United States Patent [19]
Houghton et al.

[11] Patent Number: 5,597,691
[45] Date of Patent: Jan. 28, 1997

[54] HEPATITIS C VIRUS PROTEASE

[75] Inventors: Michael Houghton, Danville; Qui-Lim Choo, El Cerrito; George Kuo, San Francisco, all of Calif.

[73] Assignee: Chiron Corporation, Emeryville, Calif.

[21] Appl. No.: 440,548

[22] Filed: May 12, 1995

Related U.S. Application Data

[62] Division of Ser. No. 350,884, Dec. 6, 1994, which is a division of Ser. No. 680,296, Apr. 4, 1991, Pat. No. 5,371,017.

[51] Int. Cl.$^6$ .............................. C12Q 1/37; C12N 9/50; C12N 15/57; C12N 15/51
[52] U.S. Cl. ..................... 435/23; 435/7.72; 435/7.6; 435/219; 536/23.2; 536/23.72
[58] Field of Search .................................. 435/5, 23, 7.6, 435/7.72

[56] References Cited

U.S. PATENT DOCUMENTS

| | | | |
|---|---|---|---|
| 4,673,634 | 6/1987 | Seto et al. | 424/228.1 |
| 4,702,909 | 10/1987 | Vallarejos et al. | 424/228.1 |
| 4,870,026 | 9/1989 | Wands et al. | 435/5 |
| 4,952,493 | 8/1990 | Kettner et al. | 435/5 |
| 5,010,175 | 4/1991 | Rutter et al. | 530/334 |
| 5,176,994 | 1/1993 | Mishiro et al. | 435/5 |
| 5,218,099 | 6/1993 | Reyes et al. | 536/23.72 |
| 5,350,671 | 9/1994 | Houghton et al. | 435/5 |
| 5,371,017 | 12/1994 | Houghton et al. | 435/320.1 |

FOREIGN PATENT DOCUMENTS

| | | |
|---|---|---|
| 0419182 | 3/1991 | European Pat. Off. . |
| WO89/04669 | 6/1989 | WIPO . |

OTHER PUBLICATIONS

Korant, B. D., "Viral proteases: An emerging therapeutic target" *CRC Critical Reviews in Biotechnology* (1988) 8:149–157.

Pichuantes, S., et al., "Expression of authentic and enzymatically active HIV–1 proteinase in bacteria and yeast" *Current Communications in Molecular Biology*, Kräusslich, H., et al., eds., Cold Spring Harbor Laboratory Press, (1989) pp. 215–222.

McQuade, T. J., et al., "A synthetic HIV–1 protease inhibitor with antiviral activity arrests HIV–like particle maturation" *Science* (1990) 247:454–456.

Kubo, Y., et al., "A cDNA fragment of hepatitis C virus isolated from an implicated donor of post–transfusion non–A, non–B hepatitis in Japan" *EMBL Data Library Accession #S06067* Submitted: (Sep. 1989) Dated: (Feb. 28, 1990).

Kubo, Y., et al., "A cDNA fragment of hepatitis C virus isolated from an implicated donor of post–transfusion non–A, non–B hepatitis in Japan" *Nucleic Acids Research* (1989) 17:10367–10372.

Miller, R. H., et al., "Hepatitis C virus shares amino acid sequence similarity with pestiviruses and flaviviruses as well as members of two plant virus supergroups" *Proceedings of the National Academy of Science USA* (1990) 87:2057–2061.

Inchauspe, G., et al., Proceedings of the National Academy of Sciences, U.S.A., vol. 88, "Genomic structure of the human prototype strain H of hepatitis C virus: comparison with American and Japanese isolates", pp. 10292–10296 1991.

Choo, Q.-L., et al., Proceedings of the National Academy of Sciences, U.S.A., vol. 88, "Genetic organization and diversity of the hepatitis C virus", pp. 2451–2455 1991.

Kato, N., et al., Proceedings of the National Academy of Sciences, U.S.A., vol. 87, "Molecular cloning of the human hepatitis C virus genome from Japanese patients with non–A, non–B hepatitis", pp. 9524–9528 1990.

Takamizawa, A., et al., Journal of Virology, vol. 65, "Structure and organization of the hepatitis C virus genome isolated from human carriers", pp. 1105–1113 1991.

Okamoto, H., et al., Journal of General Virology, vol. 72, "Nucleotide sequence of the genomic RNA of hepatitis C virus isolated from a human carrier: comparison with reported isolates for conserved and divergent regions", pp. 2697–2704 1991.

Grakoui, A., et al., Proceedings of the National Academy of Sciences, U.S.A., vol. 90, "A second hepatitis C virus–encoded proteinase", pp. 10583–10587 1993.

Chambers, T. J., et al., Proceedings of the National Academy of Science, U.S.A., vol. 87, "Evidence that the N–terminal domain of yellow fever virus NS3 protein is a serine protease . . . ", pp. 8898–8902 1990.

Hijikata, M., et al., Journal of Virology, vol. 67, "Two distinct proteinase activities required for the processing of putative nonstructural precursor protein of hepatitis C virus", pp. 4665–4675 1993.

*Primary Examiner*—Robert A. Wax
*Assistant Examiner*—William W. Moore
*Attorney, Agent, or Firm*—Kenneth M. Goldman; Alisa A. Harbin; Robert P. Blackburn

[57] ABSTRACT

The protease necessary for polyprotein processing in Hepatitis C virus is identified, cloned, and expressed. Proteases, truncated protease, and altered proteases are disclosed which are useful for cleavage of specific polypeptides, and for assay and design of antiviral agents specific for HCV.

5 Claims, 23 Drawing Sheets

```
         1                 5                      10
         Gly Thr Tyr Val Tyr Asn His Leu Thr Pro Leu Arg Asp Trp
ATT CGG GGC ACC TAT GTT TAT AAC CAT CTC ACT CCT CTT CGG GAC TGG
TAA GCC CCG TGG ATA CAA ATA TTG GTA GAG TGA GGA GAA GCC CTG ACC 15                    20                      25                    30
Ala His Asn Gly Leu Arg Asp Leu Ala Val Ala Val Glu Pro Val Val
GCG CAC AAC GGC TTG CGA GAT CTG GCC GTG GCT GTA GAG CCA GTC GTC
CGC GTG TTG CCG AAC GCT CTA GAC CGG CAC CGA CAT CTC GGT CAG CAG 35                  40                      45
Phe Ser Gln Met Glu Thr Lys Leu Ile Thr Trp Gly Ala Asp Thr Ala
TTC TCC CAA ATG GAG ACC AAG CTC ATC ACG TGG GGG GCA GAT ACC GCC
AAG AGG GTT TAC CTC TGG TTC GAG TAG TGC ACC CCC CGT CTA TGG CGG 50                      55                  60
Ala Cys Gly Asp Ile Ile Asn Gly Leu Pro Val Ser Ala Arg Arg Gly
GCG TGC GGT GAC ATC ATC AAC GGC TTG CCT GTT TCC GCC CGC AGG GGC
CGC ACG CCA CTG TAG TAG TTG CCG AAC GGA CAA AGG CGG GCG TCC CCG 65                  70                      75
Arg Glu Ile Leu Leu Gly Pro Ala Asp Gly Met Val Ser Lys Gly Trp
CGG GAG ATA CTG CTC GGG CCA GCC GAT GGA ATG GTC TCC AAG GGT TGG
GCC CTC TAT GAC GAG CCC GGT CGG CTA CCT TAC CAG AGG TTC CCA ACC 80                  85                      90
Arg Leu Leu Ala Pro Ile Thr Ala Tyr Ala Gln Gln Thr Arg Gly Leu
AGG TTG CTG GCG CCC ATC ACG GCG TAC GCC CAG CAG ACA AGG GGC CTC
TCC AAC GAC CGC GGG TAG TGC CGC ATG CGG GTC GTC TGT TCC CCG GAG 95                   100                   105                    110
Leu Gly Cys Ile Ile Thr Ser Leu Thr Gly Arg Asp Lys Asn Gln Val
CTA GGG TGC ATA ATC ACC AGC CTA ACT GGC CGG GAC AAA AAC CAA GTG
GAT CCC ACG TAT TAG TGG TCG GAT TGA CCG GCC CTG TTT TTG GTT CAC 115                   120                    125
Glu Gly Glu Val Gln Ile Val Ser Thr Ala Ala Gln Thr Phe Leu Ala
GAG GGT GAG GTC CAG ATT GTG TCA ACT GCT GCC CAA ACC TTC CTG GCA
CTC CCA CTC CAG GTC TAA CAC AGT TGA CGA CGG GTT TGG AAG GAC CGT
```

FIG. 1A

```
                    130                           135                           140
Thr Cys Ile Ile Asn Gly Val Cys Trp Thr Val Tyr His Gly Ala Gly
ACG TGC ATC ATC AAT GGG GTG TGC TGG ACT GTC TAC CAC GGG GCC GGA
TGC ACG TAG TAG TTA CCC CAC ACG ACC TGA CAG ATG GTG CCC CGG CCT 145                           150                           155
Thr Arg Thr Ile Ala Ser Pro Lys Gly Pro Val Ile Gln Met Tyr Thr
ACG AGG ACC ATC GCG TCA CCC AAG GGT CCT GTC ATC CAG ATG TAT ACC
TGC TCC TGG TAG CGC AGT GGG TTC CCA GGA CAG TAG GTC TAC ATA TGG 160                           165                           170
Asn Val Asp Gln Asp Leu Val Gly Trp Pro Ala Ser Gln Gly Thr Arg
AAT GTA GAC CAA GAC CTT GTG GGC TGG CCC GCT TCG CAA GGT ACC CGC
TTA CAT CTG GTT CTG GAA CAC CCG ACC GGG CGA AGC GTT CCA TGG GCG 175                       180                           185                           190
Ser Leu Thr Pro Cys Thr Cys Gly Ser Ser Asp Leu Tyr Leu Val Thr
TCA TTG ACA CCC TGC ACT TGC GGC TCC TCG GAC CTT TAC CTG GTC ACG
AGT AAC TGT GGG ACG TGA ACG CCG AGG AGC CTG GAA ATG GAC CAG TGC 195                           200                           205
Arg His Ala Asp Val Ile Pro Val Arg Arg Arg Gly Asp Ser Arg Gly
AGG CAC GCC GAT GTC ATT CCC GTG CGC CGG CGG GGT GAT AGC AGG GGC
TCC GTG CGG CTA CAG TAA GGG CAC GCG GCC GCC CCA CTA TCG TCC CCG
                                    ↑
                                   NaeI 210                           215                           220
Ser Leu Leu Ser Pro Arg Pro Ile Ser Tyr Leu Lys Gly Ser Ser Gly
AGC CTG CTG TCG CCC CGG CCC ATT TCC TAC TTG AAA GGC TCC TCG GGG
TCG GAC GAC AGC GGG GCC GGG TAA AGG ATG AAC TTT CCG AGG AGC CCC 225                           230                           235
Gly Pro Leu Leu Cys Pro Ala Gly His Ala Val Gly Ile Phe Arg Ala
GGT CCG CTG TTG TGC CCC GCG GGG CAC GCC GTG GGC ATA TTT AGG GCC
CCA GGC GAC AAC ACG GGG CGC CCC GTG CGG CAC CCG TAT AAA TCC CGG 240                           245                           250
Ala Val Cys Thr Arg Gly Val Ala Lys Ala Val Asp Phe Ile Pro Val
GCG GTG TGC ACC CGT GGA GTG GCT AAG GCG GTG GAC TTT ATC CCT GTG
CGC CAC ACG TGG GCA CCT CAC CGA TTC CGC CAC CTG AAA TAG GGA CAC
```

FIG. 1B

```
      255                         260                          265                          270
Glu Asn Leu Glu Thr Thr Met Arg Ser Pro Val Phe Thr Asp Asn Ser
GAG AAC CTA GAG ACA ACC ATG AGG TCC CCG GTG TTC ACG GAT AAC TCC
CTC TTG GAT CTC TGT TGG TAC TCC AGG GGC CAC AAG TGC CTA TTG AGG 275                         280                          285
Ser Pro Pro Val Val Pro Gln Ser Phe Gln Val Ala His Leu His Ala
TCT CCA CCA GTA GTG CCC CAG AGC TTC CAG GTG GCT CAC CTC CAT GCT
AGA GGT GGT CAT CAC GGG GTC TCG AAG GTC CAC CGA GTG GAG GTA CGA 290                         295                          300
Pro Thr Gly Ser Gly Lys Ser Thr Lys Val Pro Ala Ala Tyr Ala Ala
CCC ACA GGC AGC GGC AAA AGC ACC AAG GTC CCG GCT GCA TAT GCA GCT
GGG TGT CCG TCG CCG TTT TCG TGG TTC CAG GGC CGA CGT ATA CGT CGA
                                                        ↑
                                                      NdeI 305                         310                          315
Gln Gly Tyr Lys Val Leu Val Leu Asn Pro Ser Val Ala Ala Thr Leu
CAG GGC TAT AAG GTG CTA GTA CTC AAC CCC TCT GTT GCT GCA ACA CTG
GTC CCG ATA TTC CAC GAT CAT GAG TTG GGG AGA CAA CGA CGT TGT GAC 320                         325                         330
Gly Phe Gly Ala Tyr Met Ser Lys Ala His Gly Ile Asp Pro Asn Ile
GGC TTT GGT GCT TAC ATG TCC AAG GCT CAT GGG ATC GAT CCT AAC ATC
CCG AAA CCA CGA ATG TAC AGG TTC CGA GTA CCC TAG CTA GGA TTG TAG 335                         340                         345                         350
Arg Thr Gly Val Arg Thr Ile Thr Thr Gly Ser Pro Ile Thr Tyr Ser
AGG ACC GGG GTG AGA ACA ATT ACC ACT GGC AGC CCC ATC ACG TAC TCC
TCC TGG CCC CAC TCT TGT TAA TGG TGA CCG TCG GGG TAG TGC ATG AGG 355                         360                         365
Thr Tyr Gly Lys Phe Leu Ala Asp Gly Gly Cys Ser Gly Gly Ala Tyr
ACC TAC GGC AAG TTC CTT GCC GAC GGC GGG TGC TCG GGG GGC GCT TAT
TGG ATG CCG TTC AAG GAA CGG CTG CCG CCC ACG AGC CCC CCG CGA ATA 370                         375                         380
Asp Ile Ile Ile Cys Asp Glu Cys His Ser Thr Asp Ala Thr Ser Ile
GAC ATA ATA ATT TGT GAC GAG TGC CAC TCC ACG GAT GCC ACA TCC ATC
CTG TAT TAT TAA ACA CTG CTC ACG GTG AGG TGC CTA CGG TGT AGG TAG
```

FIG. 1C

```
              385                          390                         395
    Leu Gly Ile Gly Thr Val Leu Asp Gln Ala Glu Thr Ala Gly Ala Arg
    TTG GGC ATT GGC ACT GTC CTT GAC CAA GCA GAG ACT GCG GGG GCG AGA
    AAC CCG TAA CCG TGA CAG GAA CTG GTT CGT CTC TGA CGC CCC CGC TCT 400                          405                         410
    Leu Val Val Leu Ala Thr Ala Thr Pro Pro Gly Ser Val Thr Val Pro
    CTG GTT GTG CTC GCC ACC GCC ACC CCT CCG GGC TCC GTC ACT GTG CCC
    GAC CAA CAC GAG CGG TGG CGG TGG GGA GGC CCG AGG CAG TGA CAC GGG 415                          420                         425                    430
    His Pro Asn Ile Glu Glu Val Ala Leu Ser Thr Thr Gly Glu Ile Pro
    CAT CCC AAC ATC GAG GAG GTT GCT CTG TCC ACC ACC GGA GAG ATC CCT
    GTA GGG TTG TAG CTC CTC CAA CGA GAC AGG TGG TGG CCT CTC TAG GGA 435                          440                         445
    Phe Tyr Gly Lys Ala Ile Pro Leu Glu Val Ile Lys Gly Gly Arg His
    TTT TAC GGC AAG GCT ATC CCC CTC GAA GTA ATC AAG GGG GGG AGA CAT
    AAA ATG CCG TTC CGA TAG GGG GAG CTT CAT TAG TTC CCC CCC TCT GTA 450                          455                         460
    Leu Ile Phe Cys His Ser Lys Lys Lys Cys Asp Glu Leu Ala Ala Lys
    CTC ATC TTC TGT CAT TCA AAG AAG AAG TGC GAC GAA CTC GCC GCA AAG
    GAG TAG AAG ACA GTA AGT TTC TTC TTC ACG CTG CTT GAG CGG CGT TTC 465                          470                         475
    Leu Val Ala Leu Gly Ile Asn Ala Val Ala Tyr Tyr Arg Gly Leu Asp
    CTG GTC GCA TTG GGC ATC AAT GCC GTG GCC TAC TAC CGC GGT CTT GAC
    GAC CAG CGT AAC CCG TAG TTA CGG CAC CGG ATG ATG GCG CCA GAA CTG 480                          485                         490
    Val Ser Val Ile Pro Thr Ser Gly Asp Val Val Val Val Ala Thr Asp
    GTG TCC GTC ATC CCG ACC AGC GGC GAT GTT GTC GTC GTG GCA ACC GAT
    CAC AGG CAG TAG GGC TGG TCG CCG CTA CAA CAG CAG CAC CGT TGG CTA
```

FIG. 1D

```
          495                      500                      505                      510
Ala Leu Met Thr Gly Tyr Thr Gly Asp Phe Asp Ser Val Ile Asp Cys
GCC CTC ATG ACC GGC TAT ACC GGC GAC TTC GAC TCG GTG ATA GAC TGC
CGG GAG TAC TGG CCG ATA TGG CCG CTG AAG CTG AGC CAC TAT CTG ACG 515                      520                      525
Asn Thr Cys Val Thr Gln Thr Val Asp Phe Ser Leu Asp Pro Thr Phe
AAT ACG TGT GTC ACC CAG ACA GTC GAT TTC AGC CTT GAC CCT ACC TTC
TTA TGC ACA CAG TGG GTC TGT CAG CTA AAG TCG GAA CTG GGA TGG AAG 530                      535                      540
Thr Ile Glu Thr Ile Thr Leu Pro Gln Asp Ala Val Ser Arg Thr Gln
ACC ATT GAG ACA ATC ACG CTC CCC CAA GAT GCT GTC TCC CGC ACT CAA
TGG TAA CTC TGT TAG TGC GAG GGG GTT CTA CGA CAG AGG GCG TGA GTT 545                      550                      555
Arg Arg Gly Arg Thr Gly Arg Gly Lys Pro Gly Ile Tyr Arg Phe Val
CGT CGG GGC AGG ACT GGC AGG GGG AAG CCA GGC ATC TAC AGA TTT GTG
GCA GCC CCG TCC TGA CCG TCC CCC TTC GGT CCG TAG ATG TCT AAA CAC 560                      565                      570
Ala Pro Gly Glu Arg Pro Pro Gly Met Phe Asp Ser Ser Val Leu Cys
GCA CCG GGG GAG CGC CCT CCC GGC ATG TTC GAC TCG TCC GTC CTC TGT
CGT GGC CCC CTC GCG GGA GGG CCG TAC AAG CTG AGC AGG CAG GAG ACA 575                      580                      585                      590
Glu Cys Tyr Asp Ala Gly Cys Ala Trp Tyr Glu Leu Thr Pro Ala Glu
GAG TGC TAT GAC GCA GGC TGT GCT TGG TAT GAG CTC ACG CCC GCC GAG
CTC ACG ATA CTG CGT CCG ACA CGA ACC ATA CTC GAG TGC GGG CGG CTC 595                      600                      605
Thr Thr Val Arg Leu Arg Ala Tyr Met Asn Thr Pro Gly Leu Pro Val
ACT ACA GTT AGG CTA CGA GCG TAC ATG AAC ACC CCG GGC CTT CCC GTG
TGA TGT CAA TCC GAT GCT CGC ATG TAC TTG TGG GGC CCC GAA GGG CAC

FIG. IE
```

```
              610                           615                           620
Cys Gln Asp His Leu Glu Phe Trp Glu Gly Val Phe Thr Gly Leu Thr
TGC CAG GAC CAT CTT GAA TTT TGG GAG GGC GTC TTT ACA GGC CTC ACT
ACG GTC CTG GTA GAA CTT AAA ACC CTC CCG CAG AAA TGT CCG GAG TGA 625                           630                           635
His Ile Asp Ala His Phe Leu Ser Gln Thr Lys Gln Ser Gly Glu Asn
CAT ATA GAT GCC CAC TTT CTA TCC CAG ACA AAG CAG AGT GGG GAG AAC
GTA TAT CTA CGG GTG AAA GAT AGG GTC TGT TTC GTC TCA CCC CTC TTG 640                           645                           650
Leu Pro Tyr Leu Val Ala Tyr Gln Ala Thr Val Cys Ala Arg Ala Gln
CTT CCT TAC CTG GTA GCG TAC CAA GCC ACC GTG TGC GCT AGG GCT CAA
GAA GGA ATG GAC CAT CGC ATG GTT CGG TGG CAC ACG CGA TCC CGA GTT 655                       660                           665                       670
Ala Pro Pro Pro Ser Trp Asp Gln Met Trp Lys Cys Leu Ile Arg Leu
GCC CCT CCC CCA TCG TGG GAC CAG ATG TGG AAG TGT TTG ATT CGC CTC
CGG GGA GGG GGT AGC ACC CTG GTC TAC ACC TTC ACA AAC TAA GCG GAG 675                           680                           685
Lys Pro Thr Leu His Gly Pro Thr Pro Leu Leu Tyr Arg Leu Gly Ala
AAG CCC ACC CTC CAT GGG CCA ACA CCC CTG CTA TAC AGA CTG GGC GCT
TTC GGG TGG GAG GTA CCC GGT TGT GGG GAC GAT ATG TCT GAC CCG CGA
```

```
Asn Ser Glu Asn Gln Val Glu Gly Glu Val Gln Ile Val Ser Thr Ala
AAT TCG GAA AAC CAA GTG GAG GGT GAG GTC CAG ATT GTG TCA ACT GCT
TTA AGC CTT TTG GTT CAC CTC CCA CTC CAG GTC TAA CAC AGT TGA CGA
↑
EcoRI

Ala Gln Thr Phe Leu Ala Thr Cys Ile Asn Gly Val Cys Trp Thr Val
GCC CAA ACC TTC CTG GCA ACG TGC ATC AAT GGG GTG TGC TGG ACT GTC
CGG GTT TGG AAG GAC CGT TGC ACG TAG TTA CCC CAC ACG ACC TGA CAG
                               ↑
                             SfaNI

Tyr His Gly Ala Gly Thr Arg Thr Ile Ala Ser Pro Lys Gly Pro Val
TAC CAC GGG GCC GGA ACG AGG ACC ATC GCG TCA CCC AAG GGT CCT GTC
ATG GTG CCC CGG CCT TGC TCC TGG TAG CGC AGT GGG TTC CCA GGA CAG

Ile Gln Met Tyr Thr Asn Val Asp Gln Asp Leu Val Gly Trp Pro Ala
ATC CAG ATG TAT ACC AAT GTA GAC CAA GAC CTT GTG GGC TGG CCC GCT
TAG GTC TAC ATA TGG TTA CAT CTG GTT CTG GAA CAC CCG ACC GGG CGA

Ser Gln Gly Thr Arg Ser Leu Thr Pro Cys Thr Cys Gly Ser Ser Asp
TCG CAA GGT ACC CGC TCA TTG ACA CCC TGC ACT TGC GGC TCC TCG GAC
AGC GTT CCA TGG GCG AGT AAC TGT GGG ACG TGA ACG CCG AGG AGC CTG

Leu Tyr Leu Val Thr Arg His Ala Asp Val Ile Pro Val Arg Arg Arg
CTT TAC CTG GTC ACG AGG CAC GCC GAT GTC ATT CCC GTG CGC CGG CGG
GAA ATG GAC CAG TGC TCC GTG CGG CTA CAG TAA GGG CAC GCG GCC GCC
                                                        ↑
                                                      NaeI

Gly Asp Ser Arg Gly Ser Leu Val Ser Pro Arg Pro Ile Ser Tyr Leu
GGT GAT AGC AGG GGC AGC CTC GTG TCG CCC CGG CCC ATT TCC TAC TTG
CCA CTA TCG TCC CCG TCG GAG CAC AGC GGG GCC GGG TAA AGG ATG AAC

Lys Gly Ser Ser Gly Gly Pro Leu Pro Asn
AAA GGC TCC TCG GGG GGT CCG CTG CCG AAT TC
TTT CCG AGG AGC CCC CCA GGC GAC GGC TTA AG
                                        ↑
                                      EcoRI
```

```
Glu Phe Gly Gly Leu Leu Leu Cys Pro Ala Ala Ala Val Gly Ile Phe
GAA TTC GGG GGC CTG CTG TTG TGC CCC GCG GCA GCC GTG GGC ATA TTT
CTT AAG CCC CCG GAC GAC AAC ACG GGG CGC CGT CGG CAC CCG TAT AAA
  ↑
EcoRI

Arg Ala Ala Val Cys Thr Arg Gly Val Ala Lys Ala Val Asp Phe Ile
AGG GCC GCG GTG TGC ACC CGT GGA GTG GCT AAG GCG GTG GAC TTT ATC
TCC CGG CGC CAC ACG TGG GCA CCT CAC CGA TTC CGC CAC CTG AAA TAG
                                        ↑
                                       DdeI

Pro Val Glu Asn Leu Glu Thr Thr Met Arg Ser Pro Val Phe Thr Asp
CCT GTG GAG AAC CTA GAG ACA ACC ATG AGG TCC CCG GTG TTC ACG GAT
GGA CAC CTC TTG GAT CTC TGT TGG TAC TCC AGG GGC CAC AAG TGC CTA

Asn Ser Ser Pro Pro Val Val Pro Gln Ser Phe Gln Val Ala His Leu
AAC TCC TCT CCA CCA GTA GTG CCC CAG AGC TTC CAG GTG GCT CAC CTC
TTG AGG AGA GGT GGT CAT CAC GGG GTC TCG AAG GTC CAC CGA GTG GAG
                                        ↑
                                       EcoRII

His Ala Pro Arg Ile
CAT GCT CCC CGA ATT C
GTA CGA GGG GCT TAA G
              ↑
             EcoRI
```

FIG. 3 c8h:

```
Pro Cys Thr Cys Gly Ser Ser Asp Leu Tyr Leu Val Thr Arg His Ala
CCC TGC ACT TGC GGC TCC TCG GAC CTT TAC CTG GTC ACG AGG CAC GCC
GGG ACG TGA ACG CCG AGG AGC CTG GAA ATG GAC CAG TGC TCC GTG CGG

Asp Val Ile Pro Val Arg Arg Arg Gly Asp Ser Arg Gly Ser Leu Leu
GAT GTC ATT CCC GTG CGC CGG CGG GGT GAT AGC AGG GGC AGC CTG CTG
CTA CAG TAA GGG CAC GCG GCC GCC CCA CTA TCG TCC CCG TCG GAC GAC

Ser Pro Arg Pro Ile Ser Tyr Leu Lys Gly Ser Ser Gly Gly Pro Leu
TCG CCC CGG CCC ATT TCC TAC TTG AAA GGC TCC TCG GGG GGT CCG CTG
AGC GGG GCC GGG TAA AGG ATG AAC TTT CCG AGG AGC CCC CCA GGC GAC

Leu Cys Pro Ala Gly His Ala Val Gly Ile Phe Arg Ala Ala Val Cys
TTG TGC CCC GCG GGG CAC GCC GTG GGC ATA TTT AGG GCC GCG GTG TGC
AAC ACG GGG CGC CCC GTG CGG CAC CCG TAT AAA TCC CGG CGC CAC ACG

Thr Arg Gly Val Ala Lys Ala Val Asp Phe Ile Pro Val Glu Asn Leu
ACC CGT GGA GTG GCT AAG GCG GTG GAC TTT ATC CCT GTG GAG AAC CTA
TGG GCA CCT CAC CGA TTC CGC CAC CTG AAA TAG GGA CAC CTC TTG GAT
                        ↑
                      DdeI

Glu Thr Thr Met Arg Ser Pro Val Phe Thr Asp Asn Ser
GAG ACA ACC ATG AGG TCC CCG GTG TTC ACG GAT AAC TCC TC
CTC TGT TGG TAC TCC AGG GGC CAC AAG TGC CTA TTG AGG AG
```

```
Ile Arg Gly Thr Tyr Val Tyr Asn His Leu Thr Pro Leu Arg Asp Trp
ATT CGG GGC ACC TAT GTT TAT AAC CAT CTC ACT CCT CTT CGG GAC TGG
TAA GCC CCG TGG ATA CAA ATA TTG GTA GAG TGA GGA GAA GCC CTG ACC
 ↑
EcoRI

Ala His Asn Gly Leu Arg Asp Leu Ala Val Ala Val Glu Pro Val Val
GCG CAC AAC GGC TTG CGA GAT CTG GCC GTG GCT GTA GAG CCA GTC GTC
CGC GTG TTG CCG AAC GCT CTA GAC CGG CAC CGA CAT CTC GGT CAG CAG

Phe Ser Gln Met Glu Thr Lys Leu Ile Thr Trp Gly Ala Asp Thr Ala
TTC TCC CAA ATG GAG ACC AAG CTC ATC ACG TGG GGG GCA GAT ACC GCC
AAG AGG GTT TAC CTC TGG TTC GAG TAG TGC ACC CCC CGT CTA TGG CGG

Ala Cys Gly Asp Ile Ile Asn Gly Leu Pro Val Ser Ala Arg Arg Gly
GCG TGC GGT GAC ATC ATC AAC GGC TTG CCT GTT TCC GCC CGC AGG GGC
CGC ACG CCA CTG TAG TAG TTG CCG AAC GGA CAA AGG CGG GCG TCC CCG

Arg Glu Ile Leu Leu Gly Pro Ala Asp Gly Met Val Ser Lys Gly Trp
CGG GAG ATA CTG CTC GGG CCA GCC GAT GGA ATG GTC TCC AAG GGT TGG
GCC CTC TAT GAC GAG CCC GGT CGG CTA CCT TAC CAG AGG TTC CCA ACC

Arg Leu Leu Ala Pro Ile Thr Ala Tyr Ala Gln Gln Thr Arg Gly Leu
AGG TTG CTG GCG CCC ATC ACG GCG TAC GCC CAG CAG ACA AGG GGC CTC
TCC AAC GAC CGC GGG TAG TGC CGC ATG CGG GTC GTC TGT TCC CCG GAG

Leu Gly Cys Ile Ile Thr Ser Leu Thr Gly Arg Asp Lys Asn Gln Val
CTA GGG TGC ATA ATC ACC AGC CTA ACT GGC CGG GAC AAA AAC CAA GTG
GAT CCC ACG TAT TAG TGG TCG GAT TGA CCG GCC CTG TTT TTG GTT CAC

Glu Gly Glu Val Gln Ile Val Ser Thr Ala Ala Gln Thr Phe Leu Ala
GAG GGT GAG GTC CAG ATT GTG TCA ACT GCT GCC CAA ACC TTC CTG GCA
CTC CCA CTC CAG GTC TAA CAC AGT TGA CGA CGG GTT TGG AAG GAC CGT

Thr Cys Ile Asn Gly Val Cys Trp Pro Asn
ACG TGC ATC AAT GGG GTG TGC TGG CCG AAT TC
TGC ACG TAG TTA CCC CAC ACG ACC GGC TTA AG
     ↑                              ↑
   SfaNI                          EcoRI
```

Glu Phe Gly Ser Val Ile Pro Thr Ser Gly Asp Val Val Val Ala
GAA TTC GGG TCC GTC ATC CCG ACC AGC GGC GAT GTT GTC GTC GTC GCA
CTT AAG CCC AGG CAG TAG GGC TGG TCG CCG CTA CAA CAG CAG CAG CGT
↑
EcoRI

Thr Asp Ala Leu Met Thr Gly Tyr Thr Gly Asp Phe Asp Ser Val Ile
ACC GAT GCC CTC ATG ACC GGC TAT ACC GGC GAC TTC GAC TCG GTG ATA
TGG CTA CGG GAG TAC TGG CCG ATA TGG CCG CTG AAG CTG AGC CAC TAT
                                                    ↑
                                                   HinfI Asp Cys Asn Thr Cys Val Thr Gln Thr Val Asp Phe Ser Leu Asp Pro
GAC TGC AAT ACG TGT GTC ACC CAG ACA GTC GAT TTC AGC CTT GAC CCT
CTG ACG TTA TGC ACA CAG TGG GTC TGT CAG CTA AAG TCG GAA CTG GGA Thr Phe Thr Ile Glu Thr Ile Thr Leu Pro Gln Asp Ala Val Ser Arg
ACC TTC ACC ATT GAG ACA ATC ACG CTC CCC CAA GAT GCT GTC TCC CGC
TGG AAG TGG TAA CTC TGT TAG TGC GAG GGG GTT CTA CGA CAG AGG GCG Thr Gln Arg Arg Gly Arg Thr Gly Arg Gly Lys Pro Gly Ile Tyr Arg
ACT CAA CGT CGG GGC AGG ACT GGC AGG GGG AAG CCA GGC ATC TAC AGA
TGA GTT GCA GCC CCG TCC TGA CCG TCC CCC TTC GGT CCG TAG ATG TCT Phe Val Ala Pro Gly Glu Arg Pro Ser Gly Met Phe Asp Ser Ser Val
TTT GTG GCA CCG GGG GAG CGC CCC TCC GGC ATG TTC GAC TCG TCC GTC
AAA CAC CGT GGC CCC CTC GCG GGG AGG CCG TAC AAG CTG AGC AGG CAG
                    ↑                              ↑
                   BglI                          HinfI Leu Cys Glu Cys Pro Asn
CTC TGT GAG TGC CCG AAT TC
GAG ACA CTC ACG GGC TTA AG
                    ↑
                   EcoRI

```
Ile Arg Ser Ile Glu Thr Ile Thr Leu Pro Gln Asp Ala Val Ser Arg
ATT CGG TCC ATT GAG ACA ATC ACG CTC CCC CAG GAT GCT GTC TCC CGC
TAA GCC AGG TAA CTC TGT TAG TGC GAG GGG GTC CTA CGA CAG AGG GCG
↑
EcoRI

Thr Gln Arg Arg Gly Arg Thr Gly Arg Gly Lys Pro Gly Ile Tyr Arg
ACT CAA CGT CGG GGC AGG ACT GGC AGG GGG AAG CCA GGC ATC TAC AGA
TGA GTT GCA GCC CCG TCC TGA CCG TCC CCC TTC GGT CCG TAG ATG TCT

Phe Val Ala Pro Gly Glu Arg Pro Ser Gly Met Phe Asp Ser Ser Val
TTT GTG GCA CCG GGG GAG CGC CCC TCC GGC ATG TTC GAC TCG TCC GTC
AAA CAC CGT GGC CCC CTC GCG GGG AGG CCG TAC AAG CTG AGC AGG CAG
                            ↑
                          BglI

Leu Cys Glu Cys Tyr Asp Ala Gly Cys Ala Trp Tyr Glu Leu Thr Pro
CTC TGT GAG TGC TAT GAC GCA GGC TGT GCT TGG TAT GAG CTC ACG CCC
GAG ACA CTC ACG ATA CTG CGT CCG ACA CGA ACC ATA CTC GAG TGC GGG

Ala Glu Thr Thr Val Arg Leu Arg Ala Tyr Met Asn Thr Pro Gly Leu
GCC GAG ACT ACA GTT AGG CTA CGA GCG TAC ATG AAC ACC CCG GGG CTT
CGG CTC TGA TGT CAA TCC GAT GCT CGC ATG TAC TTG TGG GGC CCC GAA

Pro Val Cys Gln Asp His Leu Glu Phe Trp Glu Gly Val Phe Thr Gly
CCC GTG TGC CAG GAC CAT CTT GAA TTT TGG GAG GGC GTC TTT ACA GGC
GGG CAC ACG GTC CTG GTA GAA CTT AAA ACC CTC CCG CAG AAA TGT CCG

Leu Thr His Ile Asp Ala His Phe Leu Ser Gln Thr Lys Gln Ser Gly
CTC ACT CAT ATA GAT GCC CAC TTT CTA TCC CAG ACA AAG CAG AGT GGG
GAG TGA GTA TAT CTA CGG GTG AAA GAT AGG GTC TGT TTC GTC TCA CCC

Glu Asn Leu Pro Tyr Leu Val Ala Tyr Gln Ala Thr Val Cys Ala Arg
GAG AAC CTT CCT TAC CTG GTA GCG TAC CAA GCC ACC GTG TGC GCT AGG
CTC TTG GAA GGA ATG GAC CAT CGC ATG GTT CGG TGG CAC ACG CGA TCC

Ala Gln Ala Pro Pro Pro Ser Trp Asp Gln Met Trp Lys Cys Leu Ile
GCT CAA GCC CCT CCC CCA TCG TGG GAC CAG ATG TGG AAG TGT TTG ATT
CGA GTT CGG GGA GGG GGT AGC ACC CTG GTC TAC ACC TTC ACA AAC TAA

Arg Leu Lys Pro Thr Leu His Gly Pro Thr Pro Leu Leu Tyr Arg Leu
CGC CTC AAG CCC ACC CTC CAT GGG CCA ACA CCC CTG CTA TAC AGA CTG
GCG GAG TTC GGG TGG GAG GTA CCC GGT TGT GGG GAC GAT ATG TCT GAC

Gly Ala Ala Glu Phe
GGC GCT GCC GAA TTC
CCG CGA CGG CTT AAG
              ↑
            EcoRI
```

```
Glu Phe Gly Ala Val Asp Phe Ile Pro Val Glu Asn Leu Glu Thr Thr
GAA TTC GGG GCG GTG GAC TTT ATC CCT GTG GAG AAC CTA GAG ACA ACC
CTT AAG CCC CGC CAC CTG AAA TAG GGA CAC CTC TTG GAT CTC TGT TGG
  ↑
EcoRI

Met Arg Ser Pro Val Phe Thr Asp Asn Ser Ser Pro Pro Val Val Pro
ATG AGG TCC CCG GTG TTC ACG GAT AAC TCC TCT CCA CCA GTA GTG CCC
TAC TCC AGG GGC CAC AAG TGC CTA TTG AGG AGA GGT GGT CAT CAC GGG

Gln Ser Phe Gln Val Ala His Leu His Ala Pro Thr Gly Ser Gly Lys
CAG AGC TTC CAG GTG GCT CAC CTC CAT GCT CCC ACA GGC AGC GGC AAA
GTC TCG AAG GTC CAC CGA GTG GAG GTA CGA GGG TGT CCG TCG CCG TTT

Ser Thr Lys Val Pro Ala Ala Tyr Ala Ala Gln Gly Tyr Lys Val Leu
AGC ACC AAG GTC CCG GCT GCA TAT GCA GCT CAG GGC TAT AAG GTG CTA
TCG TGG TTC CAG GGC CGA CGT ATA CGT CGA GTC CCG ATA TTC CAC GAT

Val Leu Asn Pro Ser Val Ala Ala Thr Leu Gly Phe Gly Ala Tyr Met
GTA CTC AAC CCC TCT GTT GCT GCA ACA CTG GGC TTT GGT GCT TAC ATG
CAT GAG TTG GGG AGA CAA CGA CGT TGT GAC CCG AAA CCA CGA ATG TAC

Ser Lys Ala His Gly Ile Asp Pro Asn Ile Arg Thr Gly Val Arg Thr
TCC AAG GCT CAT GGG ATC GAT CCT AAC ATC AGG ACC GGG GTG AGA ACA
AGG TTC CGA GTA CCC TAG CTA GGA TTG TAG TCC TGG CCC CAC TCT TGT

Ile Thr Thr Gly Ser Pro Ile Thr Tyr Ser Thr Tyr Gly Lys Phe Leu
ATT ACC ACT GGC AGC CCC ATC ACG TAC TCC ACC TAC GGC AAG TTC CTT
TAA TGG TGA CCG TCG GGG TAG TGC ATG AGG TGG ATG CCG TTC AAG GAA

Ala Asp Gly Gly Cys Ser Gly Gly Ala Tyr Asp Ile Ile Ile Cys Asp
GCC GAC GGC GGG TGC TCG GGG GGC GCT TAT GAC ATA ATA ATT TGT GAC
CGG CTG CCG CCC ACG AGC CCC CCG CGA ATA CTG TAT TAT TAA ACA CTG

Glu Cys His Ser Thr Asp Ala Thr Ser Ile Leu Gly Ile Gly Thr Val
GAG TGC CAC TCC ACG GAT GCC ACA TCC ATC TTG GGC ATT GGC ACT GTC
CTC ACG GTG AGG TGC CTA CGG TGT AGG TAG AAC CCG TAA CCG TGA CAG
```

FIG. 8A

```
Leu Asp Gln Ala Glu Thr Ala Gly Ala Arg Leu Val Val Leu Ala Thr
CTT GAC CAA GCA GAG ACT GCG GGG GCG AGA CTG GTT GTG CTC GCC ACC
GAA CTG GTT CGT CTC TGA CGC CCC CGC TCT GAC CAA CAC GAG CGG TGG

Ala Thr Pro Pro Gly Ser Val Thr Val Pro His Pro Asn Ile Glu Glu
GCC ACC CCT CCG GGC TCC GTC ACT GTG CCC CAT CCC AAC ATC GAG GAG
CGG TGG GGA GGC CCG AGG CAG TGA CAC GGG GTA GGG TTG TAG CTC CTC

Val Ala Leu Ser Thr Thr Gly Glu Ile Pro Phe Tyr Gly Lys Ala Ile
GTT GCT CTG TCC ACC ACC GGA GAG ATC CCT TTT TAC GGC AAG GCT ATC
CAA CGA GAC AGG TGG TGG CCT CTC TAG GGA AAA ATG CCG TTC CGA TAG

Pro Leu Glu Val Ile Lys Gly Gly Arg His Leu Ile Phe Cys His Ser
CCC CTC GAA GTA ATC AAG GGG GGG AGA CAT CTC ATC TTC TGT CAT TCA
GGG GAG CTT CAT TAG TTC CCC CCC TCT GTA GAG TAG AAG ACA GTA AGT

Lys Lys Lys Cys Asp Glu Leu Ala Ala Lys Leu Val Ala Leu Gly Ile
AAG AAG AAG TGC GAC GAA CTC GCC GCA AAG CTG GTC GCA TTG GGC ATC
TTC TTC TTC ACG CTG CTT GAG CGG CGT TTC GAC CAG CGT AAC CCG TAG

Asn Ala Val Ala Tyr Tyr Arg Gly Leu Asp Val Ser Val Ile Pro Thr
AAT GCC GTG GCC TAC TAC CGC GGT CTT GAC GTG TCC GTC ATC CCG ACC
TTA CGG CAC CGG ATG ATG GCG CCA GAA CTG CAC AGG CAG TAG GGC TGG

Ser Gly Asp Val Val Val Val Ala Thr Asp Ala Leu Met Thr Gly Tyr
AGC GGC GAT GTT GTC GTC GTG GCA ACC GAT GCC CTC ATG ACC GGC TAT
TCG CCG CTA CAA CAG CAG CAC CGT TGG CTA CGG GAG TAC TGG CCG ATA

Thr Gly Asp Phe Asp Ser Val Ile Asp Cys Asn Thr Cys Ala Glu Phe
ACC GGC GAC TTC GAC TCG GTG ATA GAC TGC AAT ACG TGT GCC GAA TTC
TGG CCG CTG AAG CTG AGC CAC TAT CTG ACG TTA TGC ACA CGG CTT AAG
              ↑                                              ↑
            HinfI                                          EcoRI
```

FIG. 8B

```
                                    -155                      -150
                             Met Ala Thr Asn Pro Val Cys Val Leu
                             ATG GCT ACA AAC CCT GTT TGC GTT TTG
                             TAC CGA TGT TTG GGA CAA ACG CAA AAC

-145                      -140                      -135
Lys Gly Asp Gly Pro Val Gln Gly Ile Ile Asn Phe Glu Gln Lys Glu
AAG GGT GAC GGC CCA GTT CAA GGT ATT ATT AAC TTC GAG CAG AAG GAA
TTC CCA CTG CCG GGT CAA GTT CCA TAA TAA TTG AAG CTC GTC TTC CTT

-130                      -125                      -120                      -115
Ser Asn Gly Pro Val Lys Val Trp Gly Ser Ile Lys Gly Leu Thr Glu
AGT AAT GGA CCA GTG AAG GTG TGG GGA AGC ATT AAA GGA CTG ACT GAA
TCA TTA CCT GGT CAC TTC CAC ACC CCT TCG TAA TTT CCT GAC TGA CTT

-110                      -105                      -100
Gly Leu His Gly Phe His Val His Glu Phe Gly Asp Asn Thr Ala Gly
GGC CTG CAT GGA TTC CAT GTT CAT GAG TTT GGA GAT AAT ACA GCA GGC
CCG GAC GTA CCT AAG GTA CAA GTA CTC AAA CCT CTA TTA TGT CGT CCG

-95                       -90                       -85
Cys Thr Ser Pro Gly Pro His Phe Asn Pro Leu Ser Arg Lys His Gly
TGT ACC AGT CCA GGT CCT CAC TTT AAT CCT CTA TCC AGA AAA CAC GGT
ACA TGG TCA GGT CCA GGA GTG AAA TTA GGA GAT AGG TCT TTT GTG CCA

-80                       -75                       -70
Gly Pro Lys Asp Glu Glu Arg His Val Gly Asp Leu Gly Asn Val Thr
GGG CCA AAG GAT GAA GAG AGG CAT GTT GGA GAC TTG GGC AAT GTG ACT
CCC GGT TTC CTA CTT CTC TCC GTA CAA CCT CTG AAC CCG TTA CAC TGA

-65                       -60                       -55
Ala Asp Lys Asp Gly Val Ala Asp Val Ser Ile Glu Asp Ser Val Ile
GCT GAC AAA GAT GGT GTG GCC GAT GTG TCT ATT GAA GAT TCT GTG ATC
CGA CTG TTT CTA CCA CAC CGG CTA CAC AGA TAA CTT CTA AGA CAC TAG

-50                       -45                       -40                       -35
Ser Leu Ser Gly Asp His Cys Ile Ile Gly Arg Thr Leu Val Val His
TCA CTC TCA GGA GAC CAT TGC ATC ATT GGC CGC ACA CTG GTG GTC CAT
AGT GAG AGT CCT CTG GTA ACG TAG TAA CCG GCG TGT GAC CAC CAG GTA

-30                       -25                       -20
Glu Lys Ala Asp Asp Leu Gly Lys Gly Gly Asn Glu Glu Ser Thr Lys
GAA AAA GCA GAT GAC TTG GGC AAA GGT GGA AAT GAA GAA AGT ACA AAG
CTT TTT CGT CTA CTG AAC CCG TTT CCA CCT TTA CTT CTT TCA TGT TTC

-15                       -10                        -5
Thr Gly Asn Ala Gly Ser Arg Leu Ala Cys Gly Val Ile Gly Ile Arg
ACA GGA AAC GCT GGA AGT CGT TTG GCT TGT GGT GTA ATT GGG ATC CGA
TGT CCT TTG CGA CCT TCA GCA AAC CGA ACA CCA CAT TAA CCC TAG GCT
```

FIG. 10A

```
              1                    5                         10
Arg Ile Gly Thr Tyr Val Tyr Asn His Leu Thr Pro Leu Arg Asp Trp
ATT CGG GGC ACC TAT GTT TAT AAC CAT CTC ACT CCT CTT CGG GAC TGG
TAA GCC CCG TGG ATA CAA ATA TTG GTA GAG TGA GGA GAA GCC CTG ACC 15                        20                    25                    30
Ala His Asn Gly Leu Arg Asp Leu Ala Val Ala Val Glu Pro Val Val
GCG CAC AAC GGC TTG CGA GAT CTG GCC GTG GCT GTA GAG CCA GTC GTC
CGC GTG TTG CCG AAC GCT CTA GAC CGG CAC CGA CAT CTC GGT CAG CAG 35                    40                        45
Phe Ser Gln Met Glu Thr Lys Leu Ile Thr Trp Gly Ala Asp Thr Ala
TTC TCC CAA ATG GAG ACC AAG CTC ATC ACG TGG GGG GCA GAT ACC GCC
AAG AGG GTT TAC CTC TGG TTC GAG TAG TGC ACC CCC CGT CTA TGG CGG 50                        55                    60
Ala Cys Gly Asp Ile Ile Asn Gly Leu Pro Val Ser Ala Arg Arg Gly
GCG TGC GGT GAC ATC ATC AAC GGC TTG CCT GTT TCC GCC CGC AGG GGC
CGC ACG CCA CTG TAG TAG TTG CCG AAC GGA CAA AGG CGG GCG TCC CCG 65                    70                    75
Arg Glu Ile Leu Leu Gly Pro Ala Asp Gly Met Val Ser Lys Gly Trp
CGG GAG ATA CTG CTC GGG CCA GCC GAT GGA ATG GTC TCC AAG GGT TGG
GCC CTC TAT GAC GAG CCC GGT CGG CTA CCT TAC CAG AGG TTC CCA ACC 80                        85                    90
Arg Leu Leu Ala Pro Ile Thr Ala Tyr Ala Gln Gln Thr Arg Gly Leu
AGG TTG CTG GCG CCC ATC ACG GCG TAC GCC CAG CAG ACA AGG GGC CTC
TCC AAC GAC CGC GGG TAG TGC CGC ATG CGG GTC GTC TGT TCC CCG GAG 95                        100                    105                   110
Leu Gly Cys Ile Ile Thr Ser Leu Thr Gly Arg Asp Lys Asn Gln Val
CTA GGG TGC ATA ATC ACC AGC CTA ACT GGC CGG GAC AAA AAC CAA GTG
GAT CCC ACG TAT TAG TGG TCG GAT TGA CCG GCC CTG TTT TTG GTT CAC 115                   120                   125
Glu Gly Glu Val Gln Ile Val Ser Thr Ala Ala Gln Thr Phe Leu Ala
GAG GGT GAG GTC CAG ATT GTG TCA ACT GCT GCC CAA ACC TTC CTG GCA
CTC CCA CTC CAG GTC TAA CAC AGT TGA CGA CGG GTT TGG AAG GAC CGT
```

FIG. 10B

```
            130                        135                        140
Thr Cys Ile Ile Asn Gly Val Cys Trp Thr Val Tyr His Gly Ala Gly
ACG TGC ATC ATC AAT GGG GTG TGC TGG ACT GTC TAC CAC GGG GCC GGA
TGC ACG TAG TAG TTA CCC CAC ACG ACC TGA CAG ATG GTG CCC CGG CCT 145                        150                        155
Thr Arg Thr Ile Ala Ser Pro Lys Gly Pro Val Ile Gln Met Tyr Thr
ACG AGG ACC ATC GCG TCA CCC AAG GGT CCT GTC ATC CAG ATG TAT ACC
TGC TCC TGG TAG CGC AGT GGG TTC CCA GGA CAG TAG GTC TAC ATA TGG 160                        165                        170
Asn Val Asp Gln Asp Leu Val Gly Trp Pro Ala Ser Gln Gly Thr Arg
AAT GTA GAC CAA GAC CTT GTG GGC TGG CCC GCT TCG CAA GGT ACC CGC
TTA CAT CTG GTT CTG GAA CAC CCG ACC GGG CGA AGC GTT CCA TGG GCG 175                        180                        185                        190
Ser Leu Thr Pro Cys Thr Cys Gly Ser Ser Asp Leu Tyr Leu Val Thr
TCA TTG ACA CCC TGC ACT TGC GGC TCC TCG GAC CTT TAC CTG GTC ACG
AGT AAC TGT GGG ACG TGA ACG CCG AGG AGC CTG GAA ATG GAC CAG TGC 195                        200                        205
Arg His Ala Asp Val Ile Pro Val Arg Arg Arg Gly Asp Ser Arg Gly
AGG CAC GCC GAT GTC ATT CCC GTG CGC CGG CGG GGT GAT AGC AGG GGC
TCC GTG CGG CTA CAG TAA GGG CAC GCG GCC GCC CCA CTA TCG TCC CCG
                                  ↑
                                 NaeI 210                        215                        220
Ser Leu Leu Ser Pro Arg Pro Ile Ser Tyr Leu Lys Gly Ser Ser Gly
AGC CTG CTG TCG CCC CGG CCC ATT TCC TAC TTG AAA GGC TCC TCG GGG
TCG GAC GAC AGC GGG GCC GGG TAA AGG ATG AAC TTT CCG AGG AGC CCC 225                        230                        235
Gly Pro Leu Leu Cys Pro Ala Gly His Ala Val Gly Ile Phe Arg Ala
GGT CCG CTG TTG TGC CCC GCG GGG CAC GCC GTG GGC ATA TTT AGG GCC
CCA GGC GAC AAC ACG GGG CGC CCC GTG CGG CAC CCG TAT AAA TCC CGG 240                        245                        250
Ala Val Cys Thr Arg Gly Val Ala Lys Ala Val Asp Phe Ile Pro Val
GCG GTG TGC ACC CGT GGA GTG GCT AAG GCG GTG GAC TTT ATC CCT GTG
CGC CAC ACG TGG GCA CCT CAC CGA TTC CGC CAC CTG AAA TAG GGA CAC
```

FIG. 10C

```
      255                         260                         265                         270
Glu Asn Leu Glu Thr Thr Met Arg Ser Pro Val Phe Thr Asp Asn Ser
GAG AAC CTA GAG ACA ACC ATG AGG TCC CCG GTG TTC ACG GAT AAC TCC
CTC TTG GAT CTC TGT TGG TAC TCC AGG GGC CAC AAG TGC CTA TTG AGG 275                         280                         285
Ser Pro Pro Val Val Pro Gln Ser Phe Gln Val Ala His Leu His Ala
TCT CCA CCA GTA GTG CCC CAG AGC TTC CAG GTG GCT CAC CTC CAT GCT
AGA GGT GGT CAT CAC GGG GTC TCG AAG GTC CAC CGA GTG GAG GTA CGA 290                         295                         300
Pro Thr Gly Ser Gly Lys Ser Thr Lys Val Pro Ala Ala Tyr Ala Ala
CCC ACA GGC AGC GGC AAA AGC ACC AAG GTC CCG GCT GCA TAT GCA GCT
GGG TGT CCG TCG CCG TTT TCG TGG TTC CAG GGC CGA CGT ATA CGT CGA
                                                    ↑
                                                  NdeI 305                         310                         315
Gln Gly Tyr Lys Val Leu Val Leu Asn Pro Ser Val Ala Ala Thr Leu
CAG GGC TAT AAG GTG CTA GTA CTC AAC CCC TCT GTT GCT GCA ACA CTG
GTC CCG ATA TTC CAC GAT CAT GAG TTG GGG AGA CAA CGA CGT TGT GAC 320                         325                         330
Gly Phe Gly Ala Tyr Met Ser Lys Ala His Gly Ile Asp Pro Asn Ile
GGC TTT GGT GCT TAC ATG TCC AAG GCT CAT GGG ATC GAT CCT AAC ATC
CCG AAA CCA CGA ATG TAC AGG TTC CGA GTA CCC TAG CTA GGA TTG TAG 335                         340                         345                         350
Arg Thr Gly Val Arg Thr Ile Thr Thr Gly Ser Pro Ile Thr Tyr Ser
AGG ACC GGG GTG AGA ACA ATT ACC ACT GGC AGC CCC ATC ACG TAC TCC
TCC TGG CCC CAC TCT TGT TAA TGG TGA CCG TCG GGG TAG TGC ATG AGG 355                         360                         365
Thr Tyr Gly Lys Phe Leu Ala Asp Gly Gly Cys Ser Gly Gly Ala Tyr
ACC TAC GGC AAG TTC CTT GCC GAC GGC GGG TGC TCG GGG GGC GCT TAT
TGG ATG CCG TTC AAG GAA CGG CTG CCG CCC ACG AGC CCC CCG CGA ATA 370                         375                         380
Asp Ile Ile Ile Cys Asp Glu Cys His Ser Thr Asp Ala Thr Ser Ile
GAC ATA ATA ATT TGT GAC GAG TGC CAC TCC ACG GAT GCC ACA TCC ATC
CTG TAT TAT TAA ACA CTG CTC ACG GTG AGG TGC CTA CGG TGT AGG TAG
```

FIG. 10D

```
                385                         390                         395
Leu Gly Ile Gly Thr Val Leu Asp Gln Ala Glu Thr Ala Gly Ala Arg
TTG GGC ATT GGC ACT GTC CTT GAC CAA GCA GAG ACT GCG GGG GCG AGA
AAC CCG TAA CCG TGA CAG GAA CTG GTT CGT CTC TGA CGC CCC CGC TCT 400                         405                         410
Leu Val Val Leu Ala Thr Ala Thr Pro Pro Gly Ser Val Thr Val Pro
CTG GTT GTG CTC GCC ACC GCC ACC CCT CCG GGC TCC GTC ACT GTG CCC
GAC CAA CAC GAG CGG TGG CGG TGG GGA GGC CCG AGG CAG TGA CAC GGG 415                         420                         425                         430
His Pro Asn Ile Glu Glu Val Ala Leu Ser Thr Thr Gly Glu Ile Pro
CAT CCC AAC ATC GAG GAG GTT GCT CTG TCC ACC ACC GGA GAG ATC CCT
GTA GGG TTG TAG CTC CTC CAA CGA GAC AGG TGG TGG CCT CTC TAG GGA 435                         440                         445
Phe Tyr Gly Lys Ala Ile Pro Leu Glu Val Ile Lys Gly Gly Arg His
TTT TAC GGC AAG GCT ATC CCC CTC GAA GTA ATC AAG GGG GGG AGA CAT
AAA ATG CCG TTC CGA TAG GGG GAG CTT CAT TAG TTC CCC CCC TCT GTA 450                         455                         460
Leu Ile Phe Cys His Ser Lys Lys Lys Cys Asp Glu Leu Ala Ala Lys
CTC ATC TTC TGT CAT TCA AAG AAG AAG TGC GAC GAA CTC GCC GCA AAG
GAG TAG AAG ACA GTA AGT TTC TTC TTC ACG CTG CTT GAG CGG CGT TTC 465                         470                         475
Leu Val Ala Leu Gly Ile Asn Ala Val Ala Tyr Tyr Arg Gly Leu Asp
CTG GTC GCA TTG GGC ATC AAT GCC GTG GCC TAC TAC CGC GGT CTT GAC
GAC CAG CGT AAC CCG TAG TTA CGG CAC CGG ATG ATG GCG CCA GAA CTG 480                         485                         490
Val Ser Val Ile Pro Thr Ser Gly Asp Val Val Val Ala Thr Asp
GTG TCC GTC ATC CCG ACC AGC GGC GAT GTT GTC GTC GTG GCA ACC GAT
CAC AGG CAG TAG GGC TGG TCG CCG CTA CAA CAG CAG CAC CGT TGG CTA

FIG. IOE
```

```
              495                        500                        505                        510
Ala  Leu  Met  Thr  Gly  Tyr  Thr  Gly  Asp  Phe  Asp  Ser  Val  Ile  Asp  Cys
GCC  CTC  ATG  ACC  GGC  TAT  ACC  GGC  GAC  TTC  GAC  TCG  GTG  ATA  GAC  TGC
CGG  GAG  TAC  TGG  CCG  ATA  TGG  CCG  CTG  AAG  CTG  AGC  CAC  TAT  CTG  ACG 515                        520                        525
Asn  Thr  Cys  Val  Thr  Gln  Thr  Val  Asp  Phe  Ser  Leu  Asp  Pro  Thr  Phe
AAT  ACG  TGT  GTC  ACC  CAG  ACA  GTC  GAT  TTC  AGC  CTT  GAC  CCT  ACC  TTC
TTA  TGC  ACA  CAG  TGG  GTC  TGT  CAG  CTA  AAG  TCG  GAA  CTG  GGA  TGG  AAG 530                        535                        540
Thr  Ile  Glu  Thr  Ile  Thr  Leu  Pro  Gln  Asp  Ala  Val  Ser  Arg  Thr  Gln
ACC  ATT  GAG  ACA  ATC  ACG  CTC  CCC  CAA  GAT  GCT  GTC  TCC  CGC  ACT  CAA
TGG  TAA  CTC  TGT  TAG  TGC  GAG  GGG  GTT  CTA  CGA  CAG  AGG  GCG  TGA  GTT 550                        555                        560
Arg  Arg  Gly  Arg  Thr  Gly  Arg  Gly  Lys  Pro  Gly  Ile  Tyr  Arg  Phe  Val
CGT  CGG  GGC  AGG  ACT  GGC  AGG  GGG  AAG  CCA  GGC  ATC  TAC  AGA  TTT  GTG
GCA  GCC  CCG  TCC  TGA  CCG  TCC  CCC  TTC  GGT  CCG  TAG  ATG  TCT  AAA  CAC 560                        565                        570
Ala  Pro  Gly  Glu  Arg  Pro  Pro  Gly  Met  Phe  Asp  Ser  Ser  Val  Leu  Cys
GCA  CCG  GGG  GAG  CGC  CCT  CCC  GGC  ATG  TTC  GAC  TCG  TCC  GTC  CTC  TGT
CGT  GGC  CCC  CTC  GCG  GGA  GGG  CCG  TAC  AAG  CTG  AGC  AGG  CAG  GAG  ACA 575                        580                        585                        590
Glu  Cys  Tyr  Asp  Ala  Gly  Cys  Ala  Trp  Tyr  Glu  Leu  Thr  Pro  Ala  Glu
GAG  TGC  TAT  GAC  GCA  GGC  TGT  GCT  TGG  TAT  GAG  CTC  ACG  CCC  GCC  GAG
CTC  ACG  ATA  CTG  CGT  CCG  ACA  CGA  ACC  ATA  CTC  GAG  TGC  GGG  CGG  CTC 595                        600                        605
Thr  Thr  Val  Arg  Leu  Arg  Ala  Tyr  Met  Asn  Thr  Pro  Gly  Leu  Pro  Val
ACT  ACA  GTT  AGG  CTA  CGA  GCG  TAC  ATG  AAC  ACC  CCG  GGG  CTT  CCC  GTG
TGA  TGT  CAA  TCC  GAT  GCT  CGC  ATG  TAC  TTG  TGG  GGC  CCC  GAA  GGG  CAC
```

FIG. 1OF

```
            610                     615                     620
Cys Gln Asp His Leu Glu Phe Trp Glu Gly Val Phe Thr Gly Leu Thr
TGC CAG GAC CAT CTT GAA TTT TGG GAG GGC GTC TTT ACA GGC CTC ACT
ACG GTC CTG GTA GAA CTT AAA ACC CTC CCG CAG AAA TGT CCG GAG TGA 625                     630                     635
His Ile Asp Ala His Phe Leu Ser Gln Thr Lys Gln Ser Gly Glu Asn
CAT ATA GAT GCC CAC TTT CTA TCC CAG ACA AAG CAG AGT GGG GAG AAC
GTA TAT CTA CGG GTG AAA GAT AGG GTC TGT TTC GTC TCA CCC CTC TTG 640                     645                     650
Leu Pro Tyr Leu Val Ala Tyr Gln Ala Thr Val Cys Ala Arg Ala Gln
CTT CCT TAC CTG GTA GCG TAC CAA GCC ACC GTG TGC GCT AGG GCT CAA
GAA GGA ATG GAC CAT CGC ATG GTT CGG TGG CAC ACG CGA TCC CGA GTT 655                     660                     665               670
Ala Pro Pro Pro Ser Trp Asp Gln Met Trp Lys Cys Leu Ile Arg Leu
GCC CCT CCC CCA TCG TGG GAC CAG ATG TGG AAG TGT TTG ATT CGC CTC
CGG GGA GGG GGT AGC ACC CTG GTC TAC ACC TTC ACA AAC TAA GCG GAG 675                     680                     685
Lys Pro Thr Leu His Gly Pro Thr Pro Leu Leu Tyr Arg Leu Gly Ala
AAG CCC ACC CTC CAT GGG CCA ACA CCC CTG CTA TAC AGA CTG GGC GCT
TTC GGG TGG GAG GTA CCC GGT TGT GGG GAC GAT ATG TCT GAC CCG CGA
```

FIG. 10G

HEPATITIS C VIRUS PROTEASE

This application is a divisional, of application Ser. No. 08/350,884, filed Dec. 6, 1994, which is a divisional of application Ser. No. 07/680,296, filed Apr. 4, 1991, now U.S. Pat. No. 5,371,017.

TECHNICAL FIELD

This invention relates to the molecular biology and virology of the hepatitis C virus (HCV). More specifically, this invention relates to a novel protease produced by HCV, methods of expression, recombinant protease, protease mutants, and inhibitors of HCV protease.

BACKGROUND OF THE INVENTION

Non-A, Non-B hepatitis (NANBH) is a transmissible disease (or family of diseases) that is believed to be vitally induced, and is distinguishable from other forms of virus-associated liver disease, such as those caused by hepatitis A virus (HAV), hepatitis B virus (HBV), delta hepatitis virus (HDV), cytomegalovirus (CMV) or Epstein-Barr virus (EBV). Epidemiologic evidence suggests that there may be three types of NANBH: the water-borne epidemic type; the blood or needle associated type; and the sporadically occurring (community acquired) type. However, the number of causative agents is unknown. Recently, however, a new viral species, hepatitis C virus (HCV) has been identified as the primary (if not only) cause of blood-associated NANBH (BB-NANBH). See for example, PCT WO89/046699; U.S. patent application Ser. No. 7/456,637, filed 21 Dec. 1989; and U.S. patent application Ser. No. 7/456,637, filed 21 Dec. 1989, incorporated herein by reference. Hepatitis C appears to be the major form of transfusion-associated hepatitis in a number of countries, including the United States and Japan. There is also evidence implicating HCV in induction of hepatocellular carcinoma. Thus, a need exists for an effective method for treating HCV infection: currently, there is none.

Many viruses, including adenoviruses, baculoviruses, comoviruses, picornaviruses, retroviruses, and togaviruses, rely on specific, virally-encoded proteases for processing polypeptides from their initial translated form into mature, active proteins. In the case of picornaviruses, all of the viral proteins are believed to arise from cleavage of a single polyprotein (B. D. Korant, *CRC Crit Rev Biotech* (1988) 8:149–57).

S. Pichuantes et al, in "Viral Proteinases As Targets For Chemotherapy" (Cold Spring Harbor Laboratory Press, 1989) pp. 215–22, disclosed expression of a vital protease found in HIV-1. The HIV protease was obtained in the form of a fusion protein, by fusing DNA encoding an HIV protease precursor to DNA encoding human superoxide dismutase (hSOD), and expressing the product in *E. coli*. Transformed cells expressed products of 36 and 10 kDa (corresponding to the hSOD-protease fusion protein and the protease alone), suggesting that the protease was expressed in a form capable of autocatalytic proteolysis.

T. J. McQuade et al, *Science* (1990) 247:454–56 disclosed preparation of a peptide mimic capable of specifically inhibiting the HIV-1 protease. In HIV, the protease is believed responsible for cleavage of the initial p55 gag precursor transcript into the core structural proteins (p 17, p24, p8, and p7). Adding 1 µM inhibitor to HIV-infected peripheral blood lymphocytes in culture reduced the concentration of processed HIV p24 by about 70%. Viral maturation and levels of infectious virus were reduced by the protease inhibitor.

DISCLOSURE OF THE INVENTION

We have now invented recombinant HCV protease, HCV protease fusion proteins, truncated and altered HCV proteases, cloning and expression vectors therefore, and methods for identifying antiviral agents effective for treating HCV.

BRIEF DESCRIPTION OF THE DRAWINGS

FIG. 1 shows the sequence of HCV protease (SEQ ID NO:69 and SEQ ID NO:70).

FIG. 2 shows the polynucleotide sequence and deduced amino acid sequence of the clone C20c (SEQ ID NO:71 and SEQ ID NO:72).

FIG. 3 shows the polynucleotide sequence and deduced amino acid sequence of the clone C26d (SEQ ID NO:73 and SEQ ID NO:74).

FIG. 4 shows the polynucleotide sequence and deduced amino acid sequence of the clone C8h (SEQ ID NO:75 and SEQ ID NO:76).

FIG. 5 shows the polynucleotide sequence and deduced amino acid sequence of the clone C7f (SEQ ID NO:77 and SEQ ID NO:78).

FIG. 6 shows the polynucleotide sequence and deduced amino acid sequence of the clone C31 (SEQ ID NO:79 and SEQ ID NO:80).

FIG. 7 shows the polynucleotide sequence and deduced amino acid sequence of the clone C35 (SEQ ID NO:81 and SEQ ID NO:82).

FIG. 8 shows the polynucleotide sequence and deduced amino acid sequence of the clone C33c (SEQ ID NO:83 and SEQ ID NO:84).

FIG. 10 shows the sequence of vector cf1SODp600 (SEQ ID NO:85 and SEQ ID NO:86).

MODES OF CARRYING OUT THE INVENTION

A. Definitions

Figure 9A:
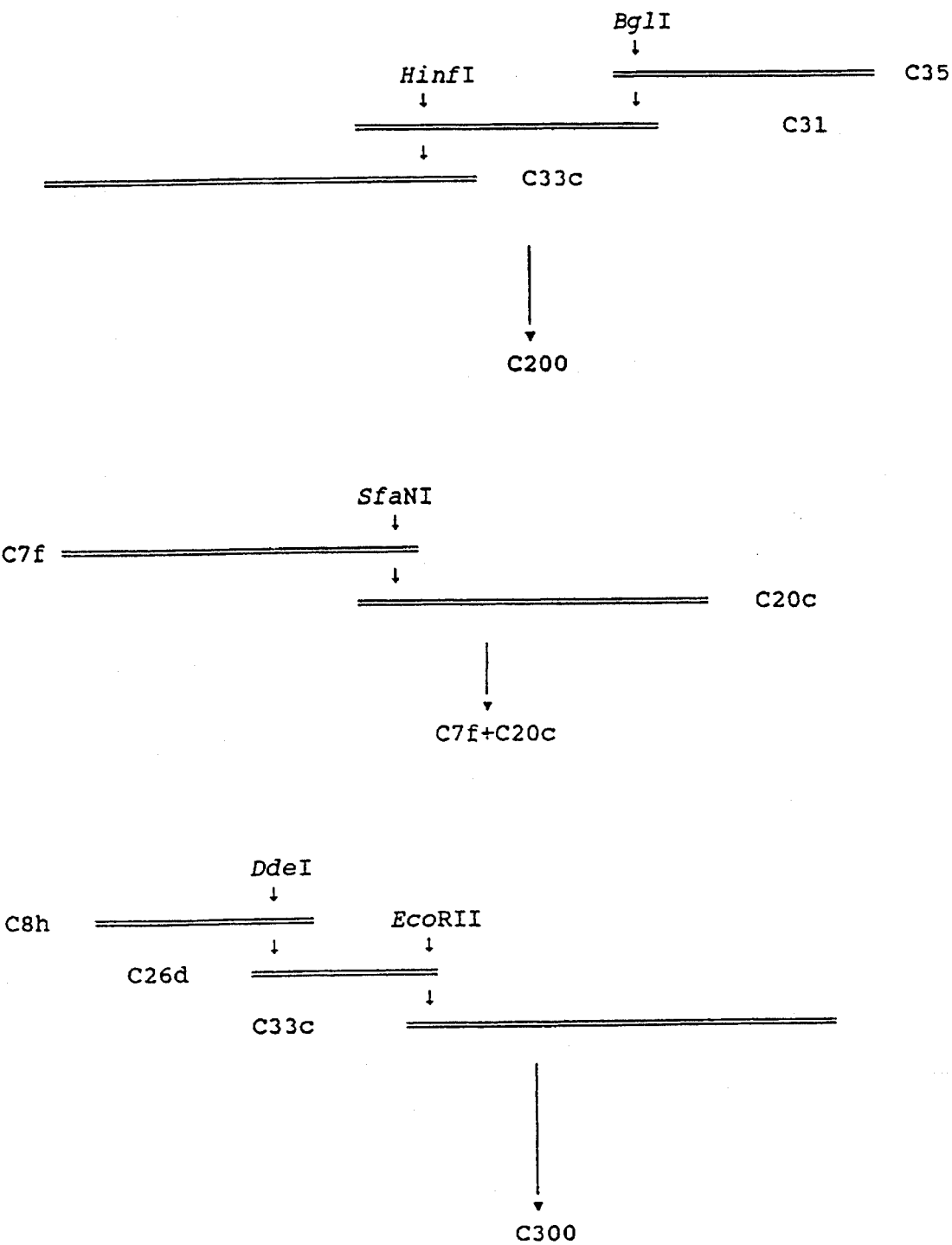
FIG. 9 schematically illustrates assembly of the vector C7fC20cC300C200.

The terms "Hepatitis C Virus" and "HCV" refer to the vital species that is the major etiological agent of BB-NANBH, the prototype isolate of which is identified in PCT WO89/046699; EPO publication 318,216; U.S. Ser. No. 7/355,008, filed 18 May 1989; and U.S. Ser. No. 7/456,637, the disclosures of which are incorporated herein by reference. "HCV" as used herein includes the pathogenic strains capable of causing hepatitis C, and attenuated strains or defective interfering particles derived therefrom. The HCV genome is comprised of RNA. It is known that RNA-containing viruses have relatively high rates of spontaneous mutation, reportedly on the order of $10^{-3}$ to $10^{-4}$ per incorporated nucleotide (Fields & Knipe, "Fundamental Virology" (1986, Raven Press, N.Y.)). As heterogeneity and fluidity of genotype are inherent characteristics of RNA viruses, there will be multiple strains/isolates, which may be virulent or avirulent, within the HCV species.

Information on several different strains/isolates of HCV is disclosed herein, particularly strain or isolate CDC/HCVI (also called HCV1). Information from one strain or isolate, such as a partial genomic sequence, is sufficient to allow those skilled in the art using standard techniques to isolate new strains/isolates and to identify whether such new strains/isolates are HCV. For example, several different strains/isolates are described below. These strains, which were obtained from a number of human sero (and from different geographical areas), were isolated utilizing the information from the genomic sequence of HCV1.

The information provided herein suggests that HCV may be distantly related to the flaviviriclae. The Flavivirus family contains a large number of viruses which are small, enveloped pathogens of man. The morphology and composition of Flavivirus particles are known, and are discussed in M. A. Brinton, in "The Viruses: The Togaviridae And Flaviviridae" (Series eds. Fraenkel-Conrat and Wagner, vol. eds. Schlesinger and Schlesinger, Plenum Press, 1986), pp. 327–374. Generally, with respect to morphology, Flaviviruses contain a central nucleocapsid surrounded by a lipid bilayer. Virions are spherical and have a diameter of about 40–50 nm. Their cores are about 25–30 nm in diameter. Along the outer surface of the virion envelope are projections measuring about 5–10 nm in length with terminal knobs about 2 nm in diameter. Typical examples of the family include Yellow Fever virus, West Nile virus, and Dengue Fever virus. They possess positive-stranded RNA genomes (about 11,000 nucleotides) that are slightly larger than that of HCV and encode a polyprotein precursor of about 3500 amino acids. Individual viral proteins are cleaved from this precursor polypeptide.

The genome of HCV appears to be single-stranded RNA containing about 10,000 nucleotides. The genome is positive-stranded, and possesses a continuous translational open reading frame (ORF) that encodes a polyprotein of about 3,000 amino acids. In the ORF, the structural proteins appear to be encoded in approximately the first quarter of the N-terminal region, with the majority of the polyprotein attributed to non-structural proteins. When compared with all known viral sequences, small but significant co-linear homologies are observed with the non-structural proteins of the Flavivirus family, and with the pestiviruses (which are now also considered to be pan of the Flavivirus family).

A schematic alignment of possible regions of a flaviviral polyprotein (using Yellow Fever Virus as an example), and of a putative polyprotein encoded in the major ORF of the HCV genome,.is shown in FIG. 1. Possible domains of the HCV polyprotein are indicated in the figure. The Yellow Fever Virus polyprotein contains, from the amino terminus to the carboxy terminus, the nucleocapsid protein (C), the matrix protein (M), the envelope protein (E), and the non-structural proteins 1, 2 (a+b), 3, 4 (a+b), and 5 (NS1, NS2, NS3, NS4, and NS5). Based upon the putative amino acids encoded in the nucleotide sequence of HCV1, a small domain at the extreme N-terminus of the HCV polyprotein appears similar both in size and high content of basic residues to the nucleocapsid protein (C) found at the N-terminus of flaviviral polyproteins. The non-structural proteins 2,3,4, and 5 (NS2–5) of HCV and of yellow fever virus (YFV) appear to have counterparks of similar size and hydropathicity, although the amino acid sequences diverge. However, the region of HCV which would correspond to the regions of YFV polyprotein which contains the M, E, and NS1 protein not only differs in sequence, but also appears to be quite different in size and hydropathicity. Thus, while certain domains of the HCV genome may be referred to herein as, for example, NS1, or NS2, it should be understood that these designations are for convenience of reference only; there may be considerable differences between the HCV family and flaviviruses that have yet to be appreciated.

Due to the evolutionary relationship of the strains or isolates of HCV, putative HCV strains and isolates are identifiable by their homology at the polypeptide level. With respect to the isolates disclosed herein, new HCV strains or isolates are expected to be at least about 40% homologous, some more than about 70% homologous, and some even more than about 80% homologous: some may be more than about 90% homologous at the polypeptide level. The techniques for determining amino acid sequence homology are known in the art. For example, the amino acid sequence may be determined directly and compared to the sequences provided herein. Alternatively the nucleotide sequence of the genomic material of the putative HCV may be determined (usually via a cDNA intermediate), the amino acid sequence encoded therein can be determined, and the corresponding regions compared.

The term "HCV protease" refers to an enzyme derived from HCV which exhibits proteolytic activity, specifically the polypeptide encoded in the NS3 domain of the HCV genome. At least one strain of HCV contains a protease believed to be substantially encoded by or within the following sequence:

| | |
|---|---|
| Arg Arg Gly Arg Glu Ile Leu Leu Gly Pro | 10 |
| Ala Asp Gly Met Val Ser Lys Gly Trp Arg | 20 |
| Leu Leu Ala Pro Ile Thr Ala Tyr Ala Gln | 30 |
| Gln Thr Arg Gly Leu Leu Gly Cys Ile Ile | 40 |
| Thr Ser Leu Thr Gly Arg Asp Lys Asn Gln | 50 |
| Val Glu Gly Glu Val Gln Ile Val Ser Thr | 60 |
| Ala Ala Gln Thr Phe Leu Ala Thr Cys Ile | 70 |
| Asn Gly Val Cys Trp Thr Val Tyr His Gly | 80 |
| Ala Gly Thr Arg Thr Ile Ala Ser Pro Lys | 90 |
| Gly Pro Val Ile Gln Met Tyr Thr Asn Val | 100 |
| Asp Gln Asp Leu Val Gly Trp Pro Ala Ser | 110 |
| Gln Gly Thr Arg Ser Leu Thr Pro Cys Thr | 120 |
| Cys Gly Ser Ser Asp Leu Tyr Leu Val Thr | 130 |
| Arg His Ala Asp Val Ile Pro Val Arg Arg | 140 |
| Arg Gly Asp Ser Arg Gly Ser Leu Leu Ser | 150 |
| Pro Arg Pro Ile Ser Tyr Leu Lys Gly Ser | 160 |
| Ser Gly Gly Pro Leu Leu Cys Pro Ala Gly | 170 |
| His Ala Val Gly Ile Phe Arg Ala Ala Val | 180 |
| Cys Thr Arg Gly Val Ala Lys Ala Val Asp | 190 |
| Phe Ile Pro Val Glu Asn Leu Glu Thr Thr | 200 |
| Met Arg (SEQ ID NO: 1)... | 202 |

The above N and C termini are putative, the actual termini being defined by expression and processing in an appropriate host of a DNA construct encoding the entire NS3 domain. It is understood that this sequence may vary from strain to strain, as RNA viruses like HCV are known to exhibit a great deal of variation. Further, the actual N and C termini may vary, as the protease is cleaved from a precursor polyprotein: variations in the protease amino acid sequence can result in cleavage from the polyprotein at different points. Thus, the amino- and carboxy-termini may differ from strain to strain of HCV. The first amino acid shown above corresponds to residue 60 in FIG. 1. However, the minimum sequence necessary for activity can be determined by routine methods. The sequence may be truncated at either end by treating an appropriate expression vector with an exonuclease (after cleavage at the 5' or 3' end of the coding sequence) to remove any desired number of base pairs. The resulting coding polynucleotide is then expressed and the sequence determined. In this manner the activity of the resulting product may be correlated with the amino acid sequence: a limited series of such experiments (removing progressively greater numbers of base pairs) determines the minimum internal sequence necessary for protease activity. We have found that the sequence may be substantially truncated, particularly at the carboxy terminus, apparently with full retention of protease activity. It is presently believed that a portion of the protein at the carboxy terminus may exhibit helicase activity. However, helicase activity is not required of the HCV proteases of the invention. The amino terminus may also be truncated to a degree without loss of protease activity.

The amino acids underlined above are believed to be the residues necessary for catalytic activity, based on sequence homology to putative flavivirus serine proteases. Table 1 shows the alignment of the three serine protease catalytic residues for HCV protease and the protease obtained from Yellow-Fever Virus, West Nile Fever virus, Murray Valley Fever virus, and Kunjin virus. Although the other four flavivirus protease sequences exhibit higher homology with each other than with HCV, a degree of homology is still observed with HCV. This homology, however, was not sufficient for indication by currently available alignment software. The indicated amino acids are numbered $His_{79}$, $Asp_{103}$, and $Ser_{161}$ in the sequence listed above ($His_{139}$, Asp163, and $Ser_{222}$ in FIG. 1).

and fusion proteins comprising HCV protease, truncated protease, or protease muteins. Alterations to form HCV protease muteins are preferably conservative amino acid substitutions, in which an amino acid is replaced with another naturally-occurring amino acid of similar character. For example, the following substitutions are considered "conservative":

| | |
|---|---|
| Gly ←→ Ala; | Asp ←→ Glu; |
| Val ←→ Ile ←→ Leu; | |
| Lys ←→ Arg; | |
| Asn ←→ Gln; and | |
| Phe ←→ Trp ←→ Tyr. | |

Nonconservative changes are generally substitutions of one of the above amino acids with an amino acid from a different group (e.g., substituting Asn for Glu), or substituting Cys, Met, His, or Pro for any of the above amino acids. Substitutions involving common amino acids are conveniently performed by site specific mutagenesis of an expression

TABLE 1

Alignment of Active Residues by Sequence

| Protease | His | Asp | Ser |
|---|---|---|---|
| HCV | CWTVYHGAG (SEQ ID NO: 2) | DQDLGWPAP (SEQ ID NO: 3) | LKGSSGGPL (SEQ ID NO: 4) |
| Yellow Fever | FHTMWHVTR (SEQ ID NO: 5) | KEDLVAYGG (SEQ ID NO: 6) | PSGTSGSPI (SEQ ID NO: 7) |
| West Nile Fever | FHTLWHTTK (SEQ ID NO: 8) | KEDRLCYGG (SEQ ID NO: 9) | PTGTSGSPI (SEQ ID NO: 10) |
| Murray Valley | FHTLWHTTR (SEQ ID NO: 11) | KEDRVTYGG (SEQ ID NO: 12) | PIGTSGSPI (SEQ ID NO: 13) |
| Kunjin Virus | FHTLWHTTK (SEQ ID NO: 14) | KEDRLCYGG (SEQ ID NO: 15) | PTGTSGSPI (SEQ ID NO: 16) |

Alternatively, one can make catalytic residue assignments based on structural homology. Table 2 shows alignment of HCV with against the catalytic sites of several well-characterized serine proteases based on structural considerations: protease A from *Streptomyces griseus*, α-lytic protease, bovine trypsin, chymotrypsin, and elastase (M. James et al, *Can J Biochem* (1978) 56:396). Again, a degree of homology is observed. The HCV residues identified are numbered $His_{79}$, $Asp_{125}$, and $Ser_{161}$ in the sequence listed above.

vector encoding the desired protein, and subsequent expression of the altered form. One may also alter amino acids by synthetic or semi-synthetic methods. For example, one may convert cysteine or serine residues to selenocysteine by appropriate chemical treatment of the isolated protein. Alternatively, one may incorporate uncommon amino acids in standard in vitro protein synthetic methods. Typically, the total number of residues changed, deleted or added to the native sequence in the muteins will be no more than about

TABLE 2

Alignment of Active Residues by Structure

| Protease | His | Asp | Ser |
|---|---|---|---|
| S. griseus A | TAGHC (SEQ ID NO: 17) | NNDYGII (SEQ ID NO: 18) | GDSGGSL (SEQ ID NO: 19) |
| α-Lytic protease | TAGHC (SEQ ID NO: 20) | GNDRAWV (SEQ ID NO: 21) | GDSGGSW (SEQ ID NO: 22) |
| Bovine Trypsin | SAAHC (SEQ ID NO: 23) | NNDIMLI (SEQ ID NO: 24) | GDSGGPV (SEQ ID NO: 25) |
| Chymotrypsin | TAAHC (SEQ ID NO: 26) | NNDITLL (SEQ ID NO: 27) | GDSGGPL (SEQ ID NO: 28) |
| Elastase | TAAHC (SEQ ID NO: 29) | GYDIALL (SEQ ID NO: 30) | GDSGGPL (SEQ ID NO: 31) |
| HCV | TVYHG (SEQ ID NO: 32) | SSDLYLV (SEQ ID NO: 33) | GSSGGPL (SEQ ID NO: 34) |

The most direct manner to verify the residues essential to the active site is to replace each residue individually with a residue of equivalent stearic size. This is easily accomplished by site-specific mutagenesis and similar methods known in the art. If replacement of a particular residue with a residue of equivalent size results in loss of activity, the essential nature of the replaced residue is confirmed.

"HCV protease analogs" refer to polypeptides which vary from the full length protease sequence by deletion, alteration and/or addition to the amino acid sequence of the native protease. HCV protease analogs include the truncated proteases described above, as well as HCV protease muteins 20, preferably no more than about 10, and most preferably no more than about 5.

The term fusion protein generally refers to a polypeptide comprising an amino acid sequence drawn from two or more individual proteins. In the present invention, "fusion protein" is used to denote a polypeptide comprising the HCV protease, truncate, mutein or a functional portion thereof, fused to a non-HCV protein or polypeptide ("fusion partner"). Fusion proteins are most conveniently produced by expression of a fused gene, which encodes a portion of one polypeptide at the 5' end and a portion of a different polypeptide at the 3' end, where the different portions are joined in one reading frame which may be expressed in a suitable host. It is presently preferred (although not required) to position the HCV protease or analog at the carboxy terminus of the fusion protein, and to employ a functional enzyme fragment at the amino terminus. As the HCV protease is normally expressed within a large polyprotein, it is not expected to include cell transport signals (e.g., export or secretion signals). Suitable functional enzyme fragments are those polypeptides which exhibit a quantifiable activity when expressed fused to the HCV protease. Exemplary enzymes include, without limitation, α-galactosidase (α-gal), α-lactamase, horseradish peroxidase (HRP), glucose oxidase (GO), human superoxide dismutase (hSOD), urease, and the like. These enzymes are convenient because the amount of fusion protein produced can be quantified by means of simple colorimetric assays. Alternatively, one may employ antigenic proteins or fragments, to permit simple detection and quantification of fusion proteins using antibodies specific for the fusion partner. The presently preferred fusion partner is hSOD.

B. General Method

The practice of the present invention generally employs conventional techniques of molecular biology, microbiology, recombinant DNA, and immunology, which are within the skill of the art. Such techniques are explained fully in the literature. See for example J. Sambrook et al, "Molecular Cloning; A Laboratory Manual (1989); "DNA Cloning", Vol. I and II (D. N. Glover ed. 1985); "Oligonucleotide Synthesis" (M. J. Gait ed, 1984); "Nucleic Acid Hybridization" (B. D. Hames & S. J. Higgins eds. 1984); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods In Enzymology" (Academic Press, Inc.); "Gene Transfer Vectors For Mammalian Cells" (J. H. Miller and M. P. Calos eds. 1987, Cold Spring Harbor Laboratory); Meth Enzymol (1987) 154 and 155 (Wu and Grossman, and Wu, eds., respectively); Mayer & Walker, eds. (1987), "Immunochemical Methods In Cell And Molecular Biology" (Academic Press, London); Scopes, "Protein Purification: Principles And Practice", 2nd Ed (Springer-Verlag, N.Y., 1987); and "Handbook Of Experimental Immunology", volumes I–IV (Weir and Blackwell, eds, 1986).

Both prokaryotic and eukaryotic host cells are useful for expressing desired coding sequences when appropriate control sequences compatible with the designated host are used.

Among prokaryotic hosts, E. coli is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These plasmids are commercially available. The markers may be used to obtain successful transformants by selection. Commonly used prokaryotic control sequences include the ε-lactamase (penicillinase) and lactose promoter systems (Chang et al, Nature (1977) 198:1056), the tryptophan (trp) promoter system (Goeddel et al, Nuc Acids Res (1980) 8:4057) and the lambda-derived $P_L$ promoter and N gene ribosome binding site (Shimatake et al, Nature (1981) 292:128) and the hybrid tac promoter (De Boer et al, Proc Nat Acad Sci USA (1983) 292:128) derived from sequences of the trp and lac UV5 promoters. The foregoing systems are particularly compatible with E. coli; if desired, other prokaryotic hosts such as strains of Bacillus or Pseudomonas may be used, with corresponding control sequences.

Eukaryotic hosts include without limitation yeast and mammalian cells in culture systems. Yeast expression hosts include Saccharomyces, Klebsiella, Picia, and the like. Saccharomyces cerevisiae and Saccharomyces carlsbergensis and K. lactis are the most commonly used yeast hosts, and are convenient fungal hosts. Yeast-compatible vectors carry markers which permit selection of successful transformants by conferring prototrophy to auxotrophic mutants or resistance to heavy metals on wild-type strains. Yeast compatible vectors may employ the 2 μ origin of replication (Broach et al, Meth Enzymol (1983) 101:307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al, J Adv Enzyme Reg (1968) 7:149; Holland et al, Biochem (1978), 17:4900), including the promoter for 3-phosphoglycerate kinase (R. Hitzeman et al, J Biol Chem (1980) 255:2073). Terminators may also be included, such as those derived from the enolase gene (Holland, J Biol Chem (1981) 256:1385). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, a leader sequence derived from yeast α-factor (see U.S. Pat. No. 4,870,008, incorporated herein by reference).

A presently preferred expression system employs the ubiquitin leader as the fusion partner. Copending application U.S. Ser. No. 7/390,599 filed 7 Aug. 1989 disclosed vectors for high expression of yeast ubiquitin fusion proteins. Yeast ubiquitin provides a 76 amino acid polypeptide which is automatically cleaved from the fused protein upon expression. The ubiquitin amino acid sequence is as follows:

| | |
|---|---|
| Gln Ile Phe Val Lys Thr Leu Thr Gly Lys Thr Ile Thr<br>Leu Glu Val Glu Ser Ser Asp Thr Ile Asp Asn Val Lys<br>Ser Lys Ile Gln Asp Lys Glu Gly Ile Pro Pro Asp Gln<br>Gln Arg Leu Ile Phe Ala Gly Lys Gln Leu Glu Asp Gly<br>Arg Thr Leu Ser Asp Tyr Asn Ile Gln Lys Glu Ser Thr<br>Leu His Leu Val Leu Arg Leu Arg Gly Gly | (SEQ ID NO: 35) |

See also Ozkaynak et at, Nature (1984) 312:663–66. Polynucleotides encoding the ubiquitin polypeptide may be synthesized by standard methods, for example following the technique of Barr et al, J Biol Chem (1988) 268:1671–78 using an Applied Biosystem 380A DNA synthesizer. Using appropriate linkers, the ubiquitin gene may be inserted into a suitable vector and ligated to a sequence encoding the HCV protease or a fragment thereof.

In addition, the transcriptional regulatory region and the transcriptional initiation region which are operably linked may be such that they are not naturally associated in the wild-type organism. These systems are described in detail in EPO 120,551, published October 3, 1984; EPO 116,201, published Aug. 22, 1984; and EPO 164,556, published Dec. 18, 1985, all of which are commonly owned with the present invention, and are hereby incorporated herein by reference in full.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include vital promoters such as that from Simian Virus 40 (SV40) (Fiers et al, *Nature* (1978) 273:113), Rous sarcoma virus (RSV), adenovirus (ADV), and bovine papilloma virus (BPV). Mammalian cells may also require terminator sequences and poly-A addition sequences. Enhancer sequences which increase expression may also be included, and sequences which promote amplification of the gene may also be desirable (for example methotrexate resistance genes). These sequences are known in the art.

Vectors suitable for replication in mammalian cells are known in the art, and may include vital replicons, or sequences which insure integration of the appropriate sequences encoding HCV epitopes into the host genome. For example, another vector used to express foreign DNA is Vaccinia virus. In this case the heterologous DNA is inserted into the Vaccinia genome. Techniques for the insertion of foreign DNA into the vaccinia virus genome are known in the art, and may utilize, for example, homologous recombination. The heterologous DNA is generally inserted into a gene which is non-essential to the virus, for example, the thyroidinc kinase gene (tk), which also provides a selectable marker. Plasmid vectors that greatly facilitate the construction of recombinant viruses have been described (see, for example, Mackett et al, *J Virol* (1984) 49:857; Chakrabarti et al, *Mol Cell Biol* (1985) 5:3403; Moss, in GENE TRANSFER VECTORS FOR MAMMALIAN CELLS (Miller and Calos, eds., Cold Spring Harbor Laboratory, N.Y., 1987), p. 10). Expression of the HCV polypeptide then occurs in cells or animals which are infected with the live recombinant vaccinia virus.

In order to detect whether or not the HCV polypeptide is expressed from the vaccinia vector, BSC 1 cells may be infected with the recombinant vector and grown on microscope slides under conditions which allow expression. The cells may then be acetone-fixed, and immunofluorescence assays performed using serum which is known to contain anti-HCV antibodies to a polypeptide(s) encoded in the region of the HCV genome from which the HCV segment in the recombinant expression vector was derived.

Other systems for expression of eukaryotic or vital genomes include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedrin gene promoter to drive expression of heterologous genes. Currently the most commonly used transfer vector for introducing foreign genes into AcNPV is pAc373 (see PCT WO89/046699 and U.S. Ser. No. 7/456,637). Many other vectors known to those of skill in the an have also been designed for improved expression. These include, for example, pVL985 (which alters the polyhedrin start codon from ATG to ATT, and introduces a BamHI cloning site 32 bp downstream from the ATT; See Luckow and Summers, *Virol* (1989) 17:31). AcNPV transfer vectors for high level expression of nonfused foreign proteins are described in copending applications PCT WO89/046699 and U.S. Ser. No. 7/456,637. A unique BamHI site is located following position −8 with respect to the translation initiation codon ATG of the polyhedrin gene. There are no cleavage sites for SmaI, PstI, BglII, XbaI or SstI. Good expression of nonfused foreign proteins usually requires foreign genes that ideally have a short leader sequence containing suitable translation initiation signals preceding an ATG start signal. The plasmid also contains the polyhedrin polyadenylation signal and the ampicillin-resistance (amp) gene and origin of replication for selection and propagation in *E. coli.*

Methods for the introduction Of heterologous DNA into the desired site in the baculovirus virus are known in the art. (See Summer and Smith, Texas Agricultural Experiment Station Bulletin No. 1555; Smith et al, *Mol Cell Biol* (1983) 3:2156–2165; and Luckow and Summers, *Virol* (1989) 17:31). For example, the heterologous DNA can be inserted into a gene such as the polyhedrin gene by homologous recombination, or into a restriction enzyme site engineered into the desired baculovirus gene. The inserted sequences may be those which encode all or varying segments of the polyprotein, or other orfs which encode viral polypeptides. For example, the insert could encode the following numbers of amino acid segments from the polyprotein: amino acids 1–1078; amino acids 332–662; amino acids 406–662; amino acids 156–328, and amino acids 199–328.

The signals for post-translational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin-2 signal ($IL2_S$) which signals for secretion from the cell, is recognized and properly removed in insect cells.

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (Cohen, *Proc Nat Acad Sci USA* (1972) 69:2110; T. Maniatis et at, "Molecular Cloning; A Laboratory Manual" (Cold Spring Harbor Press, Cold Spring Harbor, N.Y., 1982). Yeast transformation by direct uptake may be carried out using the method of Hinnen et al, *Proc Nat Acad Sci USA* (1978) 75:1929. Mammalian transformations by direct uptake may be conducted using the calcium phosphate precipitation method of Graham and Van der Eb, *Virol* (1978) 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei.

Vector construction employs techniques which are known in the art. Site-specific DNA cleavage is performed by treating with suitable restriction enzymes under conditions which generally are specified by the manufacturer of these commercially available enzymes. In general, about 1 µg of plasmid or DNA sequence is cleaved by 1 unit of enzyme in about 20 µL buffer solution by incubation for 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures described in *Meth Enzymol* (1980) 65:499–560.

Sticky-ended cleavage fragments may be blunt ended using *E. coli* DNA polymerase I (Klenow fragment) with the appropriate deoxynucleotide triphosphates (dNTPs) present in the mixture. Treatment with S1 nuclease may also be used, resulting in the hydrolysis of any single stranded DNA portions.

Ligations are carried out under standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate, thus preventing religation of the vector. Alternatively, restriction enzyme digestion of unwanted fragments can be used to prevent ligation.

Ligation mixtures are transformed into suitable cloning hosts, such as *E. coli*, and successful transformants selected using the markers incorporated (e.g., antibiotic resistance), and screened for the correct construction.

Synthetic oligonucleotides may be prepared using an automated oligonucleotide synthesizer as described by Warner, *DNA* (1984) 3:401. If desired, the synthetic strands may be labeled with $^{32}P$ by treatment with polynucleotide kinase in the presence of $^{32}P$-ATP under standard reaction conditions.

DNA sequences, including those isolated from cDNA libraries, may be modified by known techniques, for example by site directed mutagenesis (see e.g., Zoller, *Nuc Acids Res* (1982) 10:6487). Briefly, the DNA to be modified is packaged into phage as a single stranded sequence, and convened to a double stranded DNA with DNA polymerase, using as a primer a synthetic oligonucleotide complementary to the portion of the DNA to be modified, where the desired modification is included in the primer sequence. The resulting double stranded DNA is transformed into a phage-supporting host bacterium. Cultures of the transformed bacteria which contain copies of each strand of the phage are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

DNA libraries may be probed using the procedure of Grunstein and Hogness *Proc Nat Acad Sci USA* (1975) 73:3961. Briefly, in this procedure the DNA to be probed is immobilized on nitrocellulose filters, denatured, and prehybridized with a buffer containing 0–50% formamide, 0.75M NaCl, 75 mM Na citrate, 0.02% (wt/v) each of bovine serum albumin, polyvinylpyrrolidone, and Ficoll®, 50 mM $NaH_2PO_4$ (pH 6.5), 0.1% SDS, and 100 µg/mL carrier denatured DNA. The percentage of formamide in the buffer, as well as the time and temperature conditions of the prehybridization and subsequent hybridization steps depend on the stringency required. Oligomeric probes which require lower stringency conditions are generally used with low percentages of formamide, lower temperatures, and longer hybridization times. Probes containing more than 30 or 40 nucleotides, such as those derived from cDNA or genomic sequences generally employ higher temperatures, e.g., about 40°–42° C., and a high percentage formamide, e.g., 50%. Following prehybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

For routine vector constructions, ligation mixtures are transformed into *E. coli* strain HB101 or other suitable hosts, and successful transformants selected by antibiotic resistance or other markers. Plasmids from the transformants are then prepared according to the method of Clewell et al, *Proc Nat Acad Sci USA* (1969) 62:1159, usually following chloramphenicol amplification (Clewell, *J Bacteriol* (1972) 110:667). The DNA is isolated and analyzed, usually by restriction enzyme analysis and/or sequencing. Sequencing may be performed by the dideoxy method of Sanger et at, *Proc Nat Acad Sci USA* (1977) 74:5463, as further described by Messing et at, *Nuc Acids Res* (1981) 9:309, or by the method of Maxam et at, *Meth Enzymol* (1980) 65:499. Problems with band compression, which are sometimes observed in GC-rich regions, were overcome by use of T-deazoguanosine according to Barr et al, *Biotechniques* (1986) 4:428.

The enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microtiter dish, plastic cup, dipstick, plastic bead, or the like), incubated with test serum dilutions, washed, incubated with anti-immunoglobulin labeled with an enzyme, and washed again. Enzymes suitable for labeling are known in the art, and include, for example, horseradish peroxidase (HRP). Enzyme activity bound to the solid phase is usually measured by adding a specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is measured colorimetrically, and related to antigen concentration.

Proteases of the invention may be assayed for activity by cleaving a substrate which provides detectable cleavage products. As the HCV protease is believed to cleave itself from the genomic polyprotein, one can employ this auto-catalytic activity both to assay expression of the protein and determine activity. For example, of the protease is joined to its fusion partner so that the HCV protease N-terminal cleavage signal (Arg—Arg) is included, the expression product will cleave itself into fusion partner and active HCV protease. One may then assay the products, for example by western blot, to verify that the proteins produced correspond in size to the separate fusion partner and protease proteins.

It is presently preferred to employ small peptide p-nitrophenyl esters or methylcoumarins, as cleavage may then be followed by spectrophotometric or fluorescent assays. Following the method described by E. D. Matayoshi et at, *Science* (1990) 247:231–35, one may attach a fluorescent label to one end of the substrate and a quenching molecule to the other end: cleavage is then determined by measuring the resulting increase in fluorescence. If a suitable enzyme or antigen has been employed as the fusion partner, the quantity of protein produced may easily be determined. Alternatively, one may exclude the HCV protease N-terminal cleavage signal (preventing self-cleavage) and add a separate cleavage substrate, such as a fragment of the HCV NS3 domain including the native processing signal or a synthetic analog.

In the absence of this protease activity, the HCV polyprotein should remain in its unprocessed form, and thus render the virus noninfectious. Thus, the protease is useful for assaying pharmaceutical agents for control of HCV, as compounds which inhibit the protease activity sufficiently will also inhibit vital infectivity. Such inhibitors may take the form of organic compounds, particularly compounds which mimic the cleavage site of HCV recognized by the protease. Three of the putative cleavage sites of the HCV polyprotein have the following amino acid sequences:

| | |
|---|---|
| Val—Ser—Ala—Arg—Arg // Gly—Arg—Glu—Ile—Leu—Leu—Gly | (SEQ ID NO: 36) |
| Ala—Ile—Leu—Arg—Arg // His—Val—Gly—Pro— | |
| Val—Ser—Cys—Gln—Arg // Gly—Tyr | |

These sites are characterized by the presence of two basic amino acids immediately before the cleavage site, and are similar to the cleavage sites recognized by other flavivirus proteases. Thus, suitable protease inhibitors may be prepared which mimic the basic/basic/small neutral motif of the HCV cleavage sites, but substituting a nonlabile linkage for the peptide bond cleaved in the natural substrate. Suitable inhibitors include peptide trifluoromethyl ketones, peptide boronic acids, peptide α-ketoesters, peptide difluoroketo compounds, peptide aldehydes, peptide diketones, and the like. For example, the peptide aidehyde N-acetyl-phenylalanyl-glycinaldehyde is a potent inhibitor of the protease papain. One may conveniently prepare and assay large mixtures of peptides using the methods disclosed in U.S. patent application Ser. No. 7/189,318, filed 2 May 1988 (published as PCT WO89/10931), incorporated herein by reference. This application teaches methods for generating mixtures of peptides up to hexapeptides having all possible amino acid sequences, and further teaches assay methods for identifying those peptides capable of binding to proteases.

Other protease inhibitors may be proteins, particularly antibodies and antibody derivatives. Recombinant expression systems may be used to generate quantities of protease sufficient for production of monoclonal antibodies (MAbs) specific for the protease. Suitable antibodies for protease inhibition will bind to the protease in a manner reducing or eliminating the enzymatic activity, typically by obscuring the active site. Suitable MAbs may be used to generate derivatives, such as Fab fragments, chimeric antibodies, altered antibodies, univalent antibodies, and single domain antibodies, using methods known in the art.

Protease inhibitors are screened using methods of the invention. In general, a substrate is employed which mimics the enzyme's natural substrate, but which provides a quantifiable signal when cleaved. The signal is preferably detectable by colorimetric or fluorometric means: however, other methods such as HPLC or silica gel chromatography, GC-MS, nuclear magnetic resonance, and the like may also be useful. After optimum substrate and enzyme concentrations are determined, a candidate protease inhibitor is added to the reaction mixture at a range of concentrations. The assay conditions ideally should resemble the conditions under which the protease is to be inhibited in vivo, i.e., under physiologic pH, temperature, ionic strength, etc. Suitable inhibitors will exhibit strong protease inhibition at concentrations which do not raise toxic side effects in the subject. Inhibitors which compete for binding to the protease active site may require concentrations equal to or greater than the substrate concentration, while inhibitors capable of binding irreversibly to the protease active site may be added in concentrations on the order of the enzyme concentration.

In a presently preferred embodiment, an inactive protease mutein is employed rather than an active enzyme. It has been found that replacing a critical residue within the active site of a protease (e.g., replacing the active site Ser of a serine protease) does not significantly alter the structure of the enzyme, and thus preserves the binding specificity. The altered enzyme still recognizes and binds to its proper substrate, but falls to effect cleavage. Thus, in one method of the invention an inactivated HCV protease is immobilized, and a mixture of candidate inhibitors added. Inhibitors that closely mimic the enzyme's preferred recognition sequence will compete more successfully for binding than other candidate inhibitors. The poorly-binding candidates may then be separated, and the identity of the strongly-binding inhibitors determined. For example, HCV protease may be prepared substituting Ala for $Ser_{221}$ (FIG. 1), providing an enzyme capable of binding the HCV protease substrate, but incapable of cleaving it. The resulting protease mutein is then bound to a solid support, for example Sephadex® beads, and packed into a column. A mixture of candidate protease inhibitors in solution is then passed through the column and fractions collected. The last fractions to elute will contain the strongest-binding compounds, and provide the preferred protease inhibitor candidates.

Protease inhibitors may be administered by a variety of methods, such as intravenously, orally, intramuscularly, intraperitoneally, bronchially, intranasally, and so forth. The preferred route of administration will depend upon the nature of the inhibitor. Inhibitors prepared as organic compounds may often be administered orally (which is generally preferred) if well absorbed. Protein-based inhibitors (such as most antibody derivatives) must generally be administered by parenteral routes.

C. EXAMPLES

The examples presented below are provided as a further guide to the practitioner of ordinary skill in the art, and are not to be construed as limiting the invention in any way.

EXAMPLE 1

(Preparation of HCV cDNA)

A genomic library of HCV cDNA was prepared as described in PCT WO89/046699 and U.S. Ser. No. 7/456, 637. This library, ATCC accession no. 40394, has been deposited as set forth below.

EXAMPLE 2

(Expression of the Polypeptide Encoded in Clone 5-1-1.)

(A) The HCV polypeptide encoded within clone 5-1-1 (see Example 1) was expressed as a fusion polypeptide with human superoxide dismutase (SOD). This was accomplished by subcloning the clone 5-1-1 cDNA insert into the expression vector pSODCF1 (K. S. Steimer et al, *J Virol* (1986) 58:9; EPO 138,111) as follows. The SOD/5-1-1 expression vector was transformed into *E. coli* D1210 cells. These cells, named Cf1/5-1-1 in *E. coli*, were deposited as set forth below and have an ATCC accession no. of 67967.

First, DNA isolated from pSODCF1 was treated with BamHI and EcoRI, and the following linker was ligated into the linear DNA created by the restriction enzymes:

| | |
|---|---|
| GAT CCT GGA ATT CTG ATA AGA CCT TAA GAC TAT TTT AA | (SEQ ID NO: 37) |

After cloning, the plasmid containing the insert was isolated.

Plasmid containing the insert was restricted with EcoRI. The HCV cDNA insert in clone 5-1-1 was excised with EcoRI, and ligated into this EcoRI linearized plasmid DNA. The DNA mixture was used to transform *E. coli* strain D1210 (Sadler et al, *Gene* (1980) 8:279). Recombinants with the 5-1-1 cDNA in the correct orientation for expressing the ORF shown in FIG. 1 were identified by restriction mapping and nucleotide sequencing.

Recombinant bacteria from one clone were induced to express the SODHCV$_{5-1-1}$ polypeptide by growing the bacteria in the presence of IPTG.

Three separate expression vectors, pcf1AB, pcf1CD, and pcf1EF were created by ligating three new linkers, AB, CD, and EF to a BamHI-EcoRI fragment derived by digesting to completion the vector pSODCF1 with EcoRI and BamHI, followed by treatment with alkaline phosphatase. The linkers were created from six oligomers, A, B, C, D, E, and F. Each oligomer was phosphorylated by treatment with kinase in the presence of ATP prior to annealing to its complementary oligomer. The sequences of the synthetic linkers were the following:

| Name | DNA Sequence (5' to 3') |
|---|---|
| A | GATC CTG AAT TCC TGA TAA (SEQ ID NO: 38) |
| B | GAC TTA AGG ACT ATT TTA A (SEQ ID NO: 39) |
| C | GATC CGA ATT CTG TGA TAA (SEQ ID NO: 40) |
| D | GCT TAA GAC ACT ATT TTA A (SEQ ID NO: 41) |
| E | GATC CTG GAA TTC TGA TAA (SEQ ID NO: 42) |
| F | GAC CTT AAG ACT ATT TTA A (SEQ ID NO: 43) |

Each of the three linkers destroys the original EcoRI site, and creates a new EcoRI site within the linker, but within a different reading frame. Thus, the HCV cDNA EcoRI fragments isolated from the clones, when inserted into the expression vector, were in three different reading frames.

The HCV cDNA fragments in the designated λgt11 clones were excised by digestion with EcoRI; each fragment was inserted into pcf1AB, pcf1CD, and pcf1EF. These expression constructs were then transformed into D1210 *E. coli* cells, the transformants cloned, and polypeptides expressed as described in part B below.

(B) Expression products of the indicated HCV cDNAs were tested for antigenicity by direct immunological screening of the colonies, using a modification of the method described in Helfman et al, *Proc Nat Acad Sci USA* (1983), 80:31. Briefly, the bacteria were plated onto nitrocellulose filters overlaid on ampicillin plates to give approximately 40 colonies per filter. Colonies were replica plated onto nitrocellulose filters, and the replicas were regrown overnight in the presence of 2 mM IPTG and ampicillin. The bacterial colonies were lysed by suspending the nitrocellulose filters for about 15 to 20 min in an atmosphere saturated with $CHCl_3$ vapor. Each filter then was placed in an individual 100 mm Petri dish containing 10 mL of 50 mM Tris HCl, pH 7.5, 150 mM NaCl, 5 mM MgClphd 2, 3% (w/v) BSA, 40 µg/mL lysozyme, and 0.1 µg/mL DNase. The plates were agitated gently for at least 8 hours at room temperature. The filters were rinsed in TBST (50 mM Tris HCl, pH 8.0, 150 mM NaCl, 0.005% Tween® 20). After incubation, the cell residues were rinsed and incubated for one hour in TBS (TBST without Tween®) containing 10% sheep serum. The filters were then incubated with pretreated sera in TBS from individuals with NANBH, which-included 3 chimpanzees; 8 patients with chronic NANBH whose sera were positive with respect to antibodies to HCV C100-3 polypeptide (also called C100); 8 patients with chronic NANBH whose sera were negative for anti-C100 antibodies; a convalescent patient whose serum was negative for anti-C100 antibodies; and 6 patients with community-acquired NANBH, including one whose sera was strongly positive with respect to anti-C100 antibodies, and one whose sera was marginally positive with respect to anti-C100 antibodies. The sera, diluted in TBS, was pretreated by preabsorption with hSOD for at least 30 minutes at 37° C. After incubation, the filters were washed twice for 30 min with TBST. The expressed proteins which bound antibodies in the sera were labeled by incubation for 2 hours with $^{125}$I-labeled sheep anti-human antibody. After washing, the filters were washed twice for 30 min with TBST, dried, and autoradiographed.

EXAMPLE 3

(Cloning of Full-Length SOD-Protease Fusion Proteins)

(A) pBR322-C200:

The nucleotide sequences of the HCV cDNAs used below were determined essentially as described above, except that the cDNA excised from these phages were substituted for the cDNA isolated from clone 5-1-1.

Clone C33c was isolated using a hybridization probe having the following sequence:

5' ATC AGG ACC GGG GTG AGA ACA ATT ACC ACT 3' (SEQ ID NO: 44)

The sequence of the HCV cDNA in clone C33c is shown in FIG. 8, which also shows the amino acids encoded therein.

Clone 35 was isolated by screening with a synthetic polynucleotide having the sequence:

5' AAG CCA CCG TGT GCG CTA GGG CTC AAG CCC 3' (SEQ ID NO: 45)

Approximately 1 in 50,000 clones hybridized with the probe. The polynucleotide and deduced amino acid sequuences for C35 are shown in FIG. 7.

Clone C31 is shown in FIG. 6, which also shows the amino acids encoded therein. A C200 cassette was constructed by ligating together a 718 bp fragment obtained by digestion of clone C33c DNA with EcoRI and HinfI, a 179 bp fragment obtained by digestion of clone C31 DNA with HinfI and BglII, and a 377 bp fragment obtained by digesting clone C35 DNA with BglII and EcoRI. The construct of ligated fragments were inserted into the EcoRI site of pBR322, yielding the plasmid pBR322-C200.

(B) C7f+C20c:

Clone 7f was isolated using a probe having the sequence:

5'-AGC AGA CAA GGG GCC TCC TAG GGT GCA TAA T-3' (SEQ ID NO: 46)

The sequence of HCV cDNA in clone 7f and the amino acids encoded therein are shown in FIG. 5.

Clone C20c is isolated using a probe having the following sequence:

5'-TGC ATC AAT GGG GTG TGC TGG-3' (SEQ ID NO: 47)

The sequence of HCV cDNA in clone C20c, and the amino acids encoded therein are shown in FIG. 2.

Clones 7f and C20c were digested with EcoRI and SfaNI to form 400 bp and 260 bp fragments, respectively. The fragments were then cloned into the EcoRI site of pBR322 to form the vector C7f+C20c, and transformed into HB 101 cells.

(C) C300:

Clone 8h was isolated using a probe based on the sequence of nucleotides in clone 33c. The nucleotide sequence of the probe was

5'-AGA GAC AAC CAT GAG GTC CCC GGT GTT C-3'. (SEQ ID NO: 48)

The sequence of the HCV cDNA in clone 8h, and the amino acids encoded therein, are shown in FIG. 4.

Clone C26d is isolated using a probe having the following sequence:

5'-CTG TTG TGC CCC GCG GCA GCC-3' (SEQ ID NO: 49)

The sequence and amino acid translation of clone C26d is shown in FIG. 3.

Clones C26d and C33c (see part A above) were transformed into the methylation minus *E. coli* strain GM48. Clone C26d was digested with EcoRII and DdeI to provide a 100 bp fragment. Clone C33c was digested with EcoRII and EcoRI to provide a 700 bp fragment. Clone C8h was digested with EcoRI and DdeI to provide a 208 bp fragment. These three fragments were then ligated into the EcoRI site of pBR322, and transformed into *E. coli* HB101, to provide the vector C300.

(D) Preparation of Full Length Clones:

A 600 bp fragment was obtained from C7f+C20c by digestion with EcoRI and NaeI, and ligated to a 945 bp NaeI/EcoRI fragment from C300, and the construct inserted into the EcoRI site of pGEM4Z (commercially available from Promega) to form the vector C7fC20cC300.

Figure 9B:
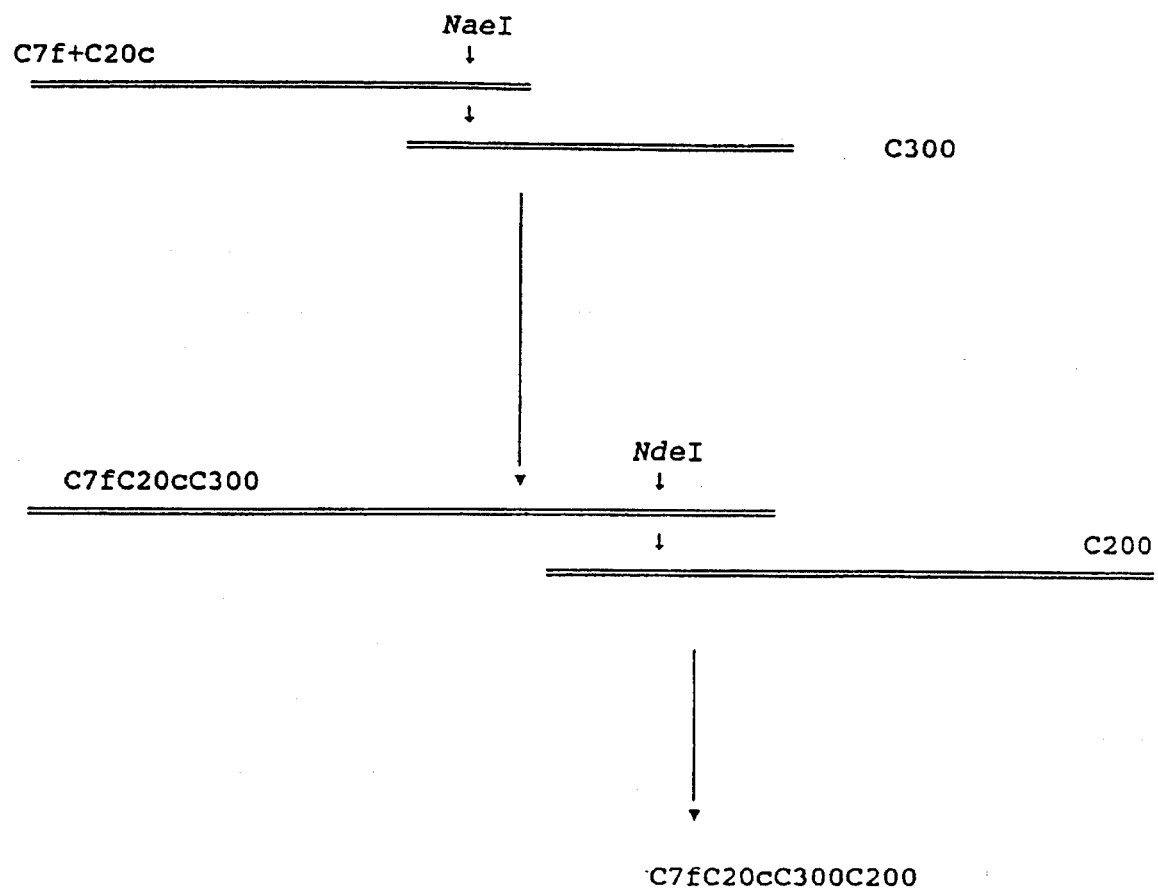

C7fC20cC300 was digested with NdeI and EcoRI to provide a 892 bp fragment, which was ligated with a 1160 bp fragment obtained by digesting C200 with NdeI and EcoRI. The resulting construct was inserted into the EcoRI site of pBR322 to provide the vector C7fC20cC300C200. Construction of this vector is illustrated schematically in FIG. 9.

EXAMPLE 4

(Preparation of E. coli Expression Vectors)

(A) cf1SODp600:

This vector contains a full-length HCV protease coding sequence fused to a functional hSOD leader. The vector C7fC20cC300C200 was cleaved with EcoRI to provide a 2000 bp fragment, which was then ligated into the EcoRI site of plasmid cf1CD (Example 2A). The resulting vector encodes amino acids 1–151 of hSOD, and amino acids 946–1630 of HCV (numbered from the beginning of the polyprotein, corresponding to amino acids 1–686 in FIG. 1). The vector was labeled cf1SODp600 (sometimes referred to as P600), and was transformed into E. coli D1210 cells. These cells, ATCC accession no. 68275, were deposited as set forth below.

(B) P190:

A truncated SOD-protease fusion polynucleotide was prepared by excising a 600 bp EcoRI/NaeI fragment from C7f+C20c, blunting the fragment with Klenow fragment, ligating the blunted fragment into the Klenow-blunted EcoRI site of cf1EF (Example 2A). This polynucleotide encodes a fusion protein having amino acids 1–151 of hSOD, and amino acids 1–199 of HCV protease.

(C) P300:

A longer truncated SOD-protease fusion polynucleotide was prepared by excising an 892 bp EcoRI/NdeI fragment from C7fC20cC300, blunting the fragment with Klenow fragment, ligating the blunted fragment into the Klenow-blunted EcoRI site of cf1EF. This polynucleotide encodes a fusion protein having amino acids 1–151 of hSOD, and amino acids 1–299 of HCV protease.

(D) P500:

A longer truncated SOD-protease fusion polynucleotide was prepared by excising a 1550 bp EcoRI/EcoRI fragment from C7fC20cC300, and ligating the fragment into the EcoRI site of cf1CD to form P500. This polynucleotide encodes a fusion protein having amino acids 1–151 of hSOD, and amino acids 946–1457 of HCV protease (amino acids 1–513 in FIG. 1).

(E) FLAG/Protease Fusion

This vector contains a full-length HCV protease coding sequence fused to the FLAG sequence, Hopp et al. (1988) Biotechnology 6:1204–1210. PCR was used to produce a HCV protease gene with special restriction ends for cloning ease. Plasmid p500 was digested with EcoRI and NdeI to yield a 900 bp fragment. This fragment and two primers were used in a polymerase chain reaction to introduce a unique BglII site at amino acid 1009 and a stop codon with a SalI site at amino acid 1262 of the HCV-1, as shown in FIG. 17 of WO 90/11089, published 4 Oct. 1990. The sequence of the primers is as follows:

5' CCC GAG CAA GAT CTC CCG GCC C 3' (SEQ ID NO: 50)
and
5'CCC GGC TGC ATA AGC AGT CGA CTT GGA 3' (SEQ ID NO: 51)

After 30 cycles of PCR, the reaction was digested with BglII and SalI, and the 710 bp fragment was isolated. This fragment was annealed and ligated to the following duplex:

MetAspTyrLysAspAspAspAspLysGlyArgGlu
CATGGACTACAAAGACGATGACGATAAAGGCCGGGA
    CTGATGTTTCTGCTACTGCTATTTCCGGCCCTCTAGG

The duplex encodes the FLAG sequence, and initiator methionine, and a 5' NcoI (SEQ ID NO:52) and SEQ ID NO:53) restriction site. The resulting NcoI/SalI fragment was ligated into a derivative of pCF1.

This construct is then transformed into E. coli D1210 cells and expression of the protease is induced by the addition of IPTG.

The FLAG sequence was fused to the HCV protease to facilitate purification. A calcium dependent monoclonal antibody, which binds to the FLAG encoded peptide, is used to purify the fusion protein without harsh eluting conditions.

EXAMPLE 5

(E. coli Expression of SOD-Protease Fusion Proteins)

(A) E. coil D1210 cells were transformed with cf1SODp600 and grown in Luria broth containing 100 µg/mL ampicillin to an OD of 0.3–0.5. IPTG was then added to a concentration of 2 mM, and the cells cultured to a final OD of 0.9 to 1.3. The cells were then lysed, and the lysate analyzed by Western blot using anti-HCV sera, as described in U.S. Ser. No. 7/456,637.

The results indicated the occurrence of cleavage, as no full length product (theoretical Mr 93 kDa) was evident on the gel. Bands corresponding to the hSOD fusion partner and the separate HCV protease appeared at relative molecular weights of about 34, 53, and 66 kDa. The 34 kDa band corresponds to the hSOD partner (about 20 kDa) with a portion of the NS3 domain, while the 53 and 66 kDa bands correspond to HCV protease with varying degrees of (possibly bacterial) processing.

(B) E. coli D1210 cells were transformed with P500 and grown in Luria broth containing 100 µg/mL ampicillin to an OD of 0.3–0.5. IPTG was then added to a concentration of 2 mM, and the cells cultured to a final OD of 0.8 to 1.0. The cells were then lysed, and the lysate analyzed as described above.

The results again indicated the occurrence of cleavage, as no full length product (theoretical Mr 73 kDa) was evident on the gel. Bands corresponding to the hSOD fusion partner and the truncated HCV protease appeared at molecular weights of about 34 and 45 kDa, respectively.

(C) E. coli D1210 cells were transformed with vectors P300 and P190 and grown as described above.

The results from P300 expression indicated the occurrence of cleavage, as no full length product (theoretical Mr 51 kDa) was evident on the gel. A band corresponding to the hSOD fusion partner appeared at a relative molecular weight of about 34. The corresponding HCV protease band was not visible, as this region of the NS3 domain is not recognized by the sera employed to detect the products. However, appearance of the hSOD band at 34 kDa rather than 51 kDa indicates that cleavage occurred.

The P190 expression product appeared only as the full (encoded) length product without cleavage, forming a band at about 40 kDa, which corresponds to the theoretical molecular weight for the uncleaved product. This may indicate that the minimum essential sequence for HCV protease extends to the region between amino acids 199 and 299.

EXAMPLE 6

(Purification of E. coli Expressed Protease)

The HCV protease and fragments expressed in Example 5 may be purified as follows:

The bacterial cells in which the polypeptide was expressed are subjected to osmotic shock and mechanical disruption, the insoluble fraction containing the protease is isolated and subjected to differential extraction with an alkaline-NaCl solution, and the polypeptide in the extract purified by chromatography on columns of S-Sepharose® and Q-Sepharose®.

The crude extract resulting from osmotic shock and mechanical disruption is prepared by suspending 1 g of the packed cells in 10 mL of a solution containing 0.02 M Tris HCl, pH 7.5, 10 mM EDTA, 20% sucrose, and incubating for 10 minutes on ice. The cells are then pelleted by centrifugation at 4,000×g for 15 min at 4° G. After the supernatant is removed, the cell pellets are resuspended in 10 mL of Buffer A1 (0.01 M Tris HCl, pH 7.5, 1 mM EDTA, 14 mM β-mercaptoethanol - "βME"), and incubated on ice for 10 minutes. The cells are again pelleted at 4,000×g for 15 minutes at 4° G. After removal of the clear supernatant (periplasmic fraction I), the cell pellets are resuspended in Buffer A1, incubated on ice for 10 minutes, and again centrifuged at 4,000×g for 15 minutes at 4° G. The clear supernatant (periplasmic fraction II) is removed, and the cell pellet resuspended in 5 mL of Buffer T2 (0.02 M Tris HCl, pH 7.5, 14 mM βME, 1 mM EDTA, 1 mM PMSF). In order to disrupt the cells, the suspension (5 mL) and 7.5 mL of Dyno-mill lead-free acid washed glass beads (0.10–0.15 mm diameter) (available from Glen-Mills, Inc.) are placed in a Falcon tube and vortexed at top speed for two minutes, followed by cooling for at least 2 min on ice. The vonexing-cooling procedure is repeated another four times. After vortexing, the slurry is filtered through a sintered glass funnel using low suction, the glass beads washed twice with Buffer A2, and the filtrate and washes combined.

The insoluble fraction of the crude extract is collected by centrifugation at 20,000×g for 15 min at 4° C., washed twice with 10 mL Buffer A2, and resuspended in 5 mL of MILLI-Q water.

A fraction containing the HCV protease is isolated from the insoluble material by adding to the suspension NaOH (2M) and NaCl (2M) to yield a final concentation of 20 mM each, vonexing the mixture for 1 minute, centrifuging it 20,000×g for 20 min at 4° C., and retaining the supernatant.

The partially purified protease is then purified by SDS-PAGE. The protease may be identified by western blot, and the band excised from the gel. The protease is then eluted from the band, and analyzed to confirm its amino acid sequence. N-terminal sequences may be analyzed using an automated amino acid sequencer, while C-terminal sequences may be analyzed by automated amino acid sequencing of a series of tryptic fragments.

EXAMPLE 7

(Preparation of Yeast Expression Vector)

(A) P650 (SOD/Protease Fusion)

This vector contains HCV sequence, which includes the wild-type full-length HCV protease coding sequence, fused at the 5' end to a SOD coding sequence. Two fragments, a 441 bp EcoRI/BglII fragment from clone 11b and a 1471 bp BglII/EcoRI fragment from expression vector P500, were used to reconstruct a wild-type, full-length HCV protease coding sequence. These two fragments were ligated together with an EcoRI digested pS356 vector to produce an expression cassette. The expression cassette encodes the ADH2/GAPDH hybrid yeast promoter, human SOD, the HCV protease, and a GAPDH transcription terminator. The resulting vector was digested with BamHI and a 4052 bp fragment was isolated. This fragment was ligated to the BamHI digested pAB24 vector to produce p650. p650 expresses a polyprotein containing, from its amino terminal end, amino acids 1–154 of hSOD, an oligopeptide -Asn-Leu-Gly-Ile-Arg-, and amino acids 819 to 1458 of HCV-1, as shown in FIG. 17 of WO 90/11089, published 4 Oct. 1990.

Clone 11b was isolated from the genomic library of HCV cDNA, ATCC accession no. 40394, as described above in Example 3A, using a hybridization probe having the following sequence:

5' CAC CTA TGT TTA TAA CCA TCT CAC TCC TCT 3'. (SEQ ID NO: 54)

This procedure is also described in EPO Pub. No. 318 216, Example IV.A.17.

The vector pS3EF, which is a pBR322 derivative, contains the ADH2/GAPDH hybrid yeast promoter upstream of the human superoxide dimutase gene, an adaptor, and a downstream yeast effective transcription terminator. A similar expression vector containing these control elements and the superoxide dismutase gene is described in Cousens et al. (1987) Gene 61:265, and in copending application EPO 196,056, published Oct. 1, 1986. pS3EF, however, differs from that in Cousens et al. in that the heterologous proinsulin gene and the immunoglobulin hinge are deleted, and $Gln_{154}$ of SOD is followed by an adaptor sequence which contains an EcoRI site. The sequence of the adaptor is:

5' AAT TTG GGA ATT CCA TAA TTA ATT AAG 3' (SEQ ID NO: 55)
3' AC CCT AAG GGT ATT AAT TAA TTC AGCT 5' (SEQ ID NO: 56)

The EcoRI site facilitates the insertion of heterologous sequences. Once inserted into pS3EF, a SOD fusion is expressed which contains an oligopeptide that links SOD to the heterologous sequences. pS3EF is exactly the same as pS356 except that pS356 contains a different adaptor. The sequence of the adaptor is shown below:

5' AAT TTG GGA ATT CCA TAA TGA G 3' (SEQ ID NO: 57)
3' AC CCT AAG GGT ATT ACT CAG CT 5' (SEQ ID NO: 58)

pS356, ATCC accession no. 67683, is deposited as set forth below.

Plasmid pAB24 is a yeast shuttle vector, which contains pBR322 sequences, the complete 2 μ sequence for DNA replication in yeast (Broach (1981) in: *Molecular Biology of the Yeast Saccharomyces,* Vol. 1, p. 445, Cold spring Harbor Press.) and the yeast $LEU^{2d}$ gene derived from plasmid pC1/1, described in EPO Pub. No. 116 201. Plasmid pAB24 was constructed by digesting YEp24 with EcoRI and re-ligating the vector to remove the partial 2 micron sequences. The resulting plasmid, YEp24deltaRI, was linearized with ClaI and ligated with the complete 2 micron plasmid which had been linearized with ClaI. The resulting plasmid, pCBou, was then digested with XbaI, and the 8605 bp vector fragment was gel isolated. This isolated XbaI fragment was ligated with a 4460 bp XbaI fragment containing the $LEU^{2d}$ gene isolated from pC1/1; the orientation of $LEU^{2d}$ gene is in the same direction as the URA3 gene.

*S. cerevisae,* 2150-2-3 (pAB24-GAP-env2), accession no. 20827, is deposited with the American Type Culture Collection as set forth below. The plasmid pAB24-GAP-env2 can be recovered from the yeast cells by known techniques. The GAP-env2 expression cassette can be removed by digesting pAB24-GAP-env2 with BamHI. pAB24 is recovered by religating the vector without the BamHI insert.

EXAMPLE 8

(Yeast Expression of SOD-Protease Fusion Protein)

p650 was transformed in *S. cerevisae* strain JSC310, Mata, leu2, ura3-52, prb1-1122, pep4-3, prc1-407, cir°: DM15 (g418 resistance). The transformation is as described by Hinnen et al. (1978) *Proc Natl Acad Sci USA* 75:1929. The transformed cells were selected on ura- plates with 8% glucose. The plates were incubated at 30° C. for 4–5 days. The tranformants were further selected on leu- plates with 8% glucose putatively for high numbers of the p650 plasmid. Colonies from the leu- plates were inoculated into leu- medium with 3% glucose. These cultures were shaken at 30° C. for 2 days and then diluted 1/20 into YEPD medium with 2% glucose and shaken for 2 more days at 30° C.

*S. cerevisae* JSC310 contains DM15 DNA, described in EPO Pub. No. 340 986, published 8 Nov. 1989. This DM15 DNA enhances ADH2 regulated expression of heterologous proteins. pDM15, accession no. 40453, is deposited with the American Type Culture Collection as set forth below.

EXAMPLE 9

(Yeast Ubiquitin Expression of Mature HCV Protease)

Mature HCV protease is prepared by cleaving vector C7fC20cC300C200 with EcoRI to obtain a 2 Kb coding sequence, and inserting the sequence with the appropriate linkers into a ubiquitin expression vector, such as that described in WO 88/02406, published 7 Apr. 1988, or U.S. Ser. No. 7/390,599 filed 7 Aug. 1989, incorporated herein by reference. Mature HCV protease is recovered upon expression of the vector in suitable hosts, particularly yeast. Specifically, the yeast expression protocol described in Example 8 is used to express a ubiquitin/HCV protease vector.

EXAMPLE 10

(Preparation of an In-Vitro Expression Vector)

(A) pGEM®-3Z/Yellow Fever Leader Vector

Four synthetic DNA fragments were annealed and ligated** together to create a EcoRI/SacI Yellow Fever leader, which was ligated to a EcoRI/SacI digested pGEM®-3Z vector from Promega®. The sequence of the four fragments are listed below:

YFK-1:

5' AAT TCG TAA ATC CTG TGT GCT AAT TGA GGT GCA TTG GTC TGC AAA TCG AGT TGC TAG GCA ATA AAC ACA TT 3' (SEQ ID NO: 59)

YFK-2:

5' TAT TGC CTA GCA ACT CGA TTT GCA GAC CAA TGC ACC TCA ATT AGC ACA CAG GAT TTA CG 3' (SEQ ID NO: 60)

YFK-3:

5' TGG ATT AAT TTT AAT CGT TCG TTG AGC GAT TAG CAG AGA ACT GAC CAG AAC ATG TCT GAG CT 3' (SEQ ID NO: 61)

YFK-4:

5' CAG ACA TGT TCT GGT CAG TTC TCT GCT AAT CGC TCA ACG AAC GAT TAA AAT TAA TCC AAA TGT GTT 3'. (SEQ ID NO: 62)

For in-vitro translation of the HCV protease, the new pGEM®-3Z/Yellow Fever leader vector was digested with BamHI and blunted with Klenow.

(B) PvuII Construct from p6000

A clone p6000 was constructed from sequences available from the genomic library of HCV cDNA, ATCC accession no. 40394. The HCV encoding DNA sequence of p6000 is identical to nucleotide −275 to nucleotide 6372 of FIG. 17 of WO 90/11089, published 4 Oct. 1990. p6000 was digested with PvuII, and from the digest, a 2,864 bp fragment was isolated. This 2,864 bp fragment was ligated to the prepared pGEM®-3Z/Yellow Fever leader vector fragment, described above.

EXAMPLE 11

(In-Vitro Expression of HCV Protease)

(A) Transcription

The pGEM®-3Z/Yellow Fever leader/PvuII vector was linearized with XbaI and transcribed using the materials and protocols from Promega's Riboprobe® Gemini II Core system.

(B) Translation

The RNA produced by the above protocol was translated using Promega's rabbit reticulocyte lysate, minus methionine, canine pancreatic microsomal membranes, as well as, other necessary materials and instructions from Promega.

Deposited Biological Materials:

The following materials were deposited with the American Type Culture Collection (ATCC), 12301 Parklawn Dr., Rockville, Md.:

| Name | Deposit Date | Accession No. |
|---|---|---|
| E. coli D1210, cf1SODp600 | 23 Mar 1990 | 68275 |
| Cf1/5-1-1 in E. coli D1210 | 11 May 1989 | 67967 |
| Bacteriophage λ-gt11 cDNA library | 01 Dec 1987 | 40394 |
| E. coli HB101, pS356 | 29 Apr 1988 | 67683 |
| plasmid DNA, pDM15 | 05 May 1988 | 40453 |
| S. cerevisae, 2150-2-3 (pAB24-GAP-env2) | 23 Dec 1986 | 20827 |

The above materials have been deposited with the ATCC under the accession numbers indicated. These deposits will be maintained under the terms of the Budapest Treaty on the International Recognition of the Deposit of Microorganisms for purposes of Patent Procedure. These deposits are provided as a convenience to those of skill in the art, and are not an admission that a deposit is required under 35 U.S.C. §112. The polynucleotide sequences contained in the deposited materials, as well as the amino acid sequence of the polypeptides encoded thereby, are incorporated herein by reference and are controlling in the event of any conflict with the sequences described herein. A license may be required to make, use or sell the deposited materials, and no such license is granted hereby.

What is claimed:

1. A method for assaying compounds for activity against hepatitis C virus comprising the steps of:
   providing an NS3 domain hepatitis C virus protease or active NS3 domain hepatitis C virus protease truncation analog and a NS3 domain hepatitis C virus protease peptide substrate;
   contacting said protease or protease truncation analog with a candidate inhibitory compound in the presence of said peptide substrate; and
   measuring the inhibition of the proteolytic activity of said NS3 domain hepatitis C virus protease or protease truncation analog.

2. The method of claim 1, wherein said NS3 domain hepatitis C virus protease peptide substrate comprises a covalently-linked marker compound.

3. The method of claim 1, wherein said NS3 domain hepatitis C virus protease or active NS3 domain hepatitis C virus protease truncation analog has a partial internal amino acid sequence comprising SEQ ID NO:63.

4. The method of claim 1, wherein said NS3 domain hepatitis C virus protease or active NS3 domain hepatitis C virus protease truncation analog has a partial internal sequence comprising SEQ ID NO:64.

5. The method of claim 1, wherein said NS3 domain hepatitis C virus protease or active NS3 domain hepatitus C virus protease truncation analog has an amino acid sequence comprising SEQ ID NO:65.

* * * * *

UNITED STATES PATENT AND TRADEMARK OFFICE
CERTIFICATE OF CORRECTION

PATENT NO. : 5,597,691
DATED : January 28, 1997
INVENTOR(S) : Houghton et al.

It is certified that error appears in the above-indentified patent and that said Letters Patent is hereby corrected as shown below:

In the specification:

Column 1, line 6 after "5,371,017" please insert:

--, which is a continuation-in-part application of U.S. Serial No. 07/505,433, filed on 4 April 1990, abandoned--.

Signed and Sealed this

Ninth Day of June, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,597,691
DATED : January 28, 1997
INVENTOR(S) : Houghton et al.

It is certified that error appears in the above-indentified patent and that said Letters Patent is hereby corrected as shown below:

Column 1, line 6 after "5,371,017" please insert:

--, which is a continuation-in-part application of U.S. Serial No. 07/505,433, filed on 4 April 1990, abandoned--.

Signed and Sealed this

Sixteenth Day of June, 1998

Attest:

BRUCE LEHMAN

Attesting Officer        Commissioner of Patents and Trademarks

US005597691B1

(12) REEXAMINATION CERTIFICATE (4503rd)
United States Patent
Houghton et al.

(10) Number: US 5,597,691 C1
(45) Certificate Issued: Dec. 11, 2001

(54) HEPATITUS C VIRUS PROTEASE

(75) Inventors: Michael Houghton, Danville; Qui-Lim Choo, El Cerrito; George Kuo, San Francisco, all of CA (US)

(73) Assignee: Chiron Corporation, Emeryville, CA (US)

Reexamination Request:
No. 90/005,514, Oct. 8, 1999

Reexamination Certificate for:
Patent No.: 5,597,691
Issued: Jan. 28, 1997
Appl. No.: 08/440,548
Filed: May 12, 1995

Certificate of Correction issued Jun. 16, 1998.

Related U.S. Application Data

(62) Division of application No. 08/350,884, filed on Dec. 6, 1994, which is a division of application No. 07/680,296, filed on Apr. 4, 1991, now Pat. No. 5,371,017.

(51) Int. Cl.[7] .............................. C12Q 1/37; C12N 9/50; C12N 15/57; C12N 15/51
(52) U.S. Cl. .......................... 435/23; 435/7.72; 435/7.6; 435/219; 435/5; 536/23.2; 536/23.72
(58) Field of Search .................................. 435/5, 23, 7.72, 435/7.6, 219; 536/23.2, 23.4, 23.72

(56) References Cited

U.S. PATENT DOCUMENTS

| | | | |
|---|---|---|---|
| 3,773,924 | 11/1973 | Ho et al. | 424/85 |
| 3,883,497 | 5/1975 | Gregory et al. | 260/112 R |
| 4,271,145 | 6/1981 | Wands et al. | 424/85 |
| 4,356,164 | 10/1982 | Tabor et al. | 424/1 |
| 4,395,395 | 7/1983 | Tabor et al. | 424/89 |
| 4,431,740 | 2/1984 | Bell et al. | 435/253 |
| 4,438,098 | 3/1984 | Tabor et al. | 424/89 |
| 4,464,474 | 8/1984 | Coursaget et al. | 436/513 |
| 4,542,016 | 9/1985 | Trepo | 424/86 |
| 4,569,794 | 2/1986 | Smith et al. | 260/113 |
| 4,620,948 | 11/1986 | Builder et al. | 530/419 |
| 4,652,525 | 3/1987 | Rutter et al. | 435/253 |
| 4,707,439 | 11/1987 | Seto et al. | 435/5 |
| 4,769,331 | 9/1988 | Roizman et al. | 435/172.3 |
| 4,777,245 | 10/1988 | Foung et al. | 530/387 |
| 4,784,950 | 11/1988 | Hagen et al. | 435/68 |
| 4,871,659 | 10/1989 | Pillot | 435/5 |
| 4,929,700 | 5/1990 | Halenbeck et al. | 530/351 |
| 4,931,543 | 6/1990 | Halenbeck et al. | 530/351 |
| 4,952,494 | 8/1990 | Zeldis et al. | 435/5 |
| 4,959,317 | 9/1990 | Saeuer | 435/172.3 |
| 4,977,248 | 12/1990 | Creighton | 530/412 |
| 5,032,511 | 7/1991 | Takahashi et al. | 435/69.1 |
| 5,077,193 | 12/1991 | Mishiro et al. | 435/5 |
| 5,108,919 | 4/1992 | Liu et al. | 435/224 |
| 5,132,213 | 7/1992 | Bachmair et al. | 435/69.7 |
| 5,162,507 | 11/1992 | Wolfe et al. | 530/412 |
| 5,166,057 | 11/1992 | Palese et al. | 435/69.1 |
| 5,252,477 | 10/1993 | Oroszlan et al. | 435/219 |
| 5,288,641 | 2/1994 | Roizman | 435/320.1 |
| 5,312,737 | 5/1994 | Bolling et al. | 435/693 |
| 5,317,086 | 5/1994 | Bartlett et al. | 530/327 |
| 5,350,671 | 9/1994 | Houghton et al. | 435/5 |
| 5,372,928 | 12/1994 | Miyamura et al. | 435/5 |
| 5,428,145 | 6/1995 | Okamoto et al. | 536/23.72 |
| 5,436,318 | 7/1995 | Reyes et al. | 530/350 |
| 5,437,974 | 8/1995 | Ryan et al. | 435/5 |
| 5,443,965 | 8/1995 | Reyes et al. | 435/69.3 |
| 5,478,727 | 12/1995 | Roizman et al. | 435/23 |
| 5,498,616 | 3/1996 | Mallamo et al. | 514/300 |
| 5,514,539 | 5/1996 | Bukh et al. | 435/3 |
| 5,527,669 | 6/1996 | Resnick et al. | 435/5 |
| 5,538,865 | 7/1996 | Reyes et al. | 435/69.3 |
| 5,550,016 | 8/1996 | Okamoto | 435/5 |
| 5,552,310 | 9/1996 | Yoshikura et al. | 435/235.1 |
| 5,585,258 | 12/1996 | Houghton et al. | 435/219 |
| 5,679,342 | 10/1997 | Houghton et al. | 424/93.21 |
| 5,698,390 | 12/1997 | Houghton et al. | 435/5 |

(List continued on next page.)

FOREIGN PATENT DOCUMENTS

| | | |
|---|---|---|
| 2079105 | 10/1991 | (CA). |
| 2264964 | 3/1998 | (CA). |
| 3819846 | 12/1989 | (DE). |
| 4240980 | 2/1994 | (DE). |
| 0 027 657 | 4/1981 | (EP). |
| 0 046 039 | 2/1982 | (EP). |
| 0 058 676 | 9/1982 | (EP). |
| 0 061 974 | 10/1982 | (EP). |
| 0 066 296 | 12/1982 | (EP). |
| 0 068 465 | 1/1983 | (EP). |
| 0 071 640 | 2/1983 | (EP). |
| 0 074 986 | 3/1983 | (EP). |
| 0 092 249 | 10/1983 | (EP). |
| 0 116 201 | 8/1984 | (EP). |
| 0 120 551 | 10/1984 | (EP). |
| 0 124 896 | 11/1984 | (EP). |
| 0 128 995 | 12/1984 | (EP). |
| 0 138 111 | 4/1985 | (EP). |
| 0 154 392 | 9/1985 | (EP). |
| 0 164 556 | 12/1985 | (EP). |
| 0 186 526 | 7/1986 | (EP). |
| 0 190 972 | 8/1986 | (EP). |

(List continued on next page.)

OTHER PUBLICATIONS

Agouron's Request for Reexamination of U.S. Patent No. 5,585,258 and appendix.

Order re: Defendant Agouron's Motion for In Camera Review of Various Chiron Documents Pursuant to the Crime–Fraud Exception to the Attorney–Client Privilege. Special Master Yanni, Case No. C–98–2974 CW, Related Action Nos. C–98–2994 CW and C–98–2995 CW. United States District Court, Northern District of California. Apr. 16, 2001.

(List continued on next page.)

*Primary Examiner*—Rebecca Prouty

(57) ABSTRACT

The protease necessary for polyprotein processing in Hepatitis C virus is identified, cloned, and expressed. Proteases, truncated protease, and altered proteases are disclosed which are useful for cleavage of specific polypeptides, and for assay and design of antiviral agents for HCV.

U.S. PATENT DOCUMENTS

| | | | |
|---|---|---|---|
| 5,712,087 | 1/1998 | Houghton et al. | 435/5 |
| 5,712,088 | 1/1998 | Houghton et al. | 435/5 |
| 5,712,145 | 1/1998 | Houghton et al. | 435/219 |
| 5,714,371 | 2/1998 | Ramanathan et al. | 435/219 |
| 5,714,596 | 2/1998 | Houghton et al. | 536/23.72 |
| 5,739,002 | 4/1998 | De Francesco et al. | 435/23 |
| 5,747,240 | 5/1998 | Kink et al. | 435/5 |
| 5,747,241 | 5/1998 | Miyamura et al. | 435/5 |
| 5,747,339 | 5/1998 | Okayama et al. | 435/350 |
| 5,759,795 | 6/1998 | Jubin | 435/21 |
| 5,766,916 | 6/1998 | Belyaev et al. | 435/219 |
| 5,767,233 | 6/1998 | Zhang et al. | 530/326 |
| 5,843,752 | 12/1998 | Dasmahapatra et al. | 435/219 |
| 5,856,437 | 1/1999 | Miyamura et al. | 530/350 |
| 5,861,267 | 1/1999 | Su | 435/23 |
| 5,863,719 | 1/1999 | Houghton et al. | 435/5 |
| 5,871,903 | 2/1999 | Miyamura et al. | 435/5 |
| 5,874,565 | 2/1999 | Rice et al. | 536/24.1 |
| 5,885,799 | 3/1999 | Houghton et al. | 435/69.1 |
| 5,959,092 | 9/1999 | Miyamura et al. | 536/23.72 |
| 5,968,775 | 10/1999 | Houghton et al. | 435/69.3 |
| 5,989,905 | 11/1999 | Houghton et al. | 435/320.1 |
| 6,027,729 | 2/2000 | Houghton et al. | 424/228.1 |
| 6,068,994 | 5/2000 | Barr | 435/69.7 |
| 6,096,541 | 8/2000 | Houghton et al. | 435/370 |
| 6,117,639 | 9/2000 | Germann et al. | 435/6 |
| 6,127,116 | 10/2000 | Rice et al. | 435/6 |
| 6,147,100 | 11/2000 | Seno et al. | 514/369 |
| 6,153,579 | 11/2000 | Kim et al. | 514/2 |
| 6,171,782 | 1/2001 | Houghton et al. | 435/5 |

FOREIGN PATENT DOCUMENTS

| | | |
|---|---|---|
| 0 194 207 | 9/1986 | (EP) . |
| 0 196 056 | 10/1986 | (EP) . |
| 0 208 672 | 1/1987 | (EP) . |
| 0 217 645 | 4/1987 | (EP) . |
| 0 219 874 | 4/1987 | (EP) . |
| 0 242 300 | 10/1987 | (EP) . |
| 0 263 761 | 4/1988 | (EP) . |
| 0 277 437 | 8/1988 | (EP) . |
| 0 279 460 | 8/1988 | (EP) . |
| 0 293 274 | 11/1988 | (EP) . |
| 0 318 216 B1 | 5/1989 | (EP) . |
| 0 335 135 | 10/1989 | (EP) . |
| 0 340 986 | 11/1989 | (EP) . |
| 0 363 025 | 4/1990 | (EP) . |
| 0 377 303 | 7/1990 | (EP) . |
| 0 388 232 | 9/1990 | (EP) . |
| 0 414 475 | 2/1991 | (EP) . |
| 0 416 725 | 3/1991 | (EP) . |
| 0 421 109 | 4/1991 | (EP) . |
| 0 433 225 | 6/1991 | (EP) . |
| 0 450 931 | 10/1991 | (EP) . |
| 0 451 891 | 10/1991 | (EP) . |
| 0 468 527 | 1/1992 | (EP) . |
| 0 468 657 | 1/1992 | (EP) . |
| 0 479 376 | 4/1992 | (EP) . |
| 0 939 128 | 9/1999 | (EP) . |
| 2 609 807 | 7/1988 | (FR) . |
| 2 239 245 | 6/1991 | (GB) . |
| 64-02576 | 1/1989 | (JP) . |
| 1-124387 | 5/1989 | (JP) . |
| 6-319583 | 11/1994 | (JP) . |
| 9-187285 | 7/1997 | (JP) . |
| WO 82/00205 | 1/1982 | (WO) . |
| WO 82/02774 | 8/1982 | (WO) . |
| WO 82/03330 | 10/1982 | (WO) . |
| WO 84/01107 | 3/1984 | (WO) . |
| WO 87/01131 | 2/1987 | (WO) . |
| WO 87/05930 | 10/1987 | (WO) . |
| WO 88/02406 | 4/1988 | (WO) . |
| WO 88/03410 | 5/1988 | (WO) . |
| WO 88/06184 | 8/1988 | (WO) . |
| WO 89/04669 | 6/1989 | (WO) . |
| WO 89/10931 | 11/1989 | (WO) . |
| WO 89/12462 | 12/1989 | (WO) . |
| WO 89/12641 | 12/1989 | (WO) . |
| WO 90/00597 | 1/1990 | (WO) . |
| WO 90/10060 | 9/1990 | (WO) . |
| WO 90/10075 | 9/1990 | (WO) . |
| WO 90/11089 | 10/1990 | (WO) . |
| WO 91/04262 | 4/1991 | (WO) . |
| WO 91/05801 | 5/1991 | (WO) . |
| WO 91/15575 | 10/1991 | (WO) . |
| WO 91/15596 | 10/1991 | (WO) . |
| WO 91/15771 | 10/1991 | (WO) . |
| WO 92/00328 | 1/1992 | (WO) . |
| WO 92/03458 | 3/1992 | (WO) . |
| WO 93/01305 | 1/1993 | (WO) . |
| WO 93/25575 | 12/1993 | (WO) . |
| WO 94/25064 | 11/1994 | (WO) . |
| WO 94/25601 | 11/1994 | (WO) . |
| WO 94/25602 | 11/1994 | (WO) . |
| WO 95/02059 | 1/1995 | (WO) . |
| WO 95/02065 | 1/1995 | (WO) . |
| WO 95/22985 | 8/1995 | (WO) . |
| WO 96/05513 | 2/1996 | (WO) . |
| WO 96/13590 | 5/1996 | (WO) . |
| WO 96/34976 | 11/1996 | (WO) . |
| WO 96/35709 | 11/1996 | (WO) . |
| WO 96/35717 | 11/1996 | (WO) . |
| WO 96/36702 | 11/1996 | (WO) . |
| WO 97/08304 | 3/1997 | (WO) . |
| WO 97/09349 | 3/1997 | (WO) . |
| WO 97/12033 | 4/1997 | (WO) . |
| WO 97/12043 | 4/1997 | (WO) . |
| WO 97/36554 | 10/1997 | (WO) . |
| WO 97/38117 | 10/1997 | (WO) . |
| WO 98/00548 | 1/1998 | (WO) . |
| WO 98/11134 | 3/1998 | (WO) . |
| WO 98/12308 | 3/1998 | (WO) . |
| WO 98/13482 | 4/1998 | (WO) . |
| WO 98/16657 | 4/1998 | (WO) . |
| WO 98/17679 | 4/1998 | (WO) . |
| WO 98/22496 | 5/1998 | (WO) . |
| WO 98/37180 | 8/1998 | (WO) . |
| WO 99/50230 | 10/1999 | (WO) . |

OTHER PUBLICATIONS

GenBank Data Base Accession No. X16543 (Aug. 5, 1995).

GenBank Data Base Accession No. D90208 (Feb. 7, 1999).

GenBank Data Base Accession No. M67463 (Aug. 2, 1993).

GenBank Data Base Accession No. S06067 (Aug. 26, 1999).

Abe et al. (1989). "Non–A, non–B hepatitis: visualization of virus–like particles from chimpanzee and human sera," *Arch. Virol.* 104(3–4):351–355.

Abdi et al. (1986). "Extended phase I study of human beta–interferon in human cancer," *Clin. Invest. Med.* 9(1):33–40.

Abrahmsén et al. (1986). "Secretion of heterologous gene products to the culture medium of *Escherichia coli,*" *Nucl. Acids Res.* 14:7487–7500.

Abrass et al. (1980). "Non–specificity of circulating immune complexes in patients with acute and chronic liver disease," *Clin. Exp. Immunol.* 40(2):292–298.

Adinolfi et al. (1996). "Solid phase synthesis of oligosaccharides," *Tetra. Letters* 37(28):5007–5010.

Alam, J.J. (1995). "Interferon–beta treatment of human disease," *Curr. Opin. Biotechnol.* 6(6):688–691.

Alberti et al. (1981). "Detection by immunofluorescence of an antigen–antibody system in patients with acute and chronic non–A, non–B hepatitis," *Liver* 1(3):183–190.

Alberti et al. (1993). "Treatment with interferon(s) of community–acquired chronic hepatitis and cirrhosis type C," *J. Hepatol.* 17(Suppl 3):S123–S126.

Allain et al. (1984). "Non–A, non–B hepatitis in hemophilic patients with inhibitor treated with activated prothrombin complex concentrates: lack of correlation with an antigen possibly related to non–A, non–B hepatitis," *Vox Sang* 47(1):47–53.

Allen et al. (1995). "Isolation of high–affinity RNA ligands to HIV–1 integrase from a random pool," *Virology* 209:327–336.

Alter et al. (1987) "Transfusion–associated Non–A, non–B hepatitis: The First decade," International Symposium vol. 21, p. 43A (Abstract No. 122).

Alter et al. (1989). "Detection of antibody to hepatitis C virus in prospectively followed transfusion recipients with acute and chronic non–A, non–B hepatits," *N. Engl. J. Med.* 321(22):1494–1500.

Alter, H.J. (1991). "Descartes before the horse: I clone, therefore I am: the hepatitis C virus in current perspective," *Ann. Intern. Med.* 115(8):644–649.

Alter et al. (1994). "The epidemiology of viral hepatitis in the United States," *Gastroenterol. Clin. North Am.* 23(3):437–55.

Alter, H.J. (1995). "To C or not to C: these are the questions," *Blood* 85(7):1681–1695.

Alter, M.J. (1995). "Epidemiology of hepatitis C in the West," *Semin. Liver Dis.* 15(1):5–14.

Alter, M.J. (1997). "Epidemiology of Hepatitis C," *Hepatology* 26(3, Suppl. 1):62S–65S.

Amerik et al. (1991). "Site–directed mutagenesis of la protease: a catalytically active serine residue," *FEBS Letters* 287(1,2):211–214.

Arankalle et al. (1988). "Aetiological association of a virus–like particle with enterically transmitted non–A, non–B hepatitis," *Lancet.* 12;1(8585):550–554.

Arima et al. (1989). "A lambda gt11–cDNA clone specific for chronic hepatitis C generated from pooled serum presumably infected by hepatitis C virus," *Gastroenterol. Jpn.* 24(5):545–548.

Arima et al. (1989). "Cloning of a cDNA associated with acute and chronic hepatitis C infection generated from patients serum RNA," *Gastroenterol Jpn.* 24(5):540–544.

Anonymous. (Jun. 1990). "Hepatitis C virus upstanding," *Lancet* 335(8703):1431–1432.

Babe LM et al. (1994). "Constitutive production of nonenveloped human immunodeficiency virus type 1 particles by a mammalian cell line and effects of a portease inhibitor on particle maturation," *Antimicrob. Agents Chemother.* 38(10):2430–2439.

Babe, L. M. and Craik, C. S. (1997). "Viral Proteases: Evolution of Diverse Structural Motifs to Optimize Function," *Cell* 91:427–430.

Babes et al. (1980). "Seropositivities in posttransfusion hepatitis," *Virologie* 31(4):315–316.

Babes et al. (1983). "New aspects of viral hepatitis plurietiology," *Virologie* 34(1):61–63.

Baggio et al. (1996). "From poor substrates to good inhibitors: design of inhibitors for serine and thiol proteases," *Biochemistry* 35(11):3351–3353.

Baker, S. C. et al. (1993). "Identification of the Catalytic Sites of a Papain–Like Cysteine Proteinase of Murine Coronavirus," *J. Virol.* 67(10):6056–6063.

Baldock et al. (1996). "A mechanism of drug action revealed by structural studies of enoyl reductase," *Science* 274(5295):2107–2110.

Bamber et al. (1981). "Short incubation non–A, non–B hepatitis transmitted by factor VIII concentrates in patients with congenital coagulation disorders: a preliminary report of an antigen/antibody system," *Med. Lab. Sci.* 38(4):373–378.

Bamber et al. (1981). "Ultrastructural features in chronic non–A, non–B (NANB) hepatitis: A controlled blind study," *J. Med. Virol.* 8(4):267–275.

Barr et al. (1986) "7–Deaza–2'–Deoxguanosine–5'–Triphosphate: Enhanced Resolution in M13 Dideoxy Sequencing," *Biotechniques* 4(5):428–432.

Barr et al. (1988). "Expression and processing of biologically active fibroblast growth factors in the yeast Saccharomyces cerevisiae," *J. Biol. Chem.* 263(31):16471–16478.

Barrett et al., (1986) "Cysteine Proteinase Inhibitors of the Cystatin Superfamily," Chapter 18 in *Protease Inhibitors.* A. J. Barret and G. Salesen, eds., Elsevier: Amsterdam, pp. 515–569.

Bartenschlager et al. (1993). "Nonstructural protein 3 of the hepatitis C virus encodes a serine–type proteinase required for cleavage at the NS3/4 and NS4/5 junctions," *J. Virol.* 67(7):3835–3844.

Bartenschlager et al. (1994). "Kinetic and structural analyses of hepatitis C virus polyprotein processing," *J. Virol.* 68(8):5045–5055.

Bartenschlager et al. (1995). "Substrate determinants for cleavage in cis and in trans by the hepatitis C virus NS3 proteinase," *J. Virol.* 69(1):198–205.

Bartenschlager et al. (1995). Structural and functional analysis of the hepatitis C virus NS3 proteinase, Abstract, p. 39.

Bartenschlager, R. et al. (1995). "Complex Formation Between the NS3 Serine–Type Proteinase of the Hepatitis C Virus and NS4A and Its Importance for Polyprotein Maturation," *Journal of Virology* 69(12):7519–7528.

Bartenschlager, R. (1997). "Candidate Targets for Hepatitis C Virus–Specific Antiviral Therapy," *Intervirology* 40:378–393.

Bartenschlager, R. (1999). "The NS3/4A Proteinase of the Hepatitis C Virus: Unravelling Struture and Function of an Unusual Enzyme and a Prime Target for antiviral Therapy," *Journal of Viral Hepatitis* 6:165–181.

Bartholomeusz et al. (1995). "Expression of the hepatitis C virus nonstructural protein NS3 in Escherichia Coli: characterisation of ATPase/GTPase activity," 3rd International Meeting on Hepatitis C Virus and Related Viruses, Australia, p. 688.

Bazan JF et al. (1990) "Structural and Catalytic Models of Trypsin–Like Viral Proteases," *Seminars in Virology* 1(5):311–322.

Behrens et al. (1996). "Identification and properties of the RNA–dependent RNA polymerase of hepatitis C virus," *EMBO J.* 15(1):12–22.

Bell et al., (1985) "Amino–terminal amino acid sequences of structural proteins of three flaviviruses," *Virology* 143:224–229.

Belyaev, A. S. et al. (1998). "Hepatitis G Virus Encodes Protease Activities Which Can Effect Processing of the Virus Putative Nonstructural Proteins," *J.1 of Virol.* 72(1):868–872.

Bennett et al. (1996). "Modeling therapeutic benefit in the midst of uncertainty: therapy for hepatitis C," *Dig Dis Sci.* 41(12 Suppl):56S–62S.

Bertolini et al. (1993). "The human bone–marrow–derived B–cell line CE, susceptible to hepatitis C virus infection," *Res Virol.* 144(4):281–285.

Bhandari, B. N. and Wright, T. L. (1995), "Hepatitis C: An Overview," *Annu. Rev. Med.* 46:309–317.

Bianchi et al. (1996). "Synthetic depsipeptide substrates for the assay of human hepatitis C virus protease," *Anal Biochem.* 237(2):239–244.

Bianchi et al. (1997). "Complex formation between the hepatitis C virus serine protease and a synthetic NS4A cofactor peptide," *Biochemistry.* 36(25):7890–7897.

Briggs et al. (1996). "Interferon–alpha in hepatitis C. Dosage, costs and benefits," *Pharmacoeconomics.* 10(3):205–9.

Di Bisceglie, A. M. and Bacon, B. R. (1999). "Some 1.8 Percent of the U.S. Adult Population are Infected with the Hepatitis C Virus, Most Without Knowing It," *Scientific American* 10:80–85.

Bodey, G.P. (1996). "Antimicrobial agents: bacterial/fungal," *Curr. Opin. Infect. Dis.* 9(6):365–366.

Bonino et al. (1988). "Delta and non–A, non–B hepatitis viruses," *Eur J Clin Microbiol Infect Dis.* 7(3):327–336.

Bonkovsky, H.L. (1997). "Therapy of hepatitis C: other Options," *Hepatology.* 26(3 Suppl 1):143S–151S.

Borowski et al. (1997). "Nonstructural protein 3 of hepatitis C virus blocks the distribution of the free catalytic subunit of cyclic AMP–dependent protein kinase," *J Virol.* 71(4):2838–2843.

Borowski P et al. (1996) "Non–structural protein 3 of hepatitis C virus inhibits phosphorylation mediated by cAMP–dependent protein kinase," *Eur J Biochem.* 237(3):611–618.

Bouffard et al. (1995). "An in vitro assay for hepatitis C virus NS3 serine proteinase," *Virology,* 209(1):52–59.

Bradley et al. (1974). "Viroids and viral hepatitis in marmosets," *Nature.* 248(444):172.

Bradley et al. (1979). "Experimental infection of chimpanzees with antihemophilic (factor VIII) materials: recovery of virus–like particles associated with non–A, non–B hepatitis," *J Med Virol.* 3(4):253–269.

Bradley et al. (1980). "Non–A/non–B hepatitis in experimentally infected chimpanzees: cross–challenge and electron microscopic studies," *J Med Virol.* 6(3):185–201.

Bradley et al. (1983). "Non–A, non–B hepatitis in chimpanzees; interference with acute hepatitis A virus and chronic hepatitis B virus infections," *J Med Virol.* 11(3):207–213.

Bradley et al. (1983). "Posttransfusion non–A, non–B hepatitis: physicochemical properties of two distinct agents," *J Infect Dis.* 148(2):254–265.

Bradley DW. (1984). "Transmission, etiology, and pathogenesis of viral hepatitis non–A non–B in non–human primates," *Adv. Hepatitis Res.* 268–280.

Bradley (1985) "The agents of Non–A, Non–B viral hepatitis," *J. Virol. Methods* 10:307–319.

Bradley et al. (1985). "Posttranstusion non–A, non–B hepatitis in chimpanzees. Physicochemical evidence that the tubule–forming agent is a small, enveloped virus," *Gastroenterology.* 88(3):773–779.

Bradley et al. (1987). "Enterically transmitted non–A, non–B hepatitis: serial passage of disease in cynomolgus macaques and tamarins and recovery of disease–associated 27–to 34–nm viruslike particles," *Proc Natl Acad Sci U S A.* 84(17):6277–6281.

Bradley et al. (Mar. 1988). "Aetiological agent of enterically transmitted non–A, non–B hepatitis," *J Gen Virol.* 69 (Pt 3):731–738.

Bradley DW (1990). "Enterically–transmitted non–A, non–B hepatitis," *Br Med Bull.* 46(2):442–461.

Bradley DW (1990). "Hepatitis non–A, non–B viruses become identified as hepatitis C and E viruses," *Prog Med Virol.* 37:101–135.

Bradley et al. (1990). "Parenterally transmitted non–A, non–B hepatitis: virus–specific antibody response patterns in hepatitis C virus–infected chimpanzees," *Gastroenterology.* 99(4):1054–1060.

Bradley et al. (1991). "Non–A, non–B hepatitis: toward the discovery of hepatitis C and E viruses," *Semin Liver Dis.* 11(2):128–146.

Brahm et al. (1988). "Lack of reverse transcriptase activity in serum in sporadic post–transfusional and presumed epidemic or water–borne forms of severe non–A, non–B hepatitis," *J Med Virol.* 25(2):157–164.

Brake et al. (1984) "α–factor–directed synthesis and scretion of mature foreign proteins in *Saccharomyces cerevisiae,*" *Proc. Natl. Acad. Sci. USA* 81:4642–4646.

Brechot et al. (1993). "Genetic variation of the hepatitis C virus (HCV) genome: random events or a clinically relevant issue?," *J Hepatol.* 17(3)265–268.

Bresters. D. et al. (1992). "Disappearance of hepatitis C virus RNA in plasma during interferon alpha–2B treatment in hemophilia patients.," *Scand. J. Gastroenterol.* 27(3):166–168.

Briand et al. (1997). "Regulation of trypsin activity by Cu2+ chelation of the substrate binding site," *Protein Eng.* 10(5):551–560.

Brinnen et al. (1996). "X–ray structures of a designed binding site in trypsin show metal–dependent geometry," *Biochemistry.* 35(19):5999–6009.

Brinton (1986) "Replication of Flaviviruses", Chapter 11 in *The Togaviridae and Flaviviridae.* S. Schelsigner and M. J. Schlesinger, eds., Plenum Press: New York, pp. 327–374.

Brotman et al. (1985). "Non–A, non–B hepatitis: is there more than a single blood–borne strain?," *J Infect Dis.* 151(4):618–625.

Brown et al. (1995). "Hepatitis C: the structure and biology of the virus and diagnostic tests," *J Infect.* 30(2):95–101.

Brown KD (Oct. 15, 1995) "Novel Emerging Therapeutics Target the Hepatitis C Virus," *Genetic Engineering News* 15(18):1, 16 35.

Butkiewicz et al. (1996). "Enhancement of hepatitis C virus NS3 proteinase activity by association with NS4A–specific synthetic peptides: identification of sequence and critical residues of NS4A for the cofactor activity," *Virology.* 225(2):328–338.

Cahour et al. (1992). "Cleavage of the dengue virus polyprotein at the NS3/NS4A and NS4B/NS5 junctions is mediated by viral protease NS2B–NS3, whereas NS4A/NSB may be processed by a cellular protease," *J Virol.* 66(3):1535–42.

Carrington et al. (1987). "Small nuclear inclusion protein encoded by a plant potyvirus genome is a protease," *J. Virol.* 61(8):2540–2548.

Castle et al. (1985) "Sequence analysis of the viral core protein and the membrane–associated proteins V1 and NV2 of the flavivirus West Nile Virus and of the genome sequences for these proteins," *Virology* 145:227–236.

Cerino et al. (1991). "Identification of an immunodominant B cell epitope on the hepatitis C virus nonstructural region defined by human monoclonal antibodies," *J Immunol.* 147(8):2692–2696.

Cerretani et al. (1999). "A high–throughput radiometric assay for hepatitis C virus NS3 protease," *Anal Biochem.* 266(2):192–197.

Cha et al. (1991). "Use of a signature nucleotide sequence of hepatitis C virus for detection of viral RNA in human serum and plasma," *J Clin Microbiol.* 29(11):2528–2534.

Chakrabarti et al. (1985). "Vaccinia virus expression vector: coexpression of beta–galactosidase provides visual screening of recombinant virus plaques," *Mol Cell Biol.* 5(12):3403–3409.

Chambers et al. (1989) "Yellow fever virus proteins NS2A, NS2B, and NS4B: Identification and partial N–terminal amino acid sequence analysis," *Virology* 169:100–109.

Chambers et al. (1991). "Processing of the yellow fever virus nonstructural polyprotein: a catalytically active NS3 proteinase domain and NS2B are required for cleavages at dibasic sites," *J Virol.* 65(11):6042–6050.

Chang et al. (1994). "Long term clinical and virologic outcome of primary hepatitis C virus infection in children: a prospective study," *Pediatr Infect Dis J.* 13(9):769–773.

Chayama, K. et al. (1994). "Nucleotide Sequence of Hepatis C Virus (Type 3B)Isolated From a Japanese Patient with Chronic Hepatitis C," *Journal of General Virology* 75:3623–3628.

Chayama, K. et al. (1997). "Pretreatment Virus Load and Multiple Amino Acid Substitutions in the Interferon Sensitivity–Determing Region Predict the Outcome of Interferon Treatment in Patients with Chronic Genotype 1B Hepatits C Virus Infection," *Hepatology* 25:745–749.

Chemello et al. (1993). "Predictors of response to interferon in chronic hepatitis C," Symposium on advances in HCV diagnosis and treatment, Barcelona, Spain, p57–58.

Chemello et al. (1995). "Randomized trial comparing three different regimens of alpha–2a–interferon in chronic hepatitis C. The TriVeneto Viral Hepatitis Group," *Hepatology.* 22(3):700–706.

Chen et al. (1990). "Hepatitis C virus infection in an area hyperendemic for hepatitis B and chronic liver disease: the Taiwan experience," *J Infect Dis.* 162(4):817–822.

Chircu et al. (1980). "Post–transfusion hepatitis: antigen/antibody systems correlated with non–A, non–B hepatitis," *J Med Virol.* 6(2):147–151.

Cho et al. (1995). "HCV–Sindbis hybrid viruses whose replication depends on the serine protease ativity of hepatitis C virus," 3rd International Meeting on Hepatitis C Virus and Related Viruses, Australia, one page.

Cho et al. (1997), "Construction of hepatitis C–SIN virus recombinants with replicative dependency on hepatitis C virus serine protease activity," *J Virol Methods.* 65(2):201–207.

Cho et al. (1998). "In vivo assay for hepatitis C viral serine protease activity using a secreted protein," *J Virol Methods.* 72(1):109–115.

Choo et al. (1992). "Identification of the major, parenteral non–A, non–B hepatitis agent (hepatitis C virus) using a recombinant cDNA approach," *Semin Liver Dis.* 12(3):279–288.

Choo et al. (1994). "Vaccination of chimpanzees against infection by the hepatitis C virus," *Proc Natl Acad Sci U S A.* 91(4):1294–1298.

Chu et al. (1996). "Structure of SCH 68631: a new hepatitis C virus proteinase inhibitor from Streptomyces sp," *Tetra Lett.* 37(40):7229–7232.

Cianci et al. (1996). "Identification of N–hydroxamic acid and N–hydroxyimide compounds that inhibit the influenza virus polymerase," *Antiviral Chem. Chemotherap.* 7(6):353–360.

Clarke B. E. (1995). "Approaches to the development of novel inhibitors of hepatitis C virus replication," *J Viral Hepat.* 2(1):1–8.

Clarke, B. (1997). "Molecular Virology of Hepatits C Virus," *J. Gen. Virol.* 78:2397–2410.

Clarke, B. and Slater, M. J. (1997). "Developments in Hepatitis C During 1996–1997," *Exp. Opin, Ther. Patents* 7(9):979–987.

Cleaves (1985) "Identification of Dengue Type 2 virus–specific high molecular weight proteins in virus–infected BHK cells," *J. Gen. Virol.* 66:2767–2771.

Clewell et al. (1969). "Supercoiled circular DNA–protein complex in Escherichia coli: purification and induced conversion to an open circular DNA form," *Proc Natl Acad Sci U S A.* 62(4):1159–1166.

Clewell DB (1972). "Nature of Col E 1 plasmid replication in Escherichia coli in the presence of the chloramphenicol," *J Bacteriol.* 110(2):667–676.

Cohen et al. (1972). "Nonchromosomal antibiotic resistance in bacteria: genetic transformation of Escherichia coli by R–factor DNA," *Proc Natl Acad Sci U S A.* 69(8):2110–2114.

Cohen, (1999) "The scientific challenge of Hepatitis C," *Science,* 285:26–30.

Collett et al. (1989) "Recent advances in pestivirus research," *J. Gen Virol.* 70:253–266.

Colombo et al. (1989). "Prevalence of antibodies to hepatitis C virus in Italian patients with hepatocellular carcinoma," *Lancet.* 2(8670):1006–1008.

Cooreman, M. P. and Schoondermark–Van De Ven E. M. E. (1996). "Hepatitis C. Virus: biological and Clinical Consequences of Genetic Heterogeneity," *Scand. J. Gastroenterol.* 218:106–115.

Corapi et al., (Aug. 1988) "Monoclonal antibody analyses of cytopathic and noncytopathic viruses from fatal bovine viral diarrhea virus infections," *J. Virol.* 62(8):2823–2827.

Coursaget et al. (1979). "Virus–like particles asociated with non–A, non–B hepatitis," *Lancet.* 2(8133):92–93.

Christensen et al. (1995) "Hepatitis C update," *Women's Health Statewide.* 5(2):10 pages.

Crute et al. (1995). "Inhibition of herpes simplex virus type 1 helicase–primase by (dichloroanilino)purines and –pyrimidines," *J Med Chem.* 38(10):1820–1825.

Cuypers et al. (1991). "Analysis of genomic variability of hepatitis C virus," *J Hepatol.* 13 Suppl 4:S15–S19.

Cuypers et al. (1993). "HCV–RNA detection by cDNA–PCR application in hepatitis C virus diagnosis Symposium on Advances in HCV Diagnosis and Treatment, Barcelona, Spain, p. 15–16.

Dasmahapatra et al. (1992). "A genetic system for studying the activity of a proteolytic enzyme," *Proc Natl Acad Sci U S A.* 89(9):4159–4162.

Dasmahapatra, (1997) "Hepatitis C virus NS3/4A proteinase as a target for antiviral drug development," Abstract, p. 5 in NMHCC's Second International Conferences: Protease Inhibitors in Infectious Diseases, Aug. 18–19, 1997, Protease Inhibitors in Inflammation, Aug. 19–20, 1997.

Davis et al. (1994). "Assessing health–related quality of life in chronic hepatitis C using the Sickness Impact Profile," *Clin Ther.* 16(2):334–43; discussion 271–2.

Devereux, J. et al. (1984). "A Comprehensive Set of Sequence Analysis Programs for the VAX," *Nucleic Acids Research* 12(1):387–395.

Di Bisceglie et al. (1991). "The role of chronic viral hepatitis in hepatocellular carcinoma in the United States," *Am J Gastroenterol.* 86(3):335–338.

Di Basceglie AM (1998). "Hepatitis C," *Lancet.* 351(9099):351–355.

Dienes et al. (1986). "Hepatitis A–like non–A, non–B hepatitis: light and electron microscopic observations of three cases," *Virchows Arch A Pathol Anat Histopathol.* 409(5):657–667.

Dienstag, J. L. (1997). "The Natural History of Chronic Hepatitis C and What We Should Do About It," *Gastroenterology* 112(2):651–655.

Diepolder, H. M. et al. (1997). "Immunodominant CD4+ T–Cell Epitope within Nonstructural Protein 3 in Acute Hepatitis C Virus Infection," *Journal of Virology* 71(8):6011–6019.

Dimasi et al. (1997). "Characterization of engineered hepatitis C virus NS3 protease inhibitors affinity selected from human pancreatic secretory trypsin inhibitor and minibody repertoires," *J Virol.* 71(10):7461–7469.

Doherty et al. (1993). "Chemical, biochemical, pharmacokinetic, and biological properties of L–680,833: a potent, orally active monocyclic beta–lactam inhibitor of human polymorphonuclear leukocyte elastase," *Proc Natl Acad Sci U S A.* 90(18):8727–8731.

Dolle et al. (1996). "First examples of peptidomimetic inhibitors of interleukin–1 beta converting enzyme," *J Med Chem.* 39(13):2438–2440.

Domingo et al. (1985). "The quasispecies (extremely heterogeneous) nature of viral RNA genome populations: Biological relevance–a review," *Gene* 40:1–8.

Donis et al. (1987). "Differences in virus–induced polypeptides in cells infected by cytopathic and noncytopathic biotypes of bovine virus diarrhea–mucosal disease virus," *Virol.* 158:168–173.

Donis et al. (1988). "Neutralizing monoclonal antibodies to bovine viral diarrhoea virus bind to the 56K to 58K glycoprotein," *J. Gen. Virol.* 69:77–86.

Doronin et al. (1993). "Expression of the gene encoding secreted placental alkaline phosphatase (SEAP) by a non-defective adenovirus vector," *Gene.* 126(2):247–250.

Dougherty WG (Dec. 1993) "Expression of virus–encoded proteinases: functional and structural similarities with cellular enzymes," *Microbiol Rev.*; 57(4):781–822.

Dougherty et al. (1989). "Characterization of the catalytic residues of the tobacco etch virus 49–kDa proteinase," *Virol.* 172(1):302–310.

Dragovich, P. S. et al. (1998). "Structure–Based Design, Synthesis, and Biological Evaluation of Irreversible Human Rhinovirus 3C Protease Inhibitors. 2. Peptide Structure–Activity Studies," *J. Med. Chem.* 41:2819–2834.

Drews, J. (1996). "Genomic Sciences and the medicine of Tomorrow," *Nature Biotechnology* 14:1515–1516.

D'Souza, E. D. A. et al. (1994). "Analysis of NS3–Mediated Processing of the Hepatitis C Virus Non–Structureal Region In Vitro," *Journal of General Virology* 75:3469–3476.

D'Souza et al. (1995). "In vitro cleavage of hepatitis C virus polyprotein substrates by purified recombinant NS3 protease," *J Gen Virol.* 76(Pt 7):1729–1736.

Dubensky et al. (1996). "Studies virus DNA–based expression vectors: utility for in vitro and in vivo gene transfer," *J Virol.* 70(1):508–519.

Dubuisson, J. et al. (1994). "Formation and Intracellular Localization of Hepatitis C Virus Envelope Glycoprotein Complexes Expressed by Recombinant Vaccinia and Sindbis Viruses," *Journal of Virology* 68(10):6147–6160.

Debuisson, J. et al. (1996). "Hepatits C Virus Glycoprotein Folding: Disulfide Bond Formation and Association with Calnexin," *Journal of Virology* 70(2):778–786.

Duermeyer et al. (1983). "An enzyme–linked immunosorbent assay for an antigen related to non–A, non–B hepatitis and its antibody: partial characterization of the antigen and chimpanzee transmission," *J Med Virol.* 11(1):11–21.

Dufour et al. (1995). "Peptide aldehydes and nitriles as transition state analog inhibitors of cysteine proteases," *Biochemistry.* 34(28):9136–9143.

Dunn et al., (1989) "Kinetic studies of synthetic cleavage site peptides by poliovirus 3C and HIV–1 and HIV–2 proteinases" in *Viral Proteinases as Targets for Chemotherapy*, CHS Press, pp. 231–235.

Dusheiko, G. M. and Rizzetto, M. eds. (1992). "The Management of Chronic Hepatits C." Synopses in *Viral Hepatitis* pp. 3–15.

Dusheiko et al. (1995). "Treatment of chronic type B and C hepatitis with interferon alfa: an economic appraisal," *Hepatology,* 22(6):1863–1873.

Dusheiko et al. (1996). "A rational approach to the management of hepatitis C infection," *BMJ.* 312(7027):357–364.

Eckart et al. (1993). "The hepatitis C virus encodes a serine protease involved in processing of the putative nonstructural proteins from the viral polyprotein precursor,"*Biochem Biophys Res Commun.* 192(2):399–406.

Enomoto et al. (1990). "There are two major types of hepatitis C virus in Japan," *Biochem Biophys Res Commun.* 170(3):1021–1025.

Enomoto et al. (1995). "Comparison of full–length sequences of interferon–sensitive and resistant hepatitis C virus 1b. Sensitivity to interferon is conferred by amino acid substitutions in the NS5A region," *J Clin Invest.* 96(1):224–230.

Enomoto et al. (1995). "Hepatitis C virus quasispecies populations during chronic hepatitis C infection," *Trends Microbiol.* 3(11):445–447.

Everhart et al. (1990). "Risk for non–A, non–B (type C) hepatitis through sexual or household contact with chronic carriers," *Ann Intern Med.* 112(7):544–545.

Ezzell C., (May 1988). "Candidate cause identified of non–A, non–B hepatitis," *Nature,* 333(6170):195.

Failla et al. (1994). "Both NS3 and NS4A are required for proteolytic processing of hepatitis C virus nonstructural proteins," *J Virol.* 68(6):3753–3760.

Failla et al. (1995). "An amino–terminal domain of the hepatitis C virus NS3 protease is essential for interaction with NS4A," *J Virol.* 69(3):1769–1777.

Failla et al. (1996). "Redesigning the substrate specificity of the hepatitis C virus NS3 protease," *Fold Des.* 1(1):35–42.

Falgout et al. (1989) "Proper processing of Dengue virus nonstructural glycoprotein NS1 requires the N–terminal hydrophobic signal sequence and the downstream nonstructural protein NS2a," *J. Virology* 63:1852–1860.

Falgout et al. (1991). "Both nonstructural proteins NS2B and NS3 are required for the proteolytic processing of dengue virus nonstructural proteins," *J Virol.* 65(5):2467–2475.

Falgout et al. (1993). "Deletion analysis of dengue virus type 4 nonstructural protein NS2B: identification of a domain required for NS2B–NS3 protease activity," *J Virol.* 67(4):2034–2042.

Farci et al. (1991). "A long–term study of hepatitis C virus replication in non–A, non–B hepatitis," *N Engl J Med.* 325(2):98–104.

Farci et al. (1992). "The natural history of infection with hepatitis C virus (HCV) in chimpanzees: comparison of serologic responses measured with first–and second–generation assays and relationship to HCV viremia," *J Infect Dis.* 165(6):1006–1011.

Farci, P. et al. (1994). "Prevention of Hepatits C Virus Infection in Chimpanzees After Antibody–Mediated in Vitro Neutralization," *Proc. Natl. Acad. Sci.* USA 91:7792–7796.

Feinstone et al. (Apr. 10, 1975). "Transfusion–associated hepatitis not due to viral hepatitis type A or B," *New Eng. J. Med.* 292(15):767–770.

Feinstone et al. (1978). "Non–A, non–B hepatitis," *Annu Rev Med.* 29:359–366.

Feinstone et al. (1981). "Non–A, non–B hepatitis in chimpanzees and marmosets," *J Infect Dis.* 144(6):588–598.

Feinstone et al. (1983). "Inactivation of hepatitis B virus and non–A, non–B hepatitis by chloroform," *Infect Immun.* 41(2):816–821.

Feinstone S.M. (1984). "Non–A, maybe–B hepatitis," *New Engl J Med.* 311(3):185–189.

Fields et al. (1983). "Unrelatedness of factor VIII–derived non–A/non–B hepatitis and hepatitis B virus," *J Med Virol.* 11(1):59–65.

Filocamo et al. (1997). "Chimeric Sindbis viruses dependent on the NS3 protease of hepatitis C virus," *J Virol.* 71(2):1417–1427.

Filocamo, G. et al. (1999). "Selection of Functional Variants of the NS3–NS4A Protease of Hepatitis C Virus by Using Chimeric Sindbis Viruses," *Journal of Virology* 73(1):561–575.

Fipaldini, C. et al. (1999). "Expression of Hepatits C Virus cDNA in Human Hepatoma Cell Line Mediated by a Hybrid Baculovirus–HCV Vector," *Virology* 255:302–311.

Fukuizumi, K. et al. (1997). "Hepatitis C Virus Seroconversion Rate in a Hyperendemic Area of HCV in Japan: A prospective Study," *Scand. J. Infect. Dis.* 29:345–347.

Fukushi et al. (1996). "A new NMR chiral derivatizing reagent for determining the absolute configurations of carboxylic acids," *Tetra Letters.* 37(27):4737–4740.

Gallinari, P. et al. (1998). "Multiple Enzymatic Activitie Associated with Recombinant NS3 Protein of Hepatitis C Virus," *Journal of Virology* 72(8):6758–6769.

Gallinari, P. et al. (1999). "Modulation of Hepatitis C Virus NS3 Protease and Helicase Activities Through the Interaction with NS4A," *Biochemistry* 38:5620–5632.

Gangarosa et al. (1998). "Impact of anti–vaccine movements on pertussis control: the untold story," *Lancet.* 351(9099):356–361.

Gerety, R.J. "Particles and antigen–antibody systems associated with non–A, non–B hepatitis and nonspecific tests to detect virus carriers," 207–28. (bookmark, non–A, non–B Hepatitis). (1981).

Geysen et al. (1988). "Cognitive features of continuous antigenic determinants," *J. Mol Recognit.* 1(1):32–41.

Giam, C–Z et al. (Oct. 1988) "In vivo and in vitro autoprocessing of human immunodeficiency virus protease expressed in Escherichia coli," *J Biol Chem.* 263(29):14617–14620.

Gibbs, C. S. and Tsiang, M. (1998). "Targeting the NS3 Protease of Hepatitis C Virus," *Internation Antiviral News* 6:2–4.

Gitnick et al. (1995). "Hepatitis C in 1994," *Scand J Gastroenterol Suppl.* 208:147–148.

Gorbalenya et al. (Aug. 1988) "Birnavirus RNA polymerase is related to polymerases of positive strand RNA viruses," *Nucl. Acids Res.* 16:7735.

Gorbalenya et al. (1989) "An NTP–binding motif is the most conserved sequence in a highly diverged monophyletic group of proteins involved in positive strand RNA viral replication," *J. Mol. Evol.* 28:256–268.

Gordeev et al. (1996). "Approaches to combinatorial synthesis of heterocycles: solid phase synthesis of pyridines and pyrido [2, 3–d] pyrimides," *Tetra Letters.* 37(27):4643–4646.

Grakoui et al. (1993). "Characterization of the hepatitis C virus–encoded serine proteinase: determination of proteinase–dependent polyprotein cleavage sites," *J Virol.* 67(5):2832–2843.

Grakoui et al. (1993). "Expression and identification of hepatitis C virus polyprotein cleavage products," *J Virol.* 67(3):1385–1395.

Groutas et al. (1997). "Structure–based design of a general class of mechanism–based inhibitors of the serine proteinases employing a novel amino acid–derived heterocyclic scaffold," *Biochemistry.* 36(16):4739–4750.

Gwack et al. (1995). "NTPase activity of hepatitis C virus NS3 protein expressed in insect cells," *Mol. Cell.* 5(2):171–175.

Gwack, Y. et al. (1996). "Characterization of RNA Binding Activity and RNA Helicase Activity of the Hepatitis C Virus NS3 Protein," *Biochemical and Biophysical Research Communications* 225:654–659.

Gwack, Y. et al. (1997). "DNA Helicase Activity of the Hepatitis C Virus Nonstructural Protein 3," *Eur. J. Biochem.* 250:47–54. p. 47 missing.

Hagedorn et al. (1995). "Further characterization of a cell culture system that propagates hepatitis C virus" 3rd International Meeting on Hepatitis C and Related Viruses, Australia, one page.

Hahm et al. (1995). "NS3–4A of hepatitis C virus is a chymotrypsin–like protease," *J Virol.* 69(4):2534–2539.

Hahm et al. (1996). "Generation of a novel poliovirus with a requirement of hepatitis C virus protease NS3 activity," *Virology.* 226(2):318–326.

Hakim AA (1986). "Isolation and functional property of mRNA coding for hepatitis A, B, and non A–non B viral particles from human sera," *Naturwissenschaften.* 73(1):45–47.

Hall et al. (1995). "Activation of the herpes simplex virus type 1 protease," *J Biol Chem.* 270(39):22697–22700.

Halstead (1988) "Pathogenesis of Dengue: Challeneges to Molecular Biology," *Science* 239:476–481.

Hamatake et al. (1996). "Establishment of an in vitro assay to characterize hepatitis C virus NS3–4A protease trans–processing activity," *Intervirology.* 39(4):249–258.

Hämmerle, T. et al. (1991). "Site–directed mutagenesis of the putative catalytic traid of poliovirus 3C proteinase," *J. Biol. Chem.* 266(9):5412–5416.

Han et al. (1988). "Isolation of intact mRNA and construction of full–length cDNA," *Genetic Eng. Principles and Methods* 10:195–219.

Han et al. (1991). "Characterization of the terminal regions of hepatitis C viral RNA: identification of conserved sequences in the 5' untranslated region and poly(A) tails at the 3' end," *Proc Natl Acad Sci U S A.* 88(5):1711–1715.

Han et al. (Jul. 1992). "Group specific sequences and conserved secondary structures at the 3' end of HCV genome and its implication for viral replication," *Nucleic Acids Res.* 20(13):3520.

Han et al. (1995). "Identification of the protease domain in NS3 of hepatitis C virus," *J Gen Virol.* 76 (Pt 4):985–993.

Harada et al. (1995). "Characterization of an established human hepatoma cell line constitutively expressing non–structural proteins of hepatitis C virus by transfection of viral cDNA," *J Gen Virol.* 76 (Pt 5):1215–1221.

Harbeson et al. (1994). "Stereospecific synthesis of peptidyl alpha–keto amides as inhibitors of calpain," *J Med Chem.* 37(18):2918–2929.

Harrison SC (1996). "Peptide–surface association: the case of PDZ and PTB domains," *Cell.* 86(3):341–343.

Haugan, I. R. et al. (1995). "Characterization of the DNA–Binding Activity of HIV–1 Integrase Using a Filter Binding Assay," *Biochemical and Biophysical Research Communications* 217(3):802–810.

Heilek et al. (1997). "A point mutation abolishes the helicase but not the nucleoside triphosphatase activity of hepatitis C virus NS3 protein," *J Virol.* 71(8):6264–6266.

Hellings JA (1986). "Non–A, non–B hepatitis: an update," *Vox Sang.* 51 Suppl 1:63–66.

Herbert et al. (1992). "Biochemical and pharmacological activities of SR 26831, a potent and selective elastase inhibitor," *J Pharmacol Exp Ther.* 260(2):809–816.

Herold, J. et al. (1998). "Proteolytic Processing at the Amino Terminus of Human Coronavirus 229E Gene 1–Encoded Polyproteins: Indentification of a Papain–Like Proteinase and Its Substrate," *Journal of Virology* 72(2):910–918.

Hijikata et al. (1991). "Gene mapping of the putative structural region of the hepatitis C virus genome by in vitro processing analysis," *Proc Natl Acad Sci U S A.* 88(13):5547–5551.

Hijikata et al. (1993). "Proteolytic processing and membrane association of putative nonstructural proteins of hepatitis C virus," *Proc Natl Acad Sci U S A.* 90(22):10773–10777.

Hiramatsu et al. (1992). "Immunohistochemical detection of hepatitis C virus–infected hepatocytes in chronic liver disease with monoclonal antibodies to core, envelope and NS3 regions of the hepatitis C virus genome," *Hepatology.* 16(2):306–311.

Hirota, M. et al. (1999). "Phosphorylation of Nonstructural 5A Protein of Hepatits C Virus: HCV Group–Specific Hyperphosphorylation," *Virology* 257:130–137.

Hirowatari Y et al. (1993) "Two proteinase activities in HCV polypeptide expressed in insect cells using baculovirus vector," *Arch Virol.*, 133(3–4):349–356.

Hirowatari et al. (1995). "A novel method for analysis of viral proteinase activity encoded by hepatitis C virus in cultured cells," *Anal Biochem.* 225(1):113–120.

Hirowatari, Y. et al. (1995). "Expression and Processing of Putative Nonstructural Proteins of Hepatits C Virus in Insect Cells, Using Baculovirus Vector," *Virus Research* 35:43–61.

Hofmann et al. (1995). "Efficient gene transfer into human hepatocytes by baculovirus vectors," *Proc Natl Acad Sci U S A.* 92(22):10099–10103.

Holland et al. (1982). "Rapid evolution of RNA genomes," *Science.* 215(4540):1577–1585.

Hong et al. (1996). "Enzymatic characterization of hepatitis C virus NS3/4A complexes expressed in mammalian cells by using the herpes simplex virus amplicon system," *J Virol.* 70(7):4261–4268.

Hoofnagle, J. H. (1997). "Hepatitis C: The Clinical Spectrum of Disease," *Hepatology* 26(3 Suppl. 1):15S–20S.

Hopp et al., (1988) "A short polypeptide marker sequence useful for recombinant protein identification and purification," *Bio/Technology* 6:1204–1210.

Hotta, H. et al., (1994) "Analysis of the core and E1 envelope region sequences of a novel variant of hepatitis C virus obtained in Indonesia," *Arch. Virol.* 136:53–62.

Houghton et al. (1991). "Molecular biology of the hepatitis C viruses: implications for diagnosis, development and control of viral disease," *Hepatology.* 14(2):381–388.

Houghton et al. (1994). "Hepatitis C virus: structure, protein products and processing of the polyprotein precursor," *Curr Stud Hematol Blood Transfus.* (61):1–11.

Houghton, M. (1996). "Chapter 32: Hepatitis C Viruses," in *Fields Virology,* eds., Lippincott–Raven Publishers: Philadelphia, 3rd edition, pp. 1035–1051.

Hwang et al. (1996). "Identification of humoral antigenic determinants in the hepatitis C virus NS3 protein," *J Infect Dis.* 174(1);173–176.

Hwang et al. (1997). "Hepatitis C virus NS5B protein is a membrane–associated phosphoprotein with a predominantly perinuclear localization," *Virology.* 227(2):439–446.

Iacovacci et al. (1993). "Replication and multiplication of hepatitis C virus genome in human foetal liver cells," *Res Virol.* 144(4):275–279.

Ide, Y. et al. (1996). "Characterization of the Nuclear Localization Signal and Subcellular Distribution of Hepatitis C Virus Nonstructural Protein NS5A," *Gene* 182:203–211.

Ide, Y. et al. (1997). "Hepatitis C Virus NS5A Protein is Phosphorylated In Vitro by a Stably Bound Protein Kinase from HeLa Cells and by cAMP–Dependent Protein Kinase A–alpha Catalytic Subunit," *Gene* 201:151–158.

Iino et al. (1994). "Current state of interferon therapy for chronic hepatitis C," *Intervirology.* 37(2):87–100.

Ingallinella et al. (1998). "Potent peptide inhibitors of human hepatitis C virus NS3 protease are obtained by optimizing the cleavage products," *Biochemistry.* 37(25):8906–8914.

Inoue et al. (1998). "Expression of a hepatitis C virus NS3 protease–NS4A fusion protein in Escherichia coli," *Biochem Biophys Res Commun.* 245(2):478–482.

Inudoh, M. et al. (1996). "Antigenicity of Hepatitis C Virus Envelope Proteins Expressed in Chinese Hamster Ovary Cells," *Vaccine* 14(17/18):1590–1596.

Ippolito et al. (1995). "Structure–assisted redesign of a protein–zinc–binding site with femtomolar affinity," *Proc Natl Acad Sci U S A.* 92(11):5017–5021.

Iwarson, S. (1994). "The Natural Course of Chronic Hepatitis C," FEMS Microbiology Review 14:201–204.

Iwarson, S. et al. (1995)."Hepatitis C: Natural History of a Unique Infection," *CID* 20:1361–1370.

Jackson et al. (1979). "Acute non–A, non–B hepatitis: specific ultrastructural alterations in endoplasmic reticulum of infected hepatocytes," *Lancet.* 1(8128):1249–1250.

Jadoul, M. (1995), "Hepatitis C Virus," *The Lancet* 345:189–191.

Jansson et al. (1996). "High–level production of uniformly 15N–and 13C–enriched fusion proteins in Escherichia coli," *J Biomol NMR.* 7(2):131–131.

Jin et al. (1995). "Use of alpha–N,N–bis[carboxymethyl] lysine–modified peroxidase in immunoassays," *Anal Biochem.* 229(1):54–60.

Jin, L. and Peterson, D.L. (1995). "Expression, Isolation, and Characterization of the Hepatitis C Virus ATPase/RNA Helicase," *Arch. Biochem. Biophys.* 323(1):47–53.

Johannes L (1996) "Biotech Firms Find Structure of Protein for Hepatitis C," *Wall Street Journal,* p. B3 (Oct. 18, 1996).

Johnson G. et al. (1992). "β–Proline Analogues as Agonists at the Strychnine–Sensitive Glycine Receptor," *J. Med. Chem.* 35:233–241.

Jung, M.C. et al. (1994). "T Cell Recognition of Hepatitis B and C Viral Antigens," *Eur. J. Clin. Invest.* 24:641–650.

Kadare et al. (1997). "Virus–encoded RNA helicases," *J. Virol.* 71(4):2583–2590.

Kakiuchi et al. (1995). "Bacterial expression and analysis of cleavage activity of HCV serine proteinase using recombinant and synthetic substrate," *Biochem Biophys Res Commun.* 210(3):1059–1065.

Kakiuchi N et al. (1997) "Cleavage activity of hepatitis C virus serine proteinase," *J Biochem* (Tokyo). 1997 Oct;122(4):749–755.

Kakiuchi et al. (1998). "Non–peptide inhibitors of HCV serine proteinase," *FEBS Lett.* 421(3):217–220.

Kakiuchi, N. et al. (1999). "A High Throughput Assay of the Hepatitis C Virus Nonstructural Protein 3 Serine Proteinase," *J. Virol. Meth.* 80:77–84.

Kamer et al. (1984). "Primary structural comparison of RNA–dependent polymerases from plant, animal and bacterial viruses," *Nucl. Acids Res.* 12(18):7269–7282.

Kaneko, T. et al. (1994). "Production of Two Phosphoproteins from the NS5A Region of the Hepatitis Viral Genome," *Biochem. Biophys. Res. Commun.* 205(1);320–326.

Kang, L.W. et al. (1998). "Crystallization and Preliminary X–Ray Crystallographic Analysis of the Helicase Domain of Hepatitis C Virus NS3 Protein," *Acta. Cryst.* D54:121–123.

Katkov et al. (1991). "Elevated serum alanine aminotransferase levels in blood donnors: the contribution of hepatitis C virus," *Ann Intern Med.* 115(11):882–884.

Katkov et al. (1991). "Role of hepatitis C virus in non–B chronic liver disease," *Arch Intern Med.* 151(8):1548–1552.

Katkov et al. (1995). "Hepatitis vaccines," *Gastroenterol Clin North Am.* 24(1):147–159.

Kato et al., (Nov. 1990) "A structural protein encoded by the 5' region of the hepatitis C virus genome efficiently detects viral infection," *Rapid Communication, Jpn. J. Cancer. Res.* 81:1092–1094.

Kato et al. (1991). "Molecular structure of the Japanese hepatitis C viral genome," *FEBS lett.* 280(2):325–328.

Kato et al. (1993). "Humoral immune response to hypervariable region 1 of the putative envelope glycoprotein (gp70) of hepatitis C virus," *J Virol.* 67(7):3923–3930.

Kato, N. et al. (1994). "Genetic Drift in Hypervariable Region 1 of the Viral Genome in Persistent Hepatitis C virus Infection," *J. Virol.* 68(8):4776–4784.

Ke et al. (1997). "Distinguishing the specificities of closely related proteases. Role of P3 in substrate and inhibitor discrimination between tissue–type plasminogen activator and urokinase," *J Biol Chem.* 272(26):16603–16609.

Kean, K. et al. (1991) "Analysis of palative active site residues of the poliovirus 3c protease," *Virol.* 181:609–619.

Kew et al. (1990). "Hepatitis C virus antibodies in southern African blacks with hepatocellular carcinoma," *Lancet.* 335(8694):873–874.

Khan et al. (1996). "Solid phase reductive alkylation of secondary amines," *Tetra Letters.* 37(27):4819–4822.

Khudyakov et al. (1995). "Linear B–cell epitopes of the NS3–NS4–NS5 proteins of the hepatitis C virus as modeled with synthetic peptides," *Virology.* 206(1):666–672.

Kim et al. (1995). "Crystal structure of HIV–1 protease in complex with VX–478, a potent and orally bioavailable inhibitor of the enzyme," *J Amer Chem Soc.* 117(3);1181–1182.

Kim et al. (1995). "C–terminal domain of the hepatitis C virus NS3 protein contains an RNA helicase activity," *Biochem Biophys Res Commun.* 215(1):160–166.

Kim et al. (1996). "Crystal structure of the hepatitis C virus NS3 protease domain complexed wth a synthetic NS4A cofactor peptide," *Cell.* 87(2):343–355.

Kim, D. W. et al. (1997). "Mutational Analysis of the Hepatitis C Virus RNA Helicase," *J. Virol.* 71(12);9400–9409.

Kim. D. W. et al.(1997). "Towards Defining a Minimal Functional Domain for NTPase and RNA Helicase Activities of the Hepatitis C Virus NS3 Protein," *Virus Res.* 49:17–25.

Kim, J. L. et al. (1998). "Hepatitis C Virus NS3 RNA Helicase Domain with a Bound Oligonucleotide: The Crystal Structure Provides Insights into the Mode of Unwinding," *Structure* 6(1):89–100.

Koch et al. (1997). "Determinants of substrate specificity in the NS3 serine proteinase of the hepatitis C virus," *Virology.* 237(1):78–88.

Koch, J.O. et al. (1996). "In Vitro Studies of the Activation of the Hepatitis C Virus NS3 Proteinase by the NS4A Cofactor," *Virology* 221:54–66.

Koff et al. (1995). "Economic modeling of treatment in chronic hepatitis B and chronic hepatitis C: promises and limitations," *Hepatology.* 22(6):1880–1882.

Koff et al. (1995), "Extrahepatic manifestations of hepatitis C and the association with alcoholic liver disease," *Semin Liver Dis.* 15(1):101–109.

Kolykhalov et al. (1994). "Specificity of the hepatitis C virus NS3 serine protease: effects of substitutions at the 3/4A, 4A/4B, 4B/5A, and 5A/5B cleavage sites on polyprotein processing," *J. Virol.* 68(11):7525–7533.

Komoda et al. (1994). "Substrate requirements of hepatitis C virus serine proteinase for intermolecular polypeptide cleavage in *Escherichia coli*," *J. Virol.* 68(11):7351–7357.

Komoda, Y. et al. (1994), "Processing of Hepatitis C Viral Polyprotein in *Escherichia coli*," *Gene* 145:221–226.

Koonin et al. (1989). "Evolution of RNA genomes: Does the high mutation rate necessitate high rate of evolution of viral proteins?," *J. Mol. Evol.* 28:524–527.

Koonin, E. V. (Apr. 6, 1989). "Tale of Two Serines," *Nature* 338:467–468.

Koonin, E. V. et al. (1992). "Computer–Assisted Assignment of Functional Domains in the Nonstructural Polyprotein of Hepatitis E Virus: Delineation of an Additional Group of Positive–Strand RNA Plant and Animal Viruses," *PNAS USA* 89:8259–8263.

Korant et al. (1986). "Viral therapy: Prospects for protease inhibitors," *J Cell Biochem.* 32(2):91–95.

Cohen, J. (Jul. 2, 1999) "The scientific challenge of hepatitis C," *Science,* 285:26–30.

Koziel, M.J. et al. (1993). "Hepatitis C Virus (HCV)–Specific Cytotoxic T Lymphocytes Recognize Epitopes in the Core and Envelope Proteins of HCV," *J. Virol.* 67(12):7522–7532.

Kremsdorf et al. (1991). "Hepatitis C virus (HCV)–RNA in non–A, non–B chronic hepatitis in France. Nucleotide sequence of a French HCV isolate," *J Hepatol.* 13 Suppl 4:S24–32.

Krishna Murthy, H.M. et al. (1999). "Dengue Virus NS3 Serine Protease," *J. Bio. Chem.* 274(9):5573–5580.

Kryger P (1983). "Non–A, non–B hepatitis, Serological, clinical, morphological and prognostic aspects," *Liver.* 3(3):176–198.

Kuida et al. (1995). "Altered cytokine export and apoptosis in mice deficient in interleukin–1 beta converting enzyme," *Science.* 267(5206):2000–2003.

Kuo et al. (1989). "An assay for circulating antibodies to a major etiologic virus of human non–A, non–B hepatitis," *Science* 244:362–364.

Kwong (1998) "Structure based drug design targets for hepatitis C virus antiviral therapy," in *Symposium on Emerging Therapies for Chronic Viral Hepatitis,* Montreal, Canada, Oct. 2–4, one page.

Kwong, A.D. (1997). "Hepatitis C virus NS3/4A protease," *Curr. Opin. Infect. Dis.* 10(6):485–490.

Kwong, A.D. et al. (1998). "Hepatitis C Virus NS3/4A Protease," *Antiviral Res.* 40(1–2):1–18.

Kwong, A.D. et al. (February 1999) "Hepatitis C virus NS3/4A protease," *Antiviral Res.* 41(1):67–84.

Kyono, K. et al. (1998). "Detection of Hepatitis C Virus Helicase Activity Using the Scintillation Proximity Assay System," *Analyt. Biochem.* 257:120–126.

Kyte et al. (1982) "A simple method for displaying the hydropathic character of a protein," *J. Mol. Biol.* 157:105–132.

La Vallie et al. (1993). "A thioredoxin gene fusion expression system that circumvents inclusion body formation in the *E. coli* cytoplasm," *Biotechnology* (N Y). 11(2):187–193.

Labonté, P. et al. (1995). "Sequence and Expression of the NS2 Protein Gene of Human Coronavirus OC43," *J. Gen. Virol.* 76:431–435.

Lagging, L.M. et al. (1995). "Immune Responses to Plasmid DNA Encoding the Hepatitis C Virus Core Protein," *J. Virol.* 69(9):5859–5863.

Leinbach, S.S. et al. (1994). "Substrate Specificity of the NS3 Serine Proteinase of Hepatitis C Virus as Determined by Mutagenisis at the NS3/NS4A Junction," *Virology* 204:163–169.

Landro et al. (1997). "Mechanistic role of an NS4A peptide cofactor with the truncated NS3 protease of hepatitis C virus: elucidation of the NS4A stimulatory effect via kinetic analysis and inhibitor mapping," *Biochemistry.* 36(31):9340–9348.

LaPlante et al. (1998). "Human cytomegalovirus protease complexes its substrate recognition sequences in an extended peptide conformation," *Biochemistry.* 37(27):9793–9801.

LaPlante, S.R. et al. (1999). "Solution Structure of Substrate–Based Ligands When Bound to Hepatitis C Virus NS3 Protease Domain," *J. Biol. Chem.* 274(26):18618–18624.

Lathe R (1985). "Synthetic oligonucleotide probes deduced from amino acid sequence data. Theoretical and practical considerations," *J Mol Biol.* 183(1):1–12.

Lavanchy, D. (1997). "The Threat to Public Health of Hepatitis C," *Res. Virol.* 148:143–145.

Lee, H.J. et al. (1991). "The Complete Sequence (22 Kilobases) of Murine Coronavirus Gene 1 Encoding the Putative Proteases and RNA Polymerase," *Virology* 180:567–582.

Leff DN (1996) "Agouron, Vertex Both Solve Hepatitis C Protease Structure," *BioWorld Today* 7(204) pp. 1 and 5.

Love, S.M. (1997). "Targeting the Achilles' Heel of Hepatitis C Virus," *Hepatology* 25(4):1035–1037.

Leontovich, A.M. et al. (1993). "Construction of the Full Local Similarity Map for Two Biopolymers," *Biosystems* 30:57–63.

Levine et al. (1997). "Measurement of specific protease activity utilizing fluorescence polarization," *Anal Biochem.* 247(1):83–88.

Lewin R (September 1987). "When does homology mean something else?," *Science.* 237(4822):1570.

Liebig H–D et al. (1991) "Proteinase trapping: screening for viral proteinase mutants by alpha complementation," *Proc Natl Acad Sci U S A.* 1991 Jul. 15;88(14):5979–5983.

Lin et al. (1993). "The hepatitis C virus genome: a guide to its conserved sequences and candidate epitopes," *Virus Res.* 30(1):27–41.

Lin et al. (1995)."The hepatitis C virus NS3 serine proteinase and NS4A cofactor: establishment of a cell–free trans–processing assay," *Proc Natl Acad Sci U S A.* 92(17):7622–7626.

Lin et al. (1994). "Hepatitis C virus NS3 serine proteinase: trans–cleavage requirements and processing kinetics," *J Virol.* 68(12):8147–8157.

Lin et al. (1995). "A central region in the hepatitis C virus NS4A protein allows formation of an active NS3–NS4A serine proteinase complex in vivo and in vitro," *J Virol.* 69(7):4373–4380.

Lin et al. (1995). "The hepatitis C virus NS3 serine proteinase and NS4A cofactor: establishment of a cell–free trans–processing assay," *Proc Natl Acad Sci U S A.* 92(17):7622–7626.

Lin et al. (1997). "The hepatitis C virus NS4A protein: interactions with the NS4B and NS5A proteins," *J Virol.* 71(9):6465–6471.

Lin, C. et al. (1994). "Hepatitis C Virus NS3 Serine Protease: Trans–Cleavage Requirements and Processing Kinetics," *J. Virol.* 68(12):8147–8157.

Lin, C. et al. (1994). "Processing in the Hepatitis C Virus E2–NS2 Region: Identification of P7 and Two Distinct E2–Specific Products with Different C Terminal," *J. Virol.* 68(8):5063–5073.

Lin, C. et al. (1995). "A Central Region in the Hepatitis C Virus NS4A Protein Allows Formation of an Active NS3–NS4A Serine Proteinase Complex In Vivo and In Vitro," *J. Virol.* 69(7):4373–4380.

Lindsay, K.L. (1997). "Therapy of Hepatitis C: Overview," *Hepatology* 26(3):71S–77S.

Lipford, J.R. et al. (1994). "Nucleotide Binding by the HIV–1 Integrase Protein In Vitro," *J. Aquired Immune Deficiency Syndromes* 7:1215–1223.

Liu, Q. et al. (1997). "Regulated Processing of Hepatitis C Virus Core Protein is Linked to Subcellular Localization," *J. Virol.* 71(1):657–662.

Liu, Q. et al. (1999). "The Hepatitis C Virus NS2 Protein Generated by NS2–3 Autocleavage is Required for NS5A Phosphorylation," *Biochem. Biophys. Res. Commun.* 254:572–577.

Llinas–Brunet et al. (1998). "Peptide–based inhibitors of the hepatitis C virus serine protease," *Bioorg Med Chem Lett.* 8(13):1713–1718.

Llinás–Brunet, M. et al. (1998). "Studies on the C–Terminal of Hexapeptide Inhibitors of the Hepatitis C Virus Serine Protease," *Bioorg. & Med. Chem. Lett.* 8:2719–2724.

Lo et al., (February 1994) "Comparative studies of the core gene products of two different hepatitis C virus isolates: two alternative forms determined by a single amino acid substitution," *Virology* 199(1):124–131.

Lobigs et al., (July 1988) "Murray Valley Encephalitis virus field strains from Australia and Papua New Guinea: Sutides on the sequence of the major envelope protein gene and virulence for mice," *Virology* 165(1):245–255.

Lobigs M (1993). "Flavivirus premembrane protein cleavage and spike heterodimer secretion require the function of the viral proteinase NS3," *Proc Natl Acad Sci U S A.* 90(13):6218–6222.

Locarnini, S.A. (1995). "Viral Hepatitis: The Challenge Ahead," *Intl. Antiviral News* 314:54–56.

Lohmann, V. et al. (1996). "Processing Pathways of the Hepatitis C Virus Proteins," *J. Hepatol.* 24 (Suppl. 2):11–19.

Lok et al. (1993). "Antibody response to core, envelope and nonstructural hepatitis C virus antigens: comparison of immunocompetent and immunosuppressed patients," *Hepatology.* 18(3):497–502.

London et al. (1992). "Infectious enveloped RNA virus antigenic chimeras," *Proc Natl Acad Sci U S A.* 89(1):207–211.

Love et al. (1996). "The crystal structure of hepatitis C virus NS3 proteinase reveals a trypsin–like fold and a structural zinc binding site," *Cell.* 87(2):331–342.

Love et al. (1998) "The conformation of hepatitis C virus NS3 proteinase with and without NS4A: A structural basis for the activation of the enzyme by its cofactor," *Clin. Diag. Virol.* 10:151–156.

Lu et al. (1996). "Poliovirus chimeras replicating under the translational control of genetic elements of hepatitis C virus reveal unusual properties of the internal ribosomal entry site of hepatitis C virus," *Proc Natl Acad Sci U S A.* 93(4):1412–1417.

Maeda et al. (1989). "Production of antibodies directed against microtubular aggregates in hepatocytes of chimpanzees with non–A, non–B hepatitis," *J Gen Virol.* 70(Pt 6):1401–1407.

Maeno et al. (1990). "A cDNA clone closely associated with non–A, non–B hepatitis," *Nucleic Acids Res.* 18(9):2685–2689.

Magrin et al. (1991). "Hepatitis C virus replication in 'autoimmune' chronic hepatitis," *J Hepatol.* 13(3):364–367.

Major et al. (1997). "The molecular virology of hepatitis C," *Hepatology.* 25(6):1527–1538.

Makris et al. (1990). "Hepatitis C antibody and chronic liver disease in haemophilia," *Lancet.* 335(8698):1117–1119.

Manabe et al. (1994). "Production of nonstructural proteins of hepatitis C virus requires a putative viral protease encoded by NS3," *Virology.* 198(2):636–644.

Manna et al. (1996). "Helicase–contrahelicase interaction and the mechanism of termination of DNA replication," *Cell.* 87(5):881–891.

Mannucci et al. (November 1985). "Non–A, non–B hepatitis after factor VIII concentrate treated by heating and chloroform," *Lancet.* 2(8462):1013.

Mansell et al. (1995). "Epidemiology of hepatitis C in the East," *Semin Liver Dis.* 15(1):15–32.

Mansour et al. (1997). "Antiviral nucleotides," *Curr. Pharm. Design* 3(2):227–264.

Markland et al. (1997). "Purfiication and characterization of the NS3 serine protease domain of hepatitis C virus expressed in *Saccharomyces cerevisiae*," *J Gen Virol.* 78 (Pt 1):39–43.

Martell, M. et al. (1992). "Hepatitis C Virus (HCV) Circulates as a Population of Different but Closely Related Genomes: Quasispecies Nature of HCV Genome Distribution," *Journal of Virology* 66(5):3225–3229.

Marth et al. (1996). "Recent advances in gene mutagenesis by site–directed recombination," *J Clin Invest.* 97(9):1999–2002.

Martin et al. (1997). "Affinity selection of a camelized V(H) domain antibody inhibitor of hepatitis C virus NS3 protease," *Protein Eng.* 10(5):607–14.

Martin et al. (1998). "Design of selective eglin inhibitors of HCV NS3 proteinase," *Biochemistry.* 37(33):11459–11468.

Martinot–Peignoux et al. (1995). "Pretreatment serum hepatitis C virus RNA levels and hepatitis C virus genotype are the main and independent prognostic factors of sustained response to interferon alfa therapy in chronic hepatitis C," *Hepatology.* 22(4 Pt 1):1050–6.

Matayoshi et al., (1990). "Novel Fluorogenic substrates for assaying retroviral proteases by resonance energy transfer" *Science* 247:954–958.

Matsumoto, M. et al. (1997). "Hepatitis C Virus Core Protein Interacts with the Cytoplasmic Tail of Lyphotoxin–B Receptor," *Journal of Virology* 71(2):1301–1309.

Matsuura et al., (1993) "The molecular biology of hepatitis C virus," in *Seminars in Virology*, vol. 4, pp. 297–304.

Matsuura, Y. et al. (1994). "Processing of E1 and E2 Glycoproteins of Hepatitis C Virus Expressed in Mammalian and Insect Cells," *Virology* 205:141–150.

Maynard et al. "Chapter 5: Transmission of non–A, non–B hepatitis by blood products and plasma derivatives," pp. 71–95.

McCall, J. et al. (1994) "A High Capacity Microbial Screen for Inhibitors of Human Rhinovirus Protease 3C," *BioTechnology* 12:1012–1016.

McGrath et al. (1993). "Structure of an engineered, metal-actuated switch in trypsin," *Biochemistry.* 32(8):1914–1919.

McHutchison et al. (1991). "Assessment of hepatitis C antibody tests in homosexual men with hyperglobulinemia," *J Infect Dis.* 164(1):217–218.

Meyers et al. (1989) "Ubiquitin in a togavirus," *Nature* 341:491.

Miller RH (1987). "Proteolytic self–cleavage of hepatitis B virus core protein may generate serum antigen," *Science.* 236(4802):722–725.

Gerin, J.L. et al., (1990). "Hepatitis B virus and liver cancer: the woodchuck as an experimental model of hepadnavirus-induced liver cancer" Abstract from 1990 International Symposium on Viral Hepatitis and Liver Disease, pp. 556–559.

Mills, J. S. (1996). "Virus Proteinase Inhibitors—What Next After HIV?," *Antiviral Chemistry and Chemotherapy* 7(6):281–293.

Mink, M.A. et al., (1994) "Characterization and mapping of a B–cell immunogenic domain in hepatitis C virus E2 glycoprotein using a yeast peptide library," *Virology* 200:246–255.

Missale, G. et al. (1996). "Different Clinical Behaviors of Acute Hepatitis C Virus Infection Are Associated with Different Vigor of the Antiviral Cell–Medeiated Immune Response," *J. Clin. Invest.* 98(3):706–714.

Mita et al. (1992). "Expression of MBP–HCV NS1/E2 fusion protein in *E. coli* and detection of anti–NS1/E2 antibody in type C chronic liver disease," *Biochem Biophys Res Commun.* 183(3):925–930.

Miyamura et al. (1990). "Detection of antibody against antigen expressed by molecularly cloned hepatitis C virus cDNA: application to diagnosis and blood screening for posttransfusion hepatitis," *Proc Natl Acad Sci U S A.* 87(3):983–987.

Saito, I. et al. (1990). "Hepatitis C virus infection is associated with the development of hepatocellular carcinoma," *Proc Natl Acad Sci U S A.* 87(17):6547–6549.

Mizushima, H. et al. (1994). "Analysis of N–Terminal Processing of Hepatitis C Virus Nonstructural Protein 2," Journal of Virology 68(4):2731–2734.

Mizutani, T. "Long–term human T–cell culture system supporting hepatitis C virus replication," *Biochem Biophys. Res. Commun.* 227:822–826 (1996), Abstract only (article available upon request).

Molla et al. (1998) "Inhibitors of HCV replication," Abstract 023, *Second International Conference on Therapies for Viral Hepatitis,* Kona, Big Island, Hawaii, Dec. 15–19, 1997.

Monath. (1986). "Pathobiology of the flaviviruses," Chapter 12 in *The Togaviridae and Flaviviridae,* Schlesinger et al., eds., Plenum Press: New York, pp. 375–441.

Mondelli, M. U. et al. (1994). "Significance of the Immune Response to a Major, Conformatrional B–Cell Epitope on the Hepatitis C Virus NS3 Region Defined by a Human Monoclonal Antibody," *Journal of Virology* 68(8):4829–4836.

Morgenstein et al. (1997). "Polynucleotide modulation of the protease, nucleoside triphosphatase, and helicase activities of a hepatitis C virus NS3–NS4A complex isolated from transfected COS cells," *J Virol.* 71(5):3767–3775.

Mori et al. (1996). "Enzymatic characterization of purified NS3 serine proteinase of hepatitis C virus expressed in *Escherichia coli,"* FEBS Lett.* 378(1):37–42.

Mori et al. (1997). "The N–terminal region of NS3 serine proteinase of hepatitis C virus is important to maintain its enzymatic integrity," *Biochem Biophys Res Commun.* 231(3):738–742.

Mosley et al. (1990). "Non–A, non–B hepatitis and antibody to hepatitis C virus," *JAMA.* 263(1):77–78.

Muller et al. (1993). "Genetic variability of German hepatitis C virus isolates," *J Med Virol.* 40(4):291–306.

Muramatsu et al. (1997). "Nuclear localization of the NS3 protein of hepatitis C virus and factors affecting the localization," *J Virol.* 71(7):4954–4961.

Murcko, (1997) "The HCV NS3–4A serine protease: Prime target for drug design,", in *NMHCC's Second International Conferences: Protease Inhibitors in Infectious Diseases,* Aug. 18–19, 1997, Protease Inhibitors in Inflammation, Aug. 19–20, 1997, Abstract, p. 8.

Murphy et al. (1996). "Demographic determinants of hepatitis C virus seroprevalence among blood donors," *JAMA.* 275(13):995–1000.

Murray et al., (1996) "Proteolytic activity of hepatitis C virus NS3 co–expressed with NS4A in *E. coli,"* 0 Abstract from *IX Triennial International Symposium on Viral Hepatitis and Liver Disease,* Apr. 21–25, 1996, Rome, Italy, Abstract (full reference provided upon request), one page.

Mustilli, A. C. et al. (1999). "Comparison of Secretion of a Hepatitis C Virus Glycoprotein in *Saccharomyces cervisiae* and *Kluyveromyces lactis,"* Res. Microbiol.* 150:179–187.

Nasoff et al. (1991). "Identification of an immanodominant epitope within the capsid protein of hepatitis C virus," *Proc Natl Acad Sci U S A.* 88(12):5462–5466.

Nassal et al. (1989). "Proteaselike sequence in hepatitis B virus core antigen is not required for e antigen generation and may not be part of an aspartic acid–type protease," *J Virol.* 63(6):2598–604.

National Institutes of Health (1997). "National Institutes of Health Consensus Development Conference Panel statement: management of hepatitis C," *Hepatology* 26(3 Suppl.1):2S–10S.

Neddermann P et al. (1997) "The nonstructural proteins of the hepatitis C virus: structure and functions," *Biol Chem.* 378(6):469–476.

Nelles M (1993). "Improved performance of a third generation multiantigen screening tests for hepatitis C virus," Symposium on advances in HCV diagnosis and Treatment, Barcelona, Spain, pp. 7–8.

Nishioka et al. (1991). "Antibody to the hepatitis C virus in acute hepatitis and chronic liver diseases in Japan," *Liver.* 11(2):65–70.

Noever D. (1996). "Naturally occurring protease inhibitors potent against the human immunodeficiency virus," *Biochem Biophys Res Commun.* 227(1):125–130.

Ogata et al. (1991). "Nucleotide sequence and mutation rate of the H strain of hepatitis C virus," *Proc Natl Acad Sci U S A.* 88(8):3392–3396.

Okamoto et al. (1990). "The 5'–terminal sequence of the hepatitis C virus genome," *Jpn J Exp Med.* 60(3):167–177.

Okamoto H (1992). "Characterization of genomic structure of hepatitis C virus," 161(5):298–302.

Okano K et al. (1990) "Functional expression of human leukocyte elastase (HLE)/medullasin in eukaryotic cells," *Biochem Biophys Res Commun.* 167(3):1326–1332.

Okuda et al. (1984). "Clinicopathological features of hepatocellular carcinoma–comparison of hepatitis B seropositive and seronegative patients," *Hepato–gastroenterol.* 31:64–68.

Ornstein, P. L. et al. (1995). "(3SR,4aRS,6SR,8aRS)–6–(1H–Tetrazol–5–yl)decahydroisoquinoline–3–carboxylic Acid, a Novel, Competitive, Systemically Active NMDA and AMPA Receptor Antagonist," *J. Med. Chem.* 38:4885–4890.

Ornstein, P. L. et al. (1996). "Structure–Activity Studies of 6–(Tetrazolylalkyl)–Substituted Decahydroisoquinoline–3–carboxylic Acid AMPA Receptor Antagonists. 1. Effects of Steriochemistry, Chain Length, and Chain Stubstitution," *J. Med Chem.* 39:2219–2231.

Orru, S. et al. (1999). "Conformational Changes in the NS3 Protease From Hepatitis C Virus Strain Bk Monitored by Limited Proteolysis and Mass Spectrometry," *Protein Science* 8:1445–1454.

Oshima et al. (1991). "cDNA clones of Japanese hepatitis C virus genomes derived from a single patient show sequence heterogeneity," *J Gen Virol.* 72 (Pt 11):2805–2809.

Ottmann M et al. (1995) "The central globular domain of the nucleocapsid protein of human immunodeficiency virus type 1 is critical for virion structure and infectivity," *J Virol.* 69(3):1778–1784.

Overton et al. (1995). "Recombinant baculovirus–expressed NS3 proteinase of hepatitis C virus shows activity in cell–based and in vitro assays," *J Gen Virol.* 76 (Pt 12):3009–3019.

Ozkaynak et al. (1984). "The yeast ubiquitin gene: head–to–tail repeats encoding a polyubiquitin precursor protein," *Nature.* 312(5995):663–666.

Parvin et al. (August 1986). "Measurement of the mutation rates of animal viruses: Influenza a virus and polivirus type 1," *J. Virol.* 59(2):377–383.

Pasquinelli, C. et al. (1997). "Hepatitis C Virus Core and E2 Protein Expression in Transgenic Mice," *Hepatology* 25(3):719–727.

Patick, A. K. and Potts, K. E. (1998). "Protease Inhibitors as Antiviral Agents," *Clinical Microbiology Reviews* 11(4):614–627.

Pecceu F et al. (1991) "Human interleukin 1 beta fused to the human growth hormone signal peptide is N–glycosylated and secreted by Chinese hamster ovary cells," *Gene.* 97(2):253–258.

Perbal, B. (1988). *A Practical Guide To Molecular Cloning.* John Wiley & Sons, New York, Table of Contents, pp. xi–xix.

Pichuantes et al. (1989). "Recombinant HIV1 protease secreted by *Saccharomyces cerevisiae* correctly processes myristylated gag polyprotein," *Proteins.* 6(3):324–337.

Pichuantes S et al. (1990) "Recombinant HIV2 protease processes HIV1 Pr53gag and analogous junction peptides in vitro," *J Biol Chem.* 265(23):13890–13898.

Pieroni et al. (1997). "In vitro study of the NS2–3 protease of hepatitis C virus," *J Virol.* 71(9):6373–6380.

Pileri et al. (1998). "Binding of hepatitis C virus to CD81," *Science.* 283(5390):938–941.

Pizzi et al. (1994). "Molecular model of the specificity pocket of the hepatitis C virus protease: implications for substrate recognition," *Proc Natl Acad Sci U S A.* 91(3):888–892.

Platt et al. (1994). "Mortality in sickle cell disease. Life expectancy and risk factors for early death," *N Engl J Med.* 330(23):1638–44.

Poch et al. (1989) "Identification of four conserved motifs among the RNA–dependent polymerase encoding elements," *EMBO J.* 8:3867–3874.

Polyak, S. J. et al. (1998). "Characterization of the effects of hepatitis C virus nonstructural 5A protein expression in human cell lines and on interferon–sensitive virus replication," Hepatology 29(4):1262–1271.

Preugschat et al. (1990) "In vitro processing of Dengue Virus Type 2 Non Structural Proteins NS2A, NS2B, and NS3," *J. Virol.* 64:4364–4374.

Preugschat et al. (1991). "Flavivirus enzyme–substrate interactions studied with chimeric proteinases: identification of an intragenic locus important for substrate recognition," *J Virol.* 65(9):4749–4758.

Prince et al. (1984). "Isolation of a virus from chimpanzee liver cell cultures inoculated with sera containing the agent of non–A, non–B hepatitis," *Lancet.* 2(8411):1071–1075.

Prince et al. (1985). "Inactivation of the Hutchinson strain of non–A, non–B hepatitis virus by combined use of beta–p–ropiolactone and ultraviolet irradiation," *J Med Virol.* 16(2):119–125.

Prince et al. (1990). "Use of anti–HCV determinations for diagnosis of chronic HCV infection," in *Proceedings of 1990 International Symposium in Viral Hepatitis and Liver Disease*, Houston, Texas, pp. 1–18.

Purcell, R. (1994). "Hepatitis C Virus: Historical Perspective and Current Concepts," *FEMS Microbiology Reviews* 14:181–191.

Purcell, R. (1997). "The Hepatitis C Virus: Overview," *Hepatology* 26(3 Suppl. 1):115–145.

Qabar et al. (1996). "Peptide secondary structure mimetics: applications to vaccines and pharmaceuticals," *Furmaco.* 51(2):87–96.

Ray, R. et al. (1994). "Peptide Immunogen Mimicry of Putative El Glycoprotein–Specific Epitopes in Hepatitis C Virus," *Journal of Virology* 4420–4426.

Read et al. (1983). "Structure of the complex of Streptomyces griseus protease B and the third domain of the turkey ovomucoid inhibitor at 1.8–A resolution," *Biochemistry.* 22(19):4420–4433.

Reanney DC (1982). "The evolution of RNA viruses," *Annu Rev Microbiol.* 36:47–73.

Rechsteiner (1987) "Ubiquitin–mediated pathways for intracellular proteolysis," *Ann. Rev. Microbiol.* 3:1–30.

Reeck et al. (1987). ""Homology," in proteins and nucleic acids: a terminology muddle and a way out of it," *Cell.* 50(5):667.

Reed et al. (1995). "Hepatitis C virus encoded NS2–3 protease: cleavage–site mutagenesis and requirements for bimolecular cleavage," *J Virol.* 69(7):4127–4136.

Reed et al. (1997). "Phosphorylation of the hepatitis C virus NS5A protein in vitro and in vivo: properties of the NS5A–associated kinase," *J Virol.* 71(10):7187–97.

Rehermann, B. et al. (1996). "Differential Cytotoxic T–Lymphocyte Responsiveness to the Hepatitis B and C Viruses in Chronically Infected Patients," *Journal of Virology* 70(10):7092–7102.

Rehermann, B. et al. (1996). "Quantitative analysis of the peripheral blood cytotoxic T lymphocyte response in patients with chronic hepatitis C virus infection," *J. Clin. Invest.* 98(6):1432–1440.

Reichard, O. et al. (1997). "Therapy of Hepatitis C: Alpha Interferon and Ribavrin," *Hepatology* 26 (3 Suppl. 1):108S–111S.

Reyes et al. (1990) "Isolation of a cDNA from the virus responsible for enterically transmitted non–A, non–B hepatitis," *Science* 247:1335–1339.

Reyes et al. (1991). "Molecular biology of non–A, non–B hepatitis agents: hepatitis C and hepatitis E viruses," *Adv Virus Res.* 40:57–102.

Rizzuto et al. (1996). "Double labelling of subcellular structure with organelle–targeted GFP mutants in vivo," *Curr Biol.* 6(2):183–8.

Roizman, B. and Palese, P. (1996). "Chapter 4: Multiplication of Viruses: An Overview," in *Fields Virology*, Third Edition, pp. 101–111.

Rumenapf et al. (1997). "N–terminal protease of pestiviruses: identification of putative catalytic residues by site–directed mutagenesis," *J Virol.* 72(3):2544–7.

Ryan, M. D. et al. (1998). "Virus–encoded Proteinases of the Flaviviridae," *Journal of General Virology* 79:947–959.

Ryff, J. (1995). "Usefulness of Interferon for Treatment of Hepatitis C," *Journal of Hepatology* 22 (Suppl. 1):101–109.

Sakamuro et al. (1995). "Hepatitis C virus nonstructural protein NS3 transforms H1H 3T3 cells," *J Virol.* 69(6):3893–3896.

Sali et al. (1998). "Serine protease of hepatitis C virus expressed in insect cells as the Ns3/4A complex," *Biochemistry.* 37(10):3392–3401.

Sällberg, M. et al. (1996). "Immunogenicity of the ATPase/Helicase Domain of the Hepatitis C Virus Non–Structural 3 Protein," *J. Gen. Virol.* 77:2721–2728.

Sambrook et al. (1989). *Molecular Cloning: A Laboratory Manual* 2nd edition, Cold Spring Harbor Laboratory Press: New York, Table of Contents, pp. v–xxxii.

Santolini, E. et al. (1995). "The NS2 Protein of Hepatitis C Virus is a Transmembrane Polypeptide," *J. Virol.* 69(12):7461–7471.

Satoh et al. (1995). "The N–terminal region of hepatitis C virus nonstructural protein 3 (NS3) is essential for stable complex formation with NS4A," *J Virol.* 69(7):4255–4260.

Scarselli et al. (1997). "GB virus B and hepatitis C virus NS3 serine proteases share substrate specificity," *J Virol.* 71(7):4985–4989.

Schlesinger et al. (October 1985). "Protection against 17D yellow fever encephalitis in mice by passive transfer of monoclonal antibodies to the nonstructural glycoprotein gp48 and by active immunization with gp48," *J. Immunol.* 135(4):2805–2809.

Schlesinger et al. (1986). "Protection against yellow fever in monkeys by immunization with yellow fever virus nonstructural protein NS1," *J Virol.* 60(3):1153–1155.

Schlesinger et al. (1987). "Protection of mice against dengue 2 virus encephalitis by immunization with the dengue 2 virus non–structural glycoprotein NS1," *J. Gen. Virol.* 68:853–857.

Scott et al. (1985). "Protease nexin. Properties and a modified purification procedure," *J Biol Chem.* 260(11):7029–7034.

Seeff, L.B. (1997). "Natural History of Hepatitis C," *Hepatol.* 26(3):21S–28S.

Selby et al. (1993) "Expression, identification and subcellular localization of the proteins encoded by the hepatitis C viral genome," *J. Gen. Virol.* 74:1103–1113.

Selby et al. (1994) "Complex processing and protein–protein interactions . . . ," *Viroly* 204:114–122.

Shank & Lomonossoff (1990). "The primary structure of the 24k protease from red clover nettle virus implications for the mode of action of comovirus protease," *J. Gen. Virol.* 172:735–738.

Shapiro et al. (1996). "19F NMR monitoring of a S(N)Ar reation on solid support," *Tetra Letters* 37(27):4671–4674.

Sharara et al. (1996). "Hepatitis C," *Ann Intern Med.* 125(8):658–668.

Shimizu et al. (1990). "Early events in hepatitis C virus infection of chimpanzees," *Proc Natl Acad Sci U S A.* 87(16):6441–6444.

Shimizu et al. (1992). "Evidence for in vitro replication of hepatitis C virus genome in a human T–cell line," *Proc Natl Acad Sci U S A.* 89(12):5477–5481.

Shimizu et al. (1995). "Identification of sequences of NS4A essential for HCV NS3 protease activation," Symposium on hepatitis C virus and related viruses in hepatitis C virus and related viruses, 3rd International Meeting, Australia.

Shimizu et al. (1996). "Identification of the sequence on NS4A required for enhanced cleavage of the NS5A/5B site by hepatitis C virus NS3 protease," *J Virol.* 70(1):127–132.

Shimotohno, K. et al. (1995). "Processing of the Hepatitis C Virus Precursor Protein," *J. Hepatol.* 22(Suppl. 1):87–92.

Shoji et al . (1995). "Proteolytic activity of NS3 serine proteinase of hepatitis C virus efficiently expressed in *Escherichia coli*," *Hepatology.* 22(6):1648–1655.

Shoji, I. et al. (1999). "Internal Processing of Hepatitis C Virus NS3 Protein," *Virology* 254:315–323.

Shukla et al. (1995). "Evaluation of complete genome sequences and sequences of individual gene products for the classification of hepatitis C viruses," *Arch Virol.* 140(10):1747–61.

Sigler et al. (1966). "An x–ray diffraction study of inhibited derivatives of alpha–chymotrypsin," *Mol Biol.* 15(1):175–192.

Simmonds et al. (1990). "Hepatitis C quantification and sequencing in blood products, haemophiliacs and drug users," *Lancet.* 336(8729):1469–1472.

Simmonds et al. (1993). "Classification of hepatitis C virus into six major genotypes and a series of subtypes by phylogenetic analysis of the NS–5 region," *J Gen Virol.* 74 (Pt 11):2391–2399.

Simmonds P (1994). "Variability of hepatitis C virus genome," *Curr Stud Hematol Blood Transfus.* (61):12–35.

Simmonds P (1995). "Variability of hepatitis C virus," *Hepatology.* 21(2):570–583.

Simmonds, P. (1996). "Virology of Hepatitis C Virus," *Clin. Therap.* 18(Suppl. B):9–36.

Smith et al. (1985) "Synthesis of proteins and glycoproteins in degue type 2 virus–infected Vero and *Aedes albopictus* cells," *J. Gen. Virol.* 66:559–571.

Smith et al. (1987). "The mutation rate and variability of eukaryotic viruses: An analytical review," *J. Gen. Virol.* 68:2729–2740.

Snijder, E.J. et al. (1996). "The Arterivirus Nsp2 Protease," *J. Biol. Chem.* 270(28):16671–16676.

Snijder, E.J. et al. (1996). "The Arterivirus Nsp4 Protease is the Prototype of a novel Group of Chymotrypsin–Like Enzymes, the 3C–Like Serine Proteases," *J. Biol. Chem.* 271(9):4864–4871.

Song et al. (1996). "Development of an in vivo assay system suitable for screening inhibitors of hepatitis C viral protease," *Mol Cells* 6(2):183–189.

Soni et al. (1995). "Genetic diversity of hepatitis C virus: implications for pathogenesis, treatment, and prevention. Report of a meeting of Physicians and Scientists," *Lancet.* 345(8949):562–6.

Spaete et al. (1992). "Characterization of the hepatitis C virus E1/NS1 gene product expressed in mammalian cells," *Virology.* 188(2):819–830.

Steimer et al. (1986). "Recombinant polypeptide from the endonuclease region of the acquired immune deficiency syndrome retrovirus polymerase (pol) gene detects serum antibodies in most infected individuals," *J Virol.* 58(1):9–16.

Steinhauer et al. (1987). "Rapid evolution of RNA viruses," *Ann. Rev. Microbiol.* 41:409–433.

Steinkuhler et al. (1995). "Enzymatic activities encoded by hepatitis C virus," Symposium on hepatitis C virus and related viruses, 5th International Meeting on Hepatitis C Virus and related viruses, Austraalia, one page.

Steinkuhler et al. (1996). "Activity of purified hepatitis C virus protease NS3 on peptide substrates," *J Virol.* 70(10):6694–6700.

Steinkuhler et al. (1996). "In vitro activity of hepatitis C virus protease NS3 purified from recombinant Baculovirus–infected sf9 cells," *J Biol Chem.* 271(11):6367–6373.

Steinkuhler et al. (1998). "Product inhibition of the hepatitis C virus NS3 protease," *Biochemistry.* 37(25):8899–8905.

Stempel, C. A. et al. (1993). "Hepatitis C—Its Prevalence in End–Stage Renal Failure Patients and Clinical Course After Kidney Transplantation," *Transplantation* 55(2):273–276.

Stempniak et al. (April 1997) "The NS3 proteinase domain of hepatitis C virus is a zinc–containing enzyme," *J. Virol.* 71(4):2881–2886.

Stevens et al. (1990). "Epidemiology of hepatitis C virus. A preliminary study in volunteer blood donors," *JAMA.* 263(1):49–53.

Strauss et al. (1985) "Chapter 6: Assembly of enveloped animal viruses," *Virus Structure and Assembly,* Casjens, ed., Jones and Bartlett: Boston, pp. 206–234.

Strauss et al. (1987). "Replication of alphaviruses and flaviviruses: Proteolytic processing of polyproteins," in *Positive Strand RNA Viruses: Proceedings of a UCLA Symposium* held in Keystone, Colorado, in April 20–26, 1986, Brinton et al., eds., Alan R. Liss, New York, pp. 209–225.

Strauss et al. (1988) "Evolution of RNA viruses," *Ann. Rev. Microbiol.* 42:657–683.

Studier, F.W. and Moffatt, B.A. (1986). "Use of Bacteriophage T7 RNA Polymerase to Direct Selective High–Level Expression of Cloned Genes," *J. Mol. Biol.* 189:113–130.

Subramanya et al. (1996). "Crystal structure of a DExx box DNA helicase," *Nature,* 384(6607):379–383.

Sudo et al. (1996). "Establishment of an in vitro assay system for screening hepatitis C virus protease inhibitors using high performance liquid chromatography," *Antiviral Res.* 32(1):9–18.

Sudo et al. (1997). "Novel hepatitis C virus protease inhibitors: thiazolidine derivatives," *Biochem Biophys Res Commun.* 238(2):643–647.

Suzich et al. (1993). "Hepatitis C virus NS3 protein polynucleotide–stimulated mucleoside triphosphatase and comparison with the related pestivirus and flavivirus enzymes," *J Virol.* 67(10):6152–6158.

Suzuki et al. (1995). "In vivo and in vitro trans–cleavage activity of hepatitis C virus serine proteinase expressed by recombinant baculoviruses," *J Gen Virol.* 76 (Pt 12):3021–3029.

Svitkin, Y.V et al. (1979). "Encephalomyocarditis Virus–Specific Polypeptide p22 Possessing a Proteolytic Activity." *FEBS Lett.* 180(1):6–9.

Swinbanks D (1989). "Hepatitis viruses. Blood donors to be screened," *Nature.* 342(6249):467.

Tai, C et al. (1996). "The Helicase Activity Associated with Hepatitis C Virus Nonstructural Protein 3 (NS3)," Journal of Virology 70(12):8477–8484.

Takahashi et al. (1992). "p26 protein and 33–nm particle associated with nucleocapsid of hepatitis C virus recovered from the circulation of infected hosts," *Virology.* 191(1):431–434.

Takano et al. (1994). "Effects of interferon beta on non–A, non–B actue hepatitis: a prospective, randomized, controlled–dose study. Japan Acute Hepatitis Cooperative Study Group," *Gastroenterology.* 107(3):805–11.

Takeshita et al. (1997) "An enzyme–linked immunosorbent assay for detecting proteolytic activity of hepatitis C virus proteinase," *Anal. Biochem.* 247(2):242–246.

Takeuchi et al. (1990). "Hepatitis C viral cDNA clones isolated from a healthy carrier donor implicated in post–transfusion non–A, non–B hepatitis," *Gene.* 91(2):287–291.

Takeuchi et al. (1990). "Nucleotide sequence of core and envelope genes of the hepatitis C virus genome derived directly from human healthy carriers," *Nucleic Acids Res.* 18(15):4626.

Takeuchi et al. (1990). "The putative nucleocapsid and envelope protein genes of hepatitis C virus determined by comparison of the nucleotide sequences of two isolates derived from an experimentally infected chimpanzee and healthy human carriers," *J Gen Virol.* 71 (Pt 12):3027–3033.

Taliani et al. (1996). "A continuous assay of hepatitis C virus protease based on resonance energy transfer depsipeptide substrates," *Anal Biochem.* 240(1):60–67.

Tan, D. et al. (1993). "Molecular Cloning, Sequencing and Expression of Core and NS3 Fragments of HCV From Patients With HCV Infection," *Chinese Medical Journal* 105(7):522–526.

Tanji et al. (1994). "Identification of the domain required for trans–cleavage activity of hepatitis C viral serine proteinase," *Gene.* 145(2):215–219.

Tanji, Y. et al. (1994). "Hepatitis C Virus Polyprotein Processing: Kinetics and Mutagenic Analysis of Serine Proteinase–Dependent Cleavage," *Journal of Virology* 68(12):8418–8422.

Tanji et al. (1995). "Hepatitis C virus–encoded nonstructural protein NS4A has versatile functions in viral protein processing," *J Virol.* 69(3):1575–1581.

Tanji, Y. et al. (1995). "Phosphorylation of Hepatitis C Virus–Encoded Nonstructural Protein NS5A," *Journal of Virology* 69(7):3980–3986.

Taremi et al. (1998). "Construction, expression, and characterization of a novel fully activated recombinant single–chain hepatitis C virus protease," *Protein Sci.* 7(10):2143–2149.

Thaler, M. M. et al. (1991). "Vertical Transmission of Hepatitis C Virus," *Lancet* 338:17–18.

Thomas et al. (1996). "Pathophysiology and treatment of hepatitis C," *Drugs.* 52 Suppl 2:1–7; discussion 7–8.

Thomson et al., "Crystal Structure of the hepatitis C NS3 protease domain complexed with a synthetic NS4A cofactor peptide," Abstract, p. 7.

Thomson (1998) "On the Machinations of the hepatitis C virus NS3/4A protein," Abstract 022, *Second International Conference on Therapies for Viral Hepatitis,* Kona, Big Island, Hawaii, Dec. 15–19, 1997, one page.

Thornberry NA (1994). "Inflammation. Key mediator takes shape," *Nature.* 370(6487):251–252.

Tokita et al. (1994). "Hepatitis C virus variants from Vietnam are classifiable into the seventh, eighth, and ninth major genetic groups," *Proc Natl Acad Sci U S A.* 91(23:11022–6.

Tomassini et al. (1994). "Inhibition of cap (m7GpppXm)–dependent endonuclease of influenza virus by 4–substituted 2,4–dioxobutanoic acid compounds," *Antimicrob Agents Chemother.* 38(12):2827–2837.

Tomassini et al. (1996). "A novel antiviral agent which inhibits the endonuclease of influenza viruses," *Antimicrob Agents Chemother.* 40(5):1189–1193.

Tomei et al. (1993). "NS3 is a serine protease required for processing of hepatitis C virus polyprotein," *J Virol.* 67(7):4017–4026.

Tomei et al. (1996). "A central hydrophobic domain of the hepatitis C virus NS4A protein is necessary and sufficient for the activation of the NS3 protease," *J Gen Virol.* 77 (Pt 5):1065–1070.

Tomei, L. et al. (1993). "NS3 is a Serine Portease Required for Processing of Hepatitis C Virus Polyprotein," *Journal of Virology* 67(7):4017–4026.

Tong, M. J. et al. (1994). "Evidence for Hepatitis C Viral Infection in Patients with Priamary Hepatocellular Carcinoma," *West. J. Med.* 160(2):133–138.

Tong, M. J. et al. (1995). "Clinical Outcomes After Transfusion–Associted Hepatitis C," *The New England Journal of Medicine* 332(22):1463–1466.

Travis et al. (1985). "Isolation and properties of recombinant DNA produced variants of human alpha 1–proteinase inhibitor," *J Biol Chem.* 260(7):4384–4389.

Tsai, S. et al. (1995). "Cellular immune responses in patients with dual infection of hepatitis B and C viruses: dominant role of hepatitis C Virus," *Hepatology* 21(4):908–912.

Tu, H. et al. (1999). "Hepatitis C Virus RNA Polymerase and NS5A Complex with a SNARE–like Protein," *Virology* 263:30–41.

Urbani et al. (1997). "Substrate specificity of the hepatitis C virus serine protease NS3," *J Biol Chem.* 272(14):9204–9209.

Urvil PT et al. (1997) "Selection of RNA aptamers that bind specifically to the NS3 protease of hepatitis C virus," *Eur J Biochem.* 248(1):130–138.

Valenzuela et al. (1990). "Hepatitis A, B, C, D and E viruses: structure of their genomes and general properties," *Gastroenterol Jpn.* 25 Suppl 2:62–71.

van Brunt J (1992) "Lilly Looks to Biotech," *BioWorld Today* 3(216):1–3.

van der Poel et al. (1989). "Anti–hepatitis C antibodies and non–A, non–B post–transfusion hepatitis in The Netherlands," *Lancet.* 2(8658):297–298.

van der Poel et al. (1991). "Confirmation of hepatitis C virus infection by new four–antigen recombinant immunoblot assay," *Lancet.* 337(8737):317–319.

van der Poel et al. (1994). "Hepatitis C virus six years on," *Lancet.* 344(8935):1475–1479.

Van Dinten, L. C. et al. (1996). "Processing of the Equine Arterivirus Virus Replicase ORF1b Protein: Identification of Clevatge Products Containing the Putative Viral Polymerase and Helicase Domains," *Journal of Virology* 70(10):6625–6633.

Van Dinten, L. C. et al. (1999). "Proteolitic Processing of the Open Reading Frame 1b–Encoded Part of Arterivirus Repolicase is Mediated by NSP4 Serine Protease and is Essential for Virus Replication," *Journal of Virology* 73(3):2027–2037.

Van Doorn, L. (1994). "Review: Molecular Biology of the Hepatitis C Virus," *Journal of Medical Virology* 43:345–356.

Verchot J et al. (Jun. 5 1995) "Evidence that the poltyvirus P1 proteinase functions in trans as an accessory factor for genome amplification," *J Virol.* 69(6):3668–3674.

Vishnuvardhan et al. (1997). "Expression of highly active recombinant NS3 protease domain of hepatitis C virus in *E. coli,*" *FEBS Lett.* 402(2–3):209–212.

Wada M et al. (Nov.; 1997) "Importance of pretreatment viral load and monitoring of serum hepatitis C virus RNA in predicting responses to interferon–alpha2a treatment of chronic hepatitis C," *J Interferon Cytokine Res.* 17(11):707–712.

Wang et al. (1986). "Structure, sequence and expression of the hepatitis delta (delta) viral genome," *Nature.* 323(6088):508–514.

Wardell, A. D. et al. (1999). "Characterization and Mutational Analysis of the Helicase and NTPase Activities of Hepatitis C Virus Full–Length NS3 Protein," *Journal of General Virology* 80:701–709.

Warrener et al. (1995). "Pestivirus NS3 (p80) protein possesses RNA helicase activity," *J Virol.* 69(3):1720–1726.

Watanabe et al. (1990). "Prevalence of anti–HCV antibody in blood donors in the Tokyo area," *Vox Sang.* 59(2):86–88.

Webber, S. et al. (1996). "Design, Synthesis, and Evaluation of Nonpeptidic Inhibitors of Human Rhinovirus 3C Protease," *J. Med. Chem.* 39:5072–5082.

Webber, S. et al. (1998). "Tripeptide Aldehyde Inhibitors of Human Rhinovirus 3C protease: Design, Synthesis, Biological Evaluation, and Coctrystal Structure Solution of P1 Glutamine Isosteric Replacements," *J. Med. Chem.* 41:2786–2805.

Wehler et al. (1996). "Magic angle spinning NMR: a valuable tool for monitoring the progress of reactions in solid phase synthesis," *Tetra Letters.* 37(27):4771–4774.

Weiland, O. (1994). "Interferon Therapy in Chronic Hepatitis C Virus Infection," *FEMS Microbiology Reviews* 14:279–288.

Weiner et al. (1987) "Hepatitis delta (δ) cDNA clones: Undetectable hybridization to nucleic acids from infectious non–A non–B hepatitis B DNA," *J. Med. Virol.* 21:239–247.

Weiner et al. (1988). "A single antigenomic open reading frame of the hepatitis delta virus encodes the epitope(s) of both hepatitis delta antigen polypeptides p24 delta and p27 delta," *J Virol.* 62(2):594–599.

Weiner et al. (1990). "HCV testing in low–risk population," *Lancet.* 336(8716):695.

Weiner et al. (1991). "Variable and hypervariable domains are found in the regions of HCV corresponding to the flavivirus envelope and NS1 proteins and the pestivirus envelope glycoproteins," *Virology* 180:842–848.

Weiner, et al. (1991) "Sequence variation in hepatitis C viral isolates," *J. Hepatol.* (13)4:S6–S14.

Wengler et al. (1985) "Sequence analysis of the membrane protein V3 of the flavivirus West Nile virus and of its gene," *Virology* 147:264–274.

Wengler et al. (1987) "Analysis of the influence of proteolytic cleavage on the structural organization of the surface of the West Nile flavivirus leads to the isolation of a protease–resistant E protein oligomer from the viral surface," *Virology* 160:210–219.

Wengler et al. (1991). "In vitro synthesis of West Nile virus proteins indicates that the amino–terminal segment of the NS3 protein contains the active centre of the protease which cleaves the viral polyprotein after multiple basic amino acids," *J Gen Virol.* 72 (Pt 4):851–858.

White, D.O. et al. (1995) "Togaviridae" *Medical Virology* Chapter 25, 4th edition, pp. 418–432.

Wilkinson CS. (1997). "Hepatitis C virus NS2–3 proteinase," *Biochem Soc Trans.* 25(4):S611.

Wilkinson et al. (1997). "Characterisation of an HCV NS3/NS4A proteinase fusion protein expressed in *E.coli* using synthetic peptide substrates," *Biochem Soc Trans.* 25(4):S624.

Willett et al. (1995). "Engineered metal regulation of trypsin specificity," *Biochemistry.* 34(7):2172–2180.

Willett et al. (1996). "Delocalizing trypsin specificity with metal activation," *Biochemistry.* 35(19):5992–5998.

Wilson et al. (1994). "Structure and mechanism of interleukin–1 beta converting enzyme," *Nature.* 370(6487):270–5.

Wong, D. K. H. et al. (1998). "Liver–Derived CTL in Hepatitis C Virus Infection: Breadth and Specificity of Responses in a Cohort of Persons with Chronic Infection," *J. Immun.* 160(3):1479–1488.

Worman HJ (1995). "Interferon treatment of viral hepatitis", 2 pages, located at <<http:cpmcnet.columbia.edu/dept/gi/intron.html>>.

Wu et al. (1998) "Mechanism of autoproteolysis at the NS2–NS3 junction of the hepatitis C virus polyprotein," *TIBS* 23:92–94.

Xu et al. (1997). "Bovine viral diarrhea virus NS3 serine proteinase: polyprotein cleavage sites, cofactor requirements, and molecular model of an enzyme essential for pestivirus replication," *J Virol.* 71(7):5312–5322.

Yamada et al. (1995). "Cloning and evaluation of the hepatitis C virus NS3 proteinase region on the basis of proteinase activity," Symposium on hepatitis C virus and related viruses, 3rd International Meeting on Hepatitis C Virus and related viruses, Australia, one page.

Yamada et al. (1996). "Genetic organization and diversity of the 3' noncoding region of the hepatitis C virus genome," *Virology.* 223(1):255–261.

Yamada et al. (1998). "Critical point mutations for hepatitis C virus NS3 proteinase," *Virology.* 246(1):104–112.

Yamashita, T. et al. (1998). "RNA–dependent RNA Polymerase Activity of the Soluble Recombinant Hepatitis C Virus NS5B Protein Truncated at the C–terminal Region," *J. Bio. Chem.* 273(25):15479–15486.

Yamshchikov et al. (1995). "Formation of the flavivirus envelope: role of the viral NS2B–NS3 protease," *J Virol.* 69(4):1995–2003.

Yamshchikov et al. (1997). "Upregulation of signalase processing and induction of prM–E secretion by the flavivirus NS2B–NS3 protease: roles of protease components," *J Virol.* 71(6):4364–71.

Yan et al. (1998). "Complex of NS3 protease and NS4A peptide of BK strain hepatitis C virus: a 2.2 Å resolution structure in a hexagonal crystal form," *Protein Sci.* 7(4):837–847.

Yan et al. (1996). "Crystal structure of hepatitis C Virus (HCV) NS3 protease–NS4A (21–34) complex at 2.8 Å resolution," oral presentation (Abstract No. 138), one page only.

Yanagi, M. et al. (1977). "Transcripts from a Single Full–Length cDNA clone of Hepatitis C Virus are Infections when Directly Transfected ino the Liver of a Chimpanzee," *Proc. Natl. Acad. Sci. USA* 94:8738–8743.

Yen, J. et al. (1995). "Cellular Proteins Specifically Bind to the 5'–Noncoding Region of Hepatitis C Virus RNA," *Virology* 208:723–732.

Yoo et al. (1992). "5' end–dependent translation initiation of hepatitis C viral RNA and the presence of putative positive and negative translational control elements within the 5' untranslated region," *Virology.* 191(1):889–899.

Yoo et al. (1995). "Transfection of a differentiated human hepatoma cell line (Huh7) with in vitro–transcribed hepatitis C virus (HCV) RNA and establishment of a long–term culture persistently infected with HCV," *J Virol.* 69(1):32–38.

Yoshikura et al. (1981). "Role of protease in mouse hepatitis virus–induced cell fusion. Studies with a cold–sensitive mutant isolated from a persistent infection," *Virology.* 113(2):503–511.

Yuasa et al. (1991). "The particle size of hepatitis C virus estimated by filtration through microporous regenerated cellulose fibre," *J Gen Virol.* 72 (Pt 8):2021–2024.

Zein et al. (1996). "Hepatitis C genotypes: current trends and future implications," *Mayo Clin Proc.* 71(5):458–62.

Zhang, Z. et al. (1994). "A Cell–Binding arg–gly–as Sequence is Present in Close Proximity to the Major Linear Antigenic Region of HCV NS3," *Biochemical and Biophysical Research Communications* 202(3):1352–1356.

Zhang et al. (1995). "Hierarchic regulation of HCV NS3 function by NS2," Symposium on hepatitis C virus and related viruses, 3rd International Meeting on Hepatitis C Virus, Australia, one page.

Zhang et al. (1997). "Probing the substrate specificity of hepatitis C virus NS3 serine protease by using synthetic peptides," *J Virol.* 71(8):6208–6213.

Zhang et al. (1999). "A continuous spectrophotometric assay for the hepatitis C virus serine protease," *Anal Biochem.* 270(2):268–75.

Answer of Defendant Eli Lilly and Company. Chiron Corporation v. Eli Lilly and Company, and Vertex Pharmaceuticals, Inc.: Case No. C–98–2974 CW ENE. In the United States District Court, Northern District of California. Sep. 21, 1998.

Defendant Gilead Sciences, Inc.'s Answer to Complaint and Counterclaims, Chiron Corporation v. Gilead Sciences, Inc.: Case No. C–98–2994 VRW, United States District Court, Northern District of California. Sep. 21, 1998.

Answer and Counterclaims of Defendant Agouron Pharmaceuticals, Inc. Chiron Corporation v. Agouron Pharmaceuticals, Inc.: Civil Action No. C–98–2995 SI. United States District Court, Northern District of California. Oct. 1, 1998.

Defendant Gilead Sciences, Inc.'s Initial Disclosure of Prior Art Pursuant to Civil Local Rule 16–7. Chiron Corporation v. Gilead Sciences, Inc. and Related Actions: Case No. C–98–2994 CW. United States District Court, Northern District of California. Nov. 10, 1998.

Vertex's Initial Disclosure of Prior Art for U.S. Pat. Nos. 5,371,017, 5,585,258 and 5,597,691 under Local Rule 16–7(d). Chiron Corporation v. Eli Lilly and Company, and Vertex Pharmaceuticals Inc. Civil No. 98–2974 CW (ENE). United States District Court, Northern District of California. Nov. 12, 1998.

Lilly's Initial Disclosure of Prior Art for U.S. Pat. Nos. 5,371,017, 5,585,258, and 5,597,691 Under Local Rule 1607(d)–(f). Nov. 12, 1998.

Agouron's Initial Disclosure of Prior Art Pursuant to Local Rules 16–7(d) and (e). Chiron Corporation v. Agouron Pharmaceuticals, Inc. Civil Action No. C–98–2995 CW. Nov. 12, 1998.

Answer of Defendant Vertex Pharmaceuticals Incorporated. Chiron Corporation v. Eli Lilly & Co., and Vertex Pharmaceuticals Incorporated. Case No.: C–98–2974 CW [PJH], Related Action Nos.: C–98–2994 CW [PJH] and C–98–2995. Feb. 1, 1999.

Vertex's First Supplemental Disclosure of Prior Art for U.S. Pat. Nos. 5,371,017, 5,585,258 and 5,597,691 Under Local Rule 16–7(d). Chiron Corporation v. Eli Lilly and Company, and Vertex Pharmaceuticals Inc. Civil No. 98–2974 CW (PJH), Related Action Nos. C–98–02994 CW [PJH] and C–98–02995 CW [PJH]. Feb. 5, 1999.

Vertex's Second Supplemental Disclosure of Prior Art for U.S. Pat. Nos. 5,371,017, 5,585,258 and 5,597,691 Under Local Rule 16–7(d). Chiron Corporation v. Eli Lilly and Vertex Pharmaceuticals Inc. Civil No. 98–2974 CW (PJH), Related Action Nos. C–98–02994 CW [PJH] and C–98–02995 CW [PJH]. Feb. 12, 1999.

Gilead Sciences, Inc.'s Response to Chiron's Proposed Claim Construction Statement on the '017, '258 and '691 Patents Pursuant to Local Rula 16–10(b). Chiron Corporation v. Gilead Sciences, Inc. Case No. C–98–2994 CW [PJH]. Mar. 22, 1999.

Response Chart to Chiron's Claim Chart on U.S. Pat. Nos. 5,371,017, 5,585,258 and 5,397,691 Pursuant to Local Rule 16–9(b) by Defendant Gilead Sciences, Inc. Case No. C–98–2994 CW [PJH]. Mar. 22, 1999.

Response Chart to Chiron's Claim Chart on U.S. Pat. Nos. 5,371,017, 5,585,258 and 5,397,691 Pursuant to Local Rule 16–9(b) by Defendant and Counterclaimant Gilead Sciences, Inc. Chiron Corporation v. Gilead Sciences Inc. Case No. C–98–2994 CW [PJH], Related Action Nos. C–98–02995 CW [PJH] and C–98–02974 CS [PJH]. Mar. 22, 1999.

Agouron's Response Chart to Chiron's Claim Chart on U.S. Pat. Nos. 5,371,017, 5,5585,258 and 5,397,691 Pursuant to Local Rule 16–9(b). Chiron Corporation v. Agouron Pharmaceuticals, Inc. Case No. C–98–2995 CW [PJH], Related Cases C–98–9874 CW and C–98–2994 CW. Aug. 4, 1999.

Eli Lilly and Company's First Supplemental Disclosure of Prior Art for U.S. Pat. Nos. 5,371,017, 5,585,258, and 5,597,691 Pursuant to Civil Local Rule 16–7(d). Chiron Corporation v. Eli Lilly and Company, and Vertex Pharmaceuticals, Inc. Case No. C–98–2974 CW, Related Action Nos. C–98–2994 CW and C–98–2995 (CW). Aug. 4, 1999.

Vertex's Third Supplemental Disclosure of Prior Art for U.S. Pat. Nos. 5,371,017, 5,585,258 and 5,597,691 Under Local Rule 16–7(d). Chiron Corporation v. Eli Lilly and Company, and Vertex Pharmaceuticals Incorporated. Civil No. 98–2974 CW (PJH), Related Action Nos. C–98–02994 CW [PJH] and C–98–02995 CW [PJH]. Aug. 4, 1999.

Joint Claim Construction Statement Pursuant to Local Rule 16–11(b). Chiron Corporation v. Eli Lilly & Co., Vertex Pharmaceuticals, Inc. No. C–98–02974 CW [PJH], Related Action Nos. C–98–02995 CW [PJH] and C–98–02994 CW [PJH]. Sep. 7, 1999.

Amended Response Chart Pursuant to Civil Local Rule 16–9(b) by Defendants Eli Lilly and Company and Vertex Pharmaceuticals Incorporated. Chiron Corporation v. Eli Lilly and Company and Vertex Pharmaceuticals Inc. Case No. C–98–2974 CW, Related Action Nos. C–98–2994 CW and C–98–2995 CW. Oct. 22, 1999.

Amended Response Chart Pursuant to Civil Local Rule 16–9(b) by Defendants Eli Lilly and Company and Vertex Pharmaceuticals Incorporated. Chiron Corporation v. Eli Lilly and Company and Vertex Pharmaceuticals, Inc. Case No. C–98–2974 CW, Related Action Nos. C–98–2994 CW and C–98–2995 CW. Nov. 18, 1999.

Findings of Fact, Conclusions of Law and Proposed Order for Motion 4A by Defendants Agouron Pharmaceuticals, Inc. Chiron Corporation v. Agouron Pharmaceuticals, Inc. Case No. C 98–2995 CW (PJH).

Eli Lilly and Company's and Vertex Pharmaceutical Incorporated's Proposed Findings of Fact and Conclusions of Law in Support of a Judgment to Pierce Attorney–Client Privilege and Work Product Immunity Under the Crime–Fraud Exception. Chiron Corporation v. Eli Lilly and Company and Vertex Pharmaceuticals, Inc. Case Nos. C–98–2974 CW and C–98–2995 CW.

Reporter's Transcript of Proceedings Before Special Masters Catherine A. Yanni and David W. Yount. Chiron Corporation v. Eli Lilly and Company and Vertex Pharmaceuticals, Inc.: Chiron Corporation v. Gilead Sciences, Inc.: Chiron Corporation v. Agouron Pharmaceuticals, Inc. Case Nos. C–98–2974 CW ENE, C–98–2994 CW and C–98–2995 CW. May 24, 2000.

Hearing Before Special Master. Chiron Corporation v. Eli Lilly and Company and Vertex Pharmaceuticals, Inc.: Chiron Corporation v. Gilead Sciences, Inc.: Chiron Corporation v. Agouron Pharmaceuticals, Inc. Case Nos. C–98–2974 CW ENE, C–98–2994 CW and C–98–2995 CW. Sep. 8, 1999.

Agouron Pharmaceuticals, Inc. for Request for Examination regarding U.S. Pat. No. 5,371,017 filed on Dec. 6, 1999 with exhibits thereto.

Vertex's Objections and Responses to Chiron's First Set of Interrogatories. Chiron Corporation v. Eli Lilly & Co. and Vertex Pharmaceuticals Inc. Civil No. C–98–2974 CW [PJH], Related Action Nos. C–98–2994 CW [PJH] and C–98–2995 CW [PJH]. Mar. 22, 1999.

Defendant Eli Lilly and Company's Response to Chiron's First Set of Interrogatories. Chiron Corporation v. Eli Lilly and Company and Vertex Pharmaceuticals Inc. Case Nos. C–98–2974 CW [PJH], Related Action Nos. C–98–2994 CW and C–98–2995 CW. Mar. 22, 1999.

Agouron's Supplemental Objections and Responses to Chiron's First Set of Interrogatories (Nos. 1–16). Chiron Corporation v. Agouron Pharmaceuticals, Inc. Case No. C–98–02995 CW [PJH], Related Action Nos. C–98–02974 CW [PJH] and C–98–02994 CW [PJH]. Aug. 19, 1999.

Chiron's Responses to Vertex's First Set of Requests to Admit (Nos. 1–9). Chiron Corporation v. Eli Lilly and Company and Vertex Pharmaceuticals Inc. No. C–98–02974 CW [PJH], Related Case Nos. C–98–02994 CW [PJH] and C–98–02995 CW [PJH]. Dec. 8, 1999.

Chiron's Answers to Agouron's First Set of Interrogatories (Nos. 1–19). Chiron Corporation v. Agouron Pharmaceuticals, Inc. No. C–98–02995 CW [PJH], Related Case No. C–98–02974 CW [PJH]. Jan. 25, 2000.

Chiron's Responses to Vertex's Second Set of Requests to Admit (Nos. 10–42). Chiron v. Eli Lilly and Company and Vertex Pharmaceuticals Inc. No. C–98–02974 CW [PJH], Related Action No. C–98–02995 CW [PJH]. Feb. 1, 2000.

Chiron's Responses to Lilly's First Set of Requests to Admit (Nos. 1–50). Chiron Corporation v. Eli Lilly and Company and Vertex Pharmaceuticals Inc. No. C–98–02974 CW [PJH], Related Action No. C–98–02995 CW [PJH]. Feb. 1, 2000.

Chiron's Responses to Agouron's First Set of Requests to Admit, and Subtended Interrogatories and Document Requests. Chiron Corporation v. Agouron Pharmaceuticals, Inc. No. C–98–02995 CW [PJH], Related Case No. C–98–02974 CW [PJH]. Feb. 4, 2000.

Chiron's Supplemental Answers to Vertex's Second Set of Interrogatories (Nos. 8, 13–15). Chiron Corporation v. Eli Lilly and Company and Vertex Pharmaceuticals Inc. No. C–98–02974 CW [PJH], Related Case No. 98–02995 CW [PJH]. Feb. 16, 2000.

Chiron's Supplemental Responses to Vertex's Second Set of Request to Admit (Nos. 23 and 37). Chiron Corporation v. Eli Lilly and Company and Vertex Pharmaceuticals Inc. No. C–98–02974 CW [PJH], Related Action No. C–98–02995 CW [PJH]. May 31, 2000.

Chiron's Supplemental Responses to Lilly's First Set of Requests to Admit (Nos. 2, 24, 37 and 49), Chiron Corporation v. Eli Lilly and Company and Vertex Pharmaceuticals Inc. No. C–98–02974 CW [PJH], Related Action No. C–98–02995 CW [PJH]. May 31, 2000.

Chiron's Supplemental Answers to Agouron's First Set of Interrogatories (Nos. 15–19). Chiron Corporation v. Agouron Pharmaceuticals, Inc. No. C–98–02995 CW [PJH], Related Case No. C–98–02974 CW [PJH]. Jun. 12, 2000.

Chiron Corporation's Responses to Defendant Eli Lilly and Company's Supplemental Interrogatories. Chiron v. Eli Lilly and Company and Vertex Pharmaceuticals Inc. No. C–98–02974 CW [PJH], Related Case No. C–98–02995 CW [PJH]. Jun. 12, 2000.

Chiron's Supplemental Responses to Agouron's First Set of Requests to Admit (Nos. 12–15 & 17–23). Chiron Corporation v. Agouron Pharmaceuticals, Inc. No. C–98–02995 CW (PJH), Related Case No. C–98–02974 CW [PJH], Related Case No. C–98–02974 CW [PJH]. Jul. 19, 2000.

Chiron's Second Supplemental Responses to Vertex's Second Set of Requests to Admit. Chiron Corporation v. Eli Lilly and Company and Vertex Pharmaceuticals Inc. No. C–98–02974 CW [PJH], Related Action No. C–98–02995 CW [PJH]. Aug. 21, 2000.

Chrion's Second Supplemental Responses to Lilly's First Set of Requests to Admit. Chiron Corporation v. Eli Lilly and Company and Vertex Pharmaceuticals Inc. No. C–98–02974 CW [PJH], Related Action No. C–98–02995 CW [PJH]. Aug. 21, 2000.

Excerpt from Laboratory Notebook of Qui–Lim Choo dated Jun. 9, 1989, p. 9.

Excerpt from Laboratory Notebook of Qui–Lim Choo dated Aug. 22, 1989, p. 25.

Civil Action No. C 98–2974 (CW) Chiron Corporation v. Eli Lilly, Subpoena in a civil case duces tecum Ex. 524 at Jan. 25, 2000 deposition of A. Gorbalenya.

Transcript of deposition of Dr. Alexander E. Gorbalenya in Civil Action No. C–98–02974 (related cases Nos. C–98–02994 CW and C–98–0295 CW) in Chiron Corp. v. Eli Lilly and Co. and Vertex Pharmaceuticals, Inc. before the U.S. District Court Northern District of California, Oakland Division (Jan. 25, 2000).

Letter from H.–J. Thiel to A. Gorbalenya dated Sep. 11, 1990, Ex. 515 at Jan. 25, 2000 deposition of A. Gorbalenya.

Letter from H.–J. Thiel to A. Gorbalenya dated Dec. 28, 1990, Ex. 519 at Jan. 25, 2000 deposition of A. Gorbalenya.

Letter from A. Gorbalenya to M. Collett dated Mar. 28, 1989, Ex. 512 at Jan. 25, 2000 deposition of A. Gorbalenya.

Letter from H.–J. Thiel to A. Gorbalenya dated Oct. 24, 1990, Ex. 517 at Jan. 25, 2000 deposition of A. Gorbalenya.

Letter from A. Gorbalenya to M. Houghton dated May 20, 1990, Ex. 514 at Jan. 25, 2000 deposition of A. Gorbalenya.

Letter from A. Gorbalenya to S. Siddell dated Feb. 17, 1991, part of Ex. 520 at Jan. 25, 2000 deposition of A. Gorbalenya.

Letter from S. Siddell to A. Gorbalenya dated Mar. 5, 1991, Ex. 521 at Jan. 25, 2000 deposition of A. Gorbalenya.

Letter from A. Gorbalenya and E. Koonin to S. Siddell dated Jun. 4, 1991, Ex. 523 at Jan. 25, 2000 deposition of A. Gorbalenya.

Letter from M. Collett to A. Gorbalenya dated Apr. 13, 1989, Ex. 513 at Jan. 25, 2000 deposition of A. Gorbalenya.

The Journal of Virology "Referee's report on Paper," Mar. 11, 1991, part of Ex. 522 at Jan. 25, 2000 deposition of A. Gorbalenya.

The Journal of General Virology, receipt of manuscript from A. Gorbalenya dated Apr. 3, 1991 and manuscript entitled "Hepatitis C virus encodes a putative serine protease related to the proteases of flavi– and pestiviruses," both of Ex. 520 at Jan. 25, 2000 deposition of A. Gorbalenya.

The Journal of Gernal Virology, "Referee's report on Paper," Feb. 28, 1991, part of Ex. 522 at Jan. 25, 2000 deposition of A. Gorbalenya.

Chiron Laboratory Notebook #1298, pp. 184–190, 192 (Nov., 1986); (previously considered in U.S. application No. 08/103,961, reference I.A.117).

Independent Legal Opinion Concerning Hepatitis C Inventorship Dispute, Jun. 1991; (previously considered in U.S. application No. 08/103,961, reference I.A.109).

Inventorship Opinion of Gladys Monroy dated Jun. 7, 1988; (previously considered in U.S. application No. 08/103,961, reference I.A.119).

Letter dated Oct. 16, 1989 from Mr. Lanman of the NIH to Robert Blackburn of Chiron Corporation.

Memorandum by Dr. Houghton, dated Nov. 10, 1987; (previously considered in U.S. application No. 08/103,961, reference I.A.118).

Memorandum dated Nov. 11, 1987 by Dr. Michael Houghton; (previously considered in U.S. application No. 08/103,961, reference I.A.115).

Memorandum Re Interview of Dr. Daniel Bradley dated Apr. 11, 1991; (previously considered in U.S. application No. 08/103,961, reference I.A.112).

Memorandum Re Interview of Dr. Lacy Overby dated Jun. 21, 1991; (previously considered in U.S. application No. 08/103,961, reference I.A.114).

Memorandum Re Interview of Dr. Michael Houghton dated May 8, 1991; (previously considered in U.S. application No. 08/103,961, reference I.A.111).

Memorandum Re Interviews of Dr. Amy Weiner and Dr. Gary Van Nest dated Apr. 30, 1991; (previously considered in U.S. application No. 08/103,961, reference I.A.113). P. 8 missing.

Memorandum Re Interviews of Dr. Qui–Lim Choo and Dr. George Kuo dated May 8, 1991; (previously considered in U.S. application No. 08/103,961, reference I.A.110).

Excerpts of the deposition testimony of Drs. Houghton, Choo and Kuo in Civil Action Nos. C–98–02995 CN and C–98–02974 CW.

Excerpts of the deposition testimony of Drs. Houghton and Choo in Civil Action Nos. C–98–02995 CN and C–98–02974 CW.

U.S. application No. 07/505,434, Rosenberg application, Apr. 4, 1990.

U.S. application No. 07/680,358, Rosenberg application, Apr. 4, 1991.

U.S. application No. 07/956,433, Rosenberg application, Sep. 28, 1992.

U.S. application No. 08/116,048, Rosenberg application, Sep. 2, 1993.

U.S. application No. 08/254,496, Rosenberg application, Jun. 6, 1994.

Genbank Data Base Accession No. GNWVC3 (May 26, 2000).

Genbank Data Base Accession No. 3114526 (Dec. 12, 1997).

Alter et al. (Nov. 1, 1975) "Clinical and serological analysis of transfusion–associated hepatitis" *Lancet* 7940:838–841.

Ayoola EA. (October 1984). "Circulating immune complexes and serum complement in Nigerian patients with non–A, non B hepatitis." *East. Afr. Med. J.* 61(10):752–756.

Bazan (1989) "Viral branches of the trypsin–like proteinase family" Viral proteinases as targets for chemotherapy: in *Current Communications in Molecular Biology,* Krausslich et al., eds., Cold Spring Laboratory Press, New York, pp. 55–62.

Blight, K. J. et al. (1998). "Molecular virology of hepatitis C virus: an update with respect to potential antiviral targets" *Antiviral Therapy* 3(Suppl. 3):71–81.

Bradley et al., (1983) "Non–A, Non–B hepatitis: Research progress and current perspectives" *Dev. Biol. Standard,* Second WHO/IABS Symposium on Viral Hepatitis, Athens, Greece, 1982, 54:463–473.

Bradley et al. (1986). "Etiology and natural history of post–transfusion and enterically–transmitted non–A, non–B hepatitis," *Semin Liver Dis.* 6(1):56–66.

Bradley et al. (April 1988). "Virus of enterically transmitted non–A, non–B hepatitis" *Lancet* 1(8589):819.

Burckhardt et al. (1988). "A hepatitis non–A, non–B associated substance in the feces—identification and cloning of a partially double–stranded circular DNA." *Immun Infekt.* 16(3):91–96, article with English abstract.

Burckhardt et al. (1988). "Hepatitis non–A, non–B–associated DNA—demonstration of DNA in proven infectious anti–D–immunoglobulin." *Immun Infekt.* 16(3):97–99, article with English abstract.

Burow, B.V. (1982) "Klinischer verlauf and prognose der virushepatitis c—prospektive studie über zwei jahre" *Klinische Medizin, Dt. Gesundh.–Wesen* 37, Heft 2, pp. 56–60, with English abstract.

Calisher et al. (1988) "Chapter 2: Arbovirus Serogroups: Definition and Geographic Distribution", *The Arboviruses: Epidemiology and Ecology,* vol. 1, Monath, T.P. ed., CRC Press, Inc., pp. 19–57.

Carloni, G. et al. (1993). "Susceptibility of human liver cell cultures to hepatitis C virus infection," *Arch Virol* [Suppl] 8:31–39.

Chambers et al. (1989) "Yellow fever virus proteins NS2A, NS2B, and NS4B: Identification and partial N–terminal amino acid sequence analysis." *Virology* 169:100–109.

Choo, Q–L et al. (1990). "Hepatitis C virus: the major causative agent of viral non–A, non–B hepatitis." *Brit. Med. Bull.* 46(2):423–441.

Chung, K. M. et al., (1997) "Hepatitis C virus nonstructural protein 5A contains potential transcriptional activator domains" *Mol. Cells* 7(5):661–667.

Craxi, A. et al. (April 1985). "Polyalbumin receptors, hepatitis B surface antigen (HBsAg), and HBsAg/IgM complexes in HBsAg positive patients with and without delta superinfection." *J Med Virol.* 15(4):383–388.

Davis, G. L. and Lau, J. Y. N. (1995). "Choice of appropriate end points of response to interferon therapy in chronic hepatitis C virus infection," *Journal of Hepatology* 22(Suppl. 1):110–114.

De Bree F.M. et al. (August 1998). "Preparation and characterization of the recombinant selenomethionine analogue of insulin–like growth factor–I." *Protein Expr Purif.* 13(3):319–325.

De Francesco, R. et al. (Oct. 15, 1996). "A zinc binding site in viral serine proteinases." *Biochemistry.* 35(41):13282–13287.

De Francesco, R. et al. (1998). "The Hepatitis C Virus NS3 Proteinase: Structure and Function of a Zinc–Containing Serine Proteinase" *Antiviral Therapy* 3(Suppl. 3):99–109.

Degott, C. et al. (1986). "Serial transmission of a human non A–non B hepatitis viral strain to HBV–protected chimpanzees: successive histological and ultrastructural studies." *Liver.* 6:17–25.

DesJarlais et al. (September 1990). "Structure–based design of nonpeptide inhibitors specific for the human immunodeficiency virus 1 protease" *Proc Natl Acad Sci U S A.* 87(17):6644–6648.

Di Bisceglie et al. (1995). "Hepatitis C and hepatocellular carcinoma." *Semin Liver Dis.* 15(1):64–69.

Dienstag et al. (1986). "Non–A, non–B hepatitis: Evolving epidemiologic and clinical perspective" *Sem. Liver Dis.* 6(1):67–81.

Dragovitch, P.S. et al., (1998) "Structure–based design, synthesis, and biological evaluation of irreversible human rhinovirus 3C protease inhibitors. 1. Michael acceptor structure–activity studies" *J. Med. Chem.* 41:2806–2818.

Drews, J. and Ryser, S. (1996). "Innovation Deficit in the Pharmaceutical Industry," *Drug Information Journal* 30:97–108.

Gubler (1988) "Chapter 23: Dengue" *The Arboviruses: Epidemiology and Ecology,* vol. 2, Monath, T.P. ed., CRC Press, Inc., pp. 223–260.

Hollinger, F.B. et al. (1991) "Tribute to Joseph L. Melnick, Ph.D." Proceedings of 1990 International *Symposium on Viral Hepatitis and Liver Disease,* The 7th Triennal Congress, pp. 3–4.

Inokuchi et al. (1994). "Correlation of quantitative HCV–RNA levels using a branched DNA enhanced level amplification assay with therapeutic effects of β–interferon in patients with chronic hepatitis C" *Int Hepatology Comm.* 2:375–382.

Iwarson, S.A. (Sep. 26, 1987) "Non–A, non–B hepatitis: dead ends or new horizons" *British Medical Journal* 295:946–948.

Joyce, C. (May 26, 1988) "Researchers find elusive hepatitis virus" *New Scientist,* Science, p. 43.

Kendrey, G. et al., (1975) Intranuclear virus–like particles in $HB_8AG$ and $IH_xAG$ negative acute hepatitis (type C?) *Acta Morphologica Acad. Sci. Hung.* 23(2):173–177.

Kim, J.P. et al., "Rapide and efficient recovery of HCV (CDC) genomic clones utilizing sequence independent single primer amplification (SISPA)" *The 1990 International Symposium on Viral Hepatitis and Liver Disease (The 7th Triennal Congress)* Apr. 4, 1990–Apr. 8, 1990, Abstract No. 361, one page.

Kohara, M. (1993). "Antigenicities of Groups I and II Hepatitis C Virus" *Nippon Rinsho* 51(2):338–343, with English abstract.

Lin, C. (1997) "The hepatitis C virus NS4A protein: interactions with the NS4B and NS5A proteins" *4th International Meeting on Hepatitis C virus and related viruses, Molecular Virology and Pathogenesis,* Mar. 6–10, 1997, Kyoto International Conference Hall, Japan, p. 20, abstract.

Maezo, M. et al., (1990) "Isolation and characterization of a cDNA that is closely associated with non–a, non–e hepatitis" *The 1990 International Symposium of Viral Hepatitis and Liver Disease,* Apr. 4, 1990–Apr. 8, 1990, Abstract No. 365, one page.

Matsuda, J.–I. (February 1998) "Transgenic mouse expressing a full–length hepatitis C virus cDNA" *Jpn. J. Cancer Res.* 89:150–158.

Moenkli, P.A. et al., (1990) "Epitope mapping of the HCV nonstructural region" *The 1990 International Symposium of Viral Hepatitis and Liver Disease, Apr. 4, 1990–Apr. 8, 1990,* Abstract No. 358, one page.

Monath TP, (1989) "Chapter 51: Yellow Fever." in *The Arboviruses: Epidemiology and Ecology,* vol. 5, Monath, T.P. ed., CRC Press, Inc., pp. 139–231.

Morgenstern, K.A. et al., (1997) "Polynucleotide modulation of the protease, NTP–protease and helicase activities of a hepatitis C virus NS3–NS4 complex isolated from transfected COS cells" *4th International Meeting on Hepatitis C virus and related viruses, Molecular Virology and Pathogenesis,* Mar. 6–10, 1997, Kyoto International Conference Hall, Japan, p. 100, abstract.

Murphy, H.M.K. et al, (Feb. 26, 1999) "Dengue virus NS3 serine protease" *J. Biol. Chem.* 274(9):5573–5580.

Nelson, D. R. et al., (Feb. 1, 1997). "The role of hepatitis C virus–specific cytotoxic T lymphocytes in chronic hepatitis C," *J. Immun.* 158(3):1473–1481.

Nicklin et al. (December 1988) "Poliovirus proteinase 3C: Large–scale expression, purification and specific cleavage activity on natural and synthetic substrates in vitro," *J. Virol.* 62:4586–4593.

Nishioka et al. (Jan. 15, 1991). "A high prevalence of antibody to the hepatitis C virus in patients with hepatocellular carcinoma in Japan." *Cancer.* 67(2):429–433.

Pasquo, A. et al., (1998) "Rational design and functional expression of a constitutively active single–chain NS4A–NS3 protein" *Fold. Des.* 3(6):433–441.

Reed, K. E. et al., (July 1998) "The NS5A/NS5 proteins of viruses from three genera of the family Flaviviridae are phosphorylated by associated serine/threonine kinases" *J. Virol.* 72(7):6199–6206.

Rice, C.M. (December 1990). "Overview of flavivirus molecular biology and future vaccine development via recombinant DNA." *Southeast Asian J Trop Med Public Health.* 21(4):670–677.

Rico–Hesse et al., (1990) "Molecular Evolution and distribution of dengue viruses types 1 and 2 in nature" *Virology* 174:479–493.

Shafran, S.D. et al. (May/June 1996). "A B C D E F G . . ." *Can. J. Infect. Dis.* 7(3):181–182.

Sherman, G. et al. (1997) "Development of a permanent cell line which expresses HCV nonstructural proteins" *Abstracts of the 37th Interscience Conference on AntimicrobialAgents and Chemotherap,* Sep. 28–Oct. 1, 1997, Toronto, Ontario, Canada 37:217, Abstract No. H–20.

Spall, et al. (1997) "Viruses employing polyprotein processing as the principal strategy of genome expression" *Seminars in Virol.* 8:16–23.

Strauss, J.H. et al. (1990). "The Structure and Function of the Flavivirus and Pestivirus Genomes," *Proceedings of the 1990 International Symposium on Viral Hepatitis and Liver Disease,* pp. 1–40.

Takeuchi, K. et al., (1990) "Molecular cloning of hepatitis C virus cDNA from plasma of an implicated donor of post–transfusion non–a, non–b hepatitis" *International Symposium of Viral Hepatitis and Liver Disease, Apr. 4, 1990–Apr. 8, 1990,* Houston, Texas, Abstract No. 363, one page.

Tramontano, A. (1998) "Homology modeling with low sequence identity" *Methods; A companion to Methods in Enzymology* 14:293–300.

Tsai, S.L. et al., (February 1997) "Detection of type–2–like T–helper cells in hepatitis C virus infection: implications for hepatitis C virus chronicity" *Hepatology* 25(2):449–458.

Tsukiyama–Kohara, K. et al. (1991). "A second group of hepatitis C viruses" *Virus Genes* 5(3):243–254.

Zuckerman, A.J., (1990) "Hepatitis C virus: a giant leap forward" *Hepatology Elsewhere* 11(2):322–323.

Response to Chiron's Claim Chart Pursuant to Civil Local Rule 16–9(b) on U.S. Pat. Nos. 5,371,017, 5,585,258 and 5,397,691 by Defendant Agouron Pharmaceuticals Incorporated. Chiron Corporation v. Agouron Pharmaceuticals, Inc.: Case No. C 98–2995 CW (PJH) (Related Cases C 98–9874 CW and C98–2994 CW). In the United States District Court, Northern District of California, Oakland Division.

Joint Response to Chiron's Claim Chart Pursuant to Civil Local Rule 16–9(b) on U.S. Pat. Nos. 5,371,017, 5,585,258 and 5,397,691 by Defendants Eli Lilly and Company and Vertex Pharmaceuticals Incorporated. Chiron Corporation v. Eli Lilly and Company, and Vertex Pharmaceuticals Inc.: Case No. C 98–2974 (Related Action Nos. C 98–2994 CW and C 98–2995 CW). In the United States District Court, Northern District of California, Oakland Division.

Bazan et al. (1988). "Viral cysteine proteases are homologous to the trypsin–like family of serine proteases: Structural and functional implications" PNAS 85:7872–7876.

Bazan et al. (1989). "Detection of a trypsin–like serine protease domain in flaviviruses and pestiviruses" Virology 171:637–639.

Bazan et al. (1989). "Viral branches of the trypsin–like protease family" in UCLA Symposia on Molecular & Cellular Biology, 18th Annual Meeting, J. Cell. Biochem. 13A:50 (Abstract A101).

Bazan et al. (1989). "Comparative analysis of viral cysteine protease structural models" FEBS Lett. 249(1):5–7.

Beach et al. (1991). "Analysis of the putative nonstructural gene region of hepatitis C virus" in Viral Hepatitis and Liver Disease: Proceedings of the 1990 International Symposium on Viral Hepatitis and Liver Disease: Contemporary Issues and Future Prospects, Hollinger et al. eds., pp. 320–328.

Biedrzycka et al. (1987). "Characterization of protease cleavage sites involved in the formation of the envelope glycoprotein and three non–structural proteins of dengue virus type 2, New Guinea C strain" J. Gen. Virol. 68:1317–1326.

Boonmar et al. (1990). "Molecular Cloning of Hepatitis C Virus cDNA from Plasma of an Implicated Donor of Post-transfusion Non–A, Non–B Hepatitis" in Proceedings of the 1990 International Symposium On Viral Hepatitis and Liver Disease. Blaine et al. eds., Williams & Wilkins: Baltimore, pp. 371–374.

Bradley et al. (1991). "Hepatitis C virus: Background and strategies for cloning a major etiologic agent for PT–NANBH" in Viral Hepatitis and Liver Disease: Proceedings of the 1990 International Symposium on Viral Hepatitis and Liver Disease: Contemporary issues and Future Prospects, Hollinger et al. eds., pp. 320–328.

Castle et al. (1986). "Primary structure of the west nile flavivirus genome region coding for all nonstructural proteins" Virology 149:10–26.

Chambers et al. (1990). "Flavivirus genome organization, expression, and replication" in 44 annual Review in Microbiology, Ornston et al. eds., 649–688.

Choo et al. (Apr. 21, 1989). "Isolation of a cDNA clone derived from a blood–borne non–A, non–B viral hepatitis genome" Science 244:359–362.

Choo et al. (1990). "Detection and mapping of immunologic epitopes expressed by bacterial cDNA clones of the hepatitis C virus" in Viral Hepatitis and Liver Disease: Proceedings of the 1990 International Symposium on Viral Hepatitis and Liver Disease: Contemporary Issues and Future Prospects, Hollinger et al. eds., pp. 3345–3346.

Choo et al. (September, 1989). "Hepatitis C virus is a distant relative of the flaviviruses and pestiviruses" Chapter 5 in Viral Hepatitis C, D and E, Shikata, ed., Excerpta Medica: New York, pp. 47–52.

Coia et al. (1988). "Nucleotide and complete amino acid sequences of kunjin Virus: Definitive gene order and characteristics of the virus–specified proteins" J. Gen. Virol. 69:1–21.

Collett et al. (1988). "Comparisons of the pestivirus bovine viral diarrhoea virus with members of the flaviviridae" J. Gen. Virol. 69:2637–2643.

Collett et al. (1988). "Molecular cloning and nucleotide sequence of the pestivirus bovine viral diarrhea virus" Virology 165:191–199.

Collett et al. (1988). "Proteins encoded by bovine viral diarrhea virus: The genomic organization of a pestivirus" Virology 165:200–208.

Dalgarno et al. (1986). "Partial nucleotide sequence of the Murray Valley Encephalitis virus genome: Comparison of the encoded polypeptides with yellow fever virus structural and non–structural proteins" J. Mol. Biol. 187:309–323.

Deubel et al. (1988). "Nucleotide sequence and deduced amino acid sequence of the nonstructural proteins of dengue type 2 virus, Jamaica genotype: Comparative analysis of the full–length genome" Virology 165:234–244.

Gorbalenya et al. (January, 1986). "Polyvirus–encoded proteinase 3C: A possible evolutionary link between cellular serine and cysteine proteinase families" FEBS Lett. 194(2):253–57.

Gorbalenya et al. (1988). "One more conserved sequence motif in helicases" Nucl. Acids Res. 16(15):7734.

Gorbalenya et al. (1989). "Two related superfamilies of putative helicases involved in replication, recombination, repair and expression of DNA and RNA genomes" Nucl. Acids Res. 17(12):4713–4730.

Gorbalenya et al. (January 1989). "Cysteine proteases of positive strand RNA viruses and chymotrypsin–like serine proteases" FEBS Lett. 243(2):103–114.

Gorbalenya. (1989). "N–terminal domains of putative helicases of flavi– and pestiviruses may be serine proteases" Nucl. Acids Res. 17(10):3889–3897.

Hahn et al. (1988). "Nucleotide sequence of dengue 2 RNA and comparison of the encoded proteins with those of other flaviviruses" Virology 162:167–180.

Houghton et al. (1991). "Hepatitis C virus (HCV): A relative of the pestiviruses and flaviviruses" in Viral Hepatitis and Liver Disease: Proceedings of the 1990 International Symposium on Viral Hepatitis and Liver Disease: Contemporary Issues and Future Prospects, Hollinger et al. eds., pp. 328–333.

James et al. (1978). "Amino acid sequence alignment of bacterial and mammalian pancreatic serine proteases based on topological equivalences" CJBIAE 56(6):396–402.

Kato et al. (1989). "Japanese isolates of the non–A, non–B hepatitis viral genome show sequence variations from the original isolate in the USA" Proc. Jap. Acad. 659(9):219–223.

Kohl et al. (July 1988). "Active human immunodeficiency virus protease is required for viral infectivity" PNAS 85:4686–4690.

Kräusslich et al. (1988). "Viral proteinases" Ann. Rev. Biochem. 57:701–754.

Kraut (1977). "Serine proteases: Structure and mechanism of catalysis" Ann. Rev. Biochem. 46:331–358.

Kubo et al. (1989). "A cDNA fragment of hepatitis C virus from an implicated donor of post–transfusion non–A, non–B hepatitis in Japan" Nucl. Acids Res. 17(24):10367–10372.

Kuo et al. (Apr. 21, 1989). An assay for circulating antibodies to a major etiologic virus of human non–A, non–B hepatitis *Science* 244:362–364.

Lain et al. (1989). "Homologous potyvirus and flavivirus proteins belonging to a superfamily of helicase–like proteins" *Gene* 82:357–362.

Mackow et al. (1987). "The nucleotide sequence of dengue type 4 virus: Analysis of genes coding for nonstructural proteins" *Virology* 159:217–228.

Mandl et al. (1989). "Genome sequence of tick–borne Encephalitis virus (western subtype) and comparative analysis of nonstructural proteins with other flaviviruses" *Virology* 173:291–301.

Markoff. (1989). "In vitro processing of dengue virus structural proteins: Cleavage of the pre–membrane protein" *J. Virol.* 63(8):3345–3352.

Meyers et al. (1989). "Molecular cloning and nucleotide sequence of the genome of hog cholera virus" *Virology* 171:555–567.

Miller et al. (1990) "Hepatitis C virus shares amino acid sequence similarity with pestiviruses and flaviviruses as well as members of two plant virus supergroups" *PNAS USA* 87:2057–2061.

Neurath. (Apr. 27, 1984). "Evolution of proteolytic enzymes" *Science* 224:350–57.

Nowak et al. (1989). "Analyses of the terminal sequences of west nile virus structural proteins and of the in vitro translation of these proteins allow the proposal of a complete scheme of the proteolytic cleavages involved in their synthesis" *Virology* 169:365–376.

Pichuantes et al. (1989). "Viral proteinases as targets for chemotherapy: Expression of authentic and enzymatically active HIV–1 proteinase in bacteria and yeast" in *Current Communications in Molecular Biology*, Kräusslich et al. eds., Cold Spring Harbor Laboratory Press: New York, pp. 215–222.

Rice et al. (1985). "Nucleotide sequence of yellow fever virus: Implications for flavivirus gene expression and evolution" *Science* 229:726–733.

Rice et al. (1986). "Partial N–terminal amino acid sequences of three nonstructural proteins of two flaviviruses" *Virology* 151:1–9.

Rice et al. (1986). "Structure of the flavivirus genome" Chapter 10, in *The Togaviridae and Flaviviridae*, Schlesinger et al., eds., Plenum Press: New York, pp. 279–326.

Ruiz–Linares et al. (1989). "Processing of yellow fever virus polyprotein: Role of cellular proteases in maturation of the structural proteins" *J. Virol.* 63(10):4199–4209.

Speight et al. (1988). "Gene mapping and positive identification of the non–structural proteins NS2A, NS2B, NS3, NS4B and NS5 of the flavivirus kunjin and their cleavage sites" *J. Gen. Virol.* 69:23–34.

Speight et al. (1989). "Carboxy–terminal analysis of nine proteins specified by the flavivirus kunjin: Evidence that only the intracellular core protein is truncated" *J. Gen. Virol.* 70:2209–2214.

Strauss et al. (1986). "Replication of alphaviruses and flaviviruses: Proteolytic processing of polyproteins" in *Positive Strand RNA Viruses: Proceedings of a UCLA Symposium held in Keystone, Colorado,* Brinton et al., eds., Alan R. Liss: New York, pp. 209–225.

Strauss et al. (1988). "Replication of the RNAs of alphaviruses and flaviviruses" Chapter 4 in RNA Genetics: RNA directed virus Replication, vol. 1, Domingo et al., eds., CRC Press: Boca Raton, Florida, pp. 71–90.

Strauss et al. (1991). "Structure and function of the flavivirus and pestivirus genomes" in *Viral Hepatitis and Liver Disease: Proceedings of the 1990 International Symposium on Viral Hepatitis and Liver Disease: Contemporary Issues and Future Prospects,* Hollinger et al. eds., pp. 333–334.

Sumiyoshi et al. (1987). "Complete nucleotide sequence of the Japanese Encephalitis virus genome RNA" *Virology* 161:497–510.

Trent et al. (1987). "Partial nucleotide sequence of St. Louis Encephalitis virus RNA: Structural proteins, NS1, ns2a, and ns2b" *Virology* 156:293–304.

Weiner et al. (1990). "Detection of hepatitis C viral sequences in non–A, non–B hepatitis" *The Lancet* 335(8680):1–3.

Wellink et al. (1988). "Proteases involved in the processing of viral polyproteins" *Arch. Virol.* 98:1–26.

Westaway et al. (1985). "Flaviviridae" *Intervirol.* 24:183–192.

Yaegashi et al. (1986). "Partial sequence analysis of cloned dengue virus type 2 genome" *Gene* 46:257–267.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 is confirmed.

* * * * *

SEQUENCE LISTING ( 1 ) GENERAL INFORMATION:

( i i i ) NUMBER OF SEQUENCES: 86

( 2 ) INFORMATION FOR SEQ ID NO:1:

( i ) SEQUENCE CHARACTERISTICS:
        ( A ) LENGTH: 202 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Arg  Arg  Gly  Arg  Glu  Ile  Leu  Leu  Gly  Pro  Ala  Asp  Gly  Met  Val  Ser
 1              5                        10                         15
```

```
Lys  Gly  Trp  Arg  Leu  Leu  Ala  Pro  Ile  Thr  Ala  Tyr  Ala  Gln  Gln  Thr
               20                  25                      30

Arg  Gly  Leu  Leu  Gly  Cys  Ile  Ile  Thr  Ser  Leu  Thr  Gly  Arg  Asp  Lys
          35                       40                      45

Asn  Gln  Val  Glu  Gly  Glu  Val  Gln  Ile  Val  Ser  Thr  Ala  Ala  Gln  Thr
     50                       55                      60

Phe  Leu  Ala  Thr  Cys  Ile  Asn  Gly  Val  Cys  Trp  Thr  Val  Tyr  His  Gly
65                       70                      75                           80

Ala  Gly  Thr  Arg  Thr  Ile  Ala  Ser  Pro  Lys  Gly  Pro  Val  Ile  Gln  Met
                    85                       90                           95

Tyr  Thr  Asn  Val  Asp  Gln  Asp  Leu  Val  Gly  Trp  Pro  Ala  Ser  Gln  Gly
               100                      105                     110

Thr  Arg  Ser  Leu  Thr  Pro  Cys  Thr  Cys  Gly  Ser  Ser  Asp  Leu  Tyr  Leu
          115                      120                     125

Val  Thr  Arg  His  Ala  Asp  Val  Ile  Pro  Val  Arg  Arg  Arg  Gly  Asp  Ser
     130                      135                     140

Arg  Gly  Ser  Leu  Leu  Ser  Pro  Arg  Pro  Ile  Ser  Tyr  Leu  Lys  Gly  Ser
145                      150                      155                          160

Ser  Gly  Gly  Pro  Leu  Leu  Cys  Pro  Ala  Gly  His  Ala  Val  Gly  Ile  Phe
                    165                      170                     175

Arg  Ala  Ala  Val  Cys  Thr  Arg  Gly  Val  Ala  Lys  Ala  Val  Asp  Phe  Ile
               180                      185                     190

Pro  Val  Glu  Asn  Leu  Glu  Thr  Thr  Met  Arg
          195                      200
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Cys  Trp  Thr  Val  Tyr  His  Gly  Ala  Gly
1                    5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Asp  Gln  Asp  Leu  Gly  Trp  Pro  Ala  Pro
1                    5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Leu  Lys  Gly  Ser  Ser  Gly  Gly  Pro  Leu
1                    5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Phe His Thr Met Trp His Val Thr Arg
1                   5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

Lys Glu Asp Leu Val Ala Tyr Gly Gly
1                   5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

Pro Ser Gly Thr Ser Gly Ser Pro Ile
1                   5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

Phe His Thr Leu Trp His Thr Thr Lys
1                   5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

Lys Glu Asp Arg Leu Cys Tyr Gly Gly
1                   5

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Pro  Thr  Gly  Thr  Ser  Gly  Ser  Pro  Ile
1                   5
```

( 2 ) INFORMATION FOR SEQ ID NO:11:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:11:

```
Phe  His  Thr  Leu  Trp  His  Thr  Thr  Arg
1                   5
```

( 2 ) INFORMATION FOR SEQ ID NO:12:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:12:

```
Lys  Glu  Asp  Arg  Val  Thr  Tyr  Gly  Gly
1                   5
```

( 2 ) INFORMATION FOR SEQ ID NO:13:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:13:

```
Pro  Ile  Gly  Thr  Ser  Gly  Ser  Pro  Ile
1                   5
```

( 2 ) INFORMATION FOR SEQ ID NO:14:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:14:

```
Phe  His  Thr  Leu  Trp  His  Thr  Thr  Lys
1                   5
```

( 2 ) INFORMATION FOR SEQ ID NO:15:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:15:

```
Lys  Glu  Asp  Arg  Leu  Cys  Tyr  Gly  Gly
1                   5
```

( 2 ) INFORMATION FOR SEQ ID NO:16:

( i ) SEQUENCE CHARACTERISTICS:
      ( A ) LENGTH: 9 amino acids
      ( B ) TYPE: amino acid
      ( C ) STRANDEDNESS: single (D) TOPOLOGY: linear (x i) SEQUENCE DESCRIPTION: SEQ ID NO:16:

Pro Thr Gly Thr Ser Gly Ser Pro Ile
1               5

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (x i) SEQUENCE DESCRIPTION: SEQ ID NO:17:

Thr Ala Gly His Cys
1               5

(2) INFORMATION FOR SEQ ID NO:18:

(i) SEQUENCE CHARACTERISTICS:
        (A) LENGTH: 7 amino acids
        (B) TYPE: amino acid
        (C) STRANDEDNESS: single
        (D) TOPOLOGY: linear (x i) SEQUENCE DESCRIPTION: SEQ ID NO:18:

Asn Asn Asp Tyr Gly Ile Ile
1               5

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (x i) SEQUENCE DESCRIPTION: SEQ ID NO:19:

Gly Asp Ser Gly Gly Ser Leu
1               5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (x i) SEQUENCE DESCRIPTION: SEQ ID NO:20:

Thr Ala Gly His Cys
1               5

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (x i) SEQUENCE DESCRIPTION: SEQ ID NO:21:

Gly Asn Asp Arg Ala Trp Val
1               5

(2) INFORMATION FOR SEQ ID NO:22:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:22:

Gly Asp Ser Gly Gly Ser Trp
1               5

( 2 ) INFORMATION FOR SEQ ID NO:23:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:23:

Ser Ala Ala His Cys
1               5

( 2 ) INFORMATION FOR SEQ ID NO:24:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:24:

Asn Asn Asp Ile Met Leu Ile
1               5

( 2 ) INFORMATION FOR SEQ ID NO:25:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:25:

Gly Asp Ser Gly Gly Pro Val
1               5

( 2 ) INFORMATION FOR SEQ ID NO:26:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:26:

Thr Ala Ala His Cys
1               5

( 2 ) INFORMATION FOR SEQ ID NO:27:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:27:

Asn Asn Asp Ile Thr Leu Leu
1               5

( 2 ) INFORMATION FOR SEQ ID NO:28:

( i ) SEQUENCE CHARACTERISTICS:
           ( A ) LENGTH: 7 amino acids
           ( B ) TYPE: amino acid
           ( C ) STRANDEDNESS: single
           ( D ) TOPOLOGY: linear ( x i ) SEQUENCE DESCRIPTION: SEQ ID NO:28:

Gly Asp Ser Gly Gly Pro Leu
1               5

( 2 ) INFORMATION FOR SEQ ID NO:29:

( i ) SEQUENCE CHARACTERISTICS:
           ( A ) LENGTH: 5 amino acids
           ( B ) TYPE: amino acid
           ( C ) STRANDEDNESS: single
           ( D ) TOPOLOGY: linear ( x i ) SEQUENCE DESCRIPTION: SEQ ID NO:29:

Thr Ala Ala His Cys
1               5

( 2 ) INFORMATION FOR SEQ ID NO:30:

( i ) SEQUENCE CHARACTERISTICS:
           ( A ) LENGTH: 7 amino acids
           ( B ) TYPE: amino acid
           ( C ) STRANDEDNESS: single
           ( D ) TOPOLOGY: linear ( x i ) SEQUENCE DESCRIPTION: SEQ ID NO:30:

Gly Tyr Asp Ile Ala Leu Leu
1               5

( 2 ) INFORMATION FOR SEQ ID NO:31:

( i ) SEQUENCE CHARACTERISTICS:
           ( A ) LENGTH: 7 amino acids
           ( B ) TYPE: amino acid
           ( C ) STRANDEDNESS: single
           ( D ) TOPOLOGY: linear ( x i ) SEQUENCE DESCRIPTION: SEQ ID NO:31:

Gly Asp Ser Gly Gly Pro Leu
1               5

( 2 ) INFORMATION FOR SEQ ID NO:32:

( i ) SEQUENCE CHARACTERISTICS:
           ( A ) LENGTH: 5 amino acids
           ( B ) TYPE: amino acid
           ( C ) STRANDEDNESS: single
           ( D ) TOPOLOGY: linear ( x i ) SEQUENCE DESCRIPTION: SEQ ID NO:32:

Thr Val Tyr His Gly
1               5

( 2 ) INFORMATION FOR SEQ ID NO:33:

( i ) SEQUENCE CHARACTERISTICS:
           ( A ) LENGTH: 7 amino acids
           ( B ) TYPE: amino acid
           ( C ) STRANDEDNESS: single
           ( D ) TOPOLOGY: linear ( x i ) SEQUENCE DESCRIPTION: SEQ ID NO:33:

Ser Ser Asp Leu Tyr Leu Val
1               5

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:34:

Gly Ser Ser Gly Gly Pro Leu
1               5

( 2 ) INFORMATION FOR SEQ ID NO:35:

( i ) SEQUENCE CHARACTERISTICS:
        ( A ) LENGTH: 75 amino acids
        ( B ) TYPE: amino acid
        ( C ) STRANDEDNESS: single
        ( D ) TOPOLOGY: linear ( x i ) SEQUENCE DESCRIPTION: SEQ ID NO:35:

Gln Ile Phe Val Lys Thr Leu Thr Gly Lys Thr Ile Thr Leu Glu Val
1               5                   10                  15

Glu Ser Ser Asp Thr Ile Asp Asn Val Lys Ser Lys Ile Gln Asp Lys
                20                  25                  30

Glu Gly Ile Pro Pro Asp Gln Gln Arg Leu Ile Phe Ala Gly Lys Gln
            35                  40                  45

Leu Glu Asp Gly Arg Thr Leu Ser Asp Tyr Asn Ile Gln Lys Glu Ser
        50                  55                  60

Thr Leu His Leu Val Leu Arg Leu Arg Gly Gly
65                  70                  75

( 2 ) INFORMATION FOR SEQ ID NO:36:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

Val Ser Ala Arg Arg Gly Arg Glu Ile Leu Leu Gly Ala Ile Leu Arg
1               5                   10                  15

Arg His Val Gly Pro Val Ser Cys Gln Arg Gly Tyr
                20                  25

( 2 ) INFORMATION FOR SEQ ID NO:37:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GATCCTGGAA TTCTGATAAG ACCTTAAGAC TATTTTAA    38

( 2 ) INFORMATION FOR SEQ ID NO:38:

( i ) SEQUENCE CHARACTERISTICS:
        ( A ) LENGTH: 19 base pairs ( B ) TYPE: nucleic acid
( C ) STRANDEDNESS: single
( D ) TOPOLOGY: linear ( x i ) SEQUENCE DESCRIPTION: SEQ ID NO:38:

GATCCTGAAT TCCTGATAA                                                                                        19

( 2 ) INFORMATION FOR SEQ ID NO:39:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:39:

GACTTAAGGA CTATTTTAA                                                                                        19

( 2 ) INFORMATION FOR SEQ ID NO:40:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:40:

GATCCGAATT CTGTGATAA                                                                                        19

( 2 ) INFORMATION FOR SEQ ID NO:41:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:41:

GCTTAAGACA CTATTTTAA                                                                                        19

( 2 ) INFORMATION FOR SEQ ID NO:42:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:42:

GATCCTGGAA TTCTGATAA                                                                                        19

( 2 ) INFORMATION FOR SEQ ID NO:43:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:43:

GACCTTAAGA CTATTTTAA                                                                                        19

( 2 ) INFORMATION FOR SEQ ID NO:44:

( i ) SEQUENCE CHARACTERISTICS:
( A ) LENGTH: 30 base pairs
( B ) TYPE: nucleic acid
( C ) STRANDEDNESS: single (D) TOPOLOGY: linear (xi) SEQUENCE DESCRIPTION: SEQ ID NO:44:

ATCAGGACCG GGGTGAGAAC AATTACCACT 30

(2) INFORMATION FOR SEQ ID NO:45:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:45:

AAGCCACCGT GTGCGCTAGG GCTCAAGCCC 30

(2) INFORMATION FOR SEQ ID NO:46:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:46:

AGCAGACAAG GGGCCTCCTA GGGTGCATAA T 31

(2) INFORMATION FOR SEQ ID NO:47:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:47:

TGCATCAATG GGGTGTGCTG G 21

(2) INFORMATION FOR SEQ ID NO:48:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO:48:

AGAGACAACC ATGAGGTCCC CGGTGTTC 28

(2) INFORMATION FOR SEQ ID NO:49:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:49:

CTGTTGTGCC CCGCGGCAGC C 21

(2) INFORMATION FOR SEQ ID NO:50:

(i) SEQUENCE CHARACTERISTICS:
(A) LENGTH: 22 base pairs
(B) TYPE: nucleic acid
(C) STRANDEDNESS: single
(D) TOPOLOGY: linear ( x i ) SEQUENCE DESCRIPTION: SEQ ID NO:50:

CCCGAGCAAG ATCTCCCGGC CC                                                                22

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

CCCGGCTGCA TAAGCAGTCG ACTTGGA                                                            27

( 2 ) INFORMATION FOR SEQ ID NO:52:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 2..37

( x i ) SEQUENCE DESCRIPTION: SEQ ID NO:52:

C ATG GAC TAC AAA GAC GAT GAC GAT AAA GGC CGG GAG                                        37
  Met Asp Tyr Lys Asp Asp Asp Asp Lys Gly Arg Glu
   1          5                 10

( 2 ) INFORMATION FOR SEQ ID NO:53:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

Met Asp Tyr Lys Asp Asp Asp Asp Lys Gly Arg Glu
 1          5                10

( 2 ) INFORMATION FOR SEQ ID NO:54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

CACCTATGTT TATAACCATC TCACTCCTCT                                                         30

( 2 ) INFORMATION FOR SEQ ID NO:55:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

AATTTGGGAA TTCCATAATT AATTAAG                                                            27

( 2 ) INFORMATION FOR SEQ ID NO:56:

( i ) SEQUENCE CHARACTERISTICS:
     ( A ) LENGTH: 27 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:56:

TCGACTTAAT TAATTATGGA ATTCCCA                                              27

( 2 ) INFORMATION FOR SEQ ID NO:57:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:57:

AATTTGGGAA TTCCATAATG AG                                                   22

( 2 ) INFORMATION FOR SEQ ID NO:58:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:58:

TCGACTCATT ATGGAATTCC CA                                                   22

( 2 ) INFORMATION FOR SEQ ID NO:59:

( i ) SEQUENCE CHARACTERISTICS:
          ( A ) LENGTH: 71 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:59:

AATTCGTAAA TCCTGTGTGC TAATTGAGGT GCATTGGTCT GCAAATCGAG TTGCTAGGCA          60

ATAAACACAT T                                                              71

( 2 ) INFORMATION FOR SEQ ID NO:60:

( i ) SEQUENCE CHARACTERISTICS:
          ( A ) LENGTH: 59 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:60:

TATTGCCTAG CAACTCGATT TGCAGACCAA TGCACCTCAA TTAGCACACA GGATTTACG           59

( 2 ) INFORMATION FOR SEQ ID NO:61:

( i ) SEQUENCE CHARACTERISTICS:
          ( A ) LENGTH: 62 base pairs
          ( B ) TYPE: nucleic acid
          ( C ) STRANDEDNESS: single
          ( D ) TOPOLOGY: linear ( x i ) SEQUENCE DESCRIPTION: SEQ ID NO:61:

TGGATTAATT TTAATCGTTC GTTGAGCGAT TAGCAGAGAA CTGACCAGAA CATGTCTGAG          60

CT                                                                        62

(2) INFORMATION FOR SEQ ID NO:62:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:62:

```
CAGACATGTT CTGGTCAGTT CTCTGCTAAT CGCTCAACGA ACGATTAAAA TTAATCCAAA    60

TGTGTT                                                                66
```

(2) INFORMATION FOR SEQ ID NO:63:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:63:

```
Trp Thr Val Tyr His Gly Ala Gly Thr Arg Thr
 1               5                   10
```

(2) INFORMATION FOR SEQ ID NO:64:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:64:

```
Leu Lys Gly Ser Ser Gly Gly Pro Leu
 1               5
```

(2) INFORMATION FOR SEQ ID NO:65:

(i) SEQUENCE CHARACTERISTICS:
        (A) LENGTH: 202 amino acids
        (B) TYPE: amino acid
        (C) STRANDEDNESS: single
        (D) TOPOLOGY: linear (xi) SEQUENCE DESCRIPTION: SEQ ID NO:65:

```
Arg Arg Gly Arg Glu Ile Leu Leu Gly Pro Ala Asp Gly Met Val Ser
 1               5                  10                  15

Lys Gly Trp Arg Leu Leu Ala Pro Ile Thr Ala Tyr Ala Gln Gln Thr
                20                  25                  30

Arg Gly Leu Leu Gly Cys Ile Ile Thr Ser Leu Thr Gly Arg Asp Lys
                35                  40                  45

Asn Gln Val Glu Gly Glu Val Gln Ile Val Ser Thr Ala Ala Gln Thr
    50                  55                      60

Phe Leu Ala Thr Cys Ile Asn Gly Val Cys Trp Thr Val Tyr His Gly
65                  70                  75                  80

Ala Gly Thr Arg Thr Ile Ala Ser Pro Lys Gly Pro Val Ile Gln Met
                85                  90                  95

Tyr Thr Asn Val Asp Gln Asp Leu Val Gly Trp Pro Ala Ser Gln Gly
                100                 105                 110

Thr Arg Ser Leu Thr Pro Cys Thr Cys Gly Ser Ser Asp Leu Tyr Leu
                115                 120                 125

Val Thr Arg His Ala Asp Val Ile Pro Val Arg Arg Arg Gly Asp Ser
                130                 135                 140
```

```
Arg Gly Ser Leu Leu Ser Pro Arg Pro Ile Ser Tyr Leu Lys Gly Ser
145                 150                 155                 160

Ser Gly Gly Pro Leu Leu Cys Pro Ala Gly His Ala Val Gly Ile Phe
                165                 170                 175

Arg Ala Ala Val Cys Thr Arg Gly Val Ala Lys Ala Val Asp Phe Ile
            180                 185                 190

Pro Val Glu Asn Leu Glu Thr Thr Met Arg
            195                 200
```

( 2 ) INFORMATION FOR SEQ ID NO:66:

( i ) SEQUENCE CHARACTERISTICS:
        ( A ) LENGTH: 299 amino acids
        ( B ) TYPE: amino acid
        ( C ) STRANDEDNESS: single
        ( D ) TOPOLOGY: linear ( x i ) SEQUENCE DESCRIPTION: SEQ ID NO:66:

```
Gly Thr Tyr Val Tyr Asn His Leu Thr Pro Leu Arg Asp Trp Ala His
1               5                   10                  15

Asn Gly Leu Arg Asp Leu Ala Val Ala Val Glu Pro Val Val Phe Ser
            20                  25                  30

Gln Met Glu Thr Lys Leu Ile Thr Trp Gly Ala Asp Thr Ala Ala Cys
        35                  40                  45

Gly Asp Ile Ile Asn Gly Leu Pro Val Ser Ala Arg Arg Gly Arg Glu
    50                  55                  60

Ile Leu Leu Gly Pro Ala Asp Gly Met Val Ser Lys Gly Trp Arg Leu
65              70                  75                  80

Leu Ala Pro Ile Thr Ala Tyr Ala Gln Gln Thr Arg Gly Leu Leu Gly
                85                  90                  95

Cys Ile Ile Thr Ser Leu Thr Gly Arg Asp Lys Asn Gln Val Glu Gly
            100                 105                 110

Glu Val Gln Ile Val Ser Thr Ala Ala Gln Thr Phe Leu Ala Thr Cys
        115                 120                 125

Ile Ile Asn Gly Val Cys Trp Thr Val Tyr His Gly Ala Gly Thr Arg
    130                 135                 140

Thr Ile Ala Ser Pro Lys Gly Pro Val Ile Gln Met Tyr Thr Asn Val
145                 150                 155                 160

Asp Gln Asp Leu Val Gly Trp Pro Ala Ser Gln Gly Thr Arg Ser Leu
                165                 170                 175

Thr Pro Cys Thr Cys Gly Ser Ser Asp Leu Tyr Leu Val Thr Arg His
            180                 185                 190

Ala Asp Val Ile Pro Val Arg Arg Arg Gly Asp Ser Arg Gly Ser Leu
        195                 200                 205

Leu Ser Pro Arg Pro Ile Ser Tyr Leu Lys Gly Ser Ser Gly Gly Pro
210                 215                 220

Leu Leu Cys Pro Ala Gly His Ala Val Gly Ile Phe Arg Ala Ala Val
225                 230                 235                 240

Cys Thr Arg Gly Val Ala Lys Ala Val Asp Phe Ile Pro Val Glu Asn
                245                 250                 255

Leu Glu Thr Thr Met Arg Ser Pro Val Phe Thr Asp Asn Ser Ser Pro
            260                 265                 270

Pro Val Val Pro Gln Ser Phe Gln Val Ala His Leu His Ala Pro Thr
        275                 280                 285

Gly Ser Gly Lys Ser Thr Lys Val Pro Ala Ala
    290                 295
```

( 2 ) INFORMATION FOR SEQ ID NO:67:

( i ) SEQUENCE CHARACTERISTICS:
        ( A ) LENGTH: 199 amino acids
        ( B ) TYPE: amino acid
        ( C ) STRANDEDNESS: single
        ( D ) TOPOLOGY: linear ( x i ) SEQUENCE DESCRIPTION: SEQ ID NO:67:

```
Gly Thr Tyr Val Tyr Asn His Leu Thr Pro Leu Arg Asp Trp Ala His
 1               5                  10                  15

Asn Gly Leu Arg Asp Leu Ala Val Ala Val Glu Pro Val Val Phe Ser
             20                  25                  30

Gln Met Glu Thr Lys Leu Ile Thr Trp Gly Ala Asp Thr Ala Ala Cys
         35                  40                  45

Gly Asp Ile Ile Asn Gly Leu Pro Val Ser Ala Arg Arg Gly Arg Glu
     50                  55                  60

Ile Leu Leu Gly Pro Ala Asp Gly Met Val Ser Lys Gly Trp Arg Leu
 65                  70                  75                  80

Leu Ala Pro Ile Thr Ala Tyr Ala Gln Gln Thr Arg Gly Leu Leu Gly
                 85                  90                  95

Cys Ile Ile Thr Ser Leu Thr Gly Arg Asp Lys Asn Gln Val Glu Gly
             100                 105                 110

Glu Val Gln Ile Val Ser Thr Ala Ala Gln Thr Phe Leu Ala Thr Cys
         115                 120                 125

Ile Ile Asn Gly Val Cys Trp Thr Val Tyr His Gly Ala Gly Thr Arg
     130                 135                 140

Thr Ile Ala Ser Pro Lys Gly Pro Val Ile Gln Met Tyr Thr Asn Val
145                 150                 155                 160

Asp Gln Asp Leu Val Gly Trp Pro Ala Ser Gln Gly Thr Arg Ser Leu
                 165                 170                 175

Thr Pro Cys Thr Cys Gly Ser Ser Asp Leu Tyr Leu Val Thr Arg His
             180                 185                 190

Ala Asp Val Ile Pro Val Arg
         195
```

( 2 ) INFORMATION FOR SEQ ID NO:68:

( i ) SEQUENCE CHARACTERISTICS:
        ( A ) LENGTH: 299 amino acids
        ( B ) TYPE: amino acid
        ( C ) STRANDEDNESS: single
        ( D ) TOPOLOGY: linear ( x i ) SEQUENCE DESCRIPTION: SEQ ID NO:68:

```
Gly Thr Tyr Val Tyr Asn His Leu Thr Pro Leu Arg Asp Trp Ala His
 1               5                  10                  15

Asn Gly Leu Arg Asp Leu Ala Val Ala Val Glu Pro Val Val Phe Ser
             20                  25                  30

Gln Met Glu Thr Lys Leu Ile Thr Trp Gly Ala Asp Thr Ala Ala Cys
         35                  40                  45

Gly Asp Ile Ile Asn Gly Leu Pro Val Ser Ala Arg Arg Gly Arg Glu
     50                  55                  60

Ile Leu Leu Gly Pro Ala Asp Gly Met Val Ser Lys Gly Trp Arg Leu
 65                  70                  75                  80

Leu Ala Pro Ile Thr Ala Tyr Ala Gln Gln Thr Arg Gly Leu Leu Gly
                 85                  90                  95

Cys Ile Ile Thr Ser Leu Thr Gly Arg Asp Lys Asn Gln Val Glu Gly
```

|     |     |     |     |     | 100 |     |     |     |     | 105 |     |     |     |     | 110 |     |
| --- | --- | --- | --- | --- | --- | --- | --- | --- | --- | --- | --- | --- | --- | --- | --- | --- |
| Glu | Val | Gln | Ile | Val | Ser | Thr | Ala | Ala | Gln | Thr | Phe | Leu | Ala | Thr | Cys |     |
|     |     | 115 |     |     |     | 120 |     |     |     | 125 |     |     |     |     |     |     |
| Ile | Ile | Asn | Gly | Val | Cys | Trp | Thr | Val | Tyr | His | Gly | Ala | Gly | Thr | Arg |     |
|     | 130 |     |     |     |     | 135 |     |     |     |     | 140 |     |     |     |     |     |
| Thr | Ile | Ala | Ser | Pro | Lys | Gly | Pro | Val | Ile | Gln | Met | Tyr | Thr | Asn | Val |     |
| 145 |     |     |     |     | 150 |     |     |     |     | 155 |     |     |     |     | 160 |     |
| Asp | Gln | Asp | Leu | Val | Gly | Trp | Pro | Ala | Ser | Gln | Gly | Thr | Arg | Ser | Leu |     |
|     |     |     |     | 165 |     |     |     |     | 170 |     |     |     |     | 175 |     |     |
| Thr | Pro | Cys | Thr | Cys | Gly | Ser | Ser | Asp | Leu | Tyr | Leu | Val | Thr | Arg | His |     |
|     |     |     | 180 |     |     |     |     | 185 |     |     |     |     | 190 |     |     |     |
| Ala | Asp | Val | Ile | Pro | Val | Arg | Arg | Arg | Gly | Asp | Ser | Arg | Gly | Ser | Leu |     |
|     |     | 195 |     |     |     |     | 200 |     |     |     |     | 205 |     |     |     |     |
| Leu | Ser | Pro | Arg | Pro | Ile | Ser | Tyr | Leu | Lys | Gly | Ser | Ser | Gly | Gly | Pro |     |
|     | 210 |     |     |     |     | 215 |     |     |     |     | 220 |     |     |     |     |     |
| Leu | Leu | Cys | Pro | Ala | Gly | His | Ala | Val | Gly | Ile | Phe | Arg | Ala | Ala | Val |     |
| 225 |     |     |     |     | 230 |     |     |     |     | 235 |     |     |     |     | 240 |     |
| Cys | Thr | Arg | Gly | Val | Ala | Lys | Ala | Val | Asp | Phe | Ile | Pro | Val | Glu | Asn |     |
|     |     |     |     | 245 |     |     |     |     | 250 |     |     |     |     | 255 |     |     |
| Leu | Glu | Thr | Thr | Met | Arg | Ser | Pro | Val | Phe | Thr | Asp | Asn | Ser | Ser | Pro |     |
|     |     |     | 260 |     |     |     |     | 265 |     |     |     |     | 270 |     |     |     |
| Pro | Val | Val | Pro | Gln | Ser | Phe | Gln | Val | Ala | His | Leu | His | Ala | Pro | Thr |     |
|     |     | 275 |     |     |     |     | 280 |     |     |     |     | 285 |     |     |     |     |
| Gly | Ser | Gly | Lys | Ser | Thr | Lys | Val | Pro | Ala | Ala |     |     |     |     |     |     |
|     |     | 290 |     |     |     | 295 |     |     |     |     |     |     |     |     |     |     |

( 2 ) INFORMATION FOR SEQ ID NO:69:

( i ) SEQUENCE CHARACTERISTICS:
        ( A ) LENGTH: 2064 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 7..2064

( x i ) SEQUENCE DESCRIPTION: SEQ ID NO:69:

| ATTCGG | GGC | ACC | TAT | GTT | TAT | AAC | CAT | CTC | ACT | CCT | CTT | CGG | GAC | TGG | 48 |
| --- | --- | --- | --- | --- | --- | --- | --- | --- | --- | --- | --- | --- | --- | --- | --- |
|     | Gly | Thr | Tyr | Val | Tyr | Asn | His | Leu | Thr | Pro | Leu | Arg | Asp | Trp |     |
|     | 1   |     |     | 5   |     |     |     |     | 10  |     |     |     |     |     |     |
| GCG | CAC | AAC | GGC | TTG | CGA | GAT | CTG | GCC | GTG | GCT | GTA | GAG | CCA | GTC | GTC | 96 |
| Ala | His | Asn | Gly | Leu | Arg | Asp | Leu | Ala | Val | Ala | Val | Glu | Pro | Val | Val |     |
| 15  |     |     |     | 20  |     |     |     |     | 25  |     |     |     |     |     | 30  |     |
| TTC | TCC | CAA | ATG | GAG | ACC | AAG | CTC | ATC | ACG | TGG | GGG | GCA | GAT | ACC | GCC | 144 |
| Phe | Ser | Gln | Met | Glu | Thr | Lys | Leu | Ile | Thr | Trp | Gly | Ala | Asp | Thr | Ala |     |
|     |     |     |     | 35  |     |     |     |     | 40  |     |     |     |     | 45  |     |     |
| GCG | TGC | GGT | GAC | ATC | ATC | AAC | GGC | TTG | CCT | GTT | TCC | GCC | CGC | AGG | GGC | 192 |
| Ala | Cys | Gly | Asp | Ile | Ile | Asn | Gly | Leu | Pro | Val | Ser | Ala | Arg | Arg | Gly |     |
|     |     |     | 50  |     |     |     |     | 55  |     |     |     |     | 60  |     |     |     |
| CGG | GAG | ATA | CTG | CTC | GGG | CCA | GCC | GAT | GGA | ATG | GTC | TCC | AAG | GGT | TGG | 240 |
| Arg | Glu | Ile | Leu | Leu | Gly | Pro | Ala | Asp | Gly | Met | Val | Ser | Lys | Gly | Trp |     |
|     |     | 65  |     |     |     |     | 70  |     |     |     |     | 75  |     |     |     |     |
| AGG | TTG | CTG | GCG | CCC | ATC | ACG | GCG | TAC | GCC | CAG | CAG | ACA | AGG | GGC | CTC | 288 |
| Arg | Leu | Leu | Ala | Pro | Ile | Thr | Ala | Tyr | Ala | Gln | Gln | Thr | Arg | Gly | Leu |     |
|     | 80  |     |     |     |     | 85  |     |     |     |     | 90  |     |     |     |     |     |
| CTA | GGG | TGC | ATA | ATC | ACC | AGC | CTA | ACT | GGC | CGG | GAC | AAA | AAC | CAA | GTG | 336 |
| Leu | Gly | Cys | Ile | Ile | Thr | Ser | Leu | Thr | Gly | Arg | Asp | Lys | Asn | Gln | Val |     |
| 95  |     |     |     | 100 |     |     |     |     | 105 |     |     |     |     | 110 |     |     |

```
GAG GGT GAG GTC CAG ATT GTG TCA ACT GCT GCC CAA ACC TTC CTG GCA      384
Glu Gly Glu Val Gln Ile Val Ser Thr Ala Ala Gln Thr Phe Leu Ala
            115                 120                 125

ACG TGC ATC ATC AAT GGG GTG TGC TGG ACT GTC TAC CAC GGG GCC GGA      432
Thr Cys Ile Ile Asn Gly Val Cys Trp Thr Val Tyr His Gly Ala Gly
                130                 135                 140

ACG AGG ACC ATC GCG TCA CCC AAG GGT CCT GTC ATC CAG ATG TAT ACC      480
Thr Arg Thr Ile Ala Ser Pro Lys Gly Pro Val Ile Gln Met Tyr Thr
            145                 150                 155

AAT GTA GAC CAA GAC CTT GTG GGC TGG CCC GCT TCG CAA GGT ACC CGC      528
Asn Val Asp Gln Asp Leu Val Gly Trp Pro Ala Ser Gln Gly Thr Arg
        160                 165                 170

TCA TTG ACA CCC TGC ACT TGC GGC TCC TCG GAC CTT TAC CTG GTC ACG      576
Ser Leu Thr Pro Cys Thr Cys Gly Ser Ser Asp Leu Tyr Leu Val Thr
175                 180                 185                 190

AGG CAC GCC GAT GTC ATT CCC GTG CGC CGG CGG GGT GAT AGC AGG GGC      624
Arg His Ala Asp Val Ile Pro Val Arg Arg Arg Gly Asp Ser Arg Gly
                195                 200                 205

AGC CTG CTG TCG CCC CGG CCC ATT TCC TAC TTG AAA GGC TCC TCG GGG      672
Ser Leu Leu Ser Pro Arg Pro Ile Ser Tyr Leu Lys Gly Ser Ser Gly
            210                 215                 220

GGT CCG CTG TTG TGC CCC GCG GGG CAC GCC GTG GGC ATA TTT AGG GCC      720
Gly Pro Leu Leu Cys Pro Ala Gly His Ala Val Gly Ile Phe Arg Ala
        225                 230                 235

GCG GTG TGC ACC CGT GGA GTG GCT AAG GCG GTG GAC TTT ATC CCT GTG      768
Ala Val Cys Thr Arg Gly Val Ala Lys Ala Val Asp Phe Ile Pro Val
240                 245                 250

GAG AAC CTA GAG ACA ACC ATG AGG TCC CCG GTG TTC ACG GAT AAC TCC      816
Glu Asn Leu Glu Thr Thr Met Arg Ser Pro Val Phe Thr Asp Asn Ser
255                 260                 265                 270

TCT CCA CCA GTA GTG CCC CAG AGC TTC CAG GTG GCT CAC CTC CAT GCT      864
Ser Pro Pro Val Val Pro Gln Ser Phe Gln Val Ala His Leu His Ala
                275                 280                 285

CCC ACA GGC AGC GGC AAA AGC ACC AAG GTC CCG GCT GCA TAT GCA GCT      912
Pro Thr Gly Ser Gly Lys Ser Thr Lys Val Pro Ala Ala Tyr Ala Ala
            290                 295                 300

CAG GGC TAT AAG GTG CTA GTA CTC AAC CCC TCT GTT GCT GCA ACA CTG      960
Gln Gly Tyr Lys Val Leu Val Leu Asn Pro Ser Val Ala Ala Thr Leu
        305                 310                 315

GGC TTT GGT GCT TAC ATG TCC AAG GCT CAT GGG ATC GAT CCT AAC ATC     1008
Gly Phe Gly Ala Tyr Met Ser Lys Ala His Gly Ile Asp Pro Asn Ile
320                 325                 330

AGG ACC GGG GTG AGA ACA ATT ACC ACT GGC AGC CCC ATC ACG TAC TCC     1056
Arg Thr Gly Val Arg Thr Ile Thr Thr Gly Ser Pro Ile Thr Tyr Ser
335                 340                 345                 350

ACC TAC GGC AAG TTC CTT GCC GAC GGC GGG TGC TCG GGG GGC GCT TAT     1104
Thr Tyr Gly Lys Phe Leu Ala Asp Gly Gly Cys Ser Gly Gly Ala Tyr
                355                 360                 365

GAC ATA ATA ATT TGT GAC GAG TGC CAC TCC ACG GAT GCC ACA TCC ATC     1152
Asp Ile Ile Ile Cys Asp Glu Cys His Ser Thr Asp Ala Thr Ser Ile
            370                 375                 380

TTG GGC ATT GGC ACT GTC CTT GAC CAA GCA GAG ACT GCG GGG GCG AGA     1200
Leu Gly Ile Gly Thr Val Leu Asp Gln Ala Glu Thr Ala Gly Ala Arg
        385                 390                 395

CTG GTT GTG CTC GCC ACC GCC ACC CCT CCG GGC TCC GTC ACT GTG CCC     1248
Leu Val Val Leu Ala Thr Ala Thr Pro Pro Gly Ser Val Thr Val Pro
400                 405                 410

CAT CCC AAC ATC GAG GAG GTT GCT CTG TCC ACC ACC GGA GAG ATC CCT     1296
His Pro Asn Ile Glu Glu Val Ala Leu Ser Thr Thr Gly Glu Ile Pro
415                 420                 425                 430
```

| | | | | | | | | | | | | | | | | |
|---|---|---|---|---|---|---|---|---|---|---|---|---|---|---|---|---|
| TTT | TAC | GGC | AAG | GCT | ATC | CCC | CTC | GAA | GTA | ATC | AAG | GGG | GGG | AGA | CAT | 1344 |
| Phe | Tyr | Gly | Lys | Ala | Ile | Pro | Leu | Glu | Val | Ile | Lys | Gly | Gly | Arg | His | |
| | | | | 435 | | | | 440 | | | | | | 445 | | |
| CTC | ATC | TTC | TGT | CAT | TCA | AAG | AAG | AAG | TGC | GAC | GAA | CTC | GCC | GCA | AAG | 1392 |
| Leu | Ile | Phe | Cys | His | Ser | Lys | Lys | Lys | Cys | Asp | Glu | Leu | Ala | Ala | Lys | |
| | | | 450 | | | | | 455 | | | | | 460 | | | |
| CTG | GTC | GCA | TTG | GGC | ATC | AAT | GCC | GTG | GCC | TAC | TAC | CGC | GGT | CTT | GAC | 1440 |
| Leu | Val | Ala | Leu | Gly | Ile | Asn | Ala | Val | Ala | Tyr | Tyr | Arg | Gly | Leu | Asp | |
| | | 465 | | | | | 470 | | | | | 475 | | | | |
| GTG | TCC | GTC | ATC | CCG | ACC | AGC | GGC | GAT | GTT | GTC | GTC | GTG | GCA | ACC | GAT | 1488 |
| Val | Ser | Val | Ile | Pro | Thr | Ser | Gly | Asp | Val | Val | Val | Val | Ala | Thr | Asp | |
| | 480 | | | | | 485 | | | | | 490 | | | | | |
| GCC | CTC | ATG | ACC | GGC | TAT | ACC | GGC | GAC | TTC | GAC | TCG | GTG | ATA | GAC | TGC | 1536 |
| Ala | Leu | Met | Thr | Gly | Tyr | Thr | Gly | Asp | Phe | Asp | Ser | Val | Ile | Asp | Cys | |
| 495 | | | | | 500 | | | | 505 | | | | | 510 | | |
| AAT | ACG | TGT | GTC | ACC | CAG | ACA | GTC | GAT | TTC | AGC | CTT | GAC | CCT | ACC | TTC | 1584 |
| Asn | Thr | Cys | Val | Thr | Gln | Thr | Val | Asp | Phe | Ser | Leu | Asp | Pro | Thr | Phe | |
| | | | 515 | | | | | 520 | | | | | 525 | | | |
| ACC | ATT | GAG | ACA | ATC | ACG | CTC | CCC | CAA | GAT | GCT | GTC | TCC | CGC | ACT | CAA | 1632 |
| Thr | Ile | Glu | Thr | Ile | Thr | Leu | Pro | Gln | Asp | Ala | Val | Ser | Arg | Thr | Gln | |
| | | | 530 | | | | | 535 | | | | | 540 | | | |
| CGT | CGG | GGC | AGG | ACT | GGC | AGG | GGG | AAG | CCA | GGC | ATC | TAC | AGA | TTT | GTG | 1680 |
| Arg | Arg | Gly | Arg | Thr | Gly | Arg | Gly | Lys | Pro | Gly | Ile | Tyr | Arg | Phe | Val | |
| | | 545 | | | | | 550 | | | | | 555 | | | | |
| GCA | CCG | GGG | GAG | CGC | CCT | CCC | GGC | ATG | TTC | GAC | TCG | TCC | GTC | CTC | TGT | 1728 |
| Ala | Pro | Gly | Glu | Arg | Pro | Pro | Gly | Met | Phe | Asp | Ser | Ser | Val | Leu | Cys | |
| | | 560 | | | | 565 | | | | | 570 | | | | | |
| GAG | TGC | TAT | GAC | GCA | GGC | TGT | GCT | TGG | TAT | GAG | CTC | ACG | CCC | GCC | GAG | 1776 |
| Glu | Cys | Tyr | Asp | Ala | Gly | Cys | Ala | Trp | Tyr | Glu | Leu | Thr | Pro | Ala | Glu | |
| 575 | | | | | 580 | | | | | 585 | | | | | 590 | |
| ACT | ACA | GTT | AGG | CTA | CGA | GCG | TAC | ATG | AAC | ACC | CCG | GGG | CTT | CCC | GTG | 1824 |
| Thr | Thr | Val | Arg | Leu | Arg | Ala | Tyr | Met | Asn | Thr | Pro | Gly | Leu | Pro | Val | |
| | | | | 595 | | | | | 600 | | | | | 605 | | |
| TGC | CAG | GAC | CAT | CTT | GAA | TTT | TGG | GAG | GGC | GTC | TTT | ACA | GGC | CTC | ACT | 1872 |
| Cys | Gln | Asp | His | Leu | Glu | Phe | Trp | Glu | Gly | Val | Phe | Thr | Gly | Leu | Thr | |
| | | | 610 | | | | | 615 | | | | | 620 | | | |
| CAT | ATA | GAT | GCC | CAC | TTT | CTA | TCC | CAG | ACA | AAG | CAG | AGT | GGG | GAG | AAC | 1920 |
| His | Ile | Asp | Ala | His | Phe | Leu | Ser | Gln | Thr | Lys | Gln | Ser | Gly | Glu | Asn | |
| | | 625 | | | | | 630 | | | | | 635 | | | | |
| CTT | CCT | TAC | CTG | GTA | GCG | TAC | CAA | GCC | ACC | GTG | TGC | GCT | AGG | GCT | CAA | 1968 |
| Leu | Pro | Tyr | Leu | Val | Ala | Tyr | Gln | Ala | Thr | Val | Cys | Ala | Arg | Ala | Gln | |
| | 640 | | | | | 645 | | | | | 650 | | | | | |
| GCC | CCT | CCC | CCA | TCG | TGG | GAC | CAG | ATG | TGG | AAG | TGT | TTG | ATT | CGC | CTC | 2016 |
| Ala | Pro | Pro | Pro | Ser | Trp | Asp | Gln | Met | Trp | Lys | Cys | Leu | Ile | Arg | Leu | |
| 655 | | | | | 660 | | | | | 665 | | | | | 670 | |
| AAG | CCC | ACC | CTC | CAT | GGG | CCA | ACA | CCC | CTA | CTA | TAC | AGA | CTG | GGC | GCT | 2064 |
| Lys | Pro | Thr | Leu | His | Gly | Pro | Thr | Pro | Leu | Leu | Tyr | Arg | Leu | Gly | Ala | |
| | | | | 675 | | | | | 680 | | | | | 685 | | |

( 2 ) INFORMATION FOR SEQ ID NO:70:

( i ) SEQUENCE CHARACTERISTICS:
        ( A ) LENGTH: 686 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

| | | | | | | | | | | | | | | |
|---|---|---|---|---|---|---|---|---|---|---|---|---|---|---|
| Gly | Thr | Tyr | Val | Tyr | Asn | His | Leu | Thr | Pro | Leu | Arg | Asp | Trp | Ala | His |
| 1 | | | | 5 | | | | | 10 | | | | | 15 | |

-continued

| | | | | | | | | | | | | | | |
|---|---|---|---|---|---|---|---|---|---|---|---|---|---|---|
|Asn|Gly|Leu|Arg 20|Asp|Leu|Ala|Val|Ala 25|Val|Glu|Pro|Val 30|Val|Phe|Ser|
|Gln|Met|Glu 35|Thr|Lys|Leu|Ile|Thr 40|Trp|Gly|Ala|Asp|Thr 45|Ala|Ala|Cys|
|Gly|Asp 50|Ile|Ile|Asn|Gly|Leu 55|Pro|Val|Ser|Ala|Arg 60|Arg|Gly|Arg|Glu|
|Ile 65|Leu|Leu|Gly|Pro|Ala 70|Asp|Gly|Met|Val|Ser 75|Lys|Gly|Trp|Arg|Leu 80|
|Leu|Ala|Pro|Ile|Thr 85|Ala|Tyr|Ala|Gln|Gln 90|Thr|Arg|Gly|Leu|Leu 95|Gly|
|Cys|Ile|Ile|Thr 100|Ser|Leu|Thr|Gly|Arg 105|Asp|Lys|Asn|Gln|Val 110|Glu|Gly|
|Glu|Val|Gln 115|Ile|Val|Ser|Thr|Ala 120|Ala|Gln|Thr|Phe|Leu 125|Ala|Thr|Cys|
|Ile|Ile 130|Asn|Gly|Val|Cys|Trp 135|Thr|Val|Tyr|His|Gly 140|Ala|Gly|Thr|Arg|
|Thr 145|Ile|Ala|Ser|Pro|Lys 150|Gly|Pro|Val|Ile|Gln 155|Met|Tyr|Thr|Asn|Val 160|
|Asp|Gln|Asp|Leu|Val 165|Gly|Trp|Pro|Ala|Ser 170|Gln|Gly|Thr|Arg|Ser 175|Leu|
|Thr|Pro|Cys|Thr 180|Cys|Gly|Ser|Ser|Asp 185|Leu|Tyr|Leu|Val|Thr 190|Arg|His|
|Ala|Asp|Val 195|Ile|Pro|Val|Arg|Arg 200|Arg|Gly|Asp|Ser|Arg 205|Gly|Ser|Leu|
|Leu|Ser 210|Pro|Arg|Pro|Ile|Ser 215|Tyr|Leu|Lys|Gly|Ser 220|Ser|Gly|Gly|Pro|
|Leu 225|Leu|Cys|Pro|Ala|Gly 230|His|Ala|Val|Gly|Ile 235|Phe|Arg|Ala|Ala|Val 240|
|Cys|Thr|Arg|Gly|Val 245|Ala|Lys|Ala|Val|Asp 250|Phe|Ile|Pro|Val|Glu 255|Asn|
|Leu|Glu|Thr|Thr 260|Met|Arg|Ser|Pro|Val 265|Phe|Thr|Asp|Asn|Ser 270|Ser|Pro|
|Pro|Val|Val 275|Pro|Gln|Ser|Phe|Gln 280|Val|Ala|His|Leu|His 285|Ala|Pro|Thr|
|Gly|Ser 290|Gly|Lys|Ser|Thr|Lys 295|Val|Pro|Ala|Ala|Tyr 300|Ala|Ala|Gln|Gly|
|Tyr 305|Lys|Val|Leu|Val|Leu 310|Asn|Pro|Ser|Val|Ala 315|Ala|Thr|Leu|Gly|Phe 320|
|Gly|Ala|Tyr|Met|Ser 325|Lys|Ala|His|Gly|Ile 330|Asp|Pro|Asn|Ile|Arg 335|Thr|
|Gly|Val|Arg|Thr 340|Ile|Thr|Thr|Gly|Ser 345|Pro|Ile|Thr|Tyr|Ser 350|Thr|Tyr|
|Gly|Lys|Phe 355|Leu|Ala|Asp|Gly|Gly 360|Cys|Ser|Gly|Gly|Ala 365|Tyr|Asp|Ile|
|Ile|Ile 370|Cys|Asp|Glu|Cys|His 375|Ser|Thr|Asp|Ala|Thr 380|Ser|Ile|Leu|Gly|
|Ile 385|Gly|Thr|Val|Leu|Asp 390|Gln|Ala|Glu|Thr|Ala 395|Gly|Ala|Arg|Leu|Val 400|
|Val|Leu|Ala|Thr|Ala 405|Thr|Pro|Pro|Gly|Ser 410|Val|Thr|Val|Pro|His 415|Pro|
|Asn|Ile|Glu|Glu 420|Val|Ala|Leu|Ser|Thr 425|Thr|Gly|Glu|Ile|Pro 430|Phe|Tyr|
|Gly|Lys|Ala|Ile|Pro 435|Leu|Glu|Val|Ile 440|Lys|Gly|Gly|Arg 445|His|Leu|Ile|

```
Phe  Cys  His  Ser  Lys  Lys  Lys  Cys  Asp  Glu  Leu  Ala  Ala  Lys  Leu  Val
     450            455                      460

Ala  Leu  Gly  Ile  Asn  Ala  Val  Ala  Tyr  Tyr  Arg  Gly  Leu  Asp  Val  Ser
465                      470                      475                           480

Val  Ile  Pro  Thr  Ser  Gly  Asp  Val  Val  Val  Ala  Thr  Asp  Ala  Leu
                    485                      490                     495

Met  Thr  Gly  Tyr  Thr  Gly  Asp  Phe  Asp  Ser  Val  Ile  Asp  Cys  Asn  Thr
               500                      505                          510

Cys  Val  Thr  Gln  Thr  Val  Asp  Phe  Ser  Leu  Asp  Pro  Thr  Phe  Thr  Ile
          515                      520                     525

Glu  Thr  Ile  Thr  Leu  Pro  Gln  Asp  Ala  Val  Ser  Arg  Thr  Gln  Arg  Arg
     530                      535                     540

Gly  Arg  Thr  Gly  Arg  Gly  Lys  Pro  Gly  Ile  Tyr  Arg  Phe  Val  Ala  Pro
545                      550                     555                          560

Gly  Glu  Arg  Pro  Pro  Gly  Met  Phe  Asp  Ser  Ser  Val  Leu  Cys  Glu  Cys
               565                     570                          575

Tyr  Asp  Ala  Gly  Cys  Ala  Trp  Tyr  Glu  Leu  Thr  Pro  Ala  Glu  Thr  Thr
               580                     585                          590

Val  Arg  Leu  Arg  Ala  Tyr  Met  Asn  Thr  Pro  Gly  Leu  Pro  Val  Cys  Gln
          595                     600                          605

Asp  His  Leu  Glu  Phe  Trp  Glu  Gly  Val  Phe  Thr  Gly  Leu  Thr  His  Ile
     610                     615                     620

Asp  Ala  His  Phe  Leu  Ser  Gln  Thr  Lys  Gln  Ser  Gly  Glu  Asn  Leu  Pro
625                      630                     635                          640

Tyr  Leu  Val  Ala  Tyr  Gln  Ala  Thr  Val  Cys  Ala  Arg  Ala  Gln  Ala  Pro
                    645                     650                          655

Pro  Pro  Ser  Trp  Asp  Gln  Met  Trp  Lys  Cys  Leu  Ile  Arg  Leu  Lys  Pro
               660                     665                          670

Thr  Leu  His  Gly  Pro  Thr  Pro  Leu  Leu  Tyr  Arg  Leu  Gly  Ala
          675                     680                     685
```

( 2 ) INFORMATION FOR SEQ ID NO:71:

( i ) SEQUENCE CHARACTERISTICS:
        ( A ) LENGTH: 368 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..366

( x i ) SEQUENCE DESCRIPTION: SEQ ID NO:71:

```
AAT  TCG  GAA  AAC  CAA  GTG  GAG  GGT  GAG  GTC  CAG  ATT  GTG  TCA  ACT  GCT     48
Asn  Ser  Glu  Asn  Gln  Val  Glu  Gly  Glu  Val  Gln  Ile  Val  Ser  Thr  Ala
 1             5                     10                      15

GCC  CAA  ACC  TTC  CTG  GCA  ACG  TGC  ATC  AAT  GGG  GTG  TGC  TGG  ACT  GTC     96
Ala  Gln  Thr  Phe  Leu  Ala  Thr  Cys  Ile  Asn  Gly  Val  Cys  Trp  Thr  Val
               20                     25                      30

TAC  CAC  GGG  GCC  GGA  ACG  AGG  ACC  ATC  GCG  TCA  CCC  AAG  GGT  CCT  GTC    144
Tyr  His  Gly  Ala  Gly  Thr  Arg  Thr  Ile  Ala  Ser  Pro  Lys  Gly  Pro  Val
               35                     40                      45

ATC  CAG  ATG  TAT  ACC  AAT  GTA  GAC  CAA  GAC  CTT  GTG  GGC  TGG  CCC  GCT    192
Ile  Gln  Met  Tyr  Thr  Asn  Val  Asp  Gln  Asp  Leu  Val  Gly  Trp  Pro  Ala
          50                     55                      60

TCG  CAA  GGT  ACC  CGC  TCA  TTG  ACA  CCC  TGC  ACT  TGC  GGC  TCC  TCG  GAC    240
Ser  Gln  Gly  Thr  Arg  Ser  Leu  Thr  Pro  Cys  Thr  Cys  Gly  Ser  Ser  Asp
65                     70                      75                           80
```

| | | | | | | | | | | | | | | | | |
|---|---|---|---|---|---|---|---|---|---|---|---|---|---|---|---|---|
|CTT|TAC|CTG|GTC|ACG|AGG|CAC|GCC|GAT|GTC|ATT|CCC|GTG|CGC|CGG|CGG|288|
|Leu|Tyr|Leu|Val|Thr 85|Arg|His|Ala|Asp|Val 90|Ile|Pro|Val|Arg|Arg 95|Arg||
|GGT|GAT|AGC|AGG|GGC|AGC|CTC|GTG|TCG|CCC|CGG|CCC|ATT|TCC|TAC|TTG|336|
|Gly|Asp|Ser|Arg 100|Gly|Ser|Leu|Val|Ser 105|Pro|Arg|Pro|Ile|Ser 110|Tyr|Leu||
|AAA|GGC|TCC|TCG|GGG|GGT|CCG|CTG|CCG|AAT|TC| | | | | |368|
|Lys|Gly|Ser 115|Ser|Gly|Gly|Pro|Leu 120|Pro|Asn| | | | | | | |

( 2 ) INFORMATION FOR SEQ ID NO:72:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

| | | | | | | | | | | | | | | | |
|---|---|---|---|---|---|---|---|---|---|---|---|---|---|---|---|
|Asn 1|Ser|Glu|Asn|Gln 5|Val|Glu|Gly|Glu|Val 10|Gln|Ile|Val|Ser|Thr 15|Ala|
|Ala|Gln|Thr|Phe 20|Leu|Ala|Thr|Cys|Ile 25|Asn|Gly|Val|Cys|Trp 30|Thr|Val|
|Tyr|His|Gly 35|Ala|Gly|Thr|Arg|Thr 40|Ile|Ala|Ser|Pro|Lys 45|Gly|Pro|Val|
|Ile|Gln 50|Met|Tyr|Thr|Asn|Val 55|Asp|Gln|Asp|Leu|Val 60|Gly|Trp|Pro|Ala|
|Ser 65|Gln|Gly|Thr|Arg|Ser 70|Leu|Thr|Pro|Cys|Thr 75|Cys|Gly|Ser|Ser|Asp 80|
|Leu|Tyr|Leu|Val|Thr 85|Arg|His|Ala|Asp|Val 90|Ile|Pro|Val|Arg|Arg 95|Arg|
|Gly|Asp|Ser|Arg 100|Gly|Ser|Leu|Val|Ser 105|Pro|Arg|Pro|Ile|Ser 110|Tyr|Leu|
|Lys|Gly|Ser 115|Ser|Gly|Gly|Pro|Leu 120|Pro|Asn| | | | | | |

( 2 ) INFORMATION FOR SEQ ID NO:73:

( i ) SEQUENCE CHARACTERISTICS:
        ( A ) LENGTH: 208 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..207

( x i ) SEQUENCE DESCRIPTION: SEQ ID NO:73:

| | | | | | | | | | | | | | | | | |
|---|---|---|---|---|---|---|---|---|---|---|---|---|---|---|---|---|
|GAA|TTC|GGG|GGC|CTG|CTG|TTG|TGC|CCC|GCG|GCA|GCC|GTG|GGC|ATA|TTT|48|
|Glu 1|Phe|Gly|Gly|Leu 5|Leu|Leu|Cys|Pro|Ala 10|Ala|Ala|Val|Gly|Ile 15|Phe||
|AGG|GCC|GCG|GTG|TGC|ACC|CGT|GGA|GTG|GCT|AAG|GCG|GTG|GAC|TTT|ATC|96|
|Arg|Ala|Ala|Val 20|Cys|Thr|Arg|Gly|Val 25|Ala|Lys|Ala|Val|Asp 30|Phe|Ile||
|CCT|GTG|GAG|AAC|CTA|GAG|ACA|ACC|ATG|AGG|TCC|CCG|GTG|TTC|ACG|GAT|144|
|Pro|Val|Glu 35|Asn|Leu|Glu|Thr|Thr 40|Met|Arg|Ser|Pro|Val 45|Phe|Thr|Asp||
|AAC|TCC|TCT|CCA|CCA|GTA|GTG|CCC|CAG|AGC|TTC|CAG|GTG|GCT|CAC|CTC|192|
|Asn|Ser|Ser 50|Pro|Pro|Val|Val 55|Pro|Gln|Ser|Phe|Gln 60|Val|Ala|His|Leu||

```
CAT GCT CCC CGA ATT C                                                                                            208
His Ala Pro Arg Ile
65
```

( 2 ) INFORMATION FOR SEQ ID NO:74:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( x i ) SEQUENCE DESCRIPTION: SEQ ID NO:74:

```
Glu Phe Gly Gly Leu Leu Leu Cys Pro Ala Ala Ala Val Gly Ile Phe
 1               5                   10                  15

Arg Ala Ala Val Cys Thr Arg Gly Val Ala Lys Ala Val Asp Phe Ile
            20                  25                  30

Pro Val Glu Asn Leu Glu Thr Thr Met Arg Ser Pro Val Phe Thr Asp
        35                  40                  45

Asn Ser Ser Pro Pro Val Val Pro Gln Ser Phe Gln Val Ala His Leu
    50                  55                  60

His Ala Pro Arg Ile
65
```

( 2 ) INFORMATION FOR SEQ ID NO:75:

( i ) SEQUENCE CHARACTERISTICS:
        ( A ) LENGTH: 281 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..279

( x i ) SEQUENCE DESCRIPTION: SEQ ID NO:75:

```
CCC TGC ACT TGC GGC TCC TCG GAC CTT TAC CTG GTC ACG AGG CAC GCC                48
Pro Cys Thr Cys Gly Ser Ser Asp Leu Tyr Leu Val Thr Arg His Ala
 1               5                   10                  15

GAT GTC ATT CCC GTG CGC GGG CGG GGT GAT AGC AGG GGC AGC CTG CTG                96
Asp Val Ile Pro Val Arg Arg Arg Gly Asp Ser Arg Gly Ser Leu Leu
            20                  25                  30

TCG CCC CGG CCC ATT TCC TAC TTG AAA GGC TCC TCG GGG GGT CCG CTG               144
Ser Pro Arg Pro Ile Ser Tyr Leu Lys Gly Ser Ser Gly Gly Pro Leu
        35                  40                  45

TTG TGC CCC GCG GGG CAC GCC GTG GGC ATA TTT AGG GCC GCG GTG TGC               192
Leu Cys Pro Ala Gly His Ala Val Gly Ile Phe Arg Ala Ala Val Cys
    50                  55                  60

ACC CGT GGA GTG GCT AAG GCG GTG GAC TTT ATC CCT GTG GAG AAC CTA               240
Thr Arg Gly Val Ala Lys Ala Val Asp Phe Ile Pro Val Glu Asn Leu
65                  70                  75                  80

GAG ACA ACC ATG AGG TCC CCG GTG TTC ACG GAT AAC TCC TC                        281
Glu Thr Thr Met Arg Ser Pro Val Phe Thr Asp Asn Ser
                85                  90
```

( 2 ) INFORMATION FOR SEQ ID NO:76:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

| Pro | Cys | Thr | Cys | Gly | Ser | Ser | Asp | Leu | Tyr | Leu | Val | Thr | Arg | His | Ala |
|---|---|---|---|---|---|---|---|---|---|---|---|---|---|---|---|
| 1 | | | | 5 | | | | | 10 | | | | | 15 | |

| Asp | Val | Ile | Pro | Val | Arg | Arg | Arg | Gly | Asp | Ser | Arg | Gly | Ser | Leu | Leu |
|---|---|---|---|---|---|---|---|---|---|---|---|---|---|---|---|
| | | | 20 | | | | | 25 | | | | | 30 | | |

| Ser | Pro | Arg | Pro | Ile | Ser | Tyr | Leu | Lys | Gly | Ser | Ser | Gly | Gly | Pro | Leu |
|---|---|---|---|---|---|---|---|---|---|---|---|---|---|---|---|
| | | 35 | | | | | 40 | | | | | 45 | | | |

| Leu | Cys | Pro | Ala | Gly | His | Ala | Val | Gly | Ile | Phe | Arg | Ala | Ala | Val | Cys |
|---|---|---|---|---|---|---|---|---|---|---|---|---|---|---|---|
| | 50 | | | | | 55 | | | | | | 60 | | | |

| Thr | Arg | Gly | Val | Ala | Lys | Ala | Val | Asp | Phe | Ile | Pro | Val | Glu | Asn | Leu |
|---|---|---|---|---|---|---|---|---|---|---|---|---|---|---|---|
| 65 | | | | | 70 | | | | | 75 | | | | | 80 |

| Glu | Thr | Thr | Met | Arg | Ser | Pro | Val | Phe | Thr | Asp | Asn | Ser |
|---|---|---|---|---|---|---|---|---|---|---|---|---|
| | | | | 85 | | | | | 90 | | | |

( 2 ) INFORMATION FOR SEQ ID NO:77:

( i ) SEQUENCE CHARACTERISTICS:
( A ) LENGTH: 416 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 1..414

( x i ) SEQUENCE DESCRIPTION: SEQ ID NO:77:

| ATT | CGG | GGC | ACC | TAT | GTT | TAT | AAC | CAT | CTC | ACT | CCT | CTT | CGG | GAC | TGG | 48 |
|---|---|---|---|---|---|---|---|---|---|---|---|---|---|---|---|---|
| Ile | Arg | Gly | Thr | Tyr | Val | Tyr | Asn | His | Leu | Thr | Pro | Leu | Arg | Asp | Trp | |
| 1 | | | | 5 | | | | | 10 | | | | | 15 | | |

| GCG | CAC | AAC | GGC | TTG | CGA | GAT | CTG | GCC | GTG | GCT | GTA | GAG | CCA | GTC | GTC | 96 |
|---|---|---|---|---|---|---|---|---|---|---|---|---|---|---|---|---|
| Ala | His | Asn | Gly | Leu | Arg | Asp | Leu | Ala | Val | Ala | Val | Glu | Pro | Val | Val | |
| | | | 20 | | | | | 25 | | | | | 30 | | | |

| TTC | TCC | CAA | ATG | GAG | ACC | AAG | CTC | ATC | ACG | TGG | GGG | GCA | GAT | ACC | GCC | 144 |
|---|---|---|---|---|---|---|---|---|---|---|---|---|---|---|---|---|
| Phe | Ser | Gln | Met | Glu | Thr | Lys | Leu | Ile | Thr | Trp | Gly | Ala | Asp | Thr | Ala | |
| | | | 35 | | | | | 40 | | | | | 45 | | | |

| GCG | TGC | GGT | GAC | ATC | ATC | AAC | GGC | TTG | CCT | GTT | TCC | GCC | CGC | AGG | GGC | 192 |
|---|---|---|---|---|---|---|---|---|---|---|---|---|---|---|---|---|
| Ala | Cys | Gly | Asp | Ile | Ile | Asn | Gly | Leu | Pro | Val | Ser | Ala | Arg | Arg | Gly | |
| | | 50 | | | | | 55 | | | | | 60 | | | | |

| CGG | GAG | ATA | CTG | CTC | GGG | CCA | GCC | GAT | GGA | ATG | GTC | TCC | AAG | GGT | TGG | 240 |
|---|---|---|---|---|---|---|---|---|---|---|---|---|---|---|---|---|
| Arg | Glu | Ile | Leu | Leu | Gly | Pro | Ala | Asp | Gly | Met | Val | Ser | Lys | Gly | Trp | |
| 65 | | | | | 70 | | | | | 75 | | | | | 80 | |

| AGG | TTG | CTG | GCG | CCC | ATC | ACG | GCG | TAC | GCC | CAG | CAG | ACA | AGG | GGC | CTC | 288 |
|---|---|---|---|---|---|---|---|---|---|---|---|---|---|---|---|---|
| Arg | Leu | Leu | Ala | Pro | Ile | Thr | Ala | Tyr | Ala | Gln | Gln | Thr | Arg | Gly | Leu | |
| | | | | 85 | | | | | 90 | | | | | 95 | | |

| CTA | GGG | TGC | ATA | ATC | ACC | AGC | CTA | ACT | GGC | CGG | GAC | AAA | AAC | CAA | GTG | 336 |
|---|---|---|---|---|---|---|---|---|---|---|---|---|---|---|---|---|
| Leu | Gly | Cys | Ile | Ile | Thr | Ser | Leu | Thr | Gly | Arg | Asp | Lys | Asn | Gln | Val | |
| | | | 100 | | | | | 105 | | | | | 110 | | | |

| GAG | GGT | GAG | GTC | CAG | ATT | GTG | TCA | ACT | GCT | GCC | CAA | ACC | TTC | CTG | GCA | 384 |
|---|---|---|---|---|---|---|---|---|---|---|---|---|---|---|---|---|
| Glu | Gly | Glu | Val | Gln | Ile | Val | Ser | Thr | Ala | Ala | Gln | Thr | Phe | Leu | Ala | |
| | | | 115 | | | | | 120 | | | | | 125 | | | |

| ACG | TGC | ATC | AAT | GGG | GTG | TGC | TGG | CCG | AAT | TC | | | | | | 416 |
|---|---|---|---|---|---|---|---|---|---|---|---|---|---|---|---|---|
| Thr | Cys | Ile | Asn | Gly | Val | Cys | Trp | Pro | Asn | | | | | | | |
| | 130 | | | | | 135 | | | | | | | | | | |

( 2 ) INFORMATION FOR SEQ ID NO:78:

( i ) SEQUENCE CHARACTERISTICS:
( A ) LENGTH: 138 amino acids
( B ) TYPE: amino acid
( D ) TOPOLOGY: linear ( i i ) MOLECULE TYPE: protein ( x i ) SEQUENCE DESCRIPTION: SEQ ID NO:78:

| Ile | Arg | Gly | Thr | Tyr | Val | Tyr | Asn | His | Leu | Thr | Pro | Leu | Arg | Asp | Trp |
|---|---|---|---|---|---|---|---|---|---|---|---|---|---|---|---|
| 1 | | | | 5 | | | | | 10 | | | | | 15 | |

| Ala | His | Asn | Gly | Leu | Arg | Asp | Leu | Ala | Val | Ala | Val | Glu | Pro | Val | Val |
|---|---|---|---|---|---|---|---|---|---|---|---|---|---|---|---|
| | | | 20 | | | | | 25 | | | | | 30 | | |

| Phe | Ser | Gln | Met | Glu | Thr | Lys | Leu | Ile | Thr | Trp | Gly | Ala | Asp | Thr | Ala |
|---|---|---|---|---|---|---|---|---|---|---|---|---|---|---|---|
| | | 35 | | | | | 40 | | | | | 45 | | | |

| Ala | Cys | Gly | Asp | Ile | Ile | Asn | Gly | Leu | Pro | Val | Ser | Ala | Arg | Arg | Gly |
|---|---|---|---|---|---|---|---|---|---|---|---|---|---|---|---|
| | 50 | | | | | 55 | | | | | 60 | | | | |

| Arg | Glu | Ile | Leu | Leu | Gly | Pro | Ala | Asp | Gly | Met | Val | Ser | Lys | Gly | Trp |
|---|---|---|---|---|---|---|---|---|---|---|---|---|---|---|---|
| 65 | | | | | 70 | | | | | 75 | | | | | 80 |

| Arg | Leu | Leu | Ala | Pro | Ile | Thr | Ala | Tyr | Ala | Gln | Gln | Thr | Arg | Gly | Leu |
|---|---|---|---|---|---|---|---|---|---|---|---|---|---|---|---|
| | | | | 85 | | | | | 90 | | | | | 95 | |

| Leu | Gly | Cys | Ile | Ile | Thr | Ser | Leu | Thr | Gly | Arg | Asp | Lys | Asn | Gln | Val |
|---|---|---|---|---|---|---|---|---|---|---|---|---|---|---|---|
| | | | 100 | | | | | 105 | | | | | 110 | | |

| Glu | Gly | Glu | Val | Gln | Ile | Val | Ser | Thr | Ala | Ala | Gln | Thr | Phe | Leu | Ala |
|---|---|---|---|---|---|---|---|---|---|---|---|---|---|---|---|
| | | 115 | | | | | 120 | | | | | 125 | | | |

| Thr | Cys | Ile | Asn | Gly | Val | Cys | Trp | Pro | Asn |
|---|---|---|---|---|---|---|---|---|---|
| | 130 | | | | | 135 | | | |

( 2 ) INFORMATION FOR SEQ ID NO:79:

( i ) SEQUENCE CHARACTERISTICS:
    ( A ) LENGTH: 308 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 1..306

( x i ) SEQUENCE DESCRIPTION: SEQ ID NO:79:

| GAA | TTC | GGG | TCC | GTC | ATC | CCG | ACC | AGC | GGC | GAT | GTT | GTC | GTC | GTC | GCA | 48 |
|---|---|---|---|---|---|---|---|---|---|---|---|---|---|---|---|---|
| Glu | Phe | Gly | Ser | Val | Ile | Pro | Thr | Ser | Gly | Asp | Val | Val | Val | Val | Ala | |
| 1 | | | | 5 | | | | | 10 | | | | | 15 | | |

| ACC | GAT | GCC | CTC | ATG | ACC | GGC | TAT | ACC | GGC | GAC | TTC | GAC | TCG | GTG | ATA | 96 |
|---|---|---|---|---|---|---|---|---|---|---|---|---|---|---|---|---|
| Thr | Asp | Ala | Leu | Met | Thr | Gly | Tyr | Thr | Gly | Asp | Phe | Asp | Ser | Val | Ile | |
| | | | 20 | | | | | 25 | | | | | 30 | | | |

| GAC | TGC | AAT | ACG | TGT | GTC | ACC | CAG | ACA | GTC | GAT | TTC | AGC | CTT | GAC | CCT | 144 |
|---|---|---|---|---|---|---|---|---|---|---|---|---|---|---|---|---|
| Asp | Cys | Asn | Thr | Cys | Val | Thr | Gln | Thr | Val | Asp | Phe | Ser | Leu | Asp | Pro | |
| | | 35 | | | | | 40 | | | | | 45 | | | | |

| ACC | TTC | ACC | ATT | GAG | ACA | ATC | ACG | CTC | CCC | CAA | GAT | GCT | GTC | TCC | CGC | 192 |
|---|---|---|---|---|---|---|---|---|---|---|---|---|---|---|---|---|
| Thr | Phe | Thr | Ile | Glu | Thr | Ile | Thr | Leu | Pro | Gln | Asp | Ala | Val | Ser | Arg | |
| | 50 | | | | | 55 | | | | | 60 | | | | | |

| ACT | CAA | CGT | CGG | GGC | AGG | ACT | GGC | AGG | GGG | AAG | CCA | GGC | ATC | TAC | AGA | 240 |
|---|---|---|---|---|---|---|---|---|---|---|---|---|---|---|---|---|
| Thr | Gln | Arg | Arg | Gly | Arg | Thr | Gly | Arg | Gly | Lys | Pro | Gly | Ile | Tyr | Arg | |
| 65 | | | | | 70 | | | | | 75 | | | | | 80 | |

| TTT | GTG | GCA | CCG | GGG | GAG | CGC | CCC | TCC | GGC | ATG | TTC | GAC | TCG | TCC | GTC | 288 |
|---|---|---|---|---|---|---|---|---|---|---|---|---|---|---|---|---|
| Phe | Val | Ala | Pro | Gly | Glu | Arg | Pro | Ser | Gly | Met | Phe | Asp | Ser | Ser | Val | |
| | | | | 85 | | | | | 90 | | | | | 95 | | |

| CTC | TGT | GAG | TGC | CCG | AAT | TC | | | | | | | | | | 308 |
|---|---|---|---|---|---|---|---|---|---|---|---|---|---|---|---|---|
| Leu | Cys | Glu | Cys | Pro | Asn | | | | | | | | | | | |
| | | | 100 | | | | | | | | | | | | | |

( 2 ) INFORMATION FOR SEQ ID NO:80:

( i ) SEQUENCE CHARACTERISTICS:
    ( A ) LENGTH: 102 amino acids
    ( B ) TYPE: amino acid
    ( D ) TOPOLOGY: linear ( i i ) MOLECULE TYPE: protein ( x i ) SEQUENCE DESCRIPTION: SEQ ID NO:80:

| Glu | Phe | Gly | Ser | Val | Ile | Pro | Thr | Ser | Gly | Asp | Val | Val | Val | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Thr | Asp | Ala | Leu | Met | Thr | Gly | Tyr | Thr | Gly | Asp | Phe | Asp | Ser | Val | Ile |
|-----|-----|-----|-----|-----|-----|-----|-----|-----|-----|-----|-----|-----|-----|-----|-----|
|     |     |     | 20  |     |     |     |     | 25  |     |     |     | 30  |     |     |     |

| Asp | Cys | Asn | Thr | Cys | Val | Thr | Gln | Thr | Val | Asp | Phe | Ser | Leu | Asp | Pro |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Phe | Thr | Ile | Glu | Thr | Ile | Thr | Leu | Pro | Gln | Asp | Ala | Val | Ser | Arg |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Gln | Arg | Arg | Gly | Arg | Thr | Gly | Arg | Gly | Lys | Pro | Gly | Ile | Tyr | Arg |
|-----|-----|-----|-----|-----|-----|-----|-----|-----|-----|-----|-----|-----|-----|-----|-----|
| 65  |     |     |     |     | 70  |     |     |     | 75  |     |     |     |     |     | 80  |

| Phe | Val | Ala | Pro | Gly | Glu | Arg | Pro | Ser | Gly | Met | Phe | Asp | Ser | Ser | Val |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Cys | Glu | Cys | Pro | Asn |
|-----|-----|-----|-----|-----|-----|
|     |     |     | 100 |     |     |

( 2 ) INFORMATION FOR SEQ ID NO:81:

( i ) SEQUENCE CHARACTERISTICS:
 ( A ) LENGTH: 495 base pairs
 ( B ) TYPE: nucleic acid
 ( C ) STRANDEDNESS: single
 ( D ) TOPOLOGY: linear ( i x ) FEATURE:
 ( A ) NAME/KEY: CDS
 ( B ) LOCATION: 1..495

( x i ) SEQUENCE DESCRIPTION: SEQ ID NO:81:

| ATT | CGG | TCC | ATT | GAG | ACA | ATC | ACG | CTC | CCC | CAG | GAT | GCT | GTC | TCC | CGC | 48 |
|-----|-----|-----|-----|-----|-----|-----|-----|-----|-----|-----|-----|-----|-----|-----|-----|-----|
| Ile | Arg | Ser | Ile | Glu | Thr | Ile | Thr | Leu | Pro | Gln | Asp | Ala | Val | Ser | Arg | |
| 1   |     |     |     | 5   |     |     |     |     | 10  |     |     |     |     | 15  |     | |

| ACT | CAA | CGT | CGG | GGC | AGG | ACT | GGC | AGG | GGG | AAG | CCA | GGC | ATC | TAC | AGA | 96 |
|-----|-----|-----|-----|-----|-----|-----|-----|-----|-----|-----|-----|-----|-----|-----|-----|-----|
| Thr | Gln | Arg | Arg | Gly | Arg | Thr | Gly | Arg | Gly | Lys | Pro | Gly | Ile | Tyr | Arg | |
|     |     |     | 20  |     |     |     |     | 25  |     |     |     |     | 30  |     |     | |

| TTT | GTG | GCA | CCG | GGG | GAG | CGC | CCC | TCC | GGC | ATG | TTC | GAC | TCG | TCC | GTC | 144 |
|-----|-----|-----|-----|-----|-----|-----|-----|-----|-----|-----|-----|-----|-----|-----|-----|-----|
| Phe | Val | Ala | Pro | Gly | Glu | Arg | Pro | Ser | Gly | Met | Phe | Asp | Ser | Ser | Val | |
|     |     |     | 35  |     |     |     |     | 40  |     |     |     |     | 45  |     |     | |

| CTC | TGT | GAG | TGC | TAT | GAC | GCA | GGC | TGT | GCT | TGG | TAT | GAG | CTC | ACG | CCC | 192 |
|-----|-----|-----|-----|-----|-----|-----|-----|-----|-----|-----|-----|-----|-----|-----|-----|-----|
| Leu | Cys | Glu | Cys | Tyr | Asp | Ala | Gly | Cys | Ala | Trp | Tyr | Glu | Leu | Thr | Pro | |
|     |     | 50  |     |     |     |     | 55  |     |     |     |     | 60  |     |     |     | |

| GCC | GAG | ACT | ACA | GTT | AGG | CTA | CGA | GCG | TAC | ATG | AAC | ACC | CCG | GGG | CTT | 240 |
|-----|-----|-----|-----|-----|-----|-----|-----|-----|-----|-----|-----|-----|-----|-----|-----|-----|
| Ala | Glu | Thr | Thr | Val | Arg | Leu | Arg | Ala | Tyr | Met | Asn | Thr | Pro | Gly | Leu | |
| 65  |     |     |     |     | 70  |     |     |     |     | 75  |     |     |     |     | 80  | |

| CCC | GTG | TGC | CAG | GAC | CAT | CTT | GAA | TTT | TGG | GAG | GGC | GTC | TTT | ACA | GGC | 288 |
|-----|-----|-----|-----|-----|-----|-----|-----|-----|-----|-----|-----|-----|-----|-----|-----|-----|
| Pro | Val | Cys | Gln | Asp | His | Leu | Glu | Phe | Trp | Glu | Gly | Val | Phe | Thr | Gly | |
|     |     |     |     | 85  |     |     |     |     | 90  |     |     |     |     | 95  |     | |

| CTC | ACT | CAT | ATA | GAT | GCC | CAC | TTT | CTA | TCC | CAG | ACA | AAG | CAG | AGT | GGG | 336 |
|-----|-----|-----|-----|-----|-----|-----|-----|-----|-----|-----|-----|-----|-----|-----|-----|-----|
| Leu | Thr | His | Ile | Asp | Ala | His | Phe | Leu | Ser | Gln | Thr | Lys | Gln | Ser | Gly | |
|     |     |     | 100 |     |     |     |     | 105 |     |     |     |     | 110 |     |     | |

| GAG | AAC | CTT | CCT | TAC | CTG | GTA | GCG | TAC | CAA | GCC | ACC | GTG | TGC | GCT | AGG | 384 |
|-----|-----|-----|-----|-----|-----|-----|-----|-----|-----|-----|-----|-----|-----|-----|-----|-----|
| Glu | Asn | Leu | Pro | Tyr | Leu | Val | Ala | Tyr | Gln | Ala | Thr | Val | Cys | Ala | Arg | |
|     |     |     | 115 |     |     |     |     | 120 |     |     |     |     | 125 |     |     | |

| GCT | CAA | GCC | CCT | CCC | CCA | TCG | TGG | GAC | CAG | ATG | TGG | AAG | TGT | TTG | ATT | 432 |
|-----|-----|-----|-----|-----|-----|-----|-----|-----|-----|-----|-----|-----|-----|-----|-----|-----|
| Ala | Gln | Ala | Pro | Pro | Pro | Ser | Trp | Asp | Gln | Met | Trp | Lys | Cys | Leu | Ile | |
|     |     | 130 |     |     |     |     | 135 |     |     |     |     | 140 |     |     |     | |

| CGC | CTC | AAG | CCC | ACC | CTC | CAT | GGG | CCA | ACA | CCC | CTG | CTA | TAC | AGA | CTG | 480 |
|-----|-----|-----|-----|-----|-----|-----|-----|-----|-----|-----|-----|-----|-----|-----|-----|-----|
| Arg | Leu | Lys | Pro | Thr | Leu | His | Gly | Pro | Thr | Pro | Leu | Leu | Tyr | Arg | Leu | |
| 145 |     |     |     |     | 150 |     |     |     |     | 155 |     |     |     |     | 160 | |

```
GGC GCT GCC GAA TTC                                                                    495
Gly Ala Ala Glu Phe
              1 6 5
```

( 2 ) INFORMATION FOR SEQ ID NO:82:

( i ) SEQUENCE CHARACTERISTICS:
        ( A ) LENGTH: 165 amino acids
        ( B ) TYPE: amino acid
        ( D ) TOPOLOGY: linear ( i i ) MOLECULE TYPE: protein ( x i ) SEQUENCE DESCRIPTION: SEQ ID NO:82:

```
Ile Arg Ser Ile Glu Thr Ile Thr Leu Pro Gln Asp Ala Val Ser Arg
 1               5                  1 0                     1 5

Thr Gln Arg Arg Gly Arg Thr Gly Arg Gly Lys Pro Gly Ile Tyr Arg
              2 0                  2 5                  3 0

Phe Val Ala Pro Gly Glu Arg Pro Ser Gly Met Phe Asp Ser Ser Val
          3 5                  4 0                  4 5

Leu Cys Glu Cys Tyr Asp Ala Gly Cys Ala Trp Tyr Glu Leu Thr Pro
      5 0                  5 5                  6 0

Ala Glu Thr Thr Val Arg Leu Arg Ala Tyr Met Asn Thr Pro Gly Leu
6 5                  7 0                  7 5                  8 0

Pro Val Cys Gln Asp His Leu Glu Phe Trp Glu Gly Val Phe Thr Gly
              8 5                  9 0                  9 5

Leu Thr His Ile Asp Ala His Phe Leu Ser Gln Thr Lys Gln Ser Gly
              1 0 0               1 0 5               1 1 0

Glu Asn Leu Pro Tyr Leu Val Ala Tyr Gln Ala Thr Val Cys Ala Arg
          1 1 5               1 2 0               1 2 5

Ala Gln Ala Pro Pro Pro Ser Trp Asp Gln Met Trp Lys Cys Leu Ile
1 3 0               1 3 5               1 4 0

Arg Leu Lys Pro Thr Leu His Gly Pro Thr Pro Leu Leu Tyr Arg Leu
1 4 5               1 5 0               1 5 5               1 6 0

Gly Ala Ala Glu Phe
              1 6 5
```

( 2 ) INFORMATION FOR SEQ ID NO:83:

( i ) SEQUENCE CHARACTERISTICS:
        ( A ) LENGTH: 816 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..816

( x i ) SEQUENCE DESCRIPTION: SEQ ID NO:83:

```
GAA TTC GGG GCG GTG GAC TTT ATC CCT GTG GAG AAC CTA GAG ACA ACC        4 8
Glu Phe Gly Ala Val Asp Phe Ile Pro Val Glu Asn Leu Glu Thr Thr
 1               5                  1 0                     1 5

ATG AGG TCC CCG GTG TTC ACG GAT AAC TCC TCT CCA CCA GTA GTG CCC        9 6
Met Arg Ser Pro Val Phe Thr Asp Asn Ser Ser Pro Pro Val Val Pro
              2 0                  2 5                  3 0

CAG AGC TTC CAG GTG GCT CAC CTC CAT GCT CCC ACA GGC AGC GGC AAA       1 4 4
Gln Ser Phe Gln Val Ala His Leu His Ala Pro Thr Gly Ser Gly Lys
          3 5                  4 0                  4 5

AGC ACC AAG GTC CCG GCT GCA TAT GCA GCT CAG GGC TAT AAG GTG CTA       1 9 2
Ser Thr Lys Val Pro Ala Ala Tyr Ala Ala Gln Gly Tyr Lys Val Leu
      5 0                  5 5                  6 0
```

| | | | | | | | | | | | | | | | | |
|---|---|---|---|---|---|---|---|---|---|---|---|---|---|---|---|---|
| GTA | CTC | AAC | CCC | TCT | GTT | GCT | GCA | ACA | CTG | GGC | TTT | GGT | GCT | TAC | ATG | 240 |
| Val | Leu | Asn | Pro | Ser | Val | Ala | Ala | Thr | Leu | Gly | Phe | Gly | Ala | Tyr | Met | |
| 65 | | | | 70 | | | | | 75 | | | | | | 80 | |
| TCC | AAG | GCT | CAT | GGG | ATC | GAT | CCT | AAC | ATC | AGG | ACC | GGG | GTG | AGA | ACA | 288 |
| Ser | Lys | Ala | His | Gly | Ile | Asp | Pro | Asn | Ile | Arg | Thr | Gly | Val | Arg | Thr | |
| | | | | 85 | | | | | 90 | | | | | 95 | | |
| ATT | ACC | ACT | GGC | AGC | CCC | ATC | ACG | TAC | TCC | ACC | TAC | GGC | AAG | TTC | CTT | 336 |
| Ile | Thr | Thr | Gly | Ser | Pro | Ile | Thr | Tyr | Ser | Thr | Tyr | Gly | Lys | Phe | Leu | |
| | | | 100 | | | | | 105 | | | | | 110 | | | |
| GCC | GAC | GGC | GGG | TGC | TCG | GGG | GGC | GCT | TAT | GAC | ATA | ATA | ATT | TGT | GAC | 384 |
| Ala | Asp | Gly | Gly | Cys | Ser | Gly | Gly | Ala | Tyr | Asp | Ile | Ile | Ile | Cys | Asp | |
| | | | 115 | | | | 120 | | | | | 125 | | | | |
| GAG | TGC | CAC | TCC | ACG | GAT | GCC | ACA | TCC | ATC | TTG | GGC | ATT | GGC | ACT | GTC | 432 |
| Glu | Cys | His | Ser | Thr | Asp | Ala | Thr | Ser | Ile | Leu | Gly | Ile | Gly | Thr | Val | |
| | 130 | | | | | 135 | | | | | 140 | | | | | |
| CTT | GAC | CAA | GCA | GAG | ACT | GCG | GGG | GCG | AGA | CTG | GTT | GTG | CTC | GCC | ACC | 480 |
| Leu | Asp | Gln | Ala | Glu | Thr | Ala | Gly | Ala | Arg | Leu | Val | Val | Leu | Ala | Thr | |
| 145 | | | | | 150 | | | | | 155 | | | | | 160 | |
| GCC | ACC | CCT | CCG | GGC | TCC | GTC | ACT | GTG | CCC | CAT | CCC | AAC | ATC | GAG | GAG | 528 |
| Ala | Thr | Pro | Pro | Gly | Ser | Val | Thr | Val | Pro | His | Pro | Asn | Ile | Glu | Glu | |
| | | | | 165 | | | | | 170 | | | | | 175 | | |
| GTT | GCT | CTG | TCC | ACC | ACC | GGA | GAG | ATC | CCT | TTT | TAC | GGC | AAG | GCT | ATC | 576 |
| Val | Ala | Leu | Ser | Thr | Thr | Gly | Glu | Ile | Pro | Phe | Tyr | Gly | Lys | Ala | Ile | |
| | | | 180 | | | | | 185 | | | | | 190 | | | |
| CCC | CTC | GAA | GTA | ATC | AAG | GGG | GGG | AGA | CAT | CTC | ATC | TTC | TGT | CAT | TCA | 624 |
| Pro | Leu | Glu | Val | Ile | Lys | Gly | Gly | Arg | His | Leu | Ile | Phe | Cys | His | Ser | |
| | | 195 | | | | | 200 | | | | | 205 | | | | |
| AAG | AAG | AAG | TGC | GAC | GAA | CTC | GCC | GCA | AAG | CTG | GTC | GCA | TTG | GGC | ATC | 672 |
| Lys | Lys | Lys | Cys | Asp | Glu | Leu | Ala | Ala | Lys | Leu | Val | Ala | Leu | Gly | Ile | |
| 210 | | | | | 215 | | | | | 220 | | | | | | |
| AAT | GCC | GTG | GCC | TAC | TAC | CGC | GGT | CTT | GAC | GTG | TCC | GTC | ATC | CCG | ACC | 720 |
| Asn | Ala | Val | Ala | Tyr | Tyr | Arg | Gly | Leu | Asp | Val | Ser | Val | Ile | Pro | Thr | |
| 225 | | | | | 230 | | | | | 235 | | | | | 240 | |
| AGC | GGC | GAT | GTT | GTC | GTC | GTG | GCA | ACC | GAT | GCC | CTC | ATG | ACC | GGC | TAT | 768 |
| Ser | Gly | Asp | Val | Val | Val | Val | Ala | Thr | Asp | Ala | Leu | Met | Thr | Gly | Tyr | |
| | | | 245 | | | | | 250 | | | | | 255 | | | |
| ACC | GGC | GAC | TTC | GAC | TCG | GTG | ATA | GAC | TGC | AAT | ACG | TGT | GCC | GAA | TTC | 816 |
| Thr | Gly | Asp | Phe | Asp | Ser | Val | Ile | Asp | Cys | Asn | Thr | Cys | Ala | Glu | Phe | |
| | | | 260 | | | | | 265 | | | | | 270 | | | |

( 2 ) INFORMATION FOR SEQ ID NO:84:

( i ) SEQUENCE CHARACTERISTICS:
        ( A ) LENGTH: 272 amino acids
        ( B ) TYPE: amino acid
        ( D ) TOPOLOGY: linear ( i i ) MOLECULE TYPE: protein ( x i ) SEQUENCE DESCRIPTION: SEQ ID NO:84:

| | | | | | | | | | | | | | | |
|---|---|---|---|---|---|---|---|---|---|---|---|---|---|---|
| Glu | Phe | Gly | Ala | Val | Asp | Phe | Ile | Pro | Val | Glu | Asn | Leu | Glu | Thr | Thr |
| 1 | | | | 5 | | | | | 10 | | | | | 15 | |
| Met | Arg | Ser | Pro | Val | Phe | Thr | Asp | Asn | Ser | Ser | Pro | Pro | Val | Val | Pro |
| | | | 20 | | | | | 25 | | | | | 30 | | |
| Gln | Ser | Phe | Gln | Val | Ala | His | Leu | His | Ala | Pro | Thr | Gly | Ser | Gly | Lys |
| | | | 35 | | | | 40 | | | | | 45 | | | |
| Ser | Thr | Lys | Val | Pro | Ala | Ala | Tyr | Ala | Ala | Gln | Gly | Tyr | Lys | Val | Leu |
| | | 50 | | | | | 55 | | | | | 60 | | | |
| Val | Leu | Asn | Pro | Ser | Val | Ala | Ala | Thr | Leu | Gly | Phe | Gly | Ala | Tyr | Met |
| 65 | | | | | 70 | | | | | 75 | | | | | 80 |

-continued

| | | | | | | | | | | | | | | |
|---|---|---|---|---|---|---|---|---|---|---|---|---|---|---|
| Ser | Lys | Ala | His | Gly<br>85 | Ile | Asp | Pro | Asn | Ile<br>90 | Arg | Thr | Gly | Val | Arg<br>95 | Thr |
| Ile | Thr | Thr | Gly<br>100 | Ser | Pro | Ile | Thr | Tyr<br>105 | Ser | Thr | Tyr | Gly | Lys<br>110 | Phe | Leu |
| Ala | Asp | Gly<br>115 | Gly | Cys | Ser | Gly | Gly<br>120 | Ala | Tyr | Asp | Ile | Ile<br>125 | Ile | Cys | Asp |
| Glu | Cys<br>130 | His | Ser | Thr | Asp | Ala<br>135 | Thr | Ser | Ile | Leu | Gly<br>140 | Ile | Gly | Thr | Val |
| Leu<br>145 | Asp | Gln | Ala | Glu | Thr<br>150 | Ala | Gly | Ala | Arg | Leu<br>155 | Val | Val | Leu | Ala | Thr<br>160 |
| Ala | Thr | Pro | Pro | Gly<br>165 | Ser | Val | Thr | Val | Pro<br>170 | His | Pro | Asn | Ile | Glu<br>175 | Glu |
| Val | Ala | Leu | Ser<br>180 | Thr | Thr | Gly | Glu | Ile<br>185 | Pro | Phe | Tyr | Gly | Lys<br>190 | Ala | Ile |
| Pro | Leu | Glu<br>195 | Val | Ile | Lys | Gly | Gly<br>200 | Arg | His | Leu | Ile | Phe<br>205 | Cys | His | Ser |
| Lys | Lys<br>210 | Lys | Cys | Asp | Glu | Leu<br>215 | Ala | Ala | Lys | Leu | Val<br>220 | Ala | Leu | Gly | Ile |
| Asn<br>225 | Ala | Val | Ala | Tyr | Tyr<br>230 | Arg | Gly | Leu | Asp | Val<br>235 | Ser | Val | Ile | Pro | Thr<br>240 |
| Ser | Gly | Asp | Val | Val<br>245 | Val | Val | Ala | Thr | Asp<br>250 | Ala | Leu | Met | Thr | Gly<br>255 | Tyr |
| Thr | Gly | Asp | Phe<br>260 | Asp | Ser | Val | Ile | Asp<br>265 | Cys | Asn | Thr | Cys | Ala<br>270 | Glu | Phe |

( 2 ) INFORMATION FOR SEQ ID NO:85:

( i ) SEQUENCE CHARACTERISTICS:
        ( A ) LENGTH: 2523 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..2523

( x i ) SEQUENCE DESCRIPTION: SEQ ID NO:85:

| | | | | | | | | | | | | | | | | |
|---|---|---|---|---|---|---|---|---|---|---|---|---|---|---|---|---|
| ATG<br>Met<br>1 | GCT<br>Ala | ACA<br>Thr | AAC<br>Asn | CCT<br>Pro<br>5 | GTT<br>Val | TGC<br>Cys | GTT<br>Val | TTG<br>Leu | AAG<br>Lys<br>10 | GGT<br>Gly | GAC<br>Asp | GGC<br>Gly | CCA<br>Pro | GTT<br>Val<br>15 | CAA<br>Gln | 48 |
| GGT<br>Gly | ATT<br>Ile | ATT<br>Ile | AAC<br>Asn<br>20 | TTC<br>Phe | GAG<br>Glu | CAG<br>Gln | AAG<br>Lys | GAA<br>Glu<br>25 | AGT<br>Ser | AAT<br>Asn | GGA<br>Gly | CCA<br>Pro | GTG<br>Val<br>30 | AAG<br>Lys | GTG<br>Val | 96 |
| TGG<br>Trp | GGA<br>Gly | AGC<br>Ser<br>35 | ATT<br>Ile | AAA<br>Lys | GGA<br>Gly | CTG<br>Leu | ACT<br>Thr<br>40 | GAA<br>Glu | GGC<br>Gly | CTG<br>Leu | CAT<br>His | GGA<br>Gly<br>45 | TTC<br>Phe | CAT<br>His | GTT<br>Val | 144 |
| CAT<br>His | GAG<br>Glu<br>50 | TTT<br>Phe | GGA<br>Gly | GAT<br>Asp | AAT<br>Asn | ACA<br>Thr<br>55 | GCA<br>Ala | GGC<br>Gly | TGT<br>Cys | ACC<br>Thr | AGT<br>Ser<br>60 | CCA<br>Pro | GGT<br>Gly | CCT<br>Pro | CAC<br>His | 192 |
| TTT<br>Phe<br>65 | AAT<br>Asn | CCT<br>Pro | CTA<br>Leu | TCC<br>Ser | AGA<br>Arg<br>70 | AAA<br>Lys | CAC<br>His | GGT<br>Gly | GGG<br>Gly | CCA<br>Pro<br>75 | AAG<br>Lys | GAT<br>Asp | GAA<br>Glu | GAG<br>Glu | AGG<br>Arg<br>80 | 240 |
| CAT<br>His | GTT<br>Val | GGA<br>Gly | GAC<br>Asp | TTG<br>Leu<br>85 | GGC<br>Gly | AAT<br>Asn | GTG<br>Val | ACT<br>Thr | GCT<br>Ala<br>90 | GAC<br>Asp | AAA<br>Lys | GAT<br>Asp | GGT<br>Gly | GTG<br>Val<br>95 | GCC<br>Ala | 288 |
| GAT<br>Asp | GTG<br>Val | TCT<br>Ser | ATT<br>Ile<br>100 | GAA<br>Glu | GAT<br>Asp | TCT<br>Ser | GTG<br>Val | ATC<br>Ile<br>105 | TCA<br>Ser | CTC<br>Leu | TCA<br>Ser | GGA<br>Gly | GAC<br>Asp<br>110 | CAT<br>His | TGC<br>Cys | 336 |
| ATC<br>Ile | ATT<br>Ile | GGC<br>Gly | CGC<br>Arg | ACA<br>Thr | CTG<br>Leu | GTG<br>Val | GTC<br>Val | CAT<br>His | GAA<br>Glu | AAA<br>Lys | GCA<br>Ala | GAT<br>Asp | GAC<br>Asp | TTG<br>Leu | GGC<br>Gly | 384 |

|  |  |  |  |  |  |  |  |  |  |  |  |  |  |  |  |
|---|---|---|---|---|---|---|---|---|---|---|---|---|---|---|---|
| Ile | Ile | Gly | Arg | Thr | Leu | Val | Val | His | Glu | Lys | Ala | Asp | Asp | Leu | Gly |
|  |  | 115 |  |  |  | 120 |  |  |  |  | 125 |  |  |  |  |

```
AAA GGT GGA AAT GAA GAA AGT ACA AAG ACA GGA AAC GCT GGA AGT CGT        432
Lys Gly Gly Asn Glu Glu Ser Thr Lys Thr Gly Asn Ala Gly Ser Arg
    130             135             140

TTG GCT TGT GGT GTA ATT GGG ATC CGA ATT CGG GGC ACC TAT GTT TAT        480
Leu Ala Cys Gly Val Ile Gly Ile Arg Ile Arg Gly Thr Tyr Val Tyr
145             150             155                             160

AAC CAT CTC ACT CCT CTT CGG GAC TGG GCG CAC AAC GGC TTG CGA GAT        528
Asn His Leu Thr Pro Leu Arg Asp Trp Ala His Asn Gly Leu Arg Asp
                165             170             175

CTG GCC GTG GCT GTA GAG CCA GTC GTC TTC TCC CAA ATG GAG ACC AAG        576
Leu Ala Val Ala Val Glu Pro Val Val Phe Ser Gln Met Glu Thr Lys
            180             185                 190

CTC ATC ACG TGG GGG GCA GAT ACC GCC GCG TGC GGT GAC ATC ATC AAC        624
Leu Ile Thr Trp Gly Ala Asp Thr Ala Ala Cys Gly Asp Ile Ile Asn
        195             200                 205

GGC TTG CCT GTT TCC GCC CGC AGG GGC CGG GAG ATA CTG CTC GGG CCA        672
Gly Leu Pro Val Ser Ala Arg Arg Gly Arg Glu Ile Leu Leu Gly Pro
    210             215             220

GCC GAT GGA ATG GTG TCC AAG GGT TGG AGG TTG CTG GCG CCC ATC ACG        720
Ala Asp Gly Met Val Ser Lys Gly Trp Arg Leu Leu Ala Pro Ile Thr
225             230             235                             240

GCG TAC GCC CAG CAG ACA AGG GGC CTC CTA GGG TGC ATA ATC ACC AGC        768
Ala Tyr Ala Gln Gln Thr Arg Gly Leu Leu Gly Cys Ile Ile Thr Ser
                245             250                 255

CTA ACT GGC CGG GAC AAA AAC CAA GTG GAG GGT GAG GTC CAG ATT GTG        816
Leu Thr Gly Arg Asp Lys Asn Gln Val Glu Gly Glu Val Gln Ile Val
            260             265                 270

TCA ACT GCT GCC CAA ACC TTC CTG GCA ACG TGC ATC ATC AAT GGG GTG        864
Ser Thr Ala Ala Gln Thr Phe Leu Ala Thr Cys Ile Ile Asn Gly Val
        275             280                 285

TGC TGG ACT GTC TAC CAC GGG GCC GGA ACG AGG ACC ATC GCG TCA CCC        912
Cys Trp Thr Val Tyr His Gly Ala Gly Thr Arg Thr Ile Ala Ser Pro
    290             295             300

AAG GGT CCT GTC ATC CAG ATG TAT ACC AAT GTA GAC CAA GAC CTT GTG        960
Lys Gly Pro Val Ile Gln Met Tyr Thr Asn Val Asp Gln Asp Leu Val
305             310             315                             320

GGC TGG CCC GCT TCG CAA GGT ACC CGC TCA TTG ACA CCC TGC ACT TGC       1008
Gly Trp Pro Ala Ser Gln Gly Thr Arg Ser Leu Thr Pro Cys Thr Cys
                325             330                 335

GGC TCC TCG GAC CTT TAC CTG GTC ACG AGG CAC GCC GAT GTC ATT CCC       1056
Gly Ser Ser Asp Leu Tyr Leu Val Thr Arg His Ala Asp Val Ile Pro
            340             345                 350

GTG CGC CGG CGG GGT GAT AGC AGG GGC AGC CTG CTG TCG CCC CGG CCC       1104
Val Arg Arg Arg Gly Asp Ser Arg Gly Ser Leu Leu Ser Pro Arg Pro
        355             360                 365

ATT TCC TAC TTG AAA GGC TCC TCG GGG GGT CCG CTG TTG TGC CCC GCG       1152
Ile Ser Tyr Leu Lys Gly Ser Ser Gly Gly Pro Leu Leu Cys Pro Ala
    370             375             380

GGG CAC GCC GTG GGC ATA TTT AGG GCC GCG GTG TGC ACC CGT GGA GTG       1200
Gly His Ala Val Gly Ile Phe Arg Ala Ala Val Cys Thr Arg Gly Val
385             390             395                             400

GCT AAG GCG GTG GAC TTT ATC CCT GTG GAG AAC CTA GAG ACA ACC ATG       1248
Ala Lys Ala Val Asp Phe Ile Pro Val Glu Asn Leu Glu Thr Thr Met
                405             410                 415

AGG TCC CCG GTG TTC ACG GAT AAC TCC TCT CCA CCA GTA GTG CCC CAG       1296
Arg Ser Pro Val Phe Thr Asp Asn Ser Ser Pro Pro Val Val Pro Gln
            420             425                 430

AGC TTC CAG GTG GCT CAC CTC CAT GCT CCC ACA GGC AGC GGC AAA AGC       1344
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ser | Phe | Gln | Val | Ala | His | Leu | His | Ala | Pro | Thr | Gly | Ser | Gly | Lys | Ser |      |
|     |     | 435 |     |     |     |     | 440 |     |     |     |     | 445 |     |     |     |      |
| ACC | AAG | GTC | CCG | GCT | GCA | TAT | GCA | GCT | CAG | GGC | TAT | AAG | GTG | CTA | GTA | 1392 |
| Thr | Lys | Val | Pro | Ala | Ala | Tyr | Ala | Ala | Gln | Gly | Tyr | Lys | Val | Leu | Val |      |
|     | 450 |     |     |     |     | 455 |     |     |     |     |     | 460 |     |     |     |      |
| CTC | AAC | CCC | TCT | GTT | GCT | GCA | ACA | CTG | GGC | TTT | GGT | GCT | TAC | ATG | TCC | 1440 |
| Leu | Asn | Pro | Ser | Val | Ala | Ala | Thr | Leu | Gly | Phe | Gly | Ala | Tyr | Met | Ser |      |
| 465 |     |     |     |     | 470 |     |     |     |     | 475 |     |     |     |     | 480 |      |
| AAG | GCT | CAT | GGG | ATC | GAT | CCT | AAC | ATC | AGG | ACC | GGG | GTG | AGA | ACA | ATT | 1488 |
| Lys | Ala | His | Gly | Ile | Asp | Pro | Asn | Ile | Arg | Thr | Gly | Val | Arg | Thr | Ile |      |
|     |     |     |     | 485 |     |     |     |     | 490 |     |     |     |     | 495 |     |      |
| ACC | ACT | GGC | AGC | CCC | ATC | ACG | TAC | TCC | ACC | TAC | GGC | AAG | TTC | CTT | GCC | 1536 |
| Thr | Thr | Gly | Ser | Pro | Ile | Thr | Tyr | Ser | Thr | Tyr | Gly | Lys | Phe | Leu | Ala |      |
|     |     |     | 500 |     |     |     |     | 505 |     |     |     |     | 510 |     |     |      |
| GAC | GGC | GGG | TGC | TCG | GGG | GGC | GCT | TAT | GAC | ATA | ATA | ATT | TGT | GAC | GAG | 1584 |
| Asp | Gly | Gly | Cys | Ser | Gly | Gly | Ala | Tyr | Asp | Ile | Ile | Ile | Cys | Asp | Glu |      |
|     |     | 515 |     |     |     |     | 520 |     |     |     |     | 525 |     |     |     |      |
| TGC | CAC | TCC | ACG | GAT | GCC | ACA | TCC | ATC | TTG | GGC | ATT | GGC | ACT | GTC | CTT | 1632 |
| Cys | His | Ser | Thr | Asp | Ala | Thr | Ser | Ile | Leu | Gly | Ile | Gly | Thr | Val | Leu |      |
|     |     | 530 |     |     |     | 535 |     |     |     |     | 540 |     |     |     |     |      |
| GAC | CAA | GCA | GAG | ACT | GCG | GGG | GCG | AGA | CTG | GTT | GTG | CTC | GCC | ACC | GCC | 1680 |
| Asp | Gln | Ala | Glu | Thr | Ala | Gly | Ala | Arg | Leu | Val | Val | Leu | Ala | Thr | Ala |      |
| 545 |     |     |     |     | 550 |     |     |     |     | 555 |     |     |     |     | 560 |      |
| ACC | CCT | CCG | GGC | TCC | GTC | ACT | GTG | CCC | CAT | CCC | AAC | ATC | GAG | GAG | GTT | 1728 |
| Thr | Pro | Pro | Gly | Ser | Val | Thr | Val | Pro | His | Pro | Asn | Ile | Glu | Glu | Val |      |
|     |     |     |     | 565 |     |     |     |     | 570 |     |     |     |     | 575 |     |      |
| GCT | CTG | TCC | ACC | ACC | GGA | GAG | ATC | CCT | TTT | TAC | GGC | AAG | GCT | ATC | CCC | 1776 |
| Ala | Leu | Ser | Thr | Thr | Gly | Glu | Ile | Pro | Phe | Tyr | Gly | Lys | Ala | Ile | Pro |      |
|     |     |     | 580 |     |     |     |     | 585 |     |     |     |     | 590 |     |     |      |
| CTC | GAA | GTA | ATC | AAG | GGG | GGG | AGA | CAT | CTC | ATC | TTC | TGT | CAT | TCA | AAG | 1824 |
| Leu | Glu | Val | Ile | Lys | Gly | Gly | Arg | His | Leu | Ile | Phe | Cys | His | Ser | Lys |      |
|     |     | 595 |     |     |     |     | 600 |     |     |     |     | 605 |     |     |     |      |
| AAG | AAG | TGC | GAC | GAA | CTC | GCC | GCA | AAG | CTG | GTC | GCA | TTG | GGC | ATC | AAT | 1872 |
| Lys | Lys | Cys | Asp | Glu | Leu | Ala | Ala | Lys | Leu | Val | Ala | Leu | Gly | Ile | Asn |      |
|     | 610 |     |     |     |     | 615 |     |     |     |     | 620 |     |     |     |     |      |
| GCC | GTG | GCC | TAC | TAC | CGC | GGT | CTT | GAC | GTG | TCC | GTC | ATC | CCG | ACC | AGC | 1920 |
| Ala | Val | Ala | Tyr | Tyr | Arg | Gly | Leu | Asp | Val | Ser | Val | Ile | Pro | Thr | Ser |      |
| 625 |     |     |     |     | 630 |     |     |     |     | 635 |     |     |     |     | 640 |      |
| GGC | GAT | GTT | GTC | GTC | GTG | GCA | ACC | GAT | GCC | CTC | ATG | ACC | GGC | TAT | ACC | 1968 |
| Gly | Asp | Val | Val | Val | Val | Ala | Thr | Asp | Ala | Leu | Met | Thr | Gly | Tyr | Thr |      |
|     |     |     |     | 645 |     |     |     |     | 650 |     |     |     |     | 655 |     |      |
| GGC | GAC | TTC | GAC | TCG | GTG | ATA | GAC | TGC | AAT | ACG | TGT | GTC | ACC | CAG | ACA | 2016 |
| Gly | Asp | Phe | Asp | Ser | Val | Ile | Asp | Cys | Asn | Thr | Cys | Val | Thr | Gln | Thr |      |
|     |     | 660 |     |     |     |     | 665 |     |     |     |     | 670 |     |     |     |      |
| GTC | GAT | TTC | AGC | CTT | GAC | CCT | ACC | TTC | ACC | ATT | GAG | ACA | ATC | ACG | CTC | 2064 |
| Val | Asp | Phe | Ser | Leu | Asp | Pro | Thr | Phe | Thr | Ile | Glu | Thr | Ile | Thr | Leu |      |
|     |     | 675 |     |     |     |     | 680 |     |     |     |     | 685 |     |     |     |      |
| CCC | CAA | GAT | GCT | GTC | TCC | CGC | ACT | CAA | CGT | CGG | GGC | AGG | ACT | GGC | AGG | 2112 |
| Pro | Gln | Asp | Ala | Val | Ser | Arg | Thr | Gln | Arg | Arg | Gly | Arg | Thr | Gly | Arg |      |
|     | 690 |     |     |     |     | 695 |     |     |     |     | 700 |     |     |     |     |      |
| GGG | AAG | CCA | GGC | ATC | TAC | AGA | TTT | GTG | GCA | CCG | GGG | GAG | CGC | CCT | CCC | 2160 |
| Gly | Lys | Pro | Gly | Ile | Tyr | Arg | Phe | Val | Ala | Pro | Gly | Glu | Arg | Pro | Pro |      |
| 705 |     |     |     |     | 710 |     |     |     |     | 715 |     |     |     |     | 720 |      |
| GGC | ATG | TTC | GAC | TCG | TCC | GTC | CTC | TGT | GAG | TGC | TAT | GAC | GCA | GGC | TGT | 2208 |
| Gly | Met | Phe | Asp | Ser | Ser | Val | Leu | Cys | Glu | Cys | Tyr | Asp | Ala | Gly | Cys |      |
|     |     |     |     | 725 |     |     |     |     | 730 |     |     |     |     | 735 |     |      |
| GCT | TGG | TAT | GAG | CTC | ACG | CCC | GCC | GAG | ACT | ACA | GTT | AGG | CTA | CGA | GCG | 2256 |
| Ala | Trp | Tyr | Glu | Leu | Thr | Pro | Ala | Glu | Thr | Thr | Val | Arg | Leu | Arg | Ala |      |
|     |     |     | 740 |     |     |     |     | 745 |     |     |     |     | 750 |     |     |      |
| TAC | ATG | AAC | ACC | CCG | GGG | CTT | CCC | GTG | TGC | CAG | GAC | CAT | CTT | GAA | TTT | 2304 |

```
           Tyr  Met  Asn  Thr  Pro  Gly  Leu  Pro  Val  Cys  Gln  Asp  His  Leu  Glu  Phe
                     755                 760                      765

TGG  GAG  GGC  GTC  TTT  ACA  GGC  CTC  ACT  CAT  ATA  GAT  GCC  CAC  TTT  CTA           2352
Trp  Glu  Gly  Val  Phe  Thr  Gly  Leu  Thr  His  Ile  Asp  Ala  His  Phe  Leu
     770                 775                      780

TCC  CAG  ACA  AAG  CAG  AGT  GGG  GAG  AAC  CTT  CCT  TAC  CTG  GTA  GCG  TAC           2400
Ser  Gln  Thr  Lys  Gln  Ser  Gly  Glu  Asn  Leu  Pro  Tyr  Leu  Val  Ala  Tyr
785                      790                      795                      800

CAA  GCC  ACC  GTG  TGC  GCT  AGG  GCT  CAA  GCC  CCT  CCC  CCA  TCG  TGG  GAC           2448
Gln  Ala  Thr  Val  Cys  Ala  Arg  Ala  Gln  Ala  Pro  Pro  Pro  Ser  Trp  Asp
                    805                      810                      815

CAG  ATG  TGG  AAG  TGT  TTG  ATT  CGC  CTC  AAG  CCC  ACC  CTC  CAT  GGG  CCA           2496
Gln  Met  Trp  Lys  Cys  Leu  Ile  Arg  Leu  Lys  Pro  Thr  Leu  His  Gly  Pro
               820                      825                      830

ACA  CCC  CTG  CTA  TAC  AGA  CTG  GGC  GCT                                              2523
Thr  Pro  Leu  Leu  Tyr  Arg  Leu  Gly  Ala
               835                      840
```

( 2 ) INFORMATION FOR SEQ ID NO:86:

( i ) SEQUENCE CHARACTERISTICS:
        ( A ) LENGTH: 841 amino acids
        ( B ) TYPE: amino acid
        ( D ) TOPOLOGY: linear ( i i ) MOLECULE TYPE: protein ( x i ) SEQUENCE DESCRIPTION: SEQ ID NO:86:

```
Met  Ala  Thr  Asn  Pro  Val  Cys  Val  Leu  Lys  Gly  Asp  Gly  Pro  Val  Gln
  1                 5                      10                      15

Gly  Ile  Ile  Asn  Phe  Glu  Gln  Lys  Glu  Ser  Asn  Gly  Pro  Val  Lys  Val
               20                      25                      30

Trp  Gly  Ser  Ile  Lys  Gly  Leu  Thr  Glu  Gly  Leu  His  Gly  Phe  His  Val
          35                      40                      45

His  Glu  Phe  Gly  Asp  Asn  Thr  Ala  Gly  Cys  Thr  Ser  Pro  Gly  Pro  His
     50                      55                      60

Phe  Asn  Pro  Leu  Ser  Arg  Lys  His  Gly  Gly  Pro  Lys  Asp  Glu  Glu  Arg
 65                      70                      75                       80

His  Val  Gly  Asp  Leu  Gly  Asn  Val  Thr  Ala  Asp  Lys  Asp  Gly  Val  Ala
                    85                      90                       95

Asp  Val  Ser  Ile  Glu  Asp  Ser  Val  Ile  Ser  Leu  Ser  Gly  Asp  His  Cys
                   100                     105                     110

Ile  Ile  Gly  Arg  Thr  Leu  Val  Val  His  Glu  Lys  Ala  Asp  Asp  Leu  Gly
              115                     120                     125

Lys  Gly  Gly  Asn  Glu  Glu  Ser  Thr  Lys  Thr  Gly  Asn  Ala  Gly  Ser  Arg
     130                     135                     140

Leu  Ala  Cys  Gly  Val  Ile  Gly  Ile  Arg  Ile  Arg  Gly  Thr  Tyr  Val  Tyr
145                      150                     155                     160

Asn  His  Leu  Thr  Pro  Leu  Arg  Asp  Trp  Ala  His  Asn  Gly  Leu  Arg  Asp
                    165                     170                     175

Leu  Ala  Val  Ala  Val  Glu  Pro  Val  Val  Phe  Ser  Gln  Met  Glu  Thr  Lys
               180                     185                     190

Leu  Ile  Thr  Trp  Gly  Ala  Asp  Thr  Ala  Ala  Cys  Gly  Asp  Ile  Ile  Asn
          195                     200                     205

Gly  Leu  Pro  Val  Ser  Ala  Arg  Arg  Gly  Arg  Glu  Ile  Leu  Leu  Gly  Pro
     210                     215                     220

Ala  Asp  Gly  Met  Val  Ser  Lys  Gly  Trp  Arg  Leu  Leu  Ala  Pro  Ile  Thr
225                      230                     235                     240
```

| | | | | | | | | | | | | | | | |
|---|---|---|---|---|---|---|---|---|---|---|---|---|---|---|---|
| Ala | Tyr | Ala | Gln | Gln | Thr | Arg | Gly | Leu | Leu | Gly | Cys | Ile | Ile | Thr | Ser |
| | | | | 245 | | | | | 250 | | | | | 255 | |
| Leu | Thr | Gly | Arg | Asp | Lys | Asn | Gln | Val | Glu | Gly | Glu | Val | Gln | Ile | Val |
| | | | 260 | | | | | 265 | | | | | 270 | | |
| Ser | Thr | Ala | Ala | Gln | Thr | Phe | Leu | Ala | Thr | Cys | Ile | Ile | Asn | Gly | Val |
| | | | 275 | | | | | 280 | | | | | 285 | | |
| Cys | Trp | Thr | Val | Tyr | His | Gly | Ala | Gly | Thr | Arg | Thr | Ile | Ala | Ser | Pro |
| | | 290 | | | | | 295 | | | | | 300 | | | |
| Lys | Gly | Pro | Val | Ile | Gln | Met | Tyr | Thr | Asn | Val | Asp | Gln | Asp | Leu | Val |
| | 305 | | | | | 310 | | | | | 315 | | | | 320 |
| Gly | Trp | Pro | Ala | Ser | Gln | Gly | Thr | Arg | Ser | Leu | Thr | Pro | Cys | Thr | Cys |
| | | | | 325 | | | | | 330 | | | | | 335 | |
| Gly | Ser | Ser | Asp | Leu | Tyr | Leu | Val | Thr | Arg | His | Ala | Asp | Val | Ile | Pro |
| | | | 340 | | | | | 345 | | | | | 350 | | |
| Val | Arg | Arg | Arg | Gly | Asp | Ser | Arg | Gly | Ser | Leu | Leu | Ser | Pro | Arg | Pro |
| | | | 355 | | | | | 360 | | | | | 365 | | |
| Ile | Ser | Tyr | Leu | Lys | Gly | Ser | Ser | Gly | Gly | Pro | Leu | Leu | Cys | Pro | Ala |
| | 370 | | | | | 375 | | | | | 380 | | | | |
| Gly | His | Ala | Val | Gly | Ile | Phe | Arg | Ala | Ala | Val | Cys | Thr | Arg | Gly | Val |
| 385 | | | | | 390 | | | | | 395 | | | | | 400 |
| Ala | Lys | Ala | Val | Asp | Phe | Ile | Pro | Val | Glu | Asn | Leu | Glu | Thr | Thr | Met |
| | | | | 405 | | | | | 410 | | | | | 415 | |
| Arg | Ser | Pro | Val | Phe | Thr | Asp | Asn | Ser | Ser | Pro | Pro | Val | Val | Pro | Gln |
| | | | 420 | | | | | 425 | | | | | 430 | | |
| Ser | Phe | Gln | Val | Ala | His | Leu | His | Ala | Pro | Thr | Gly | Ser | Gly | Lys | Ser |
| | | 435 | | | | | 440 | | | | | 445 | | | |
| Thr | Lys | Val | Pro | Ala | Ala | Tyr | Ala | Ala | Gln | Gly | Tyr | Lys | Val | Leu | Val |
| | 450 | | | | | 455 | | | | | 460 | | | | |
| Leu | Asn | Pro | Ser | Val | Ala | Ala | Thr | Leu | Gly | Phe | Gly | Ala | Tyr | Met | Ser |
| 465 | | | | | 470 | | | | | 475 | | | | | 480 |
| Lys | Ala | His | Gly | Ile | Asp | Pro | Asn | Ile | Arg | Thr | Gly | Val | Arg | Thr | Ile |
| | | | | 485 | | | | | 490 | | | | | 495 | |
| Thr | Thr | Gly | Ser | Pro | Ile | Thr | Tyr | Ser | Thr | Tyr | Gly | Lys | Phe | Leu | Ala |
| | | | 500 | | | | | 505 | | | | | 510 | | |
| Asp | Gly | Gly | Cys | Ser | Gly | Gly | Ala | Tyr | Asp | Ile | Ile | Ile | Cys | Asp | Glu |
| | | 515 | | | | | 520 | | | | | 525 | | | |
| Cys | His | Ser | Thr | Asp | Ala | Thr | Ser | Ile | Leu | Gly | Ile | Gly | Thr | Val | Leu |
| | 530 | | | | | 535 | | | | | 540 | | | | |
| Asp | Gln | Ala | Glu | Thr | Ala | Gly | Ala | Arg | Leu | Val | Val | Leu | Ala | Thr | Ala |
| 545 | | | | | 550 | | | | | 555 | | | | | 560 |
| Thr | Pro | Pro | Gly | Ser | Val | Thr | Val | Pro | His | Pro | Asn | Ile | Glu | Glu | Val |
| | | | | 565 | | | | | 570 | | | | | 575 | |
| Ala | Leu | Ser | Thr | Thr | Gly | Glu | Ile | Pro | Phe | Tyr | Gly | Lys | Ala | Ile | Pro |
| | | | 580 | | | | | 585 | | | | | 590 | | |
| Leu | Glu | Val | Ile | Lys | Gly | Gly | Arg | His | Leu | Ile | Phe | Cys | His | Ser | Lys |
| | | 595 | | | | | 600 | | | | | 605 | | | |
| Lys | Lys | Cys | Asp | Glu | Leu | Ala | Ala | Lys | Leu | Val | Ala | Leu | Gly | Ile | Asn |
| | 610 | | | | | 615 | | | | | 620 | | | | |
| Ala | Val | Ala | Tyr | Tyr | Arg | Gly | Leu | Asp | Val | Ser | Val | Ile | Pro | Thr | Ser |
| 625 | | | | | 630 | | | | | 635 | | | | | 640 |
| Gly | Asp | Val | Val | Val | Val | Ala | Thr | Asp | Ala | Leu | Met | Thr | Gly | Tyr | Thr |
| | | | | 645 | | | | | 650 | | | | | 655 | |
| Gly | Asp | Phe | Asp | Ser | Val | Ile | Asp | Cys | Asn | Thr | Cys | Val | Thr | Gln | Thr |
| | | | 660 | | | | | 665 | | | | | 670 | | |

| | | | | | | | | | | | | | | |
|---|---|---|---|---|---|---|---|---|---|---|---|---|---|---|
| Val | Asp | Phe 675 | Ser | Leu | Asp | Pro | Thr 680 | Phe | Thr | Ile | Glu | Thr 685 | Ile | Thr | Leu |
| Pro | Gln 690 | Asp | Ala | Val | Ser | Arg 695 | Thr | Gln | Arg | Arg | Gly 700 | Arg | Thr | Gly | Arg |
| Gly 705 | Lys | Pro | Gly | Ile | Tyr 710 | Arg | Phe | Val | Ala | Pro 715 | Gly | Glu | Arg | Pro | Pro 720 |
| Gly | Met | Phe | Asp | Ser 725 | Ser | Val | Leu | Cys | Glu 730 | Cys | Tyr | Asp | Ala | Gly 735 | Cys |
| Ala | Trp | Tyr | Glu 740 | Leu | Thr | Pro | Ala | Glu 745 | Thr | Thr | Val | Arg | Leu 750 | Arg | Ala |
| Tyr | Met | Asn 755 | Thr | Pro | Gly | Leu | Pro 760 | Val | Cys | Gln | Asp | His 765 | Leu | Glu | Phe |
| Trp | Glu 770 | Gly | Val | Phe | Thr | Gly 775 | Leu | Thr | His | Ile | Asp 780 | Ala | His | Phe | Leu |
| Ser 785 | Gln | Thr | Lys | Gln | Ser 790 | Gly | Glu | Asn | Leu | Pro 795 | Tyr | Leu | Val | Ala | Tyr 800 |
| Gln | Ala | Thr | Val | Cys 805 | Ala | Arg | Ala | Gln | Ala 810 | Pro | Pro | Pro | Ser | Trp 815 | Asp |
| Gln | Met | Trp | Lys 820 | Cys | Leu | Ile | Arg | Leu 825 | Lys | Pro | Thr | Leu | His 830 | Gly | Pro |
| Thr | Pro | Leu 835 | Leu | Tyr | Arg | Leu | Gly 840 | Ala | | | | | | | |